US010639364B2

(12) United States Patent
Gallei et al.

(10) Patent No.: US 10,639,364 B2
(45) Date of Patent: May 5, 2020

(54) PRRS VIRUS VARIANT, EUROPEAN PRRS VIRUS CDNA CLONE, AND USES THEREOF

(71) Applicant: Boehringer Ingelheim Vetmedica GmbH, Ingelheim am Rhein (DE)

(72) Inventors: Andreas Gallei, Hannover (DE); Christoph Keller, Burgdorf (DE); Erik Schacht, Hannover (DE); Marieke Herrel, Hannover (DE)

( * ) Notice: Subject to any disclaimer, the term of this patent is extended or adjusted under 35 U.S.C. 154(b) by 47 days.

(21) Appl. No.: 15/995,560

(22) Filed: Jun. 1, 2018

(65) Prior Publication Data

US 2019/0151432 A1 May 23, 2019

Related U.S. Application Data

(62) Division of application No. 15/105,760, filed as application No. PCT/EP2014/078929 on Dec. 19, 2014, now Pat. No. 10,010,601.

(30) Foreign Application Priority Data

Dec. 20, 2013 (EP) .................................... 13199177
Jul. 3, 2014 (EP) .................................... 14175691

(51) Int. Cl.

*A61K 39/12* (2006.01)
*C12N 15/86* (2006.01)
*C12N 7/00* (2006.01)
*C12Q 1/02* (2006.01)
*C07K 14/005* (2006.01)
*A61K 39/00* (2006.01)

(52) U.S. Cl.

CPC ............ *A61K 39/12* (2013.01); *C07K 14/005* (2013.01); *C12N 7/00* (2013.01); *C12N 15/86* (2013.01); *C12Q 1/02* (2013.01); *A61K 2039/5254* (2013.01); *A61K 2039/552* (2013.01); *C12N 2770/10021* (2013.01); *C12N 2770/10034* (2013.01); *C12N 2770/10043* (2013.01); *G01N 2333/08* (2013.01)

(58) Field of Classification Search

None
See application file for complete search history.

(56) References Cited

U.S. PATENT DOCUMENTS

| | | | |
|---|---|---|---|
| 3,137,631 | A | 6/1964 | Soloway |
| 3,959,457 | A | 5/1976 | Speaker et al. |
| 4,015,100 | A | 3/1977 | Gnanamuthu et al. |
| 4,205,060 | A | 5/1980 | Monsimer et al. |
| 5,597,721 | A | 1/1997 | Brun et al. |
| 5,620,691 | A | 4/1997 | Wensvoort et al. |
| 5,695,766 | A | 12/1997 | Paul et al. |
| 5,698,203 | A | 12/1997 | Visser et al. |
| 5,858,729 | A | 1/1999 | Van Woensel et al. |
| 5,866,401 | A | 2/1999 | Hesse |
| 5,888,513 | A | 3/1999 | Plana Duran et al. |
| 5,925,359 | A | 7/1999 | Van Woensel et al. |
| 6,001,370 | A | 12/1999 | Burch et al. |
| 6,110,467 | A | 8/2000 | Paul et al. |
| 6,197,310 | B1 | 3/2001 | Wensvoort et al. |
| 6,268,199 | B1 | 7/2001 | Meulenberg et al. |
| 6,455,245 | B1 | 9/2002 | Wensvoort et al. |
| 6,495,138 | B1 | 12/2002 | van Nieuwstadt et al. |
| 6,500,662 | B1 * | 12/2002 | Calvert ................ C07K 14/005 435/235.1 |
| 6,806,086 | B2 | 10/2004 | Wensvoort et al. |
| 7,312,030 | B2 | 12/2007 | van Rijn et al. |
| 7,335,473 | B2 | 2/2008 | Wensvoort et al. |
| 7,368,117 | B2 | 5/2008 | Fetzer et al. |
| 7,897,343 | B2 | 3/2011 | Wensvoort et al. |
| 8,765,142 | B2 | 7/2014 | Burgard et al. |
| 2002/0172690 | A1 | 11/2002 | Calvert et al. |
| 2003/0049274 | A1 | 3/2003 | Meulenberg et al. |
| 2003/0118608 | A1 | 6/2003 | Wensvoort et al. |
| 2004/0132014 | A1 | 7/2004 | Wensvoort et al. |
| 2004/0197872 | A1 | 10/2004 | Meulenberg et al. |
| 2004/0224327 | A1 | 11/2004 | Meulenberg et al. |
| 2006/0205033 | A1 | 9/2006 | Meulenberg et al. |
| 2006/0240041 | A1 | 10/2006 | Meulenberg et al. |
| 2010/0136047 | A1 | 6/2010 | Fang et al. |
| 2011/0104201 | A1 | 5/2011 | Mengeling et al. |
| 2012/0213741 | A1 | 8/2012 | Berry et al. |

(Continued)

FOREIGN PATENT DOCUMENTS

| | | | |
|---|---|---|---|
| CA | 2103460 | A1 | 12/1992 |
| EP | 587780 | A1 | 3/1994 |

(Continued)

OTHER PUBLICATIONS

Linhares et al. (Vaccine. 2012; 30: 407-413).*
Mengeling et al., "Comparison among strains of porcine reproductive and respiratory syndrome virus for their ability to cause reproductive failure", American Journal of Veterinary Research, vol. 57, No. 6, Jun. 1996, pp. 834-839.
Mengeling et al., "Strain specificity of the immune response of pigs following vaccination with various strains of porcine reproductive and respiratory syndrome virus". Veterinary Microbiology, vol. 93, 2003, pp. 13-24.

(Continued)

*Primary Examiner* — Shanon A. Foley
(74) *Attorney, Agent, or Firm* — Judy Jarecki-Black

(57) ABSTRACT

The present invention belongs to the field of animal health and provides means to study Porcine Reproductive and Respiratory Syndrome (PRRS), a viral disease affecting swine, and for the development of vaccines, therapeutics and diagnostics for the prophylaxis, treatment and diagnosis of PRRS. In a first consideration, the invention relates to a new PRRS virus variant. and, in a second consideration, to a nucleic acid sequence which comprises the genome of an infectious genotype I (EU) PRRS virus clone. Based on this, new PRRS vaccine candidates with improved properties are provided.

20 Claims, 7 Drawing Sheets

Figure 1:
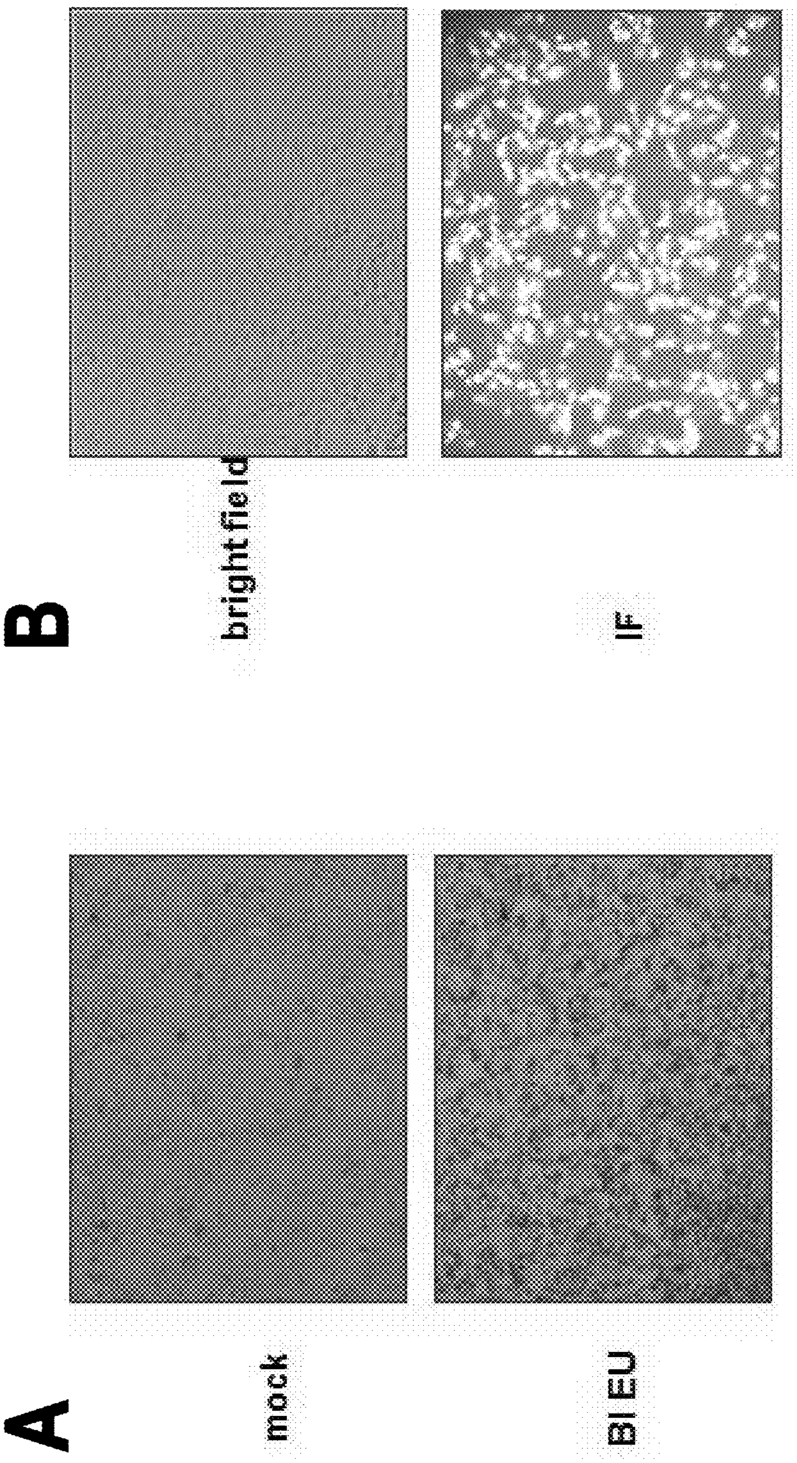

Specification includes a Sequence Listing.

(56) References Cited

U.S. PATENT DOCUMENTS

| | | | | |
|---|---|---|---|---|
| 2012/0213810 | A1 | 8/2012 | Burgard et al. | |
| 2016/0317642 | A1 | 11/2016 | Gallei et al. | |
| 2017/0065709 | A1 | 3/2017 | Burgard et al. | |
| 2019/0151432 | A1* | 5/2019 | Gallei | C12N 7/00 |

FOREIGN PATENT DOCUMENTS

| | | | |
|---|---|---|---|
| EP | 676467 | A2 | 10/1995 |
| EP | 732340 | A2 | 9/1996 |
| EP | 0835929 | A1 | 4/1998 |
| EP | 0835930 | A1 | 4/1998 |
| EP | 0839912 | A1 | 5/1998 |
| EP | 1018557 | A2 | 7/2000 |
| GB | 2282811 | A | 4/1995 |
| GB | 2289279 | A | 11/1995 |
| WO | 199221375 | A1 | 12/1992 |
| WO | 199307898 | A1 | 4/1993 |
| WO | 199314196 | A1 | 7/1993 |
| WO | 199531550 | A1 | 11/1995 |
| WO | 1996036356 | A1 | 11/1996 |
| WO | 1998018933 | A1 | 5/1998 |
| WO | 199850426 | A1 | 11/1998 |
| WO | 2000053787 | A1 | 9/2000 |
| WO | 200159077 | A1 | 8/2001 |
| WO | 200190363 | A1 | 11/2001 |
| WO | 2002095040 | A1 | 11/2002 |
| WO | 2006002193 | A2 | 1/2006 |
| WO | 2006034319 | A2 | 3/2006 |
| WO | 2006074986 | A2 | 7/2006 |
| WO | 2008121958 | A1 | 10/2008 |
| WO | 2010025109 | A1 | 3/2010 |
| WO | 20110128415 | A1 | 10/2011 |
| WO | 2012110489 | A2 | 8/2012 |
| WO | 2013/123242 | A1 | 8/2013 |
| WO | 2013/173443 | A1 | 11/2013 |
| WO | 2014150822 | A2 | 9/2014 |
| WO | 2015092058 | A1 | 6/2015 |

OTHER PUBLICATIONS

Meredith, MJ, "Porcine Reproductive and Respiratory Syndrome (PRRS)", Pig Disease Information Center, 1st North American Edition, University of Cambridge, Aug. 1994, pp. 1-57.
Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.
Meulenberg et al., "Characterization of Proteins Encoded by ORFs 2 to 7 of Lelystad Virus". Virology, vol. 206, No. 1, Jan. 1995, pp. 155-163.
Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.
Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.
Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.
Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.
Meulenberg et al., "Molecular characterization of Lelystad virus". Veterinary Microbiology, vol. 55, 1997, pp. 197-202.
Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.
Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.
Meulenberg et al., "Subgenomic RNAs of Lelystad virus contain a conserved leader-body junction sequence". Journal of General Virology, vol. 74, 1993, pp. 1697-1701.
Murtaugh et al., "Comparison of the structural protein coding sequences of the VR-2332 and Lelystad virus strains of the PRRS virus". Archives of Virology, vol. 140, No. 8, 1995, pp. 1451-1460.
Murtaugh et al., "Genetic Variation in the PRRS Virus". Coronaviruses and Arteriviruses, Plenum Press, New York, 1998, pp. 787-794.
Nam et al. "Complete genomic characterization of a European type 1 porcine reproductive and respiratory syndrome virus isolate in Korea". Archives of Virology, vol. 154, No. 4, 2009, pp. 629-638.
NCBI: Accession No. AF159149. "Porcine reproductive and respiratory syndrome virus isolate MLV RespPRRS/Repro, complete genome." Aug. 28, 2000.
NCBI: Accession No. AF176348. "Porcine reproductive and respiratory syndrome virus isolate PA8 complete genome." Sep. 3, 2002.
NCBI: Accession No. AF184212. "Porcine reproductive and respiratory syndrome virus strain SP, complete genome." Sep. 28, 2000.
NCBI: Accession No. AF325691. "Porcine reproductive and respiratory syndrome virus isolate NVSL 977985 IA 1-4-2, complete genome." Feb. 11, 2001.
NCBI: Accession No. AF331831. "Porcine reproductive and respiratory syndrome virus BJ-4, complete genome." Jan. 15, 2001.
NCBI: Accession No. B4ZWR2. "Porcine reproductive and respiratory syndrome virus (PRRSV)." May 2008, 1 page.
NCBI: Accession No. M96262.2. "Lelystad virus, complete genome." Nov. 8, 2000.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. U87392 AF030244 U00153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.
Nodelijk et al., "A quantitative assessment of the effectiveness of PRRSV vaccination in pigs under experimental conditions". Vaccine, vol. 19, 2000, pp. 3636-3644.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine reproductive and Respiratory Syndrome Virus (PRRSV) Contains Antibodies Against Structural as Well as Nonstructural Viral Proteins", Veterinary Microbiology, vol. 81, 2001, pp. 109-125.
Ostrowski et al., "Identification of Neutralizing and Nonneutralizing Epitopes on the Porcine Reproductive and Respiratory Syndrome Virus GP5 Ectodomain", Journal of Virology, vol. 76, No. 9, May 2002, pp. 4241-4250.
Pesch et al., "New insights into the genetic diversity of European porcine reproductive and respiratory syndrome virus (PRRSV)". Veterinary Microbiology, vol. 107, 2005, pp. 31-48.
Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.
Porcine Reproductive and Respiratory Syndrome: A Report on the Seminar Held in Brussels on Nov. 4-5, 1991 and Organized by the European Commission, pp. 1-74.
Prieto et al., "Similarity of European porcine reproductive and respiratory syndrome virus strains to vaccine strain is not neces-

(56) References Cited

OTHER PUBLICATIONS sarily predictive of the degree of protective immunity conferred". The Veterinary Journal, vol. 175, No. 3, Mar. 2008, pp. 356-363.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.
Shin et al., "Assessment of Porcine Reproductive and Respiratory Syndrome Virus RNA Load in Sera and Tissues during Acute Infection", Journal of Veterinary Science, vol. 3, No. 2, 2002, pp. 75-85.
Suarez et al., "Direct detection of the porcine reproductive and respiratory syndrome (PRRS) virus by reverse polymerase chain reaction (RT-PCR)", Archives ofVirology, vol. 135, No. 1-2, 1994, pp. 89-99.
Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.
Sun et al., "Crystal Structure of Porcine Reproductive and Respiratory Syndrome Virus Leader Protease Nsp1aN". Journal of Virology, vol. 83, No. 21, Nov. 2009, pp. 10931-10940.
Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.
Van Der Meer et al., "ORF1a-Encoded Replicase Subunits Are Involved in the Membrane Association of the Arterivirus Replication Complex", Journal of Virology, vol. 72, No. 8, 1998, pp. 6689-6698.
Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Verheije et al., "Safety and protective efficacy of porcine reproductive and respiratory syndrome recombinant virus vaccines in young pigs". Vaccine, vol. 21, 2003, pp. 2556-2563.
Wensvoort et al., "'Blue ear' disease in pigs", Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Wieczorek-Krohmer et al., "Porcine reproductive and respiratory syndrome virus (PRRSV): Monoclonal antibodies detect common epitopes on two viral proteins of European and U.S. isolates", Veterinary Microbiology, vol. 51, Nos. 3-4, Aug. 1996, pp. 257-266.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.
Xiao et al., "The Level of Virus-Specific T-Cell and Macrophage Recruitment in Porcine Reproductive and Respiratory Syndrome Virus Infection in Pigs Is Independent of Virus Load", Journal ofV irology, vol. 78, No. 11, Jun. 2004, pp. 6461-6471.
Xue et al., "The Crystal Structure of Porcine Reproductive and Respiratory Syndrome Virus Nonstructural Protein Nsp1b Reveals a Novel a Metal-Dependent Nuclease", Journal of Virology, vol. 84, No. 13, Jul. 2010, pp. 6461-6471.
Yang et al., "Comparative sequence analysis of open reading frames 2 to 7 of the modified live vaccine virus and other North American isolates of the porcine reproductive and respiratory syndrome virus", Archives of Virology, vol. 143, 1998, pp. 601-612.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains'[Virus Research 74 (2001) 99-110]". Virus Research, vol. 79, 2001, p. 187.
Zhou et al., "The 30-Amino-Acid Deletion in the Nsp2 of highly Pathogenic Porcine Reproductive and Respiratory Syndrome Virus Emerging in China is Not related to its Virulence", Journal of Virology, vol. 83, No. 10, May 2009, pp. 5156-5167.
Sun et al, "Differential Host Cell Gene Expression and Regulation of Cell Cycle Progression by Nonstructural Protein 11 of Porcine Reproductive and Respiratory Syndrome Virus", Biomedical research International, 2014:430508.
Sequence alignment of nt 1-10000 of SEQ ID No. 48 with Geneseq database access No. AZZ01652 by Burgard et al. in USPgPub 2012213810 on Dec. 2012.
Sequence alignment of nt 10001-14843 of SEQ ID No. 48 with Geneseq database access No. AZZ01652 by Burgard et al. in USPgPub 2012213810 on Dec. 2012.
"DutchTeam Isolates Mystery Pig Disease Agent", Animal Pharm, vol. 230, Abstract No. 00278268, Jun. 21, 1991, p. 21.
Albina et al., "Immune responses in pigs infected with porcine reproductive and respiratory syndrome virus (PRRSV)". Veterinary Immunology ans Immunopathology, vol. 61. 1998, pp. 49-66.
Allende et al., "Mutations in the genome of porcine reproductive and respiratory syndrome virus responsible for the attenuation phenotype", Archives of Virology, vol. 145, No. 6, Jun. 2000, pp. 1149-1161.
Allende et al., "North American and European porcine reproductive and respiratory syndrome viruses differ in non-structural protein coding regions", Journal of General Virology, vol. 80, 1999, pp. 307-315.
Allende et al., "Porcine Reproductive and Respiratory Syndrome Virus: Description of Persistence in Individual Pigs upon Experimental Infection", Journal of Virology, vol. 74, No. 22, Nov. 2000, pp. 10834-10837.
Andreyev et al., "Genetic variation and phylogenetic relationships of 22 porcine reproductive and respiratory syndrome virus (PRRSV) field strains based on sequence analysis of open reading frame 5", Archives of Virology, vol. 142, 1997, pp. 993-1001.
Barfoed et al., "DNA vaccination of pigs with open reading frame 1-7 of PRRS virus". Vaccine, vol. 22, 2004, pp. 3628-3641.

(56) References Cited

OTHER PUBLICATIONS

Bautista et al., "Serologic Survey for Lelystad and VR-2332 Strains of Porcine Respiratory and Reproductive Syndrome (PRRS) Virus in US Swine Herds", Journal of Veterinary Diagnostic Investigation, vol. 5, No. 4, Oct. 1992, pp. 612-614.
Bramel-Verheije et al., "Expression of a Foreign Epitope by Porcine Reproductive and Respiratory Syndrome Virus", Virology, vol. 278, 2000,pp. 380-389.
Brinton-Darnell, "Lactate Dehydrogenase-Elevating, Equine Arteritis and Lelystad Viruses", Encyclopedia of Virology, vol. 2, 1999, pp. 763-771.
Brockmeier et al., "Genomic sequence and virulence comparison of four Type 2 porcine reproductive and respiratory syndrome virus strains", Virus Research, vol. 169, No. 1, 2012, pp. 212-221.
Christianson et al., "Porcine reproductive and respiratory syndrome: A review", Journal of Swine Health and Production, vol. 2, No. 2, Mar. and Apr. 1994, pp. 10-28.
Conzelmann et al., "Molecular Characterization of Porcine Reproductive and Respiratory Syndrome Virus, a Member of the Arterivirus Group", Virology, vol. 193, 1993, pp. 329-339.
Darwich et al., "Genetic and immunobiological diversities of porcine reproductive and respiratory syndrome genotype I strains". Veterinary Microbiology, vol. 150, 2011, pp. 49-62.
Database EMBL Accession No. EU759247, "Porcine respiratory and reproductive syndrome virus isolate PRRSV2000000079 envelope glycoprotein gene, complete cds". Aug. 10, 2008, 1 page.
Database WPIL Week 8702, Derwent Publications Ltd., London, GB; AN 87-009295 [2] & EP, A,208672 (Regional Wallonne-Chiron Corp, Wallonne Regional) Jan. 14, 1987, 1 page.
Database WPIL Week 87041, Derwent Publications Ltd., London, GB; AN 87-286929 [241] & EP, A,62, 198626 (ZA Bieseibutsu Kagaku Ken) Sep. 2, 1987, 1 page.
Database WPIL Week 8821, Derwent Publications Ltd., London, GB; AN 88-147502 [21] & WO,A,8 803 410 (Inst Pasteur) May 19, 1988.
Dea et al., "Antigenic Variability among North American and European Strains of Porcine Reproductive and Respiratory Syndrome Virus as Defined by Monoclonal Antibodies to the Matrix Protein", Journal of Clinical Microbiology, vol. 34, No. 5, Jun. 1996, pp. 1488-1493.
Dea et al., "Current knowledge on the structural proteins of porcine reproductive and respiratory syndrome (PRRS) virus: comparison of the North American and European isolate", Archives of Virology, vol. 145, No. 4, Apr. 2000, pp. 659-688.
Dea et al., "Swine reproductive and respiratory syndrome in Quebec: Isolation of an enveloped virus serologically-related to Lelystad virus", Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems", Proceedings of the Mystery Swine Disease Committee Meeting, Denver, CO, Oct. 6, 1990, pp. 67-72.
Den Boon et al., "Processing and Evolution of the N-Terminal Region of the Arterivirus replicase ORF1a Protein: Identification of Two Papainlike Cysteine Proteases", Journal of Virology, vol. 69, No. 7, Jul. 1995, pp. 4500-4505.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.
Duan et al., "Identification of a putative Receptor for Porcine Reproductive and Respiratory Syndrome Virus on Porcine Alveolar Macrophages", Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts PRRS, Aug. 9 to 10, 1995, Copenhagen, Denmark, 2 pages.
Genbank Accession No. ACY56808, Version ACY56808.1 GI:262358373, Nov. 8, 2009, pp. 1-2.
Goyal, S., "Porcine Reproductive and Respiratory Syndrome", Journal of Veterinary Diagnostic Investigation, vol. 5, No. 4, 1993, pp. 656-664.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
International Search Report and Written Opinion for PCT/EP2014/078929 dated Apr. 24, 2015.
Katz et al., "Antigenic differences between European and American isolates of porcine reproductive and respiratory syndrome virus (PRRSV) are encoded by the carboxyterminal portion of viral open reading frame 3", Veterinary Microbiology, vol. 44, No. 1, Apr. 1995, pp. 65-76.
Kvisgaard et al., "Genetic and antigenic characterization of complete genomes of Type 1 Porcine Reproductive and Respiratory Syndrome viruses (PRRSV) isolated in Denmark over a period of 10 years", Virus Research, vol. 178, 2013, pp. 197-205.
Kwang et al., "Cloning, expression, and sequence analysis of the ORF4 gene of the porcine reproductive and respiratory syndrome virus MN-1b", Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Mardassi et al., "Identification of major differences in the nucleocapsid protein genes of a Québec strain and European strains of porcine reproductive and respiratory syndrome virus", vol. 75, No. 3, Mar. 1994, pp. 681-685.
Mardassi et al., "Molecular analysis of the ORFs 3 to 7 of porcine reproductive and respiratory syndrome virus, Québec reference strain", Archives of Virology, vol. 140, No. 8, 1995, pp. 1405-1418.
Mardassi et al., "Structural Gene Analysis of a Quebec Reference Strain of Porcine Reproductive and Respiratory Syndrome Virus (PRRSV)", Corona- and related Viruses, Edited by P.J. Talbot and G.A. Levy, Plenum Press, New York, 1995, pp. 277-281.
McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.
Meng et al., "Molecular cloning and nucleotide sequencing of the 3'-terminal genomic RNA of the porcine reproductive and respiratory syndrome virus (PRRSV): implication fir the existence if two genotypes if PRRSV in the U.S.A. and Europe", Archives of Virology, vol. 140, No. 4, 1995, pp. 1795-1801.
Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A and Europe". Archives of Virology, vol. 140, No. 4, 1995, pp. 745-755.
Meng, X.J., "Heterogeneity of porcine reproductive and respiratory syndrome virus: implications for current vaccine efficacy and future vaccine development". Veterinary Microbiology, vol. 74, 2000, pp. 309-329.
Mengeling et al., "An update of research at the National Animal Disease Center on current field strains of Porcine Reproductive and Respiratory Syndrome (PRRS) virus", Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS", American Journal of Veterinary Research, vol. 59, No. 12, Dec. 1998, pp. 1540-1544.
Mengeling et al., "Clinical Effects of porcine reproductive and respiratory syndrome virus on pigs during the early postnatal interval", American Journal of Veterinary Research, vol. 59, No. 1, Jan. 1998, pp. 52-55.

(56) References Cited

OTHER PUBLICATIONS

Mengeling et al., "Comparative safety and efficacy of attenuated single-strain and multi-strain vaccines for porcine reproductive and respiratory syndrome", Veterinary Microbiology, vol. 93, 2003, pp. 25-38.

* cited by examiner

SEQUENCE LISTING

```
<160> NUMBER OF SEQ ID NOS: 99

<210> SEQ ID NO 1
<211> LENGTH: 22
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(19)
<223> OTHER INFORMATION: Any naturally occurring amino acid

<400> SEQUENCE: 1

Phe Xaa Val Leu Xaa Xaa Xaa Xaa Xaa Xaa Xaa Xaa Xaa Xaa Xaa Xaa
1               5                   10                  15

Xaa Xaa Xaa Gln Cys Arg
            20


<210> SEQ ID NO 2
<211> LENGTH: 21
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(18)
<223> OTHER INFORMATION: Any naturally occurring amino acid

<400> SEQUENCE: 2

Phe Xaa Val Leu Xaa Xaa Xaa Xaa Xaa Xaa Xaa Xaa Xaa Xaa Xaa Xaa
1               5                   10                  15

Xaa Xaa Gln Cys Arg
            20


<210> SEQ ID NO 3
<211> LENGTH: 20
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(17)
<223> OTHER INFORMATION: Any naturally occurring amino acid

<400> SEQUENCE: 3

Phe Xaa Val Leu Xaa Xaa Xaa Xaa Xaa Xaa Xaa Xaa Xaa Xaa Xaa Xaa
1               5                   10                  15

Xaa Gln Cys Arg
            20
```

-continued

<210> SEQ ID NO 4
<211> LENGTH: 19
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(16)
<223> OTHER INFORMATION: Any naturally occurring amino acid

<400> SEQUENCE: 4

Phe Xaa Val Leu Xaa Xaa Xaa Xaa Xaa Xaa Xaa Xaa Xaa Xaa Xaa Xaa
1 5 10 15

Gln Cys Arg

<210> SEQ ID NO 5
<211> LENGTH: 18
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(15)
<223> OTHER INFORMATION: Any naturally occurring amino acid

<400> SEQUENCE: 5

Phe Xaa Val Leu Xaa Xaa Xaa Xaa Xaa Xaa Xaa Xaa Xaa Xaa Xaa Gln
1 5 10 15

Cys Arg

<210> SEQ ID NO 6
<211> LENGTH: 17
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(14)
<223> OTHER INFORMATION: Any naturally occurring amino acid

<400> SEQUENCE: 6

Phe Xaa Val Leu Xaa Xaa Xaa Xaa Xaa Xaa Xaa Xaa Xaa Xaa Gln Cys
1 5 10 15

Arg

<210> SEQ ID NO 7
<211> LENGTH: 16
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(13)
<223> OTHER INFORMATION: Any naturally occurring amino acid

<400> SEQUENCE: 7

Phe Xaa Val Leu Xaa Xaa Xaa Xaa Xaa Xaa Xaa Xaa Xaa Gln Cys Arg 1 5 10 15

<210> SEQ ID NO 8
<211> LENGTH: 15
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(12)
<223> OTHER INFORMATION: Any naturally occurring amino acid

<400> SEQUENCE: 8

Phe Xaa Val Leu Xaa Xaa Xaa Xaa Xaa Xaa Xaa Xaa Gln Cys Arg
1 5 10 15

<210> SEQ ID NO 9
<211> LENGTH: 14
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(11)
<223> OTHER INFORMATION: Any naturally occurring amino acid

<400> SEQUENCE: 9

Phe Xaa Val Leu Xaa Xaa Xaa Xaa Xaa Xaa Xaa Gln Cys Arg
1 5 10

<210> SEQ ID NO 10
<211> LENGTH: 13
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(10)
<223> OTHER INFORMATION: Any naturally occurring amino acid

<400> SEQUENCE: 10

Phe Xaa Val Leu Xaa Xaa Xaa Xaa Xaa Xaa Gln Cys Arg
1 5 10

<210> SEQ ID NO 11
<211> LENGTH: 12
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(9)
<223> OTHER INFORMATION: Any naturally occurring amino acid

<400> SEQUENCE: 11

Phe Xaa Val Leu Xaa Xaa Xaa Xaa Xaa Gln Cys Arg
1 5 10

<210> SEQ ID NO 12
<211> LENGTH: 11
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(8)
<223> OTHER INFORMATION: Any naturally occurring amino acid

<400> SEQUENCE: 12

```
Phe Xaa Val Leu Xaa Xaa Xaa Xaa Gln Cys Arg
1               5                   10
```

<210> SEQ ID NO 13
<211> LENGTH: 24
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(19)
<223> OTHER INFORMATION: Any naturally occurring amino acid
<220> FEATURE:
<221> NAME/KEY: MOD_RES
<222> LOCATION: (23)..(23)
<223> OTHER INFORMATION: Any naturally occurring amino acid

<400> SEQUENCE: 13

```
Phe Xaa Val Leu Xaa Xaa Ile Xaa Xaa Xaa Xaa Xaa Xaa Xaa Xaa Xaa
1               5                   10                  15

Xaa Xaa Xaa Gln Cys Arg Xaa Ala
            20
```

<210> SEQ ID NO 14
<211> LENGTH: 23
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(18)
<223> OTHER INFORMATION: Any naturally occurring amino acid
<220> FEATURE:
<221> NAME/KEY: MOD_RES
<222> LOCATION: (22)..(22)
<223> OTHER INFORMATION: Any naturally occurring amino acid

<400> SEQUENCE: 14

```
Phe Xaa Val Leu Xaa Xaa Ile Xaa Xaa Xaa Xaa Xaa Xaa Xaa Xaa Xaa
1               5                   10                  15

Xaa Xaa Gln Cys Arg Xaa Ala
            20
```

```
<210> SEQ ID NO 15
<211> LENGTH: 22
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(17)
<223> OTHER INFORMATION: Any naturally occurring amino acid
<220> FEATURE:
<221> NAME/KEY: MOD_RES
<222> LOCATION: (21)..(21)
<223> OTHER INFORMATION: Any naturally occurring amino acid

<400> SEQUENCE: 15

Phe Xaa Val Leu Xaa Xaa Ile Xaa Xaa Xaa Xaa Xaa Xaa Xaa Xaa Xaa
1               5                   10                  15

Xaa Gln Cys Arg Xaa Ala
            20


<210> SEQ ID NO 16
<211> LENGTH: 21
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(16)
<223> OTHER INFORMATION: Any naturally occurring amino acid
<220> FEATURE:
<221> NAME/KEY: MOD_RES
<222> LOCATION: (20)..(20)
<223> OTHER INFORMATION: Any naturally occurring amino acid

<400> SEQUENCE: 16

Phe Xaa Val Leu Xaa Xaa Ile Xaa Xaa Xaa Xaa Xaa Xaa Xaa Xaa Xaa
1               5                   10                  15

Gln Cys Arg Xaa Ala
            20


<210> SEQ ID NO 17
<211> LENGTH: 20
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(15)
<223> OTHER INFORMATION: Any naturally occurring amino acid
<220> FEATURE:
<221> NAME/KEY: MOD_RES
<222> LOCATION: (19)..(19)
```

-continued

<223> OTHER INFORMATION: Any naturally occurring amino acid

<400> SEQUENCE: 17

Phe Xaa Val Leu Xaa Xaa Ile Xaa Xaa Xaa Xaa Xaa Xaa Xaa Xaa Gln
1               5                   10                  15

Cys Arg Xaa Ala
            20

<210> SEQ ID NO 18
<211> LENGTH: 19
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(14)
<223> OTHER INFORMATION: Any naturally occurring amino acid
<220> FEATURE:
<221> NAME/KEY: MOD_RES
<222> LOCATION: (18)..(18)
<223> OTHER INFORMATION: Any naturally occurring amino acid

<400> SEQUENCE: 18

Phe Xaa Val Leu Xaa Xaa Ile Xaa Xaa Xaa Xaa Xaa Xaa Xaa Gln Cys
1               5                   10                  15

Arg Xaa Ala

<210> SEQ ID NO 19
<211> LENGTH: 18
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(13)
<223> OTHER INFORMATION: Any naturally occurring amino acid
<220> FEATURE:
<221> NAME/KEY: MOD_RES
<222> LOCATION: (17)..(17)
<223> OTHER INFORMATION: Any naturally occurring amino acid

<400> SEQUENCE: 19

Phe Xaa Val Leu Xaa Xaa Ile Xaa Xaa Xaa Xaa Xaa Xaa Gln Cys Arg
1               5                   10                  15

Xaa Ala

<210> SEQ ID NO 20
<211> LENGTH: 17
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(12)
<223> OTHER INFORMATION: Any naturally occurring amino acid
<220> FEATURE:
<221> NAME/KEY: MOD_RES
<222> LOCATION: (16)..(16)
<223> OTHER INFORMATION: Any naturally occurring amino acid

<400> SEQUENCE: 20

Phe Xaa Val Leu Xaa Xaa Ile Xaa Xaa Xaa Xaa Xaa Gln Cys Arg Xaa
1 5 10 15

Ala

<210> SEQ ID NO 21
<211> LENGTH: 16
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(11)
<223> OTHER INFORMATION: Any naturally occurring amino acid
<220> FEATURE:
<221> NAME/KEY: MOD_RES
<222> LOCATION: (15)..(15)
<223> OTHER INFORMATION: Any naturally occurring amino acid

<400> SEQUENCE: 21

Phe Xaa Val Leu Xaa Xaa Ile Xaa Xaa Xaa Xaa Gln Cys Arg Xaa Ala
1 5 10 15

<210> SEQ ID NO 22
<211> LENGTH: 15
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(10)
<223> OTHER INFORMATION: Any naturally occurring amino acid
<220> FEATURE:
<221> NAME/KEY: MOD_RES
<222> LOCATION: (14)..(14)
<223> OTHER INFORMATION: Any naturally occurring amino acid

<400> SEQUENCE: 22

Phe Xaa Val Leu Xaa Xaa Ile Xaa Xaa Xaa Gln Cys Arg Xaa Ala
1 5 10 15

<210> SEQ ID NO 23
<211> LENGTH: 14
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(9)
<223> OTHER INFORMATION: Any naturally occurring amino acid
<220> FEATURE:
<221> NAME/KEY: MOD_RES
<222> LOCATION: (13)..(13)
<223> OTHER INFORMATION: Any naturally occurring amino acid

<400> SEQUENCE: 23

Phe Xaa Val Leu Xaa Xaa Ile Xaa Xaa Gln Cys Arg Xaa Ala
1 5 10

<210> SEQ ID NO 24
<211> LENGTH: 13
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(6)
<223> OTHER INFORMATION: Any naturally occurring amino acid
<220> FEATURE:
<221> NAME/KEY: MOD_RES
<222> LOCATION: (8)..(8)
<223> OTHER INFORMATION: Any naturally occurring amino acid
<220> FEATURE:
<221> NAME/KEY: MOD_RES
<222> LOCATION: (12)..(12)
<223> OTHER INFORMATION: Any naturally occurring amino acid

<400> SEQUENCE: 24

Phe Xaa Val Leu Xaa Xaa Ile Xaa Gln Cys Arg Xaa Ala
1 5 10

<210> SEQ ID NO 25
<211> LENGTH: 4
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid

<400> SEQUENCE: 25

Phe Xaa Val Leu
1

<210> SEQ ID NO 26
<211> LENGTH: 7
<212> TYPE: PRT
<213> ORGANISM: Porcine reproductive and respiratory syndrome virus
<220> FEATURE:
<221> NAME/KEY: MOD_RES
<222> LOCATION: (4)..(5)
<223> OTHER INFORMATION: Any naturally occurring amino acid

<400> SEQUENCE: 26

Tyr Ile Thr Xaa Xaa Ala Asn
1 5

<210> SEQ ID NO 27

<211> LENGTH: 6
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (5)..(5)
<223> OTHER INFORMATION: Any naturally occurring amino acid

<400> SEQUENCE: 27

Phe Xaa Val Leu Xaa Asp
1               5

<210> SEQ ID NO 28
<211> LENGTH: 8
<212> TYPE: PRT
<213> ORGANISM: Porcine reproductive and respiratory syndrome virus
<220> FEATURE:
<221> NAME/KEY: MOD_RES
<222> LOCATION: (5)..(5)
<223> OTHER INFORMATION: Any naturally occurring amino acid

<400> SEQUENCE: 28

Val Tyr Ile Thr Xaa Thr Ala Asn
1               5

<210> SEQ ID NO 29
<211> LENGTH: 5
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any naturally occurring amino acid

<400> SEQUENCE: 29

Phe Xaa Val Leu Gln
1               5

<210> SEQ ID NO 30
<211> LENGTH: 8
<212> TYPE: PRT
<213> ORGANISM: Porcine reproductive and respiratory syndrome virus
<220> FEATURE:
<221> NAME/KEY: MOD_RES
<222> LOCATION: (6)..(6)
<223> OTHER INFORMATION: Any naturally occurring amino acid

<400> SEQUENCE: 30

Gln Tyr Ile Thr Ile Xaa Ala Asn
1               5

<210> SEQ ID NO 31
<211> LENGTH: 22
<212> TYPE: PRT
<213> ORGANISM: Porcine reproductive and respiratory syndrome virus

<400> SEQUENCE: 31

Phe Met Val Leu Gln Lys Ile Glu Cys Leu Gln Ala Pro Gly Thr Arg
1               5                   10                  15

Ser Gln Cys Arg Glu Ala
            20

<210> SEQ ID NO 32
<211> LENGTH: 23

<212> TYPE: PRT
<213> ORGANISM: Porcine reproductive and respiratory syndrome virus

<400> SEQUENCE: 32

```
Gln Lys Ile Glu Cys Leu Gln Ala Pro Gly Thr Arg Ser Gln Cys Arg
1               5                   10                  15

Glu Ala Ile Gly Thr Pro Gln
            20
```

<210> SEQ ID NO 33
<211> LENGTH: 21
<212> TYPE: PRT
<213> ORGANISM: Porcine reproductive and respiratory syndrome virus

<400> SEQUENCE: 33

```
Asp Ile Ser Cys Leu Arg His Gly Arg Lys Ser Arg Gln Cys Arg Thr
1               5                   10                  15

Ala Ile Gly Thr Pro
            20
```

<210> SEQ ID NO 34
<211> LENGTH: 9
<212> TYPE: PRT
<213> ORGANISM: Porcine reproductive and respiratory syndrome virus

<400> SEQUENCE: 34

```
Glu Cys Leu Gln Ala Pro Gly Thr Arg
1               5
```

<210> SEQ ID NO 35
<211> LENGTH: 10
<212> TYPE: PRT
<213> ORGANISM: Porcine reproductive and respiratory syndrome virus

<400> SEQUENCE: 35

```
Ser Cys Leu Arg His Gly His Lys Ser Arg
1               5                   10
```

<210> SEQ ID NO 36
<211> LENGTH: 172
<212> TYPE: PRT
<213> ORGANISM: Porcine reproductive and respiratory syndrome virus

<400> SEQUENCE: 36

```
Met Ala Ala Ala Ile Leu Phe Phe Leu Val Gly Ala Gln His Leu Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Ala Gly Phe Met Val Leu Gln
        35                  40                  45

Lys Ile Glu Cys Leu Gln Ala Pro Gly Thr Arg Ser Gln Cys Arg Glu
    50                  55                  60

Ala Ile Gly Thr Pro Gln Tyr Ile Thr Ile Gln Ala Asn Val Thr Asp
65                  70                  75                  80

Glu Ser Tyr Leu Tyr Asn Ala Asp Leu Leu Met Leu Ser Ala Cys Leu
                85                  90                  95

Phe Tyr Ala Ser Glu Met Ser Glu Lys Gly Phe Asn Val Ile Phe Gly
            100                 105                 110

Asn Val Ser Gly Val Val Ser Ala Cys Val Asn Phe Thr Asp Tyr Val
        115                 120                 125
```

-continued

```
Ala His Val Thr Gln His Thr Gln Gln His His Leu Val Ile Asp His
    130                 135                 140

Val Arg Leu Leu His Phe Leu Ser Pro Pro Val Met Arg Trp Ala Thr
145                 150                 155                 160

Thr Ile Ala Cys Leu Phe Ala Ile Leu Leu Ala Ile
                165                 170


<210> SEQ ID NO 37
<211> LENGTH: 519
<212> TYPE: DNA
<213> ORGANISM: Porcine reproductive and respiratory syndrome virus

<400> SEQUENCE: 37

atggctgcgg ccattctttt cttcctggtt ggtgctcaac atctcatggt ttctgaggcg     60

ttcgcctgca agccctgctt ctcgacgcat ttatcagata ttaagaccaa cacgaccgcg    120

gctgccggtt tcatggtcct tcagaaaatt gaatgcctcc aagcccctgg gacacggtcg    180

caatgtcgtg aagccatcgg taccccccag tacatcacga tacaggccaa cgtgaccgac    240

gaatcatact tgtataacgc ggacttgctg atgctctctg cgtgcctctt ctacgcctca    300

gaaatgagcg agaaaggctt caacgtcatc tttgggaatg tttctggcgt tgtttccgct    360

tgtgtcaatt tcacagatta cgtagcccac gtgactcaac acacccagca gcatcacctg    420

gtaatcgacc acgttaggct actacatttc ctgtcaccac ctgtaatgag gtgggccaca    480

accatcgctt gtttgttcgc cattcttttg gcgatatga                           519


<210> SEQ ID NO 38
<211> LENGTH: 14854
<212> TYPE: DNA
<213> ORGANISM: Porcine reproductive and respiratory syndrome virus

<400> SEQUENCE: 38

acctcttggc ccctgttcta gcccaacagg tatccttctc tctcggggcg agtgcgccgc     60

ctgctgctct cttgcagcgg gaaggacctc ccgagtattt ccggagagca cctgctttac    120

gggatctcca ccctttaacc atgtctggga ctctctcccg gtgcatgtgc accccggctg    180

ctcgggtatt ttggaacgcc ggtcaagtct tctgcacacg gtgtctcagt gcgcggtctc    240

ttctccctcc tgagcttcag gacactgacc ttgctgcaat tggtttgttt tacaagccta    300

aggacaagat caaatggaaa gttcccattg gcattcctca ggtggaatgt actccatccg    360

ggtgctgttg gctctccgct attttcccct tagcgcgcat gacctccggt aatcacaact    420

tccttcaacg gcttgtgaag gttgctgacg ttttgtaccg tgacggttac ttggcacccc    480

aacaccttcg tgaactccaa gtctacgaac gcggctgcag ctggtacccg atcacggggc    540

ctgtgcccgg aatgggtttg tatgcaaact ccatgcacgt gtctgatcag ccgtttcctg    600

gtgccactca tgtgttaacc aactcaccct tgcctcaaca ggcttgtcgg caaccattct    660

gtccatttga ggaggctcat tccgacgtgt acaggtggaa gaaatttgtg attttcgtgg    720

attctcctct taacggtcga tctcgtatga tgtggacacc ggggtccgat gactcggctg    780

ccttagaagt gcttccgcct gaactagaac gtcgagtcga aatcctcatt cgaagttttc    840

ctgctcatca ctctgttgat ctcaccgaat gggaactcac tgaatcacct gagcacggtt    900

tttccttcag cacgttccat tctagtggtc acctcgccca aaaccccgac atgtttgatg    960

gcaagtgttg gctatcttgc tttttgagcc tgccgcccga agtgtggcgc catgaagaac   1020

agctggccaa cactctcggt taccaaacca agtggggtgt gcacggtaag tacctccagc   1080
```

-continued

```
gcaggcttca aattaacggc gtccgtgctg tggttgaccc taatggtccc attcacgttg   1140
aagcgctatc ttgctcccag tcttggatca gacatctgac tctggaagat gatgtaactc   1200
cggggttcgt tcgcctaatg tctctccgta ttgtgccgaa cacagaaccc accatcctcc   1260
aggttttccg gtttggggca cacaagtggt atggtgctgc cggcaagcga gctcgcacta   1320
agcgtgcagc aaagaaaggg aaggactcga ctatcactcc cgagactgcc caaccaacct   1380
ccgcttgcga aatcatcacc tattccccac cggcggacgg atcttgtggc tggcatgttc   1440
ttgccgccat agtgaaccga atgataagtg gtgacttcac gtccccccta actcagtaca   1500
ataggccaga ggatgattgg gcttctgatt atgatcttgc tcaagcgatt caatgcctgc   1560
aactgcctgc taccctggtt cggggtcgcg cctgtcctaa cgccaagtac cttataaaac   1620
ttaacggggt tcactgggag gtagaggtga ggcctggaat ggctcctcgc tccctttccc   1680
gcgaatgcgt ggttggcgtc tgctctgaag gctgtgtcgc gccgccttat ccagaaaacg   1740
ggctaccaaa acgcgcactc gaggccttgg cgtctgctta caggctacct tccgactgcg   1800
ttagctgtgg tattgctgac tttctcgcta accctcccct tccggaattc tggaccctcg   1860
acaaaatgtt gacctccccg tcaccagaac ggtccggctt ctctagtttg tataaattac   1920
ttttggaggt tgttccgcag aaatgtggtg cctcggaggg ggcttttatt tgtgctgttg   1980
aaaggatgtt gaaggattgt ccgagctcca aacaggccat ggccctttttg gcaaaaatta   2040
gaatcccatc ctcaagggcc ccgtctgttt ccttggatga gtgttttcct acggatgtcc   2100
cagccgactt tgaatcagcg tctcaggaaa ggccccaaac ttccggtgtc gctgttgccc   2160
agtgtctacc ggatgcaaaa gagctcgagg aaacagcccc gggaaaagtt caagagaatg   2220
gtcacaaggc catccatcct gcgcctcttg ctggttgtcc taacgacgag caagtacagg   2280
tgattgccag cgagcaactg aggcccggcg actgtgtttc gacagtcagg ggtgctcgcg   2340
atgatgctcc agtctcagcc ggcctgacta acctggcagg cgggaacccc cctttttccaa   2400
accccacgga aggaaatagg ccccatgact gggaagacgg acctttggat ctatcccgac   2460
cgaaaccagt tgccgagatg acccttgtaa gagagcaagt accctacaac ccaggtccta   2520
acactgatgt ctcccccgtc gccgctccgg gctttatccc gacggggctc gtatttcgtc   2580
atgttgagca ttgtggctcg gagtccggtg agagcgactc ccctctaaac ttgtctaatg   2640
tgcaaatttc ggaccagccc ctaaaccttt ccctgaccgc atggccggtg aaggccaccg   2700
cctctgaccc cggttgggtt catggtcgac gtgagcctgt ctttgcgaag cctcgaaatg   2760
ccttctctga cggtgactca gttgttcagt tcggggagct ttctgaatcc agctccgtcg   2820
tcgagtttga ccgagcaaaa aatgttacaa cggttgacgc ccctgtcgac ttgacgactc   2880
cgaataaggc cctctctgtg gtcgatcctt tcgagttcgc tgagcccaag cgcccacgtt   2940
tctccgcgca agccctgatt gaccgaggag gtccacttgc tgatgtccac gcaaaaataa   3000
agaatcgggt atacgaacag tgcctccagg cttgcgagcc cggtagtcgc gcaaccccag   3060
ccactagaga ctggctcgac aaaatgtggg agagggtgga catgaaaact tggcgctgca   3120
cctcacagtt tcaagctggt cgcattctcg cgtccctcaa gttcctccct gacatgattc   3180
aggacacacc gcctcctgct cccaggaaga gccgggctgg tgacagcacc ggcctaaaac   3240
aactggtggc acagtgggat aggaaattga gtgcggcccc tcctccgaaa ctggttgggt   3300
cagtgcctga ccagactgtc ctcccgtccg cggacaccca gcaagaagac gctgaccctc   3360
ctgatgggcc gccccacgcg ccggacattc ctagtcgagt aggtacagtc aggaattgga   3420
aaggttgcat gctttccggc acccgttttg cggggtccat gagtcagcgc ttcatgacat   3480
```

-continued

```
gggtttttga ggttctctcc catctcccag cttttgcgct cacacttttc tcgccgcggg   3540
gctctatggc tccaggtgat tggctgtttg caggtgttgt tttacttgct ctcctgctct   3600
gtcgctctta cccaattttc gggtgccttc ccttattggg tgtcttttct ggttctgtgc   3660
ggcgcgttcg tctgggtgtt tttggttctt ggatggcttt tgctgtattt ctattctcga   3720
ctccatccaa cccagtcggt tcttcttgtg accacgattc gccggagtgt cacgctgagc   3780
ttttggctct tgagcagcgc caactttggg aacctgtgcg cggccttgtg gtgggcccct   3840
caggtctctt atgcgtcgtt cttggcaagc tactcggtgg gtcacgttat ctctggcata   3900
ttctcttacg tttatgcatg cttgcagatt tggccctttc tcttgtttat gtggtgtccc   3960
aagggcgttg tcacaagtgt tggggaaagt gtataaggac agctcctgcg gaggtggctc   4020
tcaatgtatt tcctttctcg cgcgccaccc gttcctctat tgtatcctta tgtgatcgat   4080
tccaggcgcc aaaaggggtt gatcccgtac atttggcaac gggttggcgc gggtgctggt   4140
gcggcgatag ccccatccat caaccacacc agaaacccat agcttacgcc aacttggatg   4200
aaaagaaaat atctgcccag acggtggtcg ctgttccata cgatcccagc caggccatca   4260
aatgcctgaa agtcctacag gctggaggag ctattgtaga ccagccaaca cctgaggttg   4320
ttcgtgtttc cgaaatcccc ttctcagccc catttttttcc gaaagttccg gtcaatccaa   4380
actgtagggt tgtggtagat tcggacacct ttgtggccgc ggttcgctgc ggttactcaa   4440
caacacaact ggtcctgggc cggggcaact tcgccaagtt gaatcaaaca cctcttggga   4500
actctgtctc caccaaaacg actggtggtg cctcttacac ccttgctgtg gcgcaagtgt   4560
ccgtgtggac tctcatccat ttcatcctcg gtctttggtt cacatcgcct caagtgtgcg   4620
gccgaggtac cgctgatcca tggtgttcaa atcctttttc atatcccacc tatggccctg   4680
gagttgtctg ctcctctcga ctttgcgtgt ctgccgatgg agtcaccctg ccattgttct   4740
cagccgtggc acaactctcc ggtagggagg tgggaatttt cattctggtg ctcgtctcct   4800
tgatcgcttt ggcccaccat atggctctta aagcagatat gttggtgatc tttttggctt   4860
tctgcgccta cgcctggcct atgagttctt ggttaatttg tttctttccc atgcttttga   4920
agtgggttac ccttcaccct cttaccatgc tttgggtaca ctctttctta gtgttttgtc   4980
tgccagcagc tggcatcctt tcactaggga caactggcct tctctgggca gtcggccgct   5040
tcacccaggt agccggaatt attacacctt atgacattca ccgatacact tctgggccgc   5100
gtggtgctgc cgctgtagcc acagccccag aaggcactta catggccgcc gtccgtagag   5160
ctgccttaac tgggcgaact ttgatcttca ccccgtctgc agttgggtcc cttctcgagg   5220
gtgccttcag gactcataaa ccctgcctca acaccgtgaa tgtcgtgggt tcttcttttg   5280
gttctggagg agtctttacc attgatggga aaaaactgtt gttactgcga cacatgtgtt   5340
gaacggcgac acagccaggg tcaccggtga ctcctataac cgcatgctca ccttcaggac   5400
caacggtgat tacgcctggt cccatgctga tgactggcaa ggcgttgccc cagtggtcaa   5460
gatcgcgaaa gggtatcgcg gtcgtgccta ttggcaaaca tcaactggtg tcgaacccgg   5520
tgttgttggt gaaggattcg ccttctgttt tactaactgt ggtgactcgg ggtcacccgt   5580
catttcagaa tctggtgatc tcattggaat ccacaccggt tcgaacaaac ttggttctgg   5640
tcttgtgaca acccccgaag ggagacctg cactattaaa gaaaccaagc tctctgacct   5700
ttccagacac ttcgcgggcc caagcgttcc ccttggggac ataaaattaa gcccggccat   5760
catccctgat gtgacgtcca tcccaagtga cttggcatcg ctcctggctt ccgtccctgt   5820
```

-continued

```
agtggaaggc ggtctttcga ccgttcaact cttgtgtgtc tttttccttc tctggcgtat   5880

gatggggcat gcttggacac ccattgttgc cgtgggtttc tttttgctga atgaaattct   5940

tccagcagtc ttggtccgag ccgtgttctc ttttgcgctc tttgcgtttg catggctcac   6000

cccctggtct gcgcaggtgt tgatgatcag actcctcacg gcctccctca accgcaacaa   6060

gctttctctg gcgttctacg cactcggggg tgtcgtcggt ttggccgctg agatcgggac   6120

tttcgctggt aggttgtctg aattgtctca agccatttca acatactgct ttttacctag   6180

ggtccttgct atgaccagct gtgtccccat catcatcatt ggtggactcc atgctcttgg   6240

tgtaatcctg tggttgttca aatatcggtg tctccacaac acgctagttg gtgatgggag   6300

tttttcaagc gccttcttcc tgcggtactt tgcagagggt aatctcagaa aaggtgtttc   6360

acagtcctgt ggcatgagta atgaatcctt gacggctgct ttggcttgta agttgtcaca   6420

ggctgacctt gactttctgt ccggcctaac gaatttcaag tgttttgtgt ctgcttcaaa   6480

tatgaagaat gctgctggcc aatatattga agcagcgtac gccaaggcct tgcgccacga   6540

gttggcttcc ttagttcagg tcgacaaaat gaagggggtt ttgtccaagc tagaagcttt   6600

tgctgagacg gccaccccat cccttgatac aggtgacgta gttgttctgc ttggacaaca   6660

tcctcatgga tctattcttg acattaacgt agggactgaa aggaaaactg tgtctgtgca   6720

ggagactcgg agtttgggtg gctccaaatt cagtgtctgc accgttgtgt ccaacacacc   6780

tgtagacgcc ctgaccagca tcccacttca gacaccaact ccgcttttcg agaatggccc   6840

gcgtcatcgc ggtgaggaag acgatcttaa agtcgagagg atgaagaagc actgcatatc   6900

cctcggcttt cataacatta atggcaaagt ttactgcaaa atttgggaca agtctaccgg   6960

tgacaccttc tacacggatg actcccgata cacccaagac tgtgcctttc aggacaggtc   7020

agccgactat agagacaggg attatgaagg tgtgcagacc gccccccagc acggatttga   7080

cccaaagtcc gagacccctg tcggcactgt tgtgatcggc ggcattacgt ataacaggta   7140

tctggttaaa ggtaaagagg tcttgatccc caagcctgac aactgccttg aagccgccaa   7200

gctatccctt gaacaagctc tcgctggtat gggccagact tgtgacctca cggctgctga   7260

agtggaaaag ctaaagcgca ttattagcca actccaaggc ttgaccaccg agcaggcttt   7320

aaactgctag ccgccagtgg cttgacccgc tgtggccgcg gcggcttagt tgtgactgaa   7380

acggcggtga aaattgtgaa ataccacagc agaaccttca ccctaggccc tttagacctg   7440

aaagtcacct ctgaagtgga ggtgaagaaa tcaacagagc agggccacgc cgttgtagca   7500

aacctatgct ccggtgttgt gttgatgaga cctcaccctc cgtcccttgt tgatgttctt   7560

ctaaagcctg gacttgacac gacacctggc atccaaccgg ggcatggggc tggaaacatg   7620

ggtgtgaacg gttccatttg ggattttgaa actgccccca caaaggcgga actcgagtta   7680

tccaaacaaa taatccaagc gtgtgagatt aggcgcgggg atgccccgaa cctccaactc   7740

ccttataagc tctatcctgt tagggggggat cctgagcggc atgaaggtcg ccttatcaat   7800

accaggttcg gggacttacc ttataagact cctcaagaca ccaagtccgc agtccacgcg   7860

gcttgttgcc tacaccccaa tggagccccg gtatttgacg gtaaatccat gctgggcacc   7920

actcttcagc atggttttga gctttatgtc cccactgtgc cctatagtgt tatggagtac   7980

cttgactcac gccctgacac tccttttatg tgtactaagc atggcacttc cagtgctgct   8040

gcagaggacc tccaaaagta tgacctatcc acccaaggat ttgtcttgcc tggtgtcttg   8100

cgcttagtgc gcaggttcat cttcagccat attggtaaag cgccaccatt gttcctccca   8160

tcaacttacc ccgctaagaa ctccatggca gggattaatg gtcagaggtt tccgacaaag   8220
```

-continued

```
gatattcaga gcatacctga aatcgatgaa atgtgtgccc gcgctgtcaa ggaaaattgg   8280
caaactgtta caccttgcac cctcaagaaa cagtattgtt ctaagcccaa aaccaggacc   8340
atcctgggca ctaacaactt tattgccttg gcccacagat cagcgcttag tggtgtcacc   8400
caggcgttca tgaaaaaggc ttggaattcc ccaattgcct tggggaagaa taaattcaag   8460
gagctgcatt gcaccgttgc cggcaggtgt cttgaggctg acttggcctc ctgcgaccgc   8520
agtacccccg ccattgtgag atggtttgtt gccaacctcc tgtatgaact tgcaggatgt   8580
gaagagtacc tgcccagcta cgtgcttaat tgctgccatg acctcgtggc aacacaaaat   8640
ggtgccttca caaaacgcgg tggcctgtcg tctggggacc ctgtcaccag tgtgtccaac   8700
accgtatatt cactgataat ttacgcccag cacatggtgt tgtcagccct aaaaatgggt   8760
catgagattg gtcttaagtt tcttgaggag caactcaagt tcgaagacct ccttgaaatt   8820
cagcctatgt tggtgtattc tgatgatctt gttttgtatg ctgaaaggcc ctccttcccc   8880
aattaccatt ggtgggtcga gcaccttgac ttgatgctgg gtttcaagac agacccaaag   8940
aagaccgtta taactgacaa gcccagcttt ctcggttgca gaattgaggc ggggcgacag   9000
ctagcccccca atcgtgaccg cattctggct gctctcgcat atcacatgaa agcgcaggac   9060
gcatcagagt actatgcgtc tgctgccgca attctgatgg actcgtgtgc ttgcattgac   9120
tatgatcctg agtggtatga agacctcatc tgtggcatcg ctcagtgcgc ccgccaggat   9180
ggttatcgct tcccaggacc ggcatttttc atgtccatgt gggagagact gagaagccat   9240
aatgagggga agaaattccg ccattgcggc atctgtgacg ccaaagctga tcacgcgtct   9300
gcctgtgggc ttgacttgtg cttgtttcac tcgcactttc atcaacactg ccctgttatc   9360
ttgagttgcg gccaccatgc cggttccaaa gaatgttcgc agtgtcagtc acctgttggg   9420
tctggcaaga cccctcttga tgccgtgctg aagcaaatcc catacaaacc tcctcgtaca   9480
gcaatcatga gggtaagcga caaagtgaca gccctggatc cagggaggta ccagtctcgt   9540
cggggcctcg ttgcagtcaa aaggggtatc gcaggtaatg aagttgatct ccctgatggg   9600
gactatcagg tagtgcctct tttgccgacc tgcaaagaca ttaatatggt gaaggtggct   9660
tgtaatgttc tactcagcaa attcatagtg gggccaccag gttccgggaa gacaacctgg   9720
ctgctgagtc aagtccagga tgatgatgtt atttacacac ccactcatca gaccatgttt   9780
gatatagtca gtgctctcaa agtttgcagg tattccatcc caggggcctc aggactccct   9840
ttcccaccac ctgccaggtc cgggccatgg gtcaagctca ttgccagcgg acacgtccca   9900
ggccgagtgt catacctcga tgaggctgga tattgtaatc atctggacat cctcagactg   9960
ctttccaaaa cacctcttgt gtgtttgggt gaccttcagc aacttcaccc tgttggcttt  10020
gattcctact gttatgtgtt cgatcagatg cctcagaagc agctgaccac tatttataga  10080
tttggtccta acatctgtgc agccatccag ccttgttaca gggaaaaact tgaatctaag  10140
gctaggaaca ccagggtggg tttcaccacc cggcctgtgg ccttcggtca ggtgttgaca  10200
ccataccaca aagaccgtac tggctctgcg ataaccatag attcatccca aggggccact  10260
tttgatattg tgacattgca tctaccatcg ccgaagtcct taaacaaatc ccgagcactt  10320
gtagccatta ctcgagcaag acatgggttg ttcatttatg accctcataa ccagctccag  10380
gaatttttta atttaacccc tgagagcact gattgcaacc ttgtgttttg ccacggggat  10440
gagctggtag ttttggacgc cggtaatgca gtcacaactg tggcgaaggc cctagaaact  10500
ggtccgtcgc ggttccgtgt gtcggacccg agatgcaagt ccctcttagc tgcctgttca  10560
```

-continued gccagtctgg aagggagctg catgccacta ccgcaagtgg cacataacct gggattttac 10620
ttttcccctg acagcccagc atttgcacct ctgccaaaag agctggcgcc acactggcca 10680
gtggtcactc atcagaataa tcgggcgtgg cctgatcgac ttgtcgccag catgcgcccg 10740
ctcgacaacc gttacagcaa gccaatggtc ggtgcagggt atgtggtcgg gccgtccacc 10800
tttctcggta cacccggcgt ggtgtcatac tatcttacac tatacattaa gggtgagccc 10860
caggccttac ctgaaacact cgtttccacg ggacgcatag ctacagattg tcgggagtac 10920
ctcgacacag ctgaggaaga ggcagcaaaa gaactccccc acgcattcat gggtgatgtc 10980
aaaggcacca caattggtgg ttgtcatcac attacatcaa aatacctacc caggtcccta 11040
cccaaggact ccattgccgt agttggggta agttcacctg gcaaggccgc caaagcctta 11100
tgcactctca ctgatgtgta cctcccagaa ctccggccgt atttgcaacc tgagacagcg 11160
tcgaaatgct ggaaactcaa actggacttc agggacgtcc ggctaatggt ctggaaaggg 11220
gccaccgcct acttccagtt ggaagggctc acttggtctg cactgcctga ctatgccagg 11280
tttattcagc tgcccaagaa cgccattgtg tacatcgatc cgtgcatagg accggcgaca 11340
gccaaccgta aagttgtgcg aaccacagat tggcgagctg acctggcagt gacaccgtac 11400
gactacggtg ctcaacacat tttgacaacc gcctggttcg aggacctcgg gccgcagtgg 11460
aaaattttgg ggttgcagcc cttcaggcga acatttggcc ttgaaaatac tgaagattgg 11520
gcaattcttg cacgccgtat gaatgacggt aaggactaca ctgattacaa ctggagttgc 11580
gttcgagaac gcccacacgc tatctatggg cgtgctcgtg accatacata ccactttgcc 11640
cttggcacag aattacaagt ggagctaggt aaacccagat tgtcgcctga gcaagtcccg 11700
tgaattcgga gggatgcaat ggggtcactg tggagcaaaa tcagccagtt gttcgtggac 11760
gctttcactg aattccttgt tagtgtggtt gacattgtca ttttccttgc catattgttt 11820
gggttcacag tcgcaggatg gttactggtc tttcttctca gggtggtttg ctccgcgttt 11880
ctccgttcgc gctctgccat tcactctccc gaactatcga aagtcctatg agggcttgtt 11940
acccaactgt agaccggatg ttccacaatt tgcgtttaag cacccattgg gcatgttttg 12000
gcacatgaag gtctcccact tgattgatga gatggtctct cgtcgcgtct accaaaccat 12060
ggagcattcg ggccaagcgg cctggaaaca ggtggtcgct gaggccactc tcacgaagtt 12120
gtccaggctc gacattgtca ctcacttcca acacctagcc gcagtggagg cggattcttg 12180
ccactttctt agctcgcgac tcgtgatgct aaaaaatctt gctgtaggca atgtaagtct 12240
acaatacaac accacgttgg atcgcgttga gctcattttc cccacgccag gcacgaggcc 12300
caagttgacc gattttaggc aatggctcat cagtgtgcac gcttccattt tctcctctgt 12360
ggcttcatct gttaccttgt ttgtagtgct ttggcttcga attccagctc tacgctatgt 12420
ttttggtttc cattggccca cggcaacaca tcatttgaac taactgtgaa ttacaccata 12480
tgtaagccct gccttaccag tcaagcggcc aaacaacggc tcgaacccgg tcatagcatg 12540
tggtgcagga tagggcacac cagctgcgag gagagtgacc atgatgagtt gtcaatgacc 12600
atcccgcctg ggtatgataa ccttaagctc gagggctact acgcttggct agccttcttg 12660
tccttttcct acgcggcaca gttccatccg gagctattcg gaatagggaa tgtatcgcgt 12720
gtttttgtgg acaagcaacg tcaggccatc tgtgcggagc acgacggatc caattcaacc 12780
gtgtccacta agtacaacat ctccgcatcg tatgcggcgt actatcatca ccagatagac 12840
gggggtaatt ggtttcacct agaatggctg cggccattct tttcttcctg gttggtgctc 12900
aacatctcat ggtttctgag gcgttcgcct gcaagccctg cttctcgacg catttatcag 12960

```
atattaagac caacacgacc gcggctgccg gtttcatggt ccttcagaaa attgaatgcc  13020

tccaagcccc tgggacacgg tcgcaatgtc gtgaagccat cggtaccccc cagtacatca  13080

cgatacaggc caacgtgacc gacgaatcat acttgtataa cgcggacttg ctgatgctct  13140

ctgcgtgcct cttctacgcc tcagaaatga gcgagaaagg cttcaacgtc atctttggga  13200

atgtttctgg cgttgtttcc gcttgtgtca atttcacaga ttacgtagcc cacgtgactc  13260

aacacaccca gcagcatcac ctggtaatcg accacgttag gctactacat ttcctgtcac  13320

cacctgtaat gaggtgggcc acaaccatcg cttgtttgtt cgccattctt ttggcgatat  13380

gagatgttct cacaaattgg ggcgcttctt gattccgcac tcttgctttt ggtggctttt  13440

ttgctgtgta ccggcttgtc ctggtccttt gccgatggca acggcaacag ctcgacatac  13500

caatacatat ataacttgac gatatgcgag cttaatggga ccacctggct gtctagccat  13560

tttgattggg cagtcgagac ttttgtgctc tacccggtcg cgactcacat tctctcactg  13620

ggttttctca caacaagcca tttctttgac gcgctcggtc tcagtgctgt gtccgtcaca  13680

ggattttatg accagcggta cgtgctcagc agtgtctacg gcgtctgtgc cctcgcagcg  13740

ctcgtgtgtt ttgccatccg tgctgctaaa aattgtatgg cttgtcgcta cgcccgcacc  13800

cggttcacca acttcatcgt ggacgaccgg gggaggattc atcggtggaa atccccaata  13860

gtggtggaga aattgggcaa agctgaggtc ggcagcgacc ttgtcaccat taaacatgtc  13920

gtcctcgaag ggggttaaagc tcaacccttg acgaggactt cggctgagca atgggaggcc  13980

tagatggttt ttgttatgac cctactgctg tacaaaagct tgtgttggcc ttcagcatca  14040

cgtatacacc tataatgata tatgccctta aggtgtcacg cggtcgactc ctagggctgt  14100

tgcacatcct gatatttctg aactgttcct tcactttcgg atacatgacg tatgtgcatt  14160

ttcagtccgc caaccgtgtt gtactcactt tgggggccgt tgttgccctc ctgtggggta  14220

tttacagctt cacagagtca tggaagttca tcacttccag atgcagattg tgttgccttg  14280

gccggcgata cattctggcc cctgcccacc acgtagaaag tgctgcaggt ctccatccta  14340

tcccagcgtc tggcaaccga gcatacgctg tgaggaagcc cggactaaca tcagtgaacg  14400

gcactctggt accaggactt cggagcctcg tgttgggcgg caaacgagct gttaaacgag  14460

gagtggttaa cctcgtcaaa tatggccggt aaaaaccaag gccagaagaa aaagaaaagt  14520

acagctccaa tggggaatgg ccagccagtc aatcaactgt gccagttgct gggtgcaatg  14580

ataaggaccc agcgccagca acctagggga ggacaggcca aaaagaaaag gcctgagaag  14640

ccgcattttc ccctagctgc tgaagatgac atacggcacc acctcaccca gactgaacga  14700

tccctctgtt tgcaatcgat ccagacggct tttaatcaag gcgcaggagc tgcgtcgctt  14760

tcgtccagcg ggaaagtcag ttttcaggtt gagttcatgc tgccggttgc tcatacagtg  14820

cgcctgattc gcgtgacttc cacatccgcc aatc                              14854
```

<210> SEQ ID NO 39
<211> LENGTH: 17
<212> TYPE: PRT
<213> ORGANISM: Porcine reproductive and respiratory syndrome virus

<400> SEQUENCE: 39

```
Ser Ser His Leu Gln Leu Ile Tyr Asn Leu Thr Ile Cys Glu Leu Asn
1               5                   10                  15

Gly
```

<210> SEQ ID NO 40
<211> LENGTH: 17
<212> TYPE: PRT
<213> ORGANISM: Porcine reproductive and respiratory syndrome virus

<400> SEQUENCE: 40

Gln Ser His Arg Ala Ser Thr Ala Gln Gly Thr Thr Pro Leu Arg Arg
1 5 10 15

Ser

<210> SEQ ID NO 41
<211> LENGTH: 15111
<212> TYPE: DNA
<213> ORGANISM: Porcine reproductive and respiratory syndrome virus

<400> SEQUENCE: 41
atgatgtgta gggtattccc cctacataca cgacacttct agtgtttgtg taccttggag 60
gcgtgggtac agccccgccc caccccttgg cccctgttct agcccaacag gtatccttct 120
ctctcggggc gagtgcgccg cctgctgctc ccttgcagcg ggaaggacct cccgagtatt 180
tccggagagc acctgcttta cgggatctcc accctttaac catgtctggg acgttctccc 240
ggtgcatgtg caccccggct gcccgggtat tttggaacgc cggccaagtc ttttgcacac 300
ggtgtctcag tgcgcggtct cttctctctc cagagcttca ggacactgac ctcggtgcag 360
ttggcttgtt ttacaagcct agggacaagc ttcactggaa agtccctatc ggcatccctc 420
aggtggaatg tactccatcc gggtgctgtt ggctctcagc tgttttccct ttggcgcgta 480
tgacctccgg caatcacaac ttcctccaac gacttgtgaa ggttgctgat gttttgtacc 540
gtgacggttg cttggcacct cgacaccttc gtgaactcca agtttacgag cgcggctgca 600
actggtaccc gatcacgggg cccgtgcccg ggatgggttt gtttgcgaac tccatgcacg 660
tatccgacca gccgttccct ggtgccaccc atgtgttgac taactcgcct ttgcctcaac 720
aggcttgtcg gcagccgttc tgtccatttg aggaggctca ttctagcgtg tacaggtgga 780
agaaatttgt ggttttcacg gactcctccc tcaacggtcg atctcgcatg atgtggacgc 840
cggaatccga tgattcagcc gccctggagg tactaccgcc tgagttagaa cgtcaggtcg 900
aaatcctcat tcggagtttt cctgctcatc accctgtcga cctggccgac tgggagctca 960
ctgagtcccc tgagaacggt ttttccttca acacgtctca ttcttgcggt caccttgtcc 1020
agaaccccga cgtgtttgat ggcaagtgct ggctctcctg ctttttgggc cagtcggtcg 1080
aagtgcgctg ccatgaggaa catctagctg acgccttcgg ttaccaaacc aagtggggcg 1140
tgcatggtaa gtacctccag cgcaggcttc aagttcgcgg cattcgtgct gtagtcgatc 1200
ctgatggtcc cattcacgtt gaagcgctgt cttgccccca gtcttggatc aggcacctga 1260
ctctggatga tgatgtcacc ccaggattcg ttcgcctgac atcccttcgc attgtgccga 1320
acacagagcc taccacttcc cggatctttc ggtttggagc gcataagtgg tatggcgctg 1380
ccggcaaacg ggctcgtgct aagcgtgccg ctaaaagtga gaaggattcg gctcccaccc 1440
ccaaggttgc cctgccggtc cccacctgtg gaattaccac ctactctcca ccgacagacg 1500
ggtcttgtgg ttggcatgtc cttgccgcca taatgaaccg gatgataaat ggtgacttca 1560
cgtcccctct gactcagtac aacagaccag aggatgattg ggcttctgat tatgatcttg 1620
ttcaggcgat tcaatgtcta cgactgcctg ctaccgtggt tcggaatcgc gcctgtccta 1680
acgccaagta ccttataaaa cttaacggag ttcactggga ggtagaggtg aggtctggaa 1740
tggctcctcg ctccctttct cgtgaatgtg tggttggcgt ttgctctgaa ggctgtgtcg 1800

```
caccgcctta tccagcagac gggctaccta aacgtgcact cgaggccttg gcgtctgctt   1860
acagactacc ctccgattgt gttagctctg gtattgctga ctttcttgct aatccacctc   1920
ctcaggaatt ctggaccctc gacaaaatgt tgacctcccc gtcaccagag cggtccggct   1980
tctctagttt gtataaatta ctattagagg ttgttccgca aaaatgcggt gccacggaag   2040
gggctttcat ctatgctgtt gagaggatgt tgaaggattg tccgagctcc aaacaggcca   2100
tggcccttct ggcaaaaatt aaagttccat cctcaaaggc cccgtctgtg tccctggacg   2160
agtgtttccc tacggatgtt ttagccgact tcgagccagc atctcaggaa aggccccaaa   2220
gttccggcgc tgctgttgtc ctgtgttcac cggatgcaaa agagttcgag gaagcagccc   2280
cggaagaagt tcaagagagt ggccacaagg ccgtccactc tgcactcctt gccgagggtc   2340
ctaacaatga gcaggtacag gtggttgccg gtgagcaact gaagctcggc ggttgtggtt   2400
tggcagtcgg gaatgctcat gaaggtgctc tggtctcagc tggtctaatt aacctggtag   2460
gcgggaattt gtccccctca gaccccatga aagaaaacat gctcaatagc cgggaagacg   2520
aaccactgga tttgtcccaa ccagcaccag cttccacaac gacccttgtg agagagcaaa   2580
cacccgacaa cccaggttct gatgccggtg ccctccccgt caccgttcga gaatttgtcc   2640
cgacggggcc tatactctgt catgttgagc actgcggcac ggagtcgggc gacagcagtt   2700
cgcctttgga tctatctgat gcgcaaaccc tggaccagcc tttaaatcta tccctggccg   2760
cttggccagt gagggccacc gcgtctgacc ctggctgggt ccacggtagg cgcgagcctg   2820
tctttgtaaa gcctcgaaat gctttctctg atggcgattc agcccttcag ttcggggagc   2880
tttctgaatc cagctctgtc atcgagtttg accggacaaa agatgctccg gtggttgacg   2940
cccctgtcga cttgacgact tcgaacgagg ccctctctgt agtcgatcct ttcgaatttg   3000
ccgaactcaa gcgcccgcgt ttctccgcac aagccttaat tgaccgaggc ggtccacttg   3060
ccgatgtcca tgcaaaaata aagaaccggg tatatgaaca gtgcctccaa gcttgtgagc   3120
ccggtagtcg tgcaacccca gccaccaggg agtggctcga caaaatgtgg gatagggtgg   3180
acatgaaaac ttggcgctgc acctcgcagt tccaagctgg tcgcattctt gcgtccctca   3240
aattcctccc tgacatgatt caagacacac cgcctcctgt tcccaggaag aaccgagcta   3300
gtgacaatgc cggcctgaag caactggtgg cacagtggga taggaaattg agtgtgaccc   3360
ccccccccaaa accggttggg ccagtgcttg accagatcgt ccctccgcct acggatatcc   3420
agcaagaaga tgtcaccccc tccgatgggc caccccatgc gccggatttt cctagtcgag   3480
tgagcacggg cgggagttgg aaaggcctta tgctttccgg cacccgtctc gcggggtcta   3540
tcagccagcg ccttatgaca tgggtttttg aagttttctc ccacctccca gcttttatgc   3600
tcacactttt ctcgccgcgg ggctctatgg ctccaggtga ttggttgttt gcaggtgtcg   3660
ttttacttgc tctcttgctc tgtcgttctt acccgatact cggatgcctt cccttattgg   3720
gtgtcttttc tggttctttg cggcgtgttc gtctgggtgt ttttggttct tggatggctt   3780
ttgctgtatt tttattctcg actccatcca acccagtcgg ttcttcttgt gaccacgatt   3840
cgccggagtg tcatgctgag cttttggctc ttgagcagcg ccaactttgg gaacctgtgc   3900
gcggccttgt ggtcggcccc tcaggcctct tatgtgtcat tcttggcaag ttactcggtg   3960
ggtcacgtta tctctggcat gttctcctac gtttatgcat gcttgcagat ttggcccttt   4020
ctcttgttta tgtggtgtcc caggggcgtt gtcacaagtg ttggggaaag tgtataagga   4080
cagctcctgc ggaggtggct cttaatgtat ttcctttctc gcgcgccacc cgtgtctctc   4140
```

-continued

```
ttgtatcctt gtgtgatcga ttccaaacgc caaaaggggt tgatcctgtg cacttggcaa   4200
cgggttggcg cgggtgctgg cgtggtgaga gccccatcca tcaaccacac caaaagccca   4260
tagcttatgc caatttggat gaaaagaaaa tgtctgccca aacggtggtt gctgtcccat   4320
acgatcccag tcaggctatc aaatgcctga aagttctgca ggcgggaggg gccatcgtgg   4380
accagcctac acctgaggtc gttcgtgtgt ccgagatccc cttctcagcc ccatttttcc   4440
caaaagttcc agtcaaccca gattgcaggg ttgtggtaga ttcggacact tttgtggctg   4500
cggttcgctg cggttactcg acagcacaac tggttctggg ccggggcaac tttgccaagt   4560
taaatcagac ccccccagg aactctatct ccaccaaaac gactggtggg gcctcttaca   4620
cccttgctgt ggctcaagtg tctgcgtgga ctcttgttca tttcatcctc ggtctttggt   4680
tcacatcacc tcaagtgtgt ggccgaggaa ccgctgaccc atggtgttca aatccttttt   4740
catatcctac ctatggcccc ggagttgtgt gctcctctcg actttgtgtg tctgccgacg   4800
gggtcaccct gccattgttc tcagccgtgg cacaactctc cggtagagag gtggggattt   4860
ttattttggt gctcgtctcc ttgactgctt tggcccaccg catggctctt aaggcagaca   4920
tgttagtggt cttttcggct tttgtgcttt acgcctggcc catgagctcc tggttaatct   4980
gcttctttcc tatactcttg aagtgggtta cccttcaccc tcttactatg ctttgggtgc   5040
actcattctt ggtgttttgt ctgccagcag ccggcatcct ctcactaggg ataactggcc   5100
ttctttgggc aattggccgc tttacccagg ttgccggaat tattacacct tatgacatcc   5160
accagtacac ctctgggcca cgtggtgcag ctgctgtggc cacagcccca gaaggcactt   5220
atatggccgc cgtccggaga gctgctttaa ctgggcgaac tttaatcttc accccgtctg   5280
cagttggatc ccttctcgaa ggtgctttca ggactcataa accctgcctt aacaccgtga   5340
atgttgtagg ctcttccctt ggttccggag gggttttcac cattgatggc agaagaactg   5400
tcgtcactgc tgcccatgtg ttgaacggcg acacagctag agtcaccggc gactcctaca   5460
accgcatgca cactttcaag accaatggtg attatgcctg gtcccatgct gatgactggc   5520
agggcgttgc ccctgtggtc aaggttgcga aggggtaccg cggtcgtgcc tactggcaaa   5580
catcaactgg tgtcgaaccc ggtatcattg gggaagggtt cgccttctgt tttactaact   5640
gcggcgattc ggggtcaccc gtcatctcag aatctggtga tcttattgga atccacaccg   5700
gttcaaacaa acttggttct ggtcttgtga caacccctga aggggagacc tgcaccatca   5760
aagaaaccaa gctctctgac ctttccagac attttgcagg cccaagcgtt cctcttgggg   5820
acattaaatt gagtccggcc atcatccctg atgtaacatc cattccgagt gacttggcat   5880
cgctcctagc ctccgtccct gtagtggaag gcggcctctc gaccgttcaa cttttgtgtg   5940
tctttttcct tctctggcgc atgatgggcc atgcctggac acccattgtt gccgtgggct   6000
tctttttgct gaatgaaatt cttccagcag ttttggtccg agccgtgttt tcttttgcac   6060
tctttgtgct tgcatgggcc accccctggt ctgcacaggt gttgatgatt agactcctca   6120
cggcatctct caaccgcaac aagctttctc tggcgttcta cgcactcggg ggtgtcgtcg   6180
gtttggcagc tgaaatcggg acttttgctg gcagattgtc tgaattgtct caagctcttt   6240
cgacatactg cttcttacct agggtccttg ctatgaccag ttgtgttccc accatcatca   6300
ttggtggact ccataccctc ggtgtgattc tgtggttatt caaataccgg tgcctccaca   6360
acatgctggt tggtgatggg agtttttcaa gcgccttctt cctacggtat tttgcagagg   6420
gtaatctcag aaaaggtgtt tcacagtcct gtggcatgaa taacgagtcc ctaacggctg   6480
ctttagcttg caagttgtca caggctgacc ttgatttttt gtccagctta acgaacttca   6540
```

-continued agtgctttgt atctgcttca aacatgaaaa atgctgccgg ccagtacatt gaagcagcgt 6600
atgccaaggc cctgcgccaa gagttggcct ctctagttca gattgacaaa atgaaaggag 6660
ttttgtccaa gctcgaggcc tttgctgaaa cagccacccc gtcccttgac ataggtgacg 6720
tgattgttct gcttgggcaa catcctcacg gatccatcct cgatattaat gtggggactg 6780
aaaggaaaac tgtgtccgtg caagagaccc ggagcctagg cggctccaaa ttcagtgttt 6840
gtactgtcgt gtccaacaca cccgtggacg ccttgaccgg catcccactc cagacaccaa 6900
cccctctttt tgagaatggt ccgcgtcatc gcagcgagga agacgatctt aaagtcgaga 6960
ggatgaagaa acactgtgta tccctcggct tccacaacat caatggcaaa gtttactgca 7020
aaatttggga caagtctacc ggtgacacct tttacacgga tgattcccgg tacacccaag 7080
accatgcttt tcaggacagg tcagccgact acagagacag ggactatgag ggtgtgcaaa 7140 ccaccccccca acagggattt gatccaaagt ctgaaacccc tgttggcact gttgtgatcg 7200
gcggtattac gtataacagg tatctgatca aaggtaagga ggttctggtc cccaagcctg 7260
acaactgcct tgaagctgcc aagctgtccc ttgagcaagc tctcgctggg atgggccaaa 7320
cttgcgacct tacagctgcc gaggtggaaa agctaaagcg catcattagt caactccaag 7380
gtttgaccac tgaacaggct ttaaactgtt agccgccagc ggcttgaccc gctgtggccg 7440
cggcggccta gttgtgactg aaacggcggt aaaaattata aaataccaca gcagaacttt 7500
caccttaggc cctttagacc taaaagtcac ttccgaggtg gaggtaaaga aatcaactga 7560
gcagggccac gctgttgtgg caaacttatg ttccggtgtc atcttgatga gacctcaccc 7620
accgtccctt gtcgacgttc ttctgaaacc cggacttgac acaatacccg gcattcaacc 7680
agggcatggg gccgggaata tgggcgtgga cggttctatt tgggattttg aaaccgcacc 7740
cacaaaggca gaactcgagt tatccaagca aataatccaa gcatgtgaag ttaggcgcgg 7800
ggacgccccg aacctccaac tcccttacaa gctctatcct gttagggggg atcctgagcg 7860
gcataaaggc cgccttatca ataccaggtt tggagattta ccttacaaaa ctcctcaaga 7920
caccaagtcc gcaatccacg cggcttgttg cctgcacccc aacggggccc ccgtgtctga 7980
tggtaaatcc acactaggta ccactcttca acatggtttc gagctttatg tccctactgt 8040
gccctatagt gtcatggagt accttgattc acgccctgac accccttttta tgtgtactaa 8100 acatggcact tccaaggctg ctgcagagga cctccaaaaa tacgacctat ccacccaagg 8160
atttgtcctg cctggggtcc tacgcctagt acgcagattc atctttggcc atattggtaa 8220
ggcgccgcca ttgttcctcc catcaaccta tcccgccaag aactctatgg cagggatcaa 8280
tggccagagg ttcccaacaa aggacgttca gagcatacct gaaattgatg aaatgtgtgc 8340
ccgcgctgtc aaggagaatt ggcaaactgt gacaccttgc accctcaaga aacagtactg 8400
ttccaagccc aaaaccagga ccatcctggg caccaacaac tttattgcct tggctcacag 8460
atcggcgctc agtggtgtca cccaggcatt catgaagaag gcttggaagt ccccaattgc 8520
cttggggaaa aacaaattca aggagctgca ttgcactgtc gccggcaggt gtcttgaggc 8580
cgacttggcc tcctgtgacc gcagcacccc cgccattgta agatggtttg ttgccaacct 8640
cctgtatgaa cttgcaggat gtgaagagta cttgcctagc tatgtgctta attgctgcca 8700
tgacctcgtg gcaacacagg atggtgcctt cacaaaacgc ggtggcctgt cgtccgggga 8760
ccccgtcacc agtgtgtcca acaccgtata ttcactggta atttatgccc agcacatggt 8820
attgtcggcc ttgaaaatgg gtcatgaaat tggtcttaag ttcctcgagg aacagctcaa 8880

-continued

```
gttcgaggac ctccttgaaa ttcagcctat gttggtatac tctgatgatc ttgtcttgta   8940
cgctgaaaga cccacatttc ccaattacca ctggtgggtc gagcaccttg acctgatgct   9000
gggtttcaga acggacccaa agaaaaccgt cataactgat aaacccagct tcctcggctg   9060
cagaattgag gcagggcgac agctagtccc caatcgcgac cgcatcctgg ctgctcttgc   9120
atatcacatg aaggcgcaga acgcctcaga gtattatgcg tctgctgccg caatcctgat   9180
ggattcatgt gcttgcattg accatgaccc tgagtggtat gaggacctca tctgcggtat   9240
tgcccggtgc gcccgccagg atggttatag cttcccaggt ccggcatttt tcatgtccat   9300
gtgggagaag ctgagaagtc ataatgaagg gaagaaattc cgccactgcg gcatctgcga   9360
cgccaaagcc gactatgcgt ccgcctgtgg gcttgatttg tgtttgttcc attcgcactt   9420
tcatcaacac tgccctgtca ctctgagctg cggtcaccat gccggttcaa aggaatgttc   9480
gcagtgtcag tcacctgttg gggctggcag atcccctctt gatgccgtgc taaaacaaat   9540
tccatacaaa cctcctcgta ctgtcatcat gaaggtgggt aataaaacaa cggccctcga   9600
tccggggagg taccagtccc gtcgaggtct cgttgcagtc aagaggggta ttgcaggcaa   9660
tgaagttgat ctttctgatg ggactacca agtggtgcct cttttgccga cttgcaaaga   9720
cataaacatg gtgaaggtgg cttgcaatgt actactcagc aagttcatag tagggccacc   9780
aggttccgga aagaccacct ggctactgag tcaagtccag gacgatgatg tcatttacac   9840
acccacccat cagactatgt ttgatatagt cagtgctctc aaagtttgca ggtattccat   9900
tccaggagcc tcaggactcc ctttcccacc acctgccagg tccgggccgt gggttaggct   9960
tattgccagc gggcacgtcc ctggccgagt atcatacctc gatgaggctg gatattgtaa  10020
tcatctggac attcttagac tgctttccaa aacacccctt gtgtgtttgg gtgaccttca  10080
gcaacttcac cctgtcggct ttgattccta ctgttatgtg ttcgatcaga tgcctcagaa  10140
gcagctgacc actatttaca gatttggccc taacatctgc gcagccatcc agccttgtta  10200
cagggagaaa cttgaatcta aggctaggaa cactagggtg gtttttacca cccggcctgt  10260
ggcctttggt caggtgctga caccatacca taaagatcgc atcggctctg cgataaccat  10320
agattcatcc caggggggcca cctttgatat tgtgacattg catctaccat cgccaaagtc  10380
cctaaataaa tcccgagcac ttgtagccat cactcgggca agacacgggt tgttcattta  10440
tgaccctcat aaccagctcc aggagttttt caacttaacc cctgagcgca ctgattgtaa  10500
ccttgtgttc agccgtgggg atgagctggt agttctgaat gcggataatg cagtcacaac  10560
tgtagcgaag gcccttgaga caggtccatc tcgatttcga gtatcagacc cgaggtgcaa  10620
gtctctctta gccgcttgtt cggccagtct ggaagggagc tgtatgccac taccgcaagt  10680
ggcacataac ctggggtttt acttttcccc ggacagtcca acatttgcac ctctgccaaa  10740
agagttggcg ccacattggc cagtggttac ccaccagaat aatcgggcgt ggcctgatcg  10800
acttgtcgct agtatgcgcc caattgatgc ccgctacagc aagccaatgg tcggtgcagg  10860
gtatgtggtc gggccgtcca cctttcttgg tactcctggt gtggtgtcat actatctcac  10920
actatacatc aggggtgagc cccaggcctt gccagaaaca ctcgtttcaa cagggcgtat  10980
agccacagat tgtcgggagt atctcgacgc ggctgaggaa gaggcagcaa aagaactccc  11040
ccacgcattc attggcgatg tcaaaggtac cacggttggg gggtgtcatc acattacatc  11100
aaaataccta cctaggtccc tgcctaagga ctctgttgcc gtagttggag taagttcgcc  11160
cggcagggct gctaaagccg tgtgcactct caccgatgtg tacctccccg aactccggcc  11220
atatctgcaa cctgagacgg catcaaaatg ctggaaactc aaattagact tcagggacgt  11280
```

-continued ccgactaatg gtctggaaag gagccaccgc ctatttccag ttggaagggc ttacatggtc 11340
ggcgctgccc gactatgcca ggtttattca gctgcccaag gatgccgttg tatacattga 11400
tccgtgtata ggaccggcaa cagccaaccg taaggtcgtg cgaaccacag actggcgggc 11460
cgacctggca gtgacaccgt atgattacgg tgcccagaac attttgacaa cagcctggtt 11520
cgaggacctc gggccgcagt ggaagatttt ggggttgcag ccctttaggc gagcatttgg 11580
ctttgaaaac actgaggatt gggcaatcct tgcacgccgt atgaatgacg gcaaggacta 11640
cactgactat aactggaact gtgttcgaga acgcccacac gccatctacg ggcgtgctcg 11700
tgaccatacg tatcattttg cccctggcac agaattgcag gtagagctag gtaaaccccg 11760
gctgccgcct gggcaagtgc cgtgaattcg gggtgatgca atggggtcac tgtggagtaa 11820
aatcagccag ctgttcgtgg acgccttcac tgagttcctt gttagtgtgg ttgatattgc 11880
cattttcctt gccatactgt ttgggttcac cgtcgcagga tggttactgg tctttcttct 11940
cagagtggtt tgctccgcgc ttctccgttc gcgctctgcc attcactctc ccgaactatc 12000
gaaggtccta tgaaggcttg ttgcccaact gcagaccgga tgtcccacaa tttgcagtca 12060
agcacccatt gggtatgttt tggcacatgc gagtttccca cttgattgat gagatggtct 12120
ctcgtcgcat ttaccagacc atggaacatt caggtcaagc ggcctggaag caggtggttg 12180
gtgaggccac tctcacgaag ctgtcagggc tcgatatagt tactcatttc caacacctgg 12240
ccgcagtgga ggcggattct tgccgctttc tcagctcacg actcgtgatg ctaaaaaatc 12300
ttgccgttgg caatgtgagc ctacagtaca acaccacgtt ggaccgcgtt gagctcatct 12360
tccccacgcc aggtacgagg cccaagttga ccgatttcag acaatggctc atcagtgtgc 12420
acgcttccat tttttcctct gtggcttcat ctgttacctt gttcatagtg ctttggcttc 12480
gaattccagc tctacgctat gtttttggtt tccattggcc cacggcaaca catcattcga 12540
gctgaccatc aactacacca tatgcatgcc ctgttctacc agtcaagcgg ctcgccaaag 12600
gctcgagccc ggtcgtaaca tgtggtgcaa aatagggcat gacaggtgtg aggagcgtga 12660
ccatgatgag ttgttaatgt ccatcccgtc cgggtacgac aacctcaaac ttgagggtta 12720
ttatgcttgg ctggcttttt tgtccttttc ctacgcggcc caattccatc cggagttgtt 12780
cgggataggg aatgtgtcgc gcgtcttcgt ggacaagcga caccagttca tttgtgccga 12840
gcatgatgga cacaattcaa ccgtatctac cggacacaac atctccgcat tatatgcggc 12900
atattaccac caccaaatag acgggggcaa ttggttccat ttggaatggc tgcggccact 12960
cttttcttcc tggctggtgc tcaacatatc atggtttctg aggcgttcgc ctgtaagccc 13020
tgtttctcga cgcatctatc agatattgag accaacacga ccgcggctgc cggtttcatg 13080
gtccttcagg acatcaattg tttccgacct cacggggtct cagcagcgca agagaaaatt 13140
tccttcggaa agtcgtccca atgtcgtgaa gccgtcggta ctccccagta catcacgata 13200
acggctaacg tgaccgacga atcatacttg tacaacgcgg acctgctgat gctttctgcg 13260
tgccttttct acgcctcaga aatgagcgag aaaggcttca aagtcatctt tgggaatgtc 13320
tctggcgttg tttctgcttg tgtcaatttc acagattatg tggcccatgt gacccaacat 13380
acccagcagc atcatctggt aattgatcac attcggttgc tgcatttcct gacaccatct 13440
gcaatgaggt gggctacaac cattgcttgt ttgttcgcca ttctcttggc aatatgagat 13500
gttctcacaa attggggcgt ttcttgactc cgcactcttg cttctggtgg ctttttttgc 13560
tgtgtaccgg cttgtcctgg tcctttgccg atggcaacgg cgacagctcg acataccaat 13620

-continued

```
acatatataa cttgacgata tgcgagctga atgggaccga ctggttgtcc agccattttg  13680
gttgggcagt cgagaccttt gtgctttacc cggttgccac tcatatcctc tcactgggtt  13740
ttctcacaac aagccatttt tttgacgcgc tcggtctcgg cgctgtatcc actgcaggat  13800
ttgttggcgg gcggtacgta ctctgcagcg tctacggcgc ttgtgctttc gcagcgttcg  13860
tatgttttgt catccgtgct gctaaaaatt gcatggcctg ccgctatgcc cgtacccggt  13920
ttaccaactt cattgtggac gaccggggga gagttcatcg atggaagtct ccaatagtgg  13980
tagaaaaatt gggcaaagcc gaagtcgatg gcaacctcgt caccatcaaa catgtcgtcc  14040
tcgaaggggt taaagctcaa cccttgacga ggacttcggc tgagcaatgg gaggcctaga  14100
cgatttttgc aacgatccta tcgccgcaca aaagctcgtg ctagccttta gcatcacata  14160
cacacctata atgatatacg cccttaaggt gtcacgcggc cgactcctgg ggctgttgca  14220
catcctaata tttctgaact gttcctttac attcggatac atgacatatg tgcattttca  14280
atccaccaac cgtgtcgcac ttaccctggg ggctgttgtc gcccttctgt ggggtgttta  14340
cagcttcaca gagtcatgga agtttatcac ttccagatgc agattgtgtt gccttggccg  14400
gcgatacatt ctggcccctg cccatcacgt agaaagtgct gcaggtctcc attcaatctc  14460
agcgtctggt aaccgagcat acgctgtgag aaagcccgga ctaacatcag tgaacggcac  14520
tctagtacca ggacttcgga gcctcgtgct gggcggcaaa cgagctgtta aacgaggagt  14580
ggttaacctc gtcaagtatg gccggtaaaa accagagcca gaagaaaaag aaaagtacag  14640
ctccgatggg gaatggccag ccagtcaatc aactgtgcca gttgctgggt gcaatgataa  14700
agtcccagcg ccagcaacct aggggaggac aggccaaaaa gaaaaagcct gagaagccac  14760
atttcccct ggctgctgaa gatgacatcc ggcaccacct cacccagact gaacgctccc  14820
tctgcttgca atcgatccag acggctttca atcaaggcgc aggaactgcg tcgctttcat  14880
ccagcgggaa ggtcagtttt caggttgagt ttatgctgcc ggttgctcat acagtgcgcc  14940
tgattcgcgt gacttctaca tccgccagtc agggtgcaag ttaatttgac agtcaggtga  15000
atggccgcga ttggcgtgtg gcctctgagt cacctattca attagggcga tcacatgggg  15060
gtcatactta atcaggcagg aaccatgtga ccgaaattaa aaaaaaaaaa a          15111
```

<210> SEQ ID NO 42
<211> LENGTH: 15182
<212> TYPE: DNA
<213> ORGANISM: Porcine reproductive and respiratory syndrome virus

<400> SEQUENCE: 42

```
tttctccacc cctttaacca tgtctgggat acttgatcgg tgcacgtgta cccccaatgc     60
cagggtgttt atggcggagg gccaagtcta ctgcacacga tgcctcagtg cacggtctct    120
ccttcccctg aacctccaag tttctgagct cggggtgcta ggcctattct acaggcccga    180
agagccactc cggtggacgt tgccacgtgc attccccact gttgagtgct cccccgccgg    240
ggcctgctgg ctctctgcaa tctttccaat cgcacgaatg accagtggaa acctgaactt    300
ccaacaaaga atgatacggg tcgcagctga gctttacaga gccggccagc tcacccctgc    360
agtcttgaag gctctacaag tttatgaacg gggttgccgc tggtaccccca ttgttggacc    420
tgcccctgga gtggccgttt acgccaattc cctacatgtg agtgataaac ctttcccggg    480
agcaactcac gtgttgacca acctgccgct cccgcagaga cccaagcctg aagacttttg    540
cccctttgag tgtgctatgg ctactgtcta tgacattggt catgacgccg tcatgtatgt    600
ggccgaaagg aaaatctcct gggcccctcg tggcggggat gaagtgaaat ttgaagctgt    660
```

-continued

```
ccccggggag ttgaggttga ttgcgaaccg gctccgcacc tccttcccgc cccaccacac    720
agtggacatg tctaagttcg ccttcacagc ccctgggtgt ggtgtttcta tgcgggttga    780
acgccaacac ggctgccttc ccgctgacac tgtccctgaa ggcaactgct ggtggagctt    840
gtttgactcg cttccactgg aagttcagaa caaagaaatt cgccatgcta accaatttgg    900
ctaccagacc aagcatggtg tctctggcaa gtacctacag cggaggctgc aagttaatgg    960
tctccgagca gtaactgacc taaacggacc tatcgtcgta cagtacttct ccgttaagga   1020
gagttggatc cgccatttga aactggcggg agaacccagc tactctgggt ttgaggacct   1080
cctcagaata agggttgagc ctaacacgtc gccattggct gacaaggaag aaaaaatttt   1140
ccggtttggc agtcacaagt ggtacggcgc tggaaagaga gcaagaaaag cacgctcttg   1200
tgcgactgcc acagtcgctg gccgcgcttt gtccgttcgt gaaacccggc aggccaagga   1260
gcacgaggtt gccggcgcca acaaggctga gcacctcaaa cactactccc cgcctgccga   1320
agggaattgt ggttggcatt gcatttccgc catcgccaac cggatggtga attccaaatt   1380
tgaaaccacc cttcccgaaa gagtgagacc tccagatgac tgggctactg acgaggatct   1440
tgtgaatgcc atccaaatcc tcagactccc tgcggcctta gacaggaacg gtgcttgtac   1500
tagcgccaag tacgtactta agctggaagg tgagcattgg actgtcactg tggcccctgg   1560
gatgtcccct tctttgctcc ctcttgaatg tgttcagggc tgttgtgggc acaagggcgg   1620
tcttggttcc ccagatgcag tcgaggtctc cggatttgac cctgcctgcc ttgaccggct   1680
ggctgaggtg atgcacctgc ctagcagtgc tatcccagcc gctctggccg aaatgtctgg   1740
cgattccgat cgttcggctt ctccggtcac caccgtgtgg actgtttcgc agttctttgc   1800
ccgtcacagc ggagggaatc accctgatca agtgcgctta gggaaaatta tcagcctttg   1860
tcaggtgatt gaggactgct gctgttccca gaacaaaacc aaccgggtca ccccggagga   1920
ggtcgcagca aagattgacc tgtacctccg tggtgcaaca aatcttgaag aatgcttggc   1980
caggcttgag aaagcgcgcc cgccacgcgt aatcgacacc ttctttgatt gggatgttgt   2040
gctccctggg gttgaggcgg caacccagac gatcaagctg ccccaggtca accagtgtcg   2100
tgctctggtc cctgttgtga ctcaaaagtc cttggacgac aactcggtcc ccctgaccgc   2160
cttttcactg gctaactact actaccgtgc gcaaggtgac gaagttcgtc accgtgaaag   2220
actaaccgcc gtgctctcca agttggaaaa ggttgttcga gaagaatatg ggctcatgcc   2280
aaccgagcct ggtccacggc ccacactgcc acgcgggctc gacgaactca aagaccagat   2340
ggaggaggac ttgctgaagc tggctaacgc ccagacgact tcggacatga tggcctgggc   2400
agtcgagcag gttgacctaa aaacttgggt caagaactac ccgcggtgga caccaccacc   2460
ccctccgcca aaagttcagc ctcgaaaaac gaagcctgtc aagagcttgc cggagagaaa   2520
gcctgtcccc gccccgcgca ggaaggttgg gtccgattgt ggcagcccgg tttcattagg   2580
cggcgatgtc tctaacagtt gggaagattt ggctgttagt agcccctttg atctcccgac   2640
cccacctgag ccggcaacac cttcaagtga gctggtgatt gtgtcctcac cgcaatgcat   2700
cttcaggccg gcgacaccct tgagtgagcc ggctccaatt cccgcacctc gcggaactgt   2760
gtctcgaccg gtgacaccct tgagtgagcc gatccctgtg cccgcaccgc ggcgtaagtt   2820
tcagcaggtg aaaagattga gttcggcggc ggcaatccca ccgtaccaga acgagcccct   2880
ggatttgtct gcttcctcac agactgaaca tgaggcctct cccccagcac cgccgcagag   2940
cgggggcgtt ccgggagtag aggggcatga agctgaggaa accctgagtg aaatctcgga   3000
```

-continued

```
catgtcgggt aacattaaac ctgcgtccgt gtcatcaagc agctccttgt ccagcgtgag   3060
aatcacacgc ccaaaatact cagctcaagc catcatcgac tcgggcgggc cctgcagtgg   3120
gcatctccaa gaggtaaagg aaacatgcct tagtgtcatg cgcgaggcat gtgatgcgac   3180
taagcttgat gaccctgcta cgcaggaatg gctttctcgc atgtgggatc gggtggacat   3240
gctgacttgg cgcaacacgt ctgtttacca ggcgatttgc accttagatg gcaggttaaa   3300
gttcctccca aaaatgatac tcgagacacc gccgccctat ccgtgtgagt ttgtgatgat   3360
gcctcacacg cctgcacctt ccgtaggtgc ggagagcgac cttaccattg gctcagttgc   3420
tactgaagat gttccacgca tcctcgagaa aatagaaaat gtcggcgaga tggccaacca   3480
gggacccttg gccttctccg aggataaacc ggtagatgac caacttgtca acgacccccg   3540
gatatcgtcg cggaggcctg acgagagcac atcagctccg tccgcaggca caggtggcgc   3600
cggctctttt accgatttgc cgccttcaga tggcgcggat acggacgggg gggggccgtt   3660
tcggacggca aaaagaaaag ctgaaaggct ctttgaccaa ctgagccgtc aggtttttga   3720
cctcgtctcc catctccctg ttttcttctc acgccttttc taccctggcg gtggttattc   3780
tccgggtgat tggggttttg cagcttttac tctattgtgc ctctttttat gttacagtta   3840
cccagccttt ggtattgctc ccctcttggg tgtgttttct gggtcttctc ggcgcgttcg   3900
aatgggggtt tttggctgct ggttggcttt tgctgttggt ctgttcaagc ctgtgtccga   3960
cccagtcggc gctgcttgtg agtttgactc gccagagtgt agaaacatcc ttcattcttt   4020
tgagcttctc aaaccttggg accctgttcg cagccttgtt gtgggccccg tcggtctcgg   4080
tcttgccatt cttggcaggt tactgggcgg ggcacgctgc atctggcact tttgcttag   4140
gcttggcatt gttgcagact gtatcttggc tggagcttac gtgctttctc aaggtaggtg   4200
taaaaagtgc tggggatctt gtataagaac tgctcctaat gaggtcgctt ttaacgtgtt   4260
tcctttcaca cgtgcgacca ggtcgtcact tatcgacctg tgcgatcggt tttgtgcgcc   4320
aaaaggaatg gaccccattt ttctcgccac tgggtggcgc gggtgctggg ccggccgaag   4380
ccccattgag caaccctctg aaaaacccat cgcgtttgcc caattggatg aaaagaagat   4440
tacggctagg actgtggtcg cccagcctta tgaccccaac caagccgtaa agtgcttgcg   4500
ggtattgcag gcgggtgggg cgatggtggc taaggcggtc ccaaaagtgg ttaaggtttc   4560
cgctgttcca ttccgagctc ccttctttcc cactggagtg aaagttgacc ctgattgcag   4620
ggtcgtggtt gaccctgaca ctttcactgc agctctccgg tctggctact ccaccacaaa   4680
cctcgtcctt ggtgtagggg actttgccca gctaaatgga ttaaaaatca ggcaaatttc   4740
caagccttca gggggaggcc cacatctcat ggctgccctg catgttgcct gctcgatggc   4800
tctgcacatg cttgctggga tttatgtgac tgcggtgggt tcttgcggca ccggcaccaa   4860
cgacccgtgg tgcgctaacc cgtttgccgt ccctggctac ggacctggct ctctctgtac   4920
gtccagattg tgcatttccc aacacggcct taccctgccc ttgtcagcac ttgtggcggg   4980
attcggtatt caagaaattg ccttggtcgt tttgattttt gtttccatcg gaggcatggc   5040
tcataggttg agctgtaagg ctgacatgct gtgtgttttg cttgcaattg ccagctatgt   5100
ttgggtacct cttacctggt tgctttgtgt gtttccttgc tggttgcgct gtttttcttt   5160
gcacccccctc accatcctat ggttggtgtt tttcttgatt tctgtgaata tgccttcagg   5220
aatcttggcc atggtgttgt tggtttctct ttggcttctt ggtcgttata ctaatgttgc   5280
tggccttgtc accccctacg acattcatca ttacaccagt ggccccgcg gtgttgccgc   5340
cttggctacc gcaccagatg ggacctactt ggccgctgtc cgccgcgctg cgttgactgg   5400
```

-continued

```
ccgcaccatg ctgtttaccc cgtcccagct tgggtctctt cttgagggtg ccttcagaac   5460
tcgaaagccc tcactgaaca ccgtcaatgt gatcgggtcc tccatgggct ctggcggggt   5520
gtttaccatc gacgggaaag tcaagtgcgt aactgccgca catgtcctta cgggcaattc   5580
agctcgggtt tccggggtcg gcttcaatca aatgcttgac tttgacgtaa agggagattt   5640
cgctatcgct gattgcccga attggcaagg ggctgccccc aagacccaat tctgcacgga   5700
tggatggact ggccgtgcct attggctaac atcctctggc gtcgaacccg gcgtcattgg   5760
aaaaggattc gccttctgct tcaccgcatg tggcgattcc gggtccccag tgatcaccga   5820
ggccggtgag cttgtcggcg ttcacacggg atcgaataaa caagggggggg gcattgttac   5880
gcgcccctca ggccagtttt gtaatgtggc acccatcaag ctaagcgaat taagtgaatt   5940
ctttgctggg cctaaggtcc cgctcggtga tgtgaaggtc ggcagccaca taattaaaga   6000
cataagcgag gtgccttcag atctttgtgc cttgcttgct gccaaacctg aactggaagg   6060
aggcctctcc accgtccaac ttctttgtgt gtttttttctc ctgtggagaa tgatgggaca   6120
tgcctggacg cccttggttg ctgtgagttt ctttattttg aatgaggttc tccctgccgt   6180
cctggtccgg agtgttttct cctttggaat gtttgtgcta tcctggctca cgccatggtc   6240
tgcgcaagtt ctgatgatca ggcttctgac agcagctctt aacaggaaca gatggtcact   6300
tgcctttttc agcctcggtg cagtgaccgg ttttgtcgca gatcttgcgg ccactcaggg   6360
gcatccgttg caggcagtga tgaatttgag cacctatgca ttcctgcctc ggatgatggt   6420
tgtgacctca ccagtcccag tgatcacgtg tggtgtcgtg cacctacttg ccatcatttt   6480
gtacttgttt aagtaccgtg gcctgcacca tatccttgtt ggcgatggag tgttctctgc   6540
ggctttcttc ttgagatact ttgccgaggg aaagttgagg gaaggggtgt cgcaatcctg   6600
cggaatgaat catgagtctc tgactggtgc cctcgctatg agactcaatg acgaggactt   6660
ggatttcctt atgaaatgga ctgattttaa gtgctttgtt tctgcgtcca acatgaggaa   6720
tgcagcgggt caatttatcg aggctgccta tgctaaagca cttagagtag aactggccca   6780
gttggtacag gttgataaag ttcgaggtac tttggccaaa cttgaagctt ttgctgatac   6840
cgtggctcct caactctcgc ccggtgacat tgttgtcgct ctcggccaca cgcctgttgg   6900
cagtatcttc gacctaaagg ttggtagcac caagcatacc ctccaagcca ttgagaccag   6960
agtccttgct gggtccaaaa tgaccgtggc gcgcgtcgtc gacccgaccc ccacgccccc   7020
acccgcaccc gtgcccatcc ccctcccacc gaaagttctg gagaatggcc ccaacgcttg   7080
gggggatgag gaccgtttga ataagaagaa gaggcgcagg atggaagccc tcggcatcta   7140
tgttatgggc gggaaaaagt accagaaatt ttgggacaag aattccggtg atgtgtttta   7200
tgaggaggtc cataataaca cagatgagtg ggagtgtctc agagttggcg accctgccga   7260
ctttgaccct gagaagggaa ctctgtgtgg acatgtcacc attgaaaata aggcttacca   7320
tgtttacacc tccccatctg gtaagaagtt cttggtcccc gtcaacccag agaatggaag   7380
agttcaatgg gaagctgcaa agctttccgt ggagcaggcc ctaggtatga tgaatgtcga   7440
cggcgaactg actgccaaag aactggagaa actgaaaaga ataattgaca aactccaggg   7500
cctgactaag gagcagtgtt taaactgcta gccgccagcg acttgacccg ctgtggtcgc   7560
ggcggcttgg ttgttactga aacagcggta aaaatagtca aatttcacaa ccggaccttc   7620
accctgggac ctgtgaattt aaaagtggcc agtgaggttg agctaaaaga cgcggttgag   7680
cacaaccaac acccggttgc gagaccgatc gatggtggag ttgtgctctt gcgttccgcg   7740
```

-continued

```
gttccttcgc ttatagacgt cttgatctcc ggtgctgatg catctcccaa gttacttgcc   7800
catcacgggc cgggaaacac tgggatcgat ggcacgctct gggattttga gtccgaagcc   7860
actaaagagg aagtcgcact cagtgcgcaa ataatacagg cttgtgacat taggcgcggc   7920
gacgctcctg aaattggtct cccttacaag ctgtaccctg ttaggggtaa ccctgagcgg   7980
gtgaaaggag ttctgcagaa tacaaggttt ggagacatac cttacaaaac ccccagtgac   8040
actggaagcc cagtgcacgc ggctgcctgc cttacgccca acgccactcc ggtgactgat   8100
gggcgctccg tcttggccac gaccatgccc cccgggtttg agttatatgt accgaccata   8160
ccagcgtctg tccttgatta ccttgactct aggcctgact gccctaaaca gctgacagag   8220
cacggctgcg aagatgccgc actgaaagac ctctctaaat atgacttgtc cacccaaggc   8280
tttgttttac ctggagttct tcgccttgtg cggaaatacc tgtttgccca tgtaggtaag   8340
tgcccacccg ttcatcggcc ttctacttac cctgctaaga attctatggc tggaataaat   8400
gggaacaggt tcccaaccaa ggacattcag agcgtccctg aaatcgacgt tctgtgcgca   8460
caggctgtgc gagaaaactg gcaaactgtc accccttgta ctcttaagaa acagtattgc   8520
gggaagaaga agactaggac catactcggc accaataact tcatcgcact agcccaccga   8580
gcagtgttga gtggtgttac ccagggcttc atgaaaaagg cgtttaactc gcccatcgcc   8640
ctcggaaaga acaagtttaa ggagctacag actccggtcc tgggcaggtg ccttgaagct   8700
gatctcgcat cctgcgatcg atccacgcct gcaattgtcc gctggtttgc cgccaacctt   8760
ctttatgaac ttgcctgtgc tgaagagcat ctaccgtcgt acgtgctgaa ctgctgccac   8820
gacttactgg tcacgcagtc cggcgcagtg actaagagag gtggcctgtc gtctggcgac   8880
ccgatcacct ctgtgtctaa caccatttat agtttggtga tctatgcaca gcatatggtg   8940
cttagttact tcaaaagtgg tcacccccat ggccttctgt tcttacaaga ccagctaaag   9000
tttgaggaca tgctcaaggt tcaacccctg atcgtctatt cggacgacct cgtgctgtat   9060
gccgagtctc ccaccatgcc aaactatcac tggtgggttg aacatctgaa tttgatgctg   9120
gggtttcaga cggacccaaa gaagacagca ataacagact cgccatcatt tctaggctgt   9180
agaataataa atgggcgcca gctagtcccc aaccgtgaca ggatcctcgc ggccctcgcc   9240
tatcacatga aggcgagtaa tgtttctgaa tactatgcct cagcggctgc aatactcatg   9300
gacagctgtg cttgtttgga gtatgatcct gaatggtttg aagaacttgt agttggaata   9360
gcgcagtgcg cccgcaagga cggctacagt tttcccggca cgccgttctt catgtccatg   9420
tgggaaaaac tcaggtccaa ttatgagggg aagaagtcga gagtgtgcgg gtactgcggg   9480
gccccggccc cgtacgctac tgcctgtggc ctcgacgtct gcatttacca cacccacttc   9540
caccagcatt gtccagtcac aatctggtgt ggccatccag cgggttctgg ttcttgtagt   9600
gagtgcaaat cccctgtagg gaaaggcaca agccctttag acgaggtgct ggaacaagtc   9660
ccgtataagc cccacggac cgttatcatg catgtggagc agggtctcac ccccccttgat   9720
ccaggtagat accaaactcg ccgcggacta gtctctgtca ggcgtggaat taggggaaat   9780
gaagttgaac taccagacgg tgattatgct agcaccgcct tgctccctac ctgcaaagag   9840
atcaacatgg tcgctgtcgc ttccaatgta ctgcgcagca ggttcatcat cggcccaccc   9900
ggtgctggga aaacatactg gctccttcaa caggtccagg atggtgatgt tatttacaca   9960
ccaactcacc agaccatgct tgacatgatt agggctttgg ggacgtgccg gttcaacgtc  10020
ccggcaggca caacgctgca attccccgtc ccctcccgca ccggtccgtg ggttcgcatc  10080
ctagccggcg gttggtgtcc tggcaagaat tccttcctag atgaagcagc gtattgcaat  10140
```

-continued

```
caccttgatg ttttgaggct tcttagtaaa actaccctca cctgtctagg agacttcaag  10200
caactccacc cagtgggttt tgattctcat tgctatgttt ttgacatcat gcctcaaact  10260
caactgaaga ccatctggag gtttggacag aatatctgtg atgccgttca gccagattac  10320
agggacaaac tcatgtccat ggtcaacaca acccgtgtga cctacgtgga aaaacctgtc  10380
aggtatgggc aggtcctcac cccctaccac agggaccgag aggacgacgc catcactatt  10440
gactccagtc aaggcgccac attcgatgtg gttacattgc atttgcccac taaagattca  10500
ctcaacaggc aaagagccct tgttgccatc accagggcaa gacacgctat ctttgtgtat  10560
gacccacaca ggcagctgca gggcttgttt gatcttcctg caaaaggcac acccgtcaac  10620
ctcgcagtgc accgcgacgg gcagctgatc gtgctggata gaaataacaa agaatgcacg  10680
gtcgctcagg ctctaggcaa cggggataaa tttagggcca cagataagcg tgttgtagat  10740
tctctccgcg ccatttgtgc tgatctagaa gggtcgagct ctccgctccc caaggtcgca  10800
cacaacttgg gattttattt ctcacctgat ttaacacagt ttgctaaact cccagtagaa  10860
cttgcacctc actggcccgt ggtgacaacc cagaacaatg aaaagtggcc agatcggctg  10920
gttgccagcc ttcgccctat ccataaatac agccgcgcgt gcatcggtgc cggctatatg  10980
gtgggccctt cggtgtttct aggcactcct ggggtcgtgt catactatct cacaaaattt  11040
gttaagggcg aggctcaatt gcttccggag acggttttca gcaccggccg aattgaggta  11100
gactgccggg aatatcttga tgatcgggag cgagaagttg ctgcgtccct cccacacgct  11160
ttcattggcg acgtcaaagg cactaccgtt ggaggatgtc atcatgtcac ctccagatac  11220
ctcccacgcg tccttcccaa ggaatcagtt gcggtagtcg ggtttcaagg ccccggaaaa  11280
gccgcgaaag cattgtgcac actgacagat gtgtacctcc cagatcttga cgcctatctc  11340
cacccggaga cccagtccaa gtgctggaaa atgatgttgg acttcaaaga agttcgacta  11400
atggtctgga aagacaaaac agcctatttc caacttgaag gtcgctattt cacctggtat  11460
cagcttgcca gctatgcctc gtacatccgt gttcctgtca actctacggt gtacttggac  11520
ccctgcatgg gccccgccct ttgcaacagg agagtcgtcg ggtccaccca ctggggggct  11580
gacctcgcgg tcacccctta tgattacggc gctaaaatta tcctgtctag cgcgtaccat  11640
ggtgaaatgc cccccggata caaaattctg gcgtgcgcgg agttctcgtt ggatgaccca  11700
gttaagtaca aacatacctg gggtttgaa tcggatacag cgtatctgta tgagttcacc  11760
ggaaacggtg aggactggga ggattacaat gatgcgtttc gtgcgcgcca ggaagggaaa  11820
atttataagg ccactgccac cagcttgaag ttttattttc ccccgggccc tgtcattgaa  11880
ccaactttag gcctgaattg aaatgaaatg gggtccatgc aaagcctttt ttacaaaatt  11940
ggccaacttt ttgtggatgc tttcacggag ttcttggtgt ccattgttga tatcactata  12000
tttttggcca ttttgtttgg cttcaccatc gccggttggc tggtggtctt ttgcatcaga  12060
ttggtttgct ccgcgatact ccgtacgcgc tctgccattc actctgagca attacagaag  12120
atcttatgag gcctttcttt cccagtgcca agtggacatt cccacctggg gaactaaaca  12180
tcctttgggg atgctttggc accataaggt gtcaaccctg attgatgaaa tggtgtcgcg  12240
tcgaatgtac cgcatcatgg aaaaagcagg gcaggctgcc tggaaacagg tggtgagcga  12300
ggctacgctg tctcgcatta gtagtttgga tgtggtggct cattttcagc atctagccgc  12360
cattgaagcc gagacctgta aatatttggc ctcccggctg cccatgctac acaacctgcg  12420
catgacaggt tcaaatgtaa ccatagtgta taatagcact ttgaatcagg tgtttgctat  12480
```

-continued

```
ttttccaacc cctggttccc ggccaaagct taatgatttt cagcaatggt taatagctgt  12540
acattcctcc atattttcct ctgttgcaac ttcttgtact ctttttgttg tgctgtggtt  12600
gcgggttcca atactacgta ctgcttttgg tttccgctgg ttaggggcaa tttttctttc  12660
gaactcacag tgaattacac ggtgtgtcca ccttgcctca cccggcaagc agccgcagag  12720
atctacgaac ccggtaggtc tctttggtgc aggataggt atgaccgatg tgaggaggat  12780
gatcatgacg agctagggtt tatggtaccg cctggcctct ccagcgaagg ccacttgact  12840
agtgtttacg cctggttggc gttcttgtcc ttcagctaca cggcccagtt ccatcccgag  12900
atattcggga tagggaatgt gagtcgagtt tatgttgaca tcaaacatca actcatctgc  12960
gccgaacatg acgggcagaa caccaccttg cctcgtcatg acaacatttc agccgtgttt  13020
cagacctatt accaacatca agtcgacggc ggcaattggt ttcacctaga atggcttcgt  13080
cccttctttt cctcgtggtt ggttttaaat gtctcttggt ttctcaggcg ttcgcctgca  13140
aaccatgttt cagttcgagt cttgcagata ttaagaccaa caccaccgca gcggcaagct  13200
ttgctgtcct ccaagacatc agttgcctta ggcatcgcga ctcggcctct gaggcgattc  13260
gcaaaatccc tcagtgccgt acggcgatag ggacacccgt gtatgttacc atcacagcca  13320
atgtgacaga tgagaattat ttacattctt ctgatctcct catgctttct tcttgccttt  13380
tctatgcttc tgagatgagt gaaaagggat ttaaggtggt atttggcaat gtgtcaggca  13440
tcgtggctgt gtgtgtcaat tttaccagct acgtccaaca tgtcaaggag tttacccaac  13500
gctccctggt ggtcgaccat gtgcggttgc tccatttcat gacacctgag accatgaggt  13560
gggcaactgt tttagcctgt ctttttgcca ttctgttggc aatttgaatg tttaagtatg  13620
ttggagaaat gcttgaccgc gggctgttac tcgcaattgc tttctttgtg gtgtatcgtg  13680
ccgttctgtt ttgctgtgct cgtcaacgcc agcaacgaca gcagctccca tctacagctg  13740
atttacaact tgacgctatg tgagctgaat ggcacagatt ggctagctaa caaatttgat  13800
tgggcagtgg agagttttgt catctttccc gttttgactc acattgtctc ctatggtgcc  13860
ctcactacta gccatttcct tgacacagtc gctttagtca ctgtgtctac cgccgggttt  13920
gttcacgggc ggtatgtcct aagtagcatc tacgcggtct gtgccctggc tgcgttgact  13980
tgcttcgtca ttaggtttgc aaagaattgc atgtcctggc gctacgcgtg taccagatat  14040
accaactttc ttctggacac taagggcaga ctctatcgtt ggcggtcgcc tgtcatcata  14100
gagaaaaggg gcaaagttga ggtcgaaggt catctgatcg acctcaaaag agttgtgctt  14160
gatggttccg tggcaacccc tataaccaga gtttcagcgg aacaatgggg tcgtccttag  14220
atgacttctg tcatgatagc acggctccac aaaaggtgct tttggcgttt tctattacct  14280
acacgccagt gatgatatat gccctaaagg tgagtcgcgg ccgactgcta gggcttctgc  14340
accttttgat cttcctgaat tgtgctttca ccttcgggta catgactttc gcgcactttc  14400
agagtacaaa taaggtcgcg ctcactatgg gagcagtagt tgcactcctt tggggggtgt  14460
actcagccat agaaacctgg aaattcatca cctccagatg ccgtttgtgc ttgctaggcc  14520
gcaagtacat tctggcccct gcccaccacg ttgaaagtgc cgcaggcttt catccgattg  14580
cggcaaatga taaccacgca tttgtcgtcc ggcgtcccgg ctccactacg gtcaacggca  14640
cattggtgcc cgggttaaaa agcctcgtgt tgggtggcag aaaagctgtt aaacagggag  14700
tggtaaacct tgtcaaatat gccaaataac aacggcaagc agcagaatag aaagaagggg  14760
gatggccagc cagtcaatca gctgtgccag atgctgggta agatcatcgc tcagcaaaac  14820
cagtccagag gcaagggacc gggaaagaaa aataagaaga aaaacccgga gaagccccat  14880
```

```
tttcctctag cgactgaaga tgatgtcaga catcacttta cccctagtga gcggcaattg  14940

tgtctgtcgt caatccagac cgcctttaat caaggcgctg ggacttgcac cctgtcagat  15000

tcagggagga taagttacac tgtggagttt agtttgccta cgcatcatac tgtgcgcctg  15060

attcgcgtca cagcatcacc ctcagcatga tgggctggca ttcttgaggc atctcagtgt  15120

ttgaattgga agaatgtgtg gtgaatggca ctgattgaca ttgtgcctct aagcactata  15180

tt                                                                 15182
```

```
<210> SEQ ID NO 43
<211> LENGTH: 183
<212> TYPE: PRT
<213> ORGANISM: Porcine reproductive and respiratory syndrome virus

<400> SEQUENCE: 43

Met Ala Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45

Asp Ile Asn Cys Phe Arg Pro His Gly Val Ser Ala Ala Gln Glu Lys
    50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180


<210> SEQ ID NO 44
<211> LENGTH: 178
<212> TYPE: PRT
<213> ORGANISM: Porcine reproductive and respiratory syndrome virus

<400> SEQUENCE: 44

Met Ala Ser Ser Leu Leu Phe Leu Val Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ala Ser Phe Ala Val Leu Gln
        35                  40                  45

Asp Ile Ser Cys Leu Arg His Arg Asp Ser Ala Ser Glu Ala Ile Arg
    50                  55                  60

Lys Ile Pro Gln Cys Arg Thr Ala Ile Gly Thr Pro Val Tyr Val Thr
65                  70                  75                  80
```

```
Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile


<210> SEQ ID NO 45
<211> LENGTH: 14622
<212> TYPE: DNA
<213> ORGANISM: Porcine reproductive and respiratory syndrome virus

<400> SEQUENCE: 45

atgtctggga tgttctcccg gtgcatgtgc accccggctg cccgggtatt ttggaacgcc      60

ggccaagtct attgcacacg gtgtctcagt gcacggtctc ttctctctcc agaacttcag     120

gacacggacc tcggtgcagt tggcttgttt cacaagccta aagacaagct ccattggaaa     180

gttcccattg gtatccccca ggtggaatgt tctccatctg ggtgttgctg gctgtcaacc     240

atttttcctt tagcgcgcat gacctccggc aatcacaact tccttcaacg actcgtgaag     300

gttgctgatg tattgtaccg tgacggttgc ttaaccccta gacacctccg tgaactccaa     360

gtttacgagc gtggttgcaa ttggtatccg attacggggc ctgtgcctgg gatggctgtg     420

tacgcgaact ccatgcacgt gtccgaccaa ccgttccctg gtgccactca tgtgttaaca     480

aattcccctt tgcctcaacg ggcttgtcgg cagccgttct gtccgttcga agaggcccat     540

tctagcatat acaggtggga aaaatttgta atttttatgg attcctcctc cgacggtcga     600

tctcgcatga tgtggactcc ggaatccgat gactccacgg ctttggaagt tctgccgccc     660

gagctagaac accaggtcaa ggtccttgtt cggagctttc ccgcccatca ccttgtcgac     720

cttgccgatt gggagctcac tgagtcccct gataacggtt tttccttcag cacgtcacat     780

ccttgcggct accttgttcg ggacccggct gtatccgaag gcaagtgttg gctttcctgc     840

tttttgagcc agtcagccga agtgctcagt cgcgaggcgc atctggctac cgcctatggt     900

taccaaacca agtggggtgt gcctggcaag tacatccagc gcagacttca agttcacggt     960

ctccgtgctg tggtcgaccc tgatggtccc attcacgttg aagcattgtc ttgcccccag    1020

tcttggatca ggcacttgac cctgaatgat gatgtcaccc cgggattcgt tcgcctaatg    1080

tctcttcgca ttgtgccgaa cacagagcct accacacacc ggatctttcg ttttggagtg    1140

cacaagtggt atggtgccgc cggcaaacgg gcccgtggca agcgtgccgc caaaagtgag    1200

aaagactcgg cttccaccct caaggttgcc cgaccgactt ccaccagtgg aatcgtcacc    1260

tactccccac ctgcggacgg gtcttgtggt tggcatgccc ttgccgccat actgaaccgg    1320

atgattaata atgacttcac gtcccctctg cctcggtaca acaggccgga ggacgattgg    1380

gcttctgatg gtgaccttgc tcaggccatt caatgtttgc aactacctgc cgccatagct    1440

cggaaccgcg cctgccctaa cgccaaatac ctcataaaac tcaacggagt tcattgggag    1500
```

-continued

```
gtagaggtga ggcctggaat ggctcctcgc tccctctctc gtgagtgcgt tgttggcgtc   1560
tgctctgaag gctgtgtcgc gtcgccttac ccggaggacg ggttgcctaa acgtgcactt   1620
gaggccctgg cgtctgctta tagactgcct tcagactgtg tttgtgatgg tattattgac   1680
ttccttgcca atccacctcc ccaggagttc tggactcttg acaaaatgtt gacttccccg   1740
tcaccggagc agtccggctt ctctagtctg tataaattgt tgttagagat cttgccgcag   1800
aaatgcggat ccacagaagg ggaattcatc tatactgttg agaggatgtt gaaggattgt   1860
ccgagctcca aacaggccat ggccctcctt gcaaaaatta aggtcccatc ctcaaaggcc   1920
ccatccgtga ctctgaacga gtgcttcccc acggatgttc cagtcaactc tgagttaata   1980
tcttgggaag agcccaaaga ccctggcgct gctgttgtcc tatgtccatc ggatgcaaaa   2040
gaatctaagg aaacagcccc tgaagaagct caagcgagaa accgtaaggt ccttcaccct   2100
gtggtcctta ccgaggaact tagcgagcaa caggtgcagg tggttgaggg tgatcaggat   2160
atgccactgg atttgacttg gccaacctta accgctacgg cgacccctgt tagagggccg   2220
gtaccggaca atttgagctc tggcattggt gcccagcccg ctaccgttca agaactcatt   2280
ctggcgaggc ctgcaccccg tcttgttgag cgctgtggca cggagtcgaa cggcagcagt   2340
tcatttctgg atttgcctga cgtgcagacc tcggaccagc ctttagacct gtccctggcc   2400
gcgtggcctg taagggctac cgcgtctgac cccggttgga tccacggtag gcgtgagcct   2460
gtctttgtga agcctcgagg tgttttctct gatggcgagt cggcccttca gttcggagag   2520
ctttccgaag ccagttctgt cgtcgatgac cggacaaaag aagctccggt ggttgacgcc   2580
cccatcgatt tgacaacttc gaacgagacg ctctctgggt ctgacccctt tgaattcgcc   2640
aaattcaggc gcccgcgttt ctccgcgcaa gctttaatcg accgaggtgg tccgcttgcc   2700
gatgttcatg caaagataaa gagtcgggta tatgaacaat gccttcaagc ttgtgaacct   2760
ggtagtcgtg cgaccccagc caccaagaag tggctcgaca aaatgtggga cagggtggac   2820
atgaaaactt ggcgctgcac ctcgcagttc caagctggtc acattcttga gtccctcaaa   2880
ttcctccctg acatgattca agacacaccg cctcctgttc ccaggaagaa ccgagctggt   2940
gacagtgccg gcctgaagca actggtggcg cagtgggata ggaaatcgag tgtgacaccc   3000
cccacaaaac cggttggacc ggtgcttgac caggccgtcc ctctgcctat ggacatccag   3060
caaggagatg ccatctccgc tgacaagcca ccccattcgc aaaacccttc tagtcaagta   3120
gatgtgggtg gaggttggaa aagttttatg ctctccggca cccgtttcgc ggggtccgtt   3180
agtcagcgcc ttacgacatg ggtttttgag gttctctccc atctcccagc ttttatgctc   3240
acacttttct cgccacgggg ctctatggct ccaggtgatt ggctgtttgc aggtgctgtt   3300
ctacttgctc tcctgctctg ccgttcttac ccaatactcg gatgccttcc cttattgggt   3360
gtcttttctg gttctgtgcg gtgtgttcgt ttgggtgttt ttggttcttg gatggctttt   3420
gctgtatttt tattctcgac tccacccgac ccagtcggtt cttcttgtga ccacgattcg   3480
ccggagtgtc atgctgagct tttggctctt gagcagcgcc aactttggga acctgtgcgc   3540
agccttgtgg tcgggccatc gggcctctta tgcgtcattc ttggcaagtt actcggtggg   3600
tcacgttgtc tctggtttgt tctcctacgt atatgcatgc tcgcagattt ggcaatttct   3660
cttatttatg tggtgtccca agggcgttgt cacaagtgtt ggggaaagtg tataaggacg   3720
gctcctgcag aagtggccct taatgtgttt ccttttttcgc gcgccacccg ctcatctctt   3780
gtgtccttgt gtgatcggtt ccaagcgcca aaaggagttg accccgtgca cttggcgaca   3840
ggctggcgcg ggtgctggtg tggtgagagc cctattcatc aatcacacca aaaaccgata   3900
```

-continued gcttatgcca acttggatga aaagaagata tccgcccaga cggtgattgc tgtcccgtat 3960
gatcctagtc aggccattaa atgcctgaaa gttttgcagg caggaggggc tattgtggac 4020
cagcctacgc ccgaggtcgt ccgtgtgtct gagattccct tctcggcccc attttttccg 4080
aaggtcccag tcaacccaga ctgcagggtt gtggtagatt cggacacttt tgtggctgcg 4140
gtccgctgcg gttattcgac agcacaactg gtccttggtc ggggcaactt tgccaagcta 4200
aatcagaccc ccctcaggaa ctctgtcccc accaaaacaa ctggtggggc ctcatacacc 4260
cttgccgtgg cccaggtatc tgtgtggact cttgttcatt tcatcctcgg cctttggtta 4320
acgtcacctc aagtgtgtgg tcgagggacc tctgacccgt ggtgttcgaa cccttttttcg 4380 tatcctactt atggccccgg agttgtgtgt tcctctcgac tctgcgtgtc tgccgacgga 4440
gttaccctgc cattgttctc agccgttgcc catctttccg gtagagaggt ggggattttt 4500
attttggtgc ttgcctcctt gggcgcttta gcccaccgct tggctcttaa ggcagacatg 4560
tcaatggtct ttttggcgtt ttgtgcttac gcctggccca tgagctcctg gttaatttgc 4620
ttctttccta tgctcttgag gtgggtaacc cttcatcctc tcactatgct ttgggtgcac 4680
tcatttttgg tgttttgcct accagctgcc ggcgttctct cgctgggaat aaccggtctt 4740
ctttgggcag ttggccgttt cacccaggtt gccggaatta tcacacctta tgacatccac 4800
cagtatacct ccggaccacg tggtgcagct gctgtagcaa cggctccaga aggtacttac 4860
atggcggccg ttcggagagc cgctttgact ggacggactt tgatcttcac accatctgca 4920
gtcggatccc ttcttgaagg tgctttcaga actcaaaagc cctgccttaa caccgtgaat 4980
gtcgtaggct cttcccttgg ttctggagga gttttcacca ttgatggcag aagagtcatc 5040
gtcactgcca cccatgtgtt gaatggtaac acagccaggg tcactggtga ttcctacaac 5100
cgcatgcaca cgttcaatac taatggtgat tatgcctggt cccatgctga tgactggcaa 5160
ggcgttgccc ctatggttaa gatcgctaag ggtatcgcg gtcgtgccta ctggcaaacg 5220
tcaaccggag tcgaacctgg catcatgggg gaaggattcg ccttctgttt cactaactgt 5280
ggcgactcag ggtcacctgt catttcagaa gctggtgacc ttattggagt ccataccggt 5340
tcaaacaaac tcggttctgg tcttgtgaca acccctgaag ggagacctg ctccatcaag 5400 gaaactaggc tctctgacct ttctagacat tttgcaggtc caagcgtccc tcttggggac 5460
attaagttga gcccagccat catccctgat gtgacaacta ttccgagtga cttggcatcg 5520
ctccttgctt ctgtccccgt gatggaaggt ggcctctcaa ctgtccagct tttgtgcgtc 5580
tttttccttc tctggcgcat gatgggccat gcctggacac ccattgttgc cgtaggcttc 5640
tttttgctga atgaaattct cccagcagtc ttggtccgag ctgtgttctc ttttgcactc 5700
tttgtacttg catgggccac cccctggtcg gcacaagtgt tgatgattag actcctcacg 5760
gcggctctca accgcaacag gttgtccctg gcgttctacg cattcggagg tgtcgttggc 5820
ctggccacag aaatcgggac ttttgctggt ggatggcctg aactgtccca agccctctcg 5880
acatactgct tcctgcccag gttccttgct gtgactagtt atgtccccac catcatcatc 5940
ggtgggctcc atgccctcgg cgtaattttg tggttattca aataccgatg cctccacaac 6000
atgctggttg gtgatgggag tttctcaagc gctttcttcc tacggtattt tgctgagggt 6060
aatcttagga aaggcgtgtc gcagtcctgt ggcatgaata acgaatccct gacagctgct 6120
ttggcttgca agttgtcgca agctgacctt gattttttgt ccagtttaac gaacttcaag 6180
tgctttgtgt ccgcttcaaa catgaaaaat gcagctggcc aatacatcga ggcggcgtat 6240

-continued

```
gctagagctc tgcgtcagga gctggcctcc ttggttcagg ttgacaagat gaaaggagta   6300

ttggccaagc tcgaggcttt cgctgagacg gccactccgt cacttgacac aggggacgtg   6360

attgttctgc ttgggcaaca cccccatgga tccatcctcg acattaatgt ggggggtgaa   6420

aggaaaactg tgtctgtgca agaaacacga tgcctgggtg gttccaaatt cagtgtctgc   6480

actgtcgtgt ccaacacgcc cgtggatacc ttgaccggta tcccacttca gacgccaacc   6540

ccactttttg aaaatggccc gcgccatcgc agcgaggacg acgacctcaa agttgagaga   6600

atgaaaaaac actgtgtatc cctcggcttc cacaaaatca atggtaaagt ttactgcaaa   6660

atttgggaca agtctaacgg cgacaccttt tacacggatg attcccgata cactcaagac   6720

catgcttttc aggacaggtc aaccgactat agagacaggg attatgaagg tgtacagacc   6780

gccccccaac agggattcga tccaaagtcc gaagcccctg ttggcactgt tgtaatcggt   6840

ggcattacgt ataacaggca tctggtcaaa ggtaaggagg tcctagttcc caaacctgac   6900

aactgccttg aagctgccag actgtccctt gagcaagctc ttgctgggat gggccaaact   6960

tgtgacctta cagctaccga agtggagaaa ctaaagcgca tcattagtca actccaaggt   7020

ctgaccactg aacaggcttt aaactgctag ccgccagcgg cttgacccgc tgtggccgcg   7080

gcggcctagt tgtaactgaa acggcggtaa aaatcgtaaa ataccacagc agaactttca   7140

ccttaggctc tttagaccta aaagtcacct ccgaggtgga ggtgaagaaa tcaactgagc   7200

aggggcacgc tgtcgtggcg aacttatgtt ccggtgtcgt cttgatgagg cctcacccac   7260

cgtcccttgt tgacgttctc ctcaaacccg gacttgacac aacacccggc attcaaccag   7320

ggcatggggc cgggaatatg ggcgtgaacg gttctatttg ggattttgaa actgcaccca   7380

caaaggtaga actagagttg tccaagcaaa taatccaagc atgtgaagtc aggcgcgggg   7440

acgcccctaa cctccaactc ccctacaagc tttatcctgt caggggggac cccgagcggc   7500

gtaaaggtcg ccttgtcaac actaggtttg gagatttacc ttacaaaact ccccaagaca   7560

ccaagtccgc aattcatgcg gcttgttgcc tgcatcccaa tggggtcctc gtgtctgatg   7620

gcaaatccac gctgggtacc actcttcaac atggtttcga gctttatgtc cccactgtac   7680

cttatagtgt catggaatac cttgattcac gccctgacac cccttttatg tgtactaaac   7740

atggcacttc caaggctgct gcagaggacc tccaaaaata tgacctatcc actcaagggt   7800

ttgtcttgcc tggggtccta cgcctagtgc gcaggttcat ctttagccat gttggtaagg   7860

cgccaccact gttccttcca tcaacctacc ctgccaagaa ctccatggca ggggtcaatg   7920

gccagaggtt cccaacaaag gatgtccaga gcatacctga aattgatgaa atgtgcgccc   7980

gtgccgtcaa ggaaaattgg cagactgtga caccttgcac cctcaaaaaa cagtactgtt   8040

ccaaacctaa aactagaacc atcctaggta ccaacaactt catagccttg gctcacaggt   8100

cagcactcag tggtgtcacc caggcgttca tgaagaaggc ctggaagtcc ccaattgcct   8160

tggggaaaaa caagtttaag gaattgcatt gcactgtcgc cggcagatgc cttgaggctg   8220

acctggcttc ctgcgatcgc agcacccccg ccattgtgag gtggtttgtt gccaacctcc   8280

tgtatgaact tgcaggatgt gaagagtact tgcctagcta cgtgctcaac tgttgccatg   8340

accttgtggc aacgcaggat ggcgctttca caaaacgcgg tggcctgtcg tccggggacc   8400

ccgtcaccag tgtgtccaac accgtctact cactgataat ttacgcccag cacatggtgc   8460

tttcggcctt gaagatgggt catgaaattg gtctcaagtt ccttgaggaa cagctcaaat   8520

ttgaggacct tcttgaaatc cagcccatgt tagtgtattc tgatgacctc gtcttgtatg   8580

cggaaagacc cacttttccc aactaccatt ggtgggtcga gcatcttgac ctgatgttgg   8640
```

-continued gctttaaaac ggacccaaag aaaactgtca taactgataa acccagtttt ctcggctgca 8700
gaattgaagc aggacggcag ttagtcccca atcgcgaccg tattctggct gctcttgcat 8760
atcatatgaa ggcgcagaac gcctcagagt attatgcgtc cgctgccgca attctgatgg 8820
attcgtgtgc ttgcattgac catgaccccg agtggtatga ggatcttatc tgcggcatcg 8880
cccggtgtgc tcgccaggac ggttaccgtt ttccaggccc ggcatttttc atgtccatgt 8940
gggagaagct gaaaagtcat aatgaaggga agaaatgccg tcactgcggc atctgcgacg 9000
ccaaagccga ctatgcgtcc gcctgtggac ttgatttgtg tttgttccat tcacactttc 9060
atcaacactg cccagtcact ctgagctgtg gccaccatgc cggttcaaag gaatgttcgc 9120
agtgtcagtc acctgtcggg gctggcaaat ccccccttga cgctgtgctg aaacaaatcc 9180
cgtacaaacc tcctcgtacc attatcatga aggtggacaa caaaacaacg acccttgacc 9240
cgggaagata tcagtcccgt cgaggtcttg ttgcagtcaa aagaggtatt gcaggtaatg 9300
aggttgatct ttctgatgga gactaccaag tggtgcctct tttgccgact tgcaaagaca 9360
taaacatggt gaaggtggct tgcaacgtac tactcagcaa gtttatagta gggccgccag 9420
gttccggaaa aaccacctgg ctactgaacc aagtccagga cgatgatgtc atttacacac 9480
ctactcatca gacaatgttt gacatagtca gtgctcttaa agtttgcagg tattccatcc 9540
caggagcctc aggactccct tttccaccac ctgccaggtc cgggccgtgg gttaggctca 9600
tcgccagcgg acatgtccct ggccgagtgt catatctcga tgaggcagga tattgcaatc 9660
atctagacat tctaaggctg ctttccaaaa cacccccttgt gtgtttgggt gaccttcagc 9720
aacttcaccc ggtcggcttt gattcctatt gttatgtgtt cgatcagatg cctcagaagc 9780
agctgaccac catttataga tttggcccta acatctgtgc agccatccag ccttgttaca 9840
gggagaaact tgaatccaag gccaggaaca ccagagtggt tttcaccacc cggcctgtgg 9900
cctttggtca ggtcctgaca ccgtaccaca aagatcgtac cggctctgca ataactatag 9960
attcatccca gggggcgacc ttcgacattg tgacattgca tctaccatcg ccaaagtccc 10020
taaacaaatc ccgagcactt gtagccatca ctcgggcaag acatgggttg ttcatttatg 10080
accctcatga ccaactccag gagtttttca acttaacccc cgagcgcact gattgtaacc 10140
ttgcgttcag ccgtggggat gagctggttg ttttgaatgt ggataatgcg gtcacaactg 10200
tagcgaaggc cctagagaca ggttcacccc gatttcgagt atcggacccg aggtgcaagt 10260
ctctcttagc cgcttgttcg gccagtctag aagggagctg catgccacta ccacaagtag 10320
cacataacct ggggttttac ttttccccgg acagcccagc ttttgcaccc ctgccaaaag 10380
agctggcgcc acattggcca gtggtcaccc accagaataa tcgagcgtgg cctgatcgac 10440
ttgtcgctag tatgcgccca attgatgccc gctacagcaa gccaatggtc ggtgcagggt 10500
atgtggtcgg gccatccatt tttcttggca ctcctggtgt ggtgtcatac tatctcacat 10560
tatacatcgg gggcgagcct caggccctgc cagaaacact cgtttcaaca ggacgtatag 10620
ccacagattg tcgggaatat ctcgacgcgg ctgaggaaga ggcagcgaga gaacttcccc 10680
acgcatttat tggcgatgtc aaaggcacta cgatcggggg gtgtcaccac attacatcga 10740
aatacctacc taggtccctg cctaaagact ctgttgctgt ggttggggtg agttcgcccg 10800
gtagggctgc taaagccgtg tgcactctca ccgatgtgta cctccccgaa ctccgaccat 10860
atttgcaacc ggagacggca tcaaaatgct ggaaacttaa actggatttc agggatgttc 10920
gactgatggt ctggaaaggc gccacagcct atttccagtt ggaagggctg acatggtcag 10980

-continued

```
cgctgcccga ttatgctagg ttcattcagc tacccaagga tgccgttgtg tacatcgatc  11040
cgtgtatagg gccggcaaca gccaatcgca aggttgtgcg aaccacagac tggcgggccg  11100
acctggcagt gacaccgtat gattacggtg ctcaggtcat tttgacaaca gcctggttcg  11160
aggaccttgg gccgcagtgg aagattttgg ggttgcagcc tttcagacga acatttggct  11220
ttgagaacac tgaagattgg gcaattctcg cacgccgtat gaatgacggc aaagattaca  11280
ctgactataa ttggcattgt gtacgagaac gcccacacgc aatttacggg cgcgcccgtg  11340
accatacgta tcattttgcc cttggcactg aactgcaagt agagctgggc agaccccggc  11400
tgcctcctga gcaagtgccg tgaacgcgga gtgatgcaat gggtttactg tggagtaaaa  11460
tcagtcagtt gttcgtggat gccttcactg agttccttgt tagtgtggtt gacattgtca  11520
tctttctcgc catattgttt gggttcactg ttgcaggctg gttattggtc ttccttctca  11580
gagtggtttg ctccgcgttt ctccgttcgc gctctgccat tcactcttcc gaactatcga  11640
aggtcctatg agggcttgct acccaactgc agaccggatg tcccacaatt cgcagttaag  11700
cacccgttgg gtatactttg gcatatgcga gtctcccacc taattgacga aatggtctct  11760
cgccgcattt accggaccat ggaacattcg ggtcaagcgg cctggaagca ggttgttagt  11820
gaagccactc tcacaaaact gtcaaggctt gacgtagtca ctcatttcca acacctggcc  11880
gcagtggagg ctgattcttg ccgcttcctt agctcacgac tcgcgatgct gaaaaacctt  11940
gccgttggca atgtgagcct ggagtacaac actactttgg accgcgttga gctcatcttt  12000
cccacaccag gtacgaggcc caagttgacc gattttaggc aatggcttat cagcgtgcac  12060
gcttccatct tctcctctgt ggcttcgtct gttaccttgt tcacagtgct ttggcttcga  12120
attccagctc tacgctatgt ttttggtttc cattggccca cggcaacaca tcattcgaac  12180
taactatcaa ttacactata tgtaagccat gccctaccag tcaagctgcc caacaaagac  12240
tcgagcctgg ccgtaacgtg tggtgcaaaa tagggcacga caggtgtgag gaacgtgacc  12300
atgatgagtt gtcaatgtcc attccgtccg ggtacgacaa cctcaaactt gagggttatt  12360
atgcttggct ggctttttg tcctttttcct acgcggccca attccatccg gagctgttcg  12420
gaataggaaa cgtgtcgcgc gtctttgtgg ataagcgaca ccagttcatt tgcgccgagc  12480
atgatggaca aaattcaacc atatctgcca gacacaacat ctccgcgtcg tatgcggtgt  12540
attaccatca tcaaatagac gggggcaatt ggtttcattt ggaatggctg cgaccattct  12600
tttcctcctg gctggtgctc aacatctcat ggtttctgag gcgttcgcct gcaagccctg  12660
cttctcgacg catctatcag atattaagac caacacgacc gcggctgccg gtttcatggt  12720
ccttcagaac atcaattgtt tccaatctca cagggcctca acagcgcaag gtaccactcc  12780
cctcaggagg tcgtcccaat gtcgtgaagc cgtcggcatt ccccagtaca tcacgataac  12840
ggctaatgtg accgatgaat cgtatttgta caacgcggac ttgctgatgc tttccgcgtg  12900
ccttttctac gcctcggaaa tgagcgagaa aggcttcaaa gtcatctttg ggaatatttc  12960
tggcgttgtt tccgcttgtg ttaatttcac agattatgtg gcccatgtga cccaacacac  13020
tcagcagcac catttggtaa ttgatcacat tcggttacta cacttcttga caccgtctac  13080
gatgaggtgg gctacaacca ttgcttgttt gcttgccatt cttttggcgg tatgaaatgt  13140
tcttgcaagt tggggcattt cttgactcct cactcttgct tctggtggct ttttttgctg  13200
tgtaccggct tgtcttggtc ctttgtcgat ggcaacgacg acagctcgac atcccaatac  13260
atatataatt tgacgatatg cgagctgaat gggaccgaat ggttgtccgg tcattttgat  13320
tgggcagtcg aaacctttgt gctttaccca gttgccactc atatcatttc actgggtttt  13380
```

ctcacaacaa gccatttcct tgatgcgctc ggtctcggcg ctgtgtccgc cacaggattc 13440
attggcgagc ggtatgtact tagcagcatg tacggcgttt gcgccttcgc ggcgttcgta 13500
tgttttgtca tccgtgctgc taaaaattgc atggcttgcc gctatgcccg cacccggttt 13560
accaacttca tcgtggacga ccggggaaga atccatcgat ggaagtcttc aatagtggtg 13620
gagaaattgg gcaaagctga agtcggtggt gaccttgtca acattaagca tgttgtcctc 13680
gaaggggtta aagctcaacc tttgacgagg acttcggctg agcaatggga agcctagacg 13740
acttttgcaa cgatcccacc gccgcacaaa aactcgtgct ggcctttagc atcacatata 13800
cacccataat gatatacgcc cttaaggtgt cacgcggccg actcctgggg ctgttgcaca 13860
tcttgatatt tctgaattgt tcctttactt ttgggtacat gacatatgtg cattttcaat 13920
ccaccaaccg tgtcgcattc actctggggg ctgtagtcgc ccttttgtgg ggtgtttaca 13980
gcctcacaga gtcatggaag ttcatcactt ccagatgcag attgtgttgc ctaggccggc 14040
gatacattct ggcccctgcc catcacgtag aaagtgctgc aggcctccat tcaatcccag 14100
cgtctggtaa ccgagcatac gctgtgagaa agcccggact aacatcagtg aacggcactc 14160
tagtacctgg gcttcggagc ctcgtgctgg gcggcaaacg agctgttaaa cgaggagtgg 14220
ttaacctcgt caagtatggc cggtaagaac cagagccaga agaaaagaag aaatgcagct 14280
ccgatgggga aaggccagcc agtcaatcaa ctgtgccagt tgctgggtac aatgataaag 14340
tcccagcgcc agcaatctag gggaggacag gccaaaaaga agaagcctga gaagccacat 14400
tttcccctag ctgctgaaga tgacattcgg caccatctca cccaggccga acgttccctc 14460
tgcttgcaat cgatccagac ggctttcaat caaggcgcag gaactgcgtc gctttcatcc 14520
agcgggaagg tcagtttcca ggttgagttc atgctgccgg ttgctcatac agtgcgcctg 14580
attcgcgtga cttctacatc cgccagtcag ggtgcaaatt aa 14622

<210> SEQ ID NO 46
<211> LENGTH: 221
<212> TYPE: DNA
<213> ORGANISM: Porcine reproductive and respiratory syndrome virus

<400> SEQUENCE: 46
atgatgtgta gggtattccc cctacataca cgacactctt agtgtttgtg taccttggag 60
gcgtgggtac agccctgccc caccctttgg tccctgttct agcccgacag gtacccttct 120
ctctcggggc gagcgcgccg cctgctgctc ccttgcggcg ggaaggacct cccgagtatt 180
tccggagagc acctgcttta cggatctcc gccctttaac c 221

<210> SEQ ID NO 47
<211> LENGTH: 114
<212> TYPE: DNA
<213> ORGANISM: Porcine reproductive and respiratory syndrome virus

<400> SEQUENCE: 47
tttgacagtc aggtgaatgg ccgcgattga cgtgtggcct ctaagtcacc tattcaatta 60
gggcgatcac atgggggtca aacttaatta ggcaggaacc atgtgaccga aatt 114

<210> SEQ ID NO 48
<211> LENGTH: 14984
<212> TYPE: DNA
<213> ORGANISM: Porcine reproductive and respiratory syndrome virus

<400> SEQUENCE: 48

-continued

```
atgatgtgta gggtattccc cctacataca cgacactctt agtgtttgtg taccttggag     60
gcgtgggtac agccctgccc caccctttgg tccctgttct agcccgacag gtacccttct    120
ctctcggggc gagcgcgccg cctgctgctc ccttgcggcg ggaaggacct cccgagtatt    180
tccggagagc acctgcttta cgggatctcc gccctttaac catgtctggg atgttctccc    240
ggtgcatgtg caccccggct gcccgggtat tttggaacgc cggccaagtc tattgcacac    300
ggtgtctcag tgcacggtct cttctctctc cagaacttca ggacacggac ctcggtgcag    360
ttggcttgtt tcacaagcct aaagacaagc tccattggaa agttcccatt ggtatccccc    420
aggtggaatg ttctccatct gggtgttgct ggctgtcaac catttttcct ttagcgcgca    480
tgacctccgg caatcacaac ttccttcaac gactcgtgaa ggttgctgat gtattgtacc    540
gtgacggttg cttaacccct agacacctcc gtgaactcca agtttacgag cgtggttgca    600
attggtatcc gattacgggg cctgtgcctg ggatggctgt gtacgcgaac tccatgcacg    660
tgtccgacca accgttccct ggtgccactc atgtgttaac aaattcccct ttgcctcaac    720
gggcttgtcg gcagccgttc tgtccgttcg aagaggccca ttctagcata tacaggtggg    780
aaaaatttgt aatttttatg gattcctcct ccgacggtcg atctcgcatg atgtggactc    840
cggaatccga tgactccacg gctttggaag ttctgccgcc cgagctagaa caccaggtca    900
aggtccttgt tcggagcttt cccgcccatc accttgtcga ccttgccgat tgggagctca    960
ctgagtcccc tgataacggt ttttccttca gcacgtcaca tccttgcggc taccttgttc   1020
gggacccggc tgtatccgaa ggcaagtgtt ggctttcctg ctttttgagc cagtcagccg   1080
aagtgctcag tcgcgaggcg catctggcta ccgcctatgg ttaccaaacc aagtggggtg   1140
tgcctggcaa gtacatccag cgcagacttc aagttcacgg tctccgtgct gtggtcgacc   1200
ctgatggtcc cattcacgtt gaagcattgt cttgccccca gtcttggatc aggcacttga   1260
ccctgaatga tgatgtcacc ccgggattcg ttcgcctaat gtctcttcgc attgtgccga   1320
acacagagcc taccacacac cggatctttc gttttggagt gcacaagtgg tatggtgccg   1380
ccggcaaacg ggcccgtggc aagcgtgccg ccaaaagtga gaaagactcg gcttccaccc   1440
tcaaggttgc ccgaccgact tccaccagtg gaatcgtcac ctactcccca cctgcggacg   1500
ggtcttgtgg ttggcatgcc cttgccgcca tactgaaccg gatgattaat aatgacttca   1560
cgtcccctct gcctcggtac aacaggccgg aggacgattg ggcttctgat ggtgaccttg   1620
ctcaggccat tcaatgtttg caactacctg ccgccatagc tcggaaccgc gcctgcccta   1680
acgccaaata cctcataaaa ctcaacggag ttcattggga ggtagaggtg aggcctggaa   1740
tggctcctcg ctccctctct cgtgagtgcg ttgttggcgt ctgctctgaa ggctgtgtcg   1800
cgtcgcctta cccggaggac gggttgccta aacgtgcact tgaggccctg gcgtctgctt   1860
atagactgcc ttcagactgt gtttgtgatg gtattattga cttccttgcc aatccacctc   1920
cccaggagtt ctggactctt gacaaaatgt tgacttcccc gtcaccggag cagtccggct   1980
tctctagtct gtataaattg ttgttagaga tcttgccgca gaaatgcgga tccacagaag   2040
gggaattcat ctatactgtt gagaggatgt tgaaggattg tccgagctcc aaacaggcca   2100
tggccctcct tgcaaaaatt aaggtcccat cctcaaaggc cccatccgtg actctgaacg   2160
agtgcttccc cacggatgtt ccagtcaact ctgagttaat atcttgggaa gagcccaaag   2220
accctggcgc tgctgttgtc ctatgtccat cggatgcaaa agaatctaag gaaacagccc   2280
ctgaagaagc tcaagcgaga aaccgtaagg tccttcaccc tgtggtcctt accgaggaac   2340
ttagcgagca acaggtgcag gtggttgagg gtgatcagga tatgccactg gatttgactt   2400
```

```
ggccaacctt aaccgctacg gcgacccctg ttagagggcc ggtaccggac aatttgagct   2460
ctggcattgg tgcccagccc gctaccgttc aagaactcat tctggcgagg cctgcacccc   2520
gtcttgttga gcgctgtggc acggagtcga acggcagcag ttcatttctg gatttgcctg   2580
acgtgcagac ctcggaccag cctttagacc tgtccctggc cgcgtggcct gtaagggcta   2640
ccgcgtctga ccccggttgg atccacggta ggcgtgagcc tgtctttgtg aagcctcgag   2700
gtgttttctc tgatggcgag tcggcccttc agttcggaga gctttccgaa gccagttctg   2760
tcgtcgatga ccggacaaaa gaagctccgg tggttgacgc cccatcgat ttgacaactt   2820
cgaacgagac gctctctggg tctgacccct ttgaattcgc caaattcagg cgcccgcgtt   2880
tctccgcgca agctttaatc gaccgaggtg gtccgcttgc cgatgttcat gcaaagataa   2940
agagtcgggt atatgaacaa tgccttcaag cttgtgaacc tggtagtcgt gcgaccccag   3000
ccaccaagaa gtggctcgac aaaatgtggg acagggtgga catgaaaact tggcgctgca   3060
cctcgcagtt ccaagctggt cacattcttg agtccctcaa attcctccct gacatgattc   3120
aagacacacc gcctcctgtt cccaggaaga accgagctgg tgacagtgcc ggcctgaagc   3180
aactggtggc gcagtgggat aggaaatcga gtgtgacacc ccccacaaaa ccggttggac   3240
cggtgcttga ccaggccgtc cctctgccta tggacatcca gcaaggagat gccatctccg   3300
ctgacaagcc accccattcg caaaaccctt ctagtcaagt agatgtgggt ggaggttgga   3360
aaagttttat gctctccggc acccgtttcg cggggtccgt tagtcagcgc cttacgacat   3420
gggtttttga ggttctctcc catctcccag cttttatgct cacacttttc tcgccacggg   3480
gctctatggc tccaggtgat tggctgtttg caggtgctgt tctacttgct ctcctgctct   3540
gccgttctta cccaatactc ggatgccttc ccttattggg tgtcttttct ggttctgtgc   3600
ggtgtgttcg tttgggtgtt tttggttctt ggatggcttt tgctgtattt ttattctcga   3660
ctccacccga cccagtcggt tcttcttgtg accacgattc gccggagtgt catgctgagc   3720
ttttggctct tgagcagcgc caactttggg aacctgtgcg cagccttgtg gtcgggccat   3780
cgggcctctt atgcgtcatt cttggcaagt tactcggtgg gtcacgttgt ctctggtttg   3840
ttctcctacg tatatgcatg ctcgcagatt tggcaatttc tcttatttat gtggtgtccc   3900
aagggcgttg tcacaagtgt tggggaaagt gtataaggac ggctcctgca gaagtggccc   3960
ttaatgtgtt tcctttttcg cgcgccaccc gctcatctct tgtgtccttg tgtgatcggt   4020
tccaagcgcc aaaaggagtt gaccccgtgc acttggcgac aggctggcgc gggtgctggt   4080
gtggtgagag ccctattcat caatcacacc aaaaaccgat agcttatgcc aacttggatg   4140
aaaagaagat atccgcccag acggtgattg ctgtcccgta tgatcctagt caggccatta   4200
aatgcctgaa agttttgcag gcaggagggg ctattgtgga ccagcctacg cccgaggtcg   4260
tccgtgtgtc tgagattccc ttctcggccc catttttcc gaaggtccca gtcaacccag   4320
actgcagggt tgtggtagat tcggacactt ttgtggctgc ggtccgctgc ggttattcga   4380
cagcacaact ggtccttggt cggggcaact ttgccaagct aaatcagacc cccctcagga   4440
actctgtccc caccaaaaca actggtgggg cctcatacac ccttgccgtg gcccaggtat   4500
ctgtgtggac tcttgttcat ttcatcctcg gcctttggtt aacgtcacct caagtgtgtg   4560
gtcgagggac ctctgacccg tggtgttcga accctttttc gtatcctact tatggccccg   4620
gagttgtgtg ttcctctcga ctctgcgtgt ctgccgacgg agttaccctg ccattgttct   4680
cagccgttgc ccatctttcc ggtagagagg tggggatttt tattttggtg cttgcctcct   4740
```

-continued

```
tgggcgcttt agcccaccgc ttggctctta aggcagacat gtcaatggtc tttttggcgt   4800
tttgtgctta cgcctggccc atgagctcct ggttaatttg cttctttcct atgctcttga   4860
ggtgggtaac ccttcatcct ctcactatgc tttgggtgca ctcatttttg gtgttttgcc   4920
taccagctgc cggcgttctc tcgctgggaa taaccggtct tctttgggca gttggccgtt   4980
tcacccaggt tgccggaatt atcacacctt atgacatcca ccagtatacc tccggaccac   5040
gtggtgcagc tgctgtagca acggctccag aaggtactta catggcggcc gttcggagag   5100
ccgctttgac tggacggact ttgatcttca caccatctgc agtcggatcc cttcttgaag   5160
gtgctttcag aactcaaaag ccctgcctta acaccgtgaa tgtcgtaggc tcttcccttg   5220
gttctggagg agttttcacc attgatggca gaagagtcat cgtcactgcc acccatgtgt   5280
tgaatggtaa cacagccagg gtcactggtg attcctacaa ccgcatgcac acgttcaata   5340
ctaatggtga ttatgcctgg tcccatgctg atgactggca aggcgttgcc cctatggtta   5400
agatcgctaa ggggtatcgc ggtcgtgcct actggcaaac gtcaaccgga gtcgaacctg   5460
gcatcatggg ggaaggattc gccttctgtt tcactaactg tggcgactca gggtcacctg   5520
tcatttcaga agctggtgac cttattggag tccataccgg ttcaaacaaa ctcggttctg   5580
gtcttgtgac aacccctgaa ggggagacct gctccatcaa ggaaactagg ctctctgacc   5640
tttctagaca ttttgcaggt ccaagcgtcc ctcttgggga cattaagttg agcccagcca   5700
tcatccctga tgtgacaact attccgagtg acttggcatc gctccttgct tctgtccccg   5760
tgatggaagg tggcctctca actgtccagc ttttgtgcgt ctttttcctt ctctggcgca   5820
tgatgggcca tgcctggaca cccattgttg ccgtaggctt ctttttgctg aatgaaattc   5880
tcccagcagt cttggtccga gctgtgttct cttttgcact ctttgtactt gcatgggcca   5940
ccccctggtc ggcacaagtg ttgatgatta gactcctcac ggcggctctc aaccgcaaca   6000
ggttgtccct ggcgttctac gcattcggag gtgtcgttgg cctggccaca gaaatcggga   6060
cttttgctgg tggatggcct gaactgtccc aagccctctc gacatactgc ttcctgccca   6120
ggttccttgc tgtgactagt tatgtcccca ccatcatcat cggtgggctc catgccctcg   6180
gcgtaatttt gtggttattc aaataccgat gcctccacaa catgctggtt ggtgatggga   6240
gtttctcaag cgctttcttc ctacggtatt ttgctgaggg taatcttagg aaaggcgtgt   6300
cgcagtcctg tggcatgaat aacgaatccc tgacagctgc tttggcttgc aagttgtcgc   6360
aagctgacct tgatttttttg tccagtttaa cgaacttcaa gtgctttgtg tccgcttcaa   6420
acatgaaaaa tgcagctggc caatacatcg aggcggcgta tgctagagct ctgcgtcagg   6480
agctggcctc cttggttcag gttgacaaga tgaaaggagt attggccaag ctcgaggctt   6540
tcgctgagac ggccactccg tcacttgaca caggggacgt gattgttctg cttgggcaac   6600
acccccatgg atccatcctc gacattaatg tgggggggtga aaggaaaact gtgtctgtgc   6660
aagaaacacg atgcctgggt ggttccaaat tcagtgtctg cactgtcgtg tccaacacgc   6720
ccgtggatac cttgaccggt atcccacttc agacgccaac ccccactttt gaaaatggcc   6780
cgcgccatcg cagcgaggac gacgacctca aagttgagag aatgaaaaaa cactgtgtat   6840
ccctcggctt ccacaaaatc aatggtaaag tttactgcaa aatttgggac aagtctaacg   6900
gcgacacctt ttacacggat gattcccgat acactcaaga ccatgctttt caggacaggt   6960
caaccgacta tagagacagg gattatgaag gtgtacagac cgcccccccaa cagggattcg   7020
atccaaagtc cgaagcccct gttggcactg ttgtaatcgg tggcattacg tataacaggc   7080
atctggtcaa aggtaaggag gtcctagttc ccaaacctga caactgcctt gaagctgcca   7140
```

-continued

```
gactgtccct tgagcaagct cttgctggga tgggccaaac ttgtgacctt acagctaccg   7200
aagtggagaa actaaagcgc atcattagtc aactccaagg tctgaccact gaacaggctt   7260
taaactgcta gccgccagcg gcttgacccg ctgtggccgc ggcggcctag ttgtaactga   7320
aacggcggta aaaatcgtaa aataccacag cagaactttc accttaggct ctttagacct   7380
aaaagtcacc tccgaggtgg aggtgaagaa atcaactgag caggggcacg ctgtcgtggc   7440
gaacttatgt tccggtgtcg tcttgatgag gcctcaccca ccgtcccttg ttgacgttct   7500
cctcaaaccc ggacttgaca caacacccgg cattcaacca gggcatgggg ccgggaatat   7560
gggcgtgaac ggttctattt gggattttga aactgcaccc acaaaggtag aactagagtt   7620
gtccaagcaa ataatccaag catgtgaagt caggcgcggg gacgccccta acctccaact   7680
cccctacaag ctttatcctg tcagggggga ccccgagcgg cgtaaaggtc gccttgtcaa   7740
cactaggttt ggagatttac cttacaaaac tccccaagac accaagtccg caattcatgc   7800
ggcttgttgc ctgcatccca atggggtcct cgtgtctgat ggcaaatcca cgctgggtac   7860
cactcttcaa catggtttcg agctttatgt ccccactgta ccttatagtg tcatggaata   7920
ccttgattca cgccctgaca cccctttat gtgtactaaa catggcactt ccaaggctgc   7980
tgcagaggac ctccaaaaat atgacctatc cactcaaggg tttgtcttgc ctggggtcct   8040
acgcctagtg cgcaggttca tctttagcca tgttggtaag gcgccaccac tgttccttcc   8100
atcaacctac cctgccaaga actccatggc aggggtcaat ggccagaggt tcccaacaaa   8160
ggatgtccag agcatacctg aaattgatga aatgtgcgcc cgtgccgtca aggaaaattg   8220
gcagactgtg acaccttgca ccctcaaaaa acagtactgt tccaaaccta aaactagaac   8280
catcctaggt accaacaact tcatagcctt ggctcacagg tcagcactca gtggtgtcac   8340
ccaggcgttc atgaagaagg cctggaagtc cccaattgcc ttggggaaaa acaagtttaa   8400
ggaattgcat tgcactgtcg ccggcagatg ccttgaggct gacctggctt cctgcgatcg   8460
cagcaccccc gccattgtga ggtggtttgt tgccaacctc ctgtatgaac ttgcaggatg   8520
tgaagagtac ttgcctagct acgtgctcaa ctgttgccat gaccttgtgg caacgcagga   8580
tggcgctttc acaaaacgcg gtggcctgtc gtccggggac cccgtcacca gtgtgtccaa   8640
caccgtctac tcactgataa tttacgccca gcacatggtg ctttcggcct tgaagatggg   8700
tcatgaaatt ggtctcaagt tccttgagga acagctcaaa tttgaggacc ttcttgaaat   8760
ccagcccatg ttagtgtatt ctgatgacct cgtcttgtat gcggaaagac ccacttttcc   8820
caactaccat tggtgggtcg agcatcttga cctgatgttg ggctttaaaa cggacccaaa   8880
gaaaactgtc ataactgata aacccagttt tctcggctgc agaattgaag caggacggca   8940
gttagtcccc aatcgcgacc gtattctggc tgctcttgca tatcatatga aggcgcagaa   9000
cgcctcagag tattatgcgt ccgctgccgc aattctgatg gattcgtgtg cttgcattga   9060
ccatgacccc gagtggtatg aggatcttat ctgcggcatc gcccggtgtg ctcgccagga   9120
cggttaccgt tttccaggcc cggcattttt catgtccatg tgggagaagc tgaaaagtca   9180
taatgaaggg aagaaatgcc gtcactgcgg catctgcgac gccaaagccg actatgcgtc   9240
cgcctgtgga cttgatttgt gtttgttcca ttcacacttt catcaacact gcccagtcac   9300
tctgagctgt ggccaccatg ccggttcaaa ggaatgttcg cagtgtcagt cacctgtcgg   9360
ggctggcaaa tccccccttg acgctgtgct gaaacaaatc ccgtacaaac ctcctcgtac   9420
cattatcatg aaggtggaca acaaaacaac gacccttgac ccgggaagat atcagtcccg   9480
```

-continued

```
tcgaggtctt gttgcagtca aaagaggtat tgcaggtaat gaggttgatc tttctgatgg   9540
agactaccaa gtggtgcctc ttttgccgac ttgcaaagac ataaacatgg tgaaggtggc   9600
ttgcaacgta ctactcagca agtttatagt agggccgcca ggttccggaa aaaccacctg   9660
gctactgaac caagtccagg acgatgatgt catttacaca cctactcatc agacaatgtt   9720
tgacatagtc agtgctctta aagtttgcag gtattccatc ccaggagcct caggactccc   9780
ttttccacca cctgccaggt ccgggccgtg ggttaggctc atcgccagcg gacatgtccc   9840
tggccgagtg tcatatctcg atgaggcagg atattgcaat catctagaca ttctaaggct   9900
gctttccaaa acaccccttg tgtgtttggg tgaccttcag caacttcacc cggtcggctt   9960
tgattcctat tgttatgtgt tcgatcagat gcctcagaag cagctgacca ccatttatag  10020
atttggccct aacatctgtg cagccatcca gccttgttac agggagaaac ttgaatccaa  10080
ggccaggaac accagagtgg ttttcaccac ccggcctgtg gcctttggtc aggtcctgac  10140
accgtaccac aaagatcgta ccggctctgc aataactata gattcatccc aggggggcgac  10200
cttcgacatt gtgacattgc atctaccatc gccaaagtcc ctaaacaaat cccgagcact  10260
tgtagccatc actcgggcaa gacatgggtt gttcatttat gaccctcatg accaactcca  10320
ggagtttttc aacttaaccc ccgagcgcac tgattgtaac cttgcgttca gccgtgggga  10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta gaagggagct gcatgccact accacaagta gcacataacc tggggtttta  10560
cttttccccg gacagcccag cttttgcacc cctgccaaaa gagctggcgc cacattggcc  10620
agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg gggcgagcc   10800
tcaggccctg ccagaaacac tcgtttcaac aggacgtata gccacagatt gtcgggaata  10860
tctcgacgcg gctgaggaag aggcagcgag agaacttccc cacgcattta ttggcgatgt  10920
caaaggcact acgatcgggg ggtgtcacca cattacatcg aaatacctac ctaggtccct  10980
gcctaaagac tctgttgctg tggttggggt gagttcgccc ggtagggctg ctaaagccgt  11040
gtgcactctc accgatgtgt acctccccga actccgacca tatttgcaac cggagacggc  11100
atcaaaatgc tggaaactta aactggattt cagggatgtt cgactgatgg tctggaaagg  11160
cgccacagcc tatttccagt tggaagggct gacatggtca gcgctgcccg attatgctag  11220
gttcattcag ctacccaagg atgccgttgt gtacatcgat ccgtgtatag ggccggcaac  11280
agccaatcgc aaggttgtgc gaaccacaga ctggcgggcc gacctggcag tgacaccgta  11340
tgattacggt gctcaggtca ttttgacaac agcctggttc gaggaccttg ggccgcagtg  11400
gaagatttg gggttgcagc ctttcagacg aacatttggc tttgagaaca ctgaagattg  11460
ggcaattctc gcacgccgta tgaatgacgg caaagattac actgactata attggcattg  11520
tgtacgagaa cgcccacacg caatttacgg gcgcgcccgt gaccatacgt atcattttgc  11580
ccttggcact gaactgcaag tagagctggg cagaccccgg ctgcctcctg agcaagtgcc  11640
gtgaacgcgg agtgatgcaa tgggtttact gtggagtaaa atcagtcagt tgttcgtgga  11700
tgccttcact gagttccttg ttagtgtggt tgacattgtc atctttctcg ccatattgtt  11760
tgggttcact gttgcaggct ggttattggt cttccttctc agagtggttt gctccgcgtt  11820
tctccgttcg cgctctgcca ttcactcttc cgaactatcg aaggtcctat gagggcttgc  11880
```

tacccaactg cagaccggat gtcccacaat tcgcagttaa gcacccgttg ggtatacttt 11940
ggcatatgcg agtctcccac ctaattgacg aaatggtctc tcgccgcatt taccggacca 12000
tggaacattc gggtcaagcg gcctggaagc aggttgttag tgaagccact ctcacaaaac 12060
tgtcaaggct tgacgtagtc actcatttcc aacacctggc cgcagtggag gctgattctt 12120
gccgcttcct tagctcacga ctcgcgatgc tgaaaaacct tgccgttggc aatgtgagcc 12180
tggagtacaa cactactttg gaccgcgttg agctcatctt tcccacacca ggtacgaggc 12240
ccaagttgac cgattttagg caatggctta tcagcgtgca cgcttccatc ttctcctctg 12300
tggcttcgtc tgttaccttg ttcacagtgc tttggcttcg aattccagct ctacgctatg 12360
tttttggttt ccattggccc acggcaacac atcattcgaa ctaactatca attacactat 12420
atgtaagcca tgccctacca gtcaagctgc ccaacaaaga ctcgagcctg gccgtaacgt 12480
gtggtgcaaa atagggcacg acaggtgtga ggaacgtgac catgatgagt tgtcaatgtc 12540
cattccgtcc gggtacgaca acctcaaact tgagggttat tatgcttggc tggctttttt 12600
gtccttttcc tacgcggccc aattccatcc ggagctgttc ggaataggaa acgtgtcgcg 12660
cgtctttgtg gataagcgac accagttcat ttgcgccgag catgatggac aaaattcaac 12720
catatctgcc agacacaaca tctccgcgtc gtatgcggtg tattaccatc atcaaataga 12780
cgggggcaat tggtttcatt tggaatggct gcgaccattc ttttcctcct ggctggtgct 12840
caacatctca tggtttctga ggcgttcgcc tgcaagccct gcttctcgac gcatctatca 12900
gatattaaga ccaacacgac cgcggctgcc ggtttcatgg tccttcagaa catcaattgt 12960
ttccaatctc acagggcctc aacagcgcaa ggtaccactc ccctcaggag gtcgtcccaa 13020
tgtcgtgaag ccgtcggcat tccccagtac atcacgataa cggctaatgt gaccgatgaa 13080
tcgtatttgt acaacgcgga cttgctgatg ctttccgcgt gccttttcta cgcctcggaa 13140
atgagcgaga aaggcttcaa agtcatcttt gggaatattt ctggcgttgt ttccgcttgt 13200
gttaatttca cagattatgt ggcccatgtg acccaacaca ctcagcagca ccatttggta 13260
attgatcaca ttcggttact acacttcttg acaccgtcta cgatgaggtg ggctacaacc 13320
attgcttgtt tgcttgccat tcttttggcg gtatgaaatg ttcttgcaag ttggggcatt 13380
tcttgactcc tcactcttgc ttctggtggc ttttttttgct gtgtaccggc ttgtcttggt 13440
cctttgtcga tggcaacgac gacagctcga catcccaata catatataat ttgacgatat 13500
gcgagctgaa tgggaccgaa tggttgtccg gtcattttga ttgggcagtc gaaacctttg 13560
tgctttaccc agttgccact catatcattt cactgggttt tctcacaaca agccatttcc 13620
ttgatgcgct cggtctcggc gctgtgtccg ccacaggatt cattggcgag cggtatgtac 13680
ttagcagcat gtacggcgtt tgcgccttcg cggcgttcgt atgttttgtc atccgtgctg 13740
ctaaaaattg catggcttgc cgctatgccc gcacccggtt taccaacttc atcgtggacg 13800
accggggaag aatccatcga tggaagtctt caatagtggt ggagaaattg ggcaaagctg 13860
aagtcggtgg tgaccttgtc aacattaagc atgttgtcct cgaaggggtt aaagctcaac 13920
ctttgacgag gacttcggct gagcaatggg aagcctagac gacttttgca acgatcccac 13980
cgccgcacaa aaactcgtgc tggcctttag catcacatat acacccataa tgatatacgc 14040
ccttaaggtg tcacgcggcc gactcctggg gctgttgcac atcttgatat ttctgaattg 14100
ttcctttact tttgggtaca tgacatatgt gcattttcaa tccaccaacc gtgtcgcatt 14160
cactctgggg gctgtagtcg cccttttgtg gggtgtttac agcctcacag agtcatggaa 14220

-continued

```
gttcatcact tccagatgca gattgtgttg cctaggccgg cgatacattc tggcccctgc  14280

ccatcacgta gaaagtgctg caggcctcca ttcaatccca gcgtctggta accgagcata  14340

cgctgtgaga aagcccggac taacatcagt gaacggcact ctagtacctg ggcttcggag  14400

cctcgtgctg ggcggcaaac gagctgttaa acgaggagtg gttaacctcg tcaagtatgg  14460

ccggtaagaa ccagagccag aagaaaagaa gaaatgcagc tccgatgggg aaaggccagc  14520

cagtcaatca actgtgccag ttgctgggta caatgataaa gtcccagcgc cagcaatcta  14580

ggggaggaca ggccaaaaag aagaagcctg agaagccaca ttttccccta gctgctgaag  14640

atgacattcg gcaccatctc acccaggccg aacgttccct ctgcttgcaa tcgatccaga  14700

cggctttcaa tcaaggcgca ggaactgcgt cgctttcatc cagcgggaag gtcagtttcc  14760

aggttgagtt catgctgccg gttgctcata cagtgcgcct gattcgcgtg acttctacat  14820

ccgccagtca gggtgcaaat taatttgaca gtcaggtgaa tggccgcgat tgacgtgtgg  14880

cctctaagtc acctattcaa ttagggcgat cacatggggg tcaaacttaa ttaggcagga  14940

accatgtgac cgaaattaaa aaaaaaaaaa aaaaaaaaaa aaaa                  14984
```

```
<210> SEQ ID NO 49
<211> LENGTH: 14945
<212> TYPE: DNA
<213> ORGANISM: Porcine reproductive and respiratory syndrome virus

<400> SEQUENCE: 49

atgatgtgta gggtattccc cctacataca cgacactctt agtgtttgtg taccttggag     60

gcgtgggtac agccctgccc caccctttgg tccctgttct agcccgacag gtacccttct    120

ctctcggggc gagcgcgccg cctgctgctc ccttgcggcg ggaaggacct cccgagtatt    180

tccggagagc acctgcttta cgggatctcc gccctttaac catgtctggg atgttctccc    240

ggtgcatgtg caccccggct gcccgggtat tttggaacgc cggccaagtc tattgcacac    300

ggtgtctcag tgcacggtct cttctctctc cagaacttca ggacacggac ctcggtgcag    360

ttggcttgtt tcacaagcct aaagacaagc tccattggaa agttcccatt ggtatccccc    420

aggtggaatg ttctccatct gggtgttgct ggctgtcaac catttttcct ttagcgcgca    480

tgacctccgg caatcacaac ttccttcaac gactcgtgaa ggttgctgat gtattgtacc    540

gtgacggttg cttaacccct agacacctcc gtgaactcca agtttacgag cgtggttgca    600

attggtatcc gattacgggg cctgtgcctg ggatggctgt gtacgcgaac tccatgcacg    660

tgtccgacca accgttccct ggtgccactc atgtgttaac aaattcccct ttgcctcaac    720

gggcttgtcg gcagccgttc tgtccgttcg aagaggccca ttctagcata tacaggtggg    780

aaaaatttgt aatttttatg gattcctcct ccgacggtcg atctcgcatg atgtggactc    840

cggaatccga tgactccacg gctttggaag ttctgccgcc cgagctagaa caccaggtca    900

aggtccttgt tcggagcttt cccgcccatc accttgtcga ccttgccgat tgggagctca    960

ctgagtcccc tgataacggt tttccttca gcacgtcaca tccttgcggc taccttgttc    1020

gggacccggc tgtatccgaa ggcaagtgtt ggctttcctg ctttttgagc cagtcagccg   1080

aagtgctcag tcgcgaggcg catctggcta ccgcctatgg ttaccaaacc aagtggggtg   1140

tgcctggcaa gtacatccag cgcagacttc aagttcacgg tctccgtgct gtggtcgacc   1200

ctgatggtcc cattcacgtt gaagcattgt cttgccccca gtcttggatc aggcacttga   1260

ccctgaatga tgatgtcacc ccgggattcg ttcgcctaat gtctcttcgc attgtgccga   1320

acacagagcc taccacacac cggatctttc gttttggagt gcacaagtgg tatggtgccg   1380
```

ccggcaaacg ggcccgtggc aagcgtgccg ccaaaagtga gaaagactcg gcttccaccc 1440
tcaaggttgc ccgaccgact tccaccagtg gaatcgtcac ctactcccca cctgcggacg 1500
ggtcttgtgg ttggcatgcc cttgccgcca tactgaaccg gatgattaat aatgacttca 1560
cgtcccctct gcctcggtac aacaggccgg aggacgattg ggcttctgat ggtgaccttg 1620
ctcaggccat tcaatgtttg caactacctg ccgccatagc tcggaaccgc gcctgcccta 1680
acgccaaata cctcataaaa ctcaacggag ttcattggga ggtagaggtg aggcctggaa 1740
tggctcctcg ctccctctct cgtgagtgcg ttgttggcgt ctgctctgaa ggctgtgtcg 1800
cgtcgcctta cccggaggac gggttgccta aacgtgcact tgaggccctg gcgtctgctt 1860
atagactgcc ttcagactgt gtttgtgatg gtattattga cttccttgcc aatccacctc 1920
cccaggagtt ctggactctt gacaaaatgt tgacttcccc gtcaccggag cagtccggct 1980
tctctagtct gtataaattg ttgttagaga tcttgccgca gaaatgcgga tccacagaag 2040
gggaattcat ctatactgtt gagaggatgt tgaaggattg tccgagctcc aaacaggcca 2100
tggccctcct tgcaaaaatt aaggtcccat cctcaaaggc cccatccgtg actctgaacg 2160
agtgcttccc cacggatgtt ccagtcaact ctgagttaat atcttgggaa gagcccaaag 2220
accctggcgc tgctgttgtc ctatgtccat cggatgcaaa agaatctaag gaaacagccc 2280
ctgaagaagc tcaagcgaga aaccgtaagg tccttcaccc tgtggtcctt accgaggaac 2340
ttagcgagca acaggtgcag gtggttgagg gtgatcagga tatgccactg gatttgactt 2400
ggccaacctt aaccgctacg gcgacccctg ttagagggcc ggtaccggac aatttgagct 2460
ctggcattgg tgcccagccc gctaccgttc aagaactcat tctggcgagg cctgcacccc 2520
gtcttgttga gcgctgtggc acggagtcga acggcagcag ttcatttctg gatttgcctg 2580
acgtgcagac ctcggaccag cctttagacc tgtccctggc cgcgtggcct gtaagggcta 2640
ccgcgtctga ccccggttgg atccacggta ggcgtgagcc tgtctttgtg aagcctcgag 2700
gtgttttctc tgatggcgag tcggcccttc agttcggaga gctttccgaa gccagttctg 2760
tcgtcgatga ccggacaaaa gaagctccgg tggttgacgc cccccatcgat ttgacaactt 2820
cgaacgagac gctctctggg tctgacccct ttgaattcgc caaattcagg cgcccgcgtt 2880
tctccgcgca agctttaatc gaccgaggtg gtccgcttgc cgatgttcat gcaaagataa 2940
agagtcgggt atatgaacaa tgccttcaag cttgtgaacc tggtagtcgt gcgaccccag 3000
ccaccaagaa gtggctcgac aaaatgtggg acagggtgga catgaaaact tggcgctgca 3060
cctcgcagtt ccaagctggt cacattcttg agtccctcaa attcctccct gacatgattc 3120
aagacacacc gcctcctgtt cccaggaaga accgagctgg tgacagtgcc ggcctgaagc 3180
aactggtggc gcagtgggat aggaaatcga gtgtgacacc ccccacaaaa ccggttggac 3240
cggtgcttga ccaggccgtc cctctgccta tggacatcca gcaaggagat gccatctccg 3300
ctgacaagcc accccattcg caaaaccctt ctagtcaagt agatgtgggt ggaggttgga 3360
aaagttttat gctctccggc acccgtttcg cggggtccgt tagtcagcgc cttacgacat 3420
gggtttttga ggttctctcc catctcccag cttttatgct cacacttttc tcgccacggg 3480
gctctatggc tccaggtgat tggctgtttg caggtgctgt tctacttgct ctcctgctct 3540
gccgttctta cccaatactc ggatgccttc ccttattggg tgtcttttct ggttctgtgc 3600
ggtgtgttcg tttgggtgtt tttggttctt ggatggcttt tgctgtattt ttattctcga 3660
ctccacccga cccagtcggt tcttcttgtg accacgattc gccggagtgt catgctgagc 3720

-continued

```
ttttggctct tgagcagcgc caactttggg aacctgtgcg cagccttgtg gtcgggccat   3780

cgggcctctt atgcgtcatt cttggcaagt tactcggtgg gtcacgttgt ctctggtttg   3840

ttctcctacg tatatgcatg ctcgcagatt tggcaatttc tcttatttat gtggtgtccc   3900

aagggcgttg tcacaagtgt tggggaaagt gtataaggac ggctcctgca gaagtggccc   3960

ttaatgtgtt tcctttttcg cgcgccaccc gctcatctct tgtgtccttg tgtgatcggt   4020

tccaagcgcc aaaaggagtt gaccccgtgc acttggcgac aggctggcgc gggtgctggt   4080

gtggtgagag ccctattcat caatcacacc aaaaaccgat agcttatgcc aacttggatg   4140

aaaagaagat atccgcccag acggtgattg ctgtcccgta tgatcctagt caggccatta   4200

aatgcctgaa agttttgcag gcaggagggg ctattgtgga ccagcctacg cccgaggtcg   4260

tccgtgtgtc tgagattccc ttctcggccc catttttcc gaaggtccca gtcaacccag   4320

actgcagggt tgtggtagat tcggacactt ttgtggctgc ggtccgctgc ggttattcga   4380

cagcacaact ggtccttggt cggggcaact ttgccaagct aaatcagacc cccctcagga   4440

actctgtccc caccaaaaca actggtgggg cctcatacac ccttgccgtg gcccaggtat   4500

ctgtgtggac tcttgttcat ttcatcctcg gcctttggtt aacgtcacct caagtgtgtg   4560

gtcgagggac ctctgacccg tggtgttcga acccttttc gtatcctact tatggccccg   4620

gagttgtgtg ttcctctcga ctctgcgtgt ctgccgacgg agttaccctg ccattgttct   4680

cagccgttgc ccatctttcc ggtagagagg tggggatttt tattttggtg cttgcctcct   4740

tgggcgcttt agcccaccgc ttggctctta aggcagacat gtcaatggtc tttttggcgt   4800

tttgtgctta cgcctggccc atgagctcct ggttaatttg cttctttcct atgctcttga   4860

ggtgggtaac ccttcatcct ctcactatgc tttgggtgca ctcatttttg gtgttttgcc   4920

taccagctgc cggcgttctc tcgctgggaa taaccggtct tctttgggca gttggccgtt   4980

tcacccaggt tgccggaatt atcacacctt atgacatcca ccagtatacc tccggaccac   5040

gtggtgcagc tgctgtagca acggctccag aaggtactta catggcggcc gttcggagag   5100

ccgctttgac tggacggact ttgatcttca caccatctgc agtcggatcc cttcttgaag   5160

gtgctttcag aactcaaaag ccctgcctta acaccgtgaa tgtcgtaggc tcttcccttg   5220

gttctggagg agttttcacc attgatggca gaagagtcat cgtcactgcc acccatgtgt   5280

tgaatggtaa cacagccagg gtcactggtg attcctacaa ccgcatgcac acgttcaata   5340

ctaatggtga ttatgcctgg tcccatgctg atgactggca aggcgttgcc cctatggtta   5400

agatcgctaa ggggtatcgc ggtcgtgcct actggcaaac gtcaaccgga gtcgaacctg   5460

gcatcatggg ggaaggattc gccttctgtt tcactaactg tggcgactca gggtcacctg   5520

tcatttcaga agctggtgac cttattggag tccataccgg ttcaaacaaa ctcggttctg   5580

gtcttgtgac aacccctgaa ggggagacct gctccatcaa ggaaactagg ctctctgacc   5640

tttctagaca ttttgcaggt ccaagcgtcc ctcttgggga cattaagttg agcccagcca   5700

tcatccctga tgtgacaact attccgagtg acttggcatc gctccttgct tctgtccccg   5760

tgatggaagg tggcctctca actgtccagc ttttgtgcgt ctttttcctt ctctggcgca   5820

tgatgggcca tgcctggaca cccattgttg ccgtaggctt ctttttgctg aatgaaattc   5880

tcccagcagt cttggtccga gctgtgttct cttttgcact ctttgtactt gcatgggcca   5940

ccccctggtc ggcacaagtg ttgatgatta gactcctcac ggcggctctc aaccgcaaca   6000

ggttgtccct ggcgttctac gcattcggag gtgtcgttgg cctggccaca gaaatcggga   6060

cttttgctgg tggatggcct gaactgtccc aagccctctc gacatactgc ttcctgccca   6120
```

```
ggttccttgc tgtgactagt tatgtcccca ccatcatcat cggtgggctc catgccctcg   6180
gcgtaatttt gtggttattc aaataccgat gcctccacaa catgctggtt ggtgatggga   6240
gtttctcaag cgctttcttc ctacggtatt ttgctgaggg taatcttagg aaaggcgtgt   6300
cgcagtcctg tggcatgaat aacgaatccc tgacagctgc tttggcttgc aagttgtcgc   6360
aagctgacct tgatttttg tccagtttaa cgaacttcaa gtgctttgtg tccgcttcaa   6420
acatgaaaaa tgcagctggc caatacatcg aggcggcgta tgctagagct ctgcgtcagg   6480
agctggcctc cttggttcag gttgacaaga tgaaaggagt attggccaag ctcgaggctt   6540
tcgctgagac ggccactccg tcacttgaca caggggacgt gattgttctg cttgggcaac   6600
acccccatgg atccatcctc gacattaatg tggggggtga aaggaaaact gtgtctgtgc   6660
aagaaacacg atgcctgggt ggttccaaat tcagtgtctg cactgtcgtg tccaacacgc   6720
ccgtggatac cttgaccggt atcccacttc agacgccaac cccacttttt gaaaatggcc   6780
cgcgccatcg cagcgaggac gacgacctca aagttgagag aatgaaaaaa cactgtgtat   6840
ccctcggctt ccacaaaatc aatggtaaag tttactgcaa aatttgggac aagtctaacg   6900
gcgacacctt ttacacggat gattcccgat acactcaaga ccatgctttt caggacaggt   6960
caaccgacta tagagacagg gattatgaag gtgtacagac cgcccccaa cagggattcg   7020
atccaaagtc cgaagcccct gttggcactg ttgtaatcgg tggcattacg tataacaggc   7080
atctggtcaa aggtaaggag gtcctagttc ccaaacctga caactgcctt gaagctgcca   7140
gactgtccct tgagcaagct cttgctggga tgggccaaac ttgtgacctt acagctaccg   7200
aagtggagaa actaaagcgc atcattagtc aactccaagg tctgaccact gaacaggctt   7260
taaactgcta gccgccagcg gcttgacccg ctgtggccgc ggcggcctag ttgtaactga   7320
aacggcggta aaaatcgtaa aataccacag cagaactttc accttaggct ctttagacct   7380
aaaagtcacc tccgaggtgg aggtgaagaa atcaactgag caggggcacg ctgtcgtggc   7440
gaacttatgt tccggtgtcg tcttgatgag gcctcaccca ccgtcccttg ttgacgttct   7500
cctcaaaccc ggacttgaca caacacccgg cattcaacca gggcatgggg ccgggaatat   7560
gggcgtgaac ggttctattt gggattttga aactgcaccc acaaaggtag aactagagtt   7620
gtccaagcaa ataatccaag catgtgaagt caggcgcggg gacgccccta acctccaact   7680
cccctacaag ctttatcctg tcaggggga ccccgagcgg cgtaaaggtc gccttgtcaa   7740
cactaggttt ggagatttac cttacaaaac tccccaagac accaagtccg caattcatgc   7800
ggcttgttgc ctgcatccca atggggtcct cgtgtctgat ggcaaatcca cgctgggtac   7860
cactcttcaa catggtttcg agctttatgt ccccactgta ccttatagtg tcatggaata   7920
ccttgattca cgccctgaca cccctttat gtgtactaaa catggcactt ccaaggctgc   7980
tgcagaggac ctccaaaaat atgacctatc cactcaaggg tttgtcttgc ctggggtcct   8040
acgcctagtg cgcaggttca tctttagcca tgttggtaag gcgccaccac tgttccttcc   8100
atcaacctac cctgccaaga actccatggc aggggtcaat ggccagaggt tcccaacaaa   8160
ggatgtccag agcatacctg aaattgatga aatgtgcgcc cgtgccgtca aggaaaattg   8220
gcagactgtg acaccttgca ccctcaaaaa acagtactgt tccaaaccta aaactagaac   8280
catcctaggt accaacaact tcatagcctt ggctcacagg tcagcactca gtggtgtcac   8340
ccaggcgttc atgaagaagg cctggaagtc cccaattgcc ttggggaaaa acaagtttaa   8400
ggaattgcat tgcactgtcg ccggcagatg ccttgaggct gacctggctt cctgcgatcg   8460
```

-continued

```
cagcaccccc gccattgtga ggtggtttgt tgccaacctc ctgtatgaac ttgcaggatg   8520
tgaagagtac ttgcctagct acgtgctcaa ctgttgccat gaccttgtgg caacgcagga   8580
tggcgctttc acaaaacgcg gtggcctgtc gtccggggac cccgtcacca gtgtgtccaa   8640
caccgtctac tcactgataa tttacgccca gcacatggtg ctttcggcct tgaagatggg   8700
tcatgaaatt ggtctcaagt tccttgagga acagctcaaa tttgaggacc ttcttgaaat   8760
ccagcccatg ttagtgtatt ctgatgacct cgtcttgtat gcggaaagac ccactttcc    8820
caactaccat tggtgggtcg agcatcttga cctgatgttg ggctttaaaa cggacccaaa   8880
gaaaactgtc ataactgata aacccagttt tctcggctgc agaattgaag caggacggca   8940
gttagtcccc aatcgcgacc gtattctggc tgctcttgca tatcatatga aggcgcagaa   9000
cgcctcagag tattatgcgt ccgctgccgc aattctgatg gattcgtgtg cttgcattga   9060
ccatgacccc gagtggtatg aggatcttat ctgcggcatc gcccggtgtg ctcgccagga   9120
cggttaccgt tttccaggcc cggcattttt catgtccatg tgggagaagc tgaaaagtca   9180
taatgaaggg aagaaatgcc gtcactgcgg catctgcgac gccaaagccg actatgcgtc   9240
cgcctgtgga cttgatttgt gtttgttcca ttcacacttt catcaacact gcccagtcac   9300
tctgagctgt ggccaccatg ccggttcaaa ggaatgttcg cagtgtcagt cacctgtcgg   9360
ggctggcaaa tccccccttg acgctgtgct gaaacaaatc ccgtacaaac ctcctcgtac   9420
cattatcatg aaggtggaca acaaaacaac gacccttgac ccgggaagat atcagtcccg   9480
tcgaggtctt gttgcagtca aaagaggtat tgcaggtaat gaggttgatc tttctgatgg   9540
agactaccaa gtggtgcctc ttttgccgac ttgcaaagac ataaacatgg tgaaggtggc   9600
ttgcaacgta ctactcagca agtttatagt agggccgcca ggttccggaa aaaccacctg   9660
gctactgaac caagtccagg acgatgatgt catttacaca cctactcatc agacaatgtt   9720
tgacatagtc agtgctctta aagtttgcag gtattccatc ccaggagcct caggactccc   9780
ttttccacca cctgccaggt ccgggccgtg ggttaggctc atcgccagcg gacatgtccc   9840
tggccgagtg tcatatctcg atgaggcagg atattgcaat catctagaca ttctaaggct   9900
gctttccaaa acaccccttg tgtgtttggg tgaccttcag caacttcacc cggtcggctt   9960
tgattcctat tgttatgtgt tcgatcagat gcctcagaag cagctgacca ccatttatag  10020
atttggccct aacatctgtg cagccatcca gccttgttac agggagaaac ttgaatccaa  10080
ggccaggaac accagagtgg ttttcaccac ccggcctgtg gcctttggtc aggtcctgac  10140
accgtaccac aaagatcgta ccggctctgc aataactata gattcatccc agggggcgac  10200
cttcgacatt gtgacattgc atctaccatc gccaaagtcc ctaaacaaat cccgagcact  10260
tgtagccatc actcgggcaa gacatgggtt gttcatttat gaccctcatg accaactcca  10320
ggagtttttc aacttaaccc ccgagcgcac tgattgtaac cttgcgttca gccgtgggga  10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta gaagggagct gcatgccact accacaagta gcacataacc tggggtttta  10560
cttttccccg gacagcccag cttttgcacc cctgccaaaa gagctggcgc cacattggcc  10620
agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg gggcgagcc   10800
tcaggccctg ccagaaacac tcgtttcaac aggacgtata gccacagatt gtcgggaata  10860
```

```
tctcgacgcg gctgaggaag aggcagcgag agaacttccc cacgcattta ttggcgatgt  10920
caaaggcact acgatcgggg ggtgtcacca cattacatcg aaatacctac ctaggtccct  10980
gcctaaagac tctgttgctg tggttggggt gagttcgccc ggtagggctg ctaaagccgt  11040
gtgcactctc accgatgtgt acctccccga actccgacca tatttgcaac cggagacggc  11100
atcaaaatgc tggaaactta aactggattt cagggatgtt cgactgatgg tctggaaagg  11160
cgccacagcc tatttccagt tggaagggct gacatggtca gcgctgcccg attatgctag  11220
gttcattcag ctacccaagg atgccgttgt gtacatcgat ccgtgtatag ggccggcaac  11280
agccaatcgc aaggttgtgc gaaccacaga ctggcgggcc gacctggcag tgacaccgta  11340
tgattacggt gctcaggtca ttttgacaac agcctggttc gaggaccttg ggccgcagtg  11400
gaagattttg gggttgcagc ctttcagacg aacatttggc tttgagaaca ctgaagattg  11460
ggcaattctc gcacgccgta tgaatgacgg caaagattac actgactata attggcattg  11520
tgtacgagaa cgcccacacg caatttacgg gcgcgcccgt gaccatacgt atcattttgc  11580
ccttggcact gaactgcaag tagagctggg cagaccccgg ctgcctcctg agcaagtgcc  11640
gtgaacgcgg agtgatgcaa tgggtttact gtggagtaaa atcagtcagt tgttcgtgga  11700
tgccttcact gagttccttg ttagtgtggt tgacattgtc atctttctcg ccatattgtt  11760
tgggttcact gttgcaggct ggttattggt cttccttctc agagtggttt gctccgcgtt  11820
tctccgttcg cgctctgcca ttcactcttc cgaactatcg aaggtcctat gagggcttgc  11880
tacccaactg cagaccggat gtcccacaat tcgcagttaa gcacccgttg ggtatacttt  11940
ggcatatgcg agtctcccac ctaattgacg aaatggtctc tcgccgcatt taccggacca  12000
tggaacattc gggtcaagcg gcctggaagc aggttgttag tgaagccact ctcacaaaac  12060
tgtcaaggct tgacgtagtc actcatttcc aacacctggc cgcagtggag gctgattctt  12120
gccgcttcct tagctcacga ctcgcgatgc tgaaaaacct tgccgttggc aatgtgagcc  12180
tggagtacaa cactactttg gaccgcgttg agctcatctt tcccacacca ggtacgaggc  12240
ccaagttgac cgattttagg caatggctta tcagcgtgca cgcttccatc ttctcctctg  12300
tggcttcgtc tgttaccttg ttcacagtgc tttggcttcg aattccagct ctacgctatg  12360
tttttggttt ccattggccc acggcaacac atcattcgaa ctaactatca attacactat  12420
atgtaagcca tgccctacca gtcaagctgc ccaacaaaga ctcgagcctg gccgtaacgt  12480
gtggtgcaaa atagggcacg acaggtgtga ggaacgtgac catgatgagt tgtcaatgtc  12540
cattccgtcc gggtacgaca acctcaaact tgagggttat tatgcttggc tggctttttt  12600
gtccttttcc tacgcggccc aattccatcc ggagctgttc ggaataggaa acgtgtcgcg  12660
cgtctttgtg gataagcgac accagttcat ttgcgccgag catgatggac aaaattcaac  12720
catatctgcc agacacaaca tctccgcgtc gtatgcggtg tattaccatc atcaaataga  12780
cgggggcaat tggtttcatt tggaatggct gcgaccattc ttttcctcct ggctggtgct  12840
caacatctca tggtttctga ggcgttcgcc tgcaagccct gcttctcgac gcatctatca  12900
gatattaaga ccaacacgac cgcggctgcc ggtttcatgg tccttcagaa catcaattgt  12960
ttccaatctc actcgtccca atgtcgtgaa gccgtcggca ttccccagta catcacgata  13020
acggctaatg tgaccgatga atcgtatttg tacaacgcgg acttgctgat gctttccgcg  13080
tgccttttct acgcctcgga aatgagcgag aaaggcttca aagtcatctt tgggaatatt  13140
tctggcgttg tttccgcttg tgttaatttc acagattatg tggcccatgt gacccaacac  13200
```

actcagcagc accatttggt aattgatcac attcggttac tacacttctt gacaccgtct 13260
acgatgaggt gggctacaac cattgcttgt ttgcttgcca ttcttttggc ggtatgaaat 13320
gttcttgcaa gttggggcat ttcttgactc ctcactcttg cttctggtgg cttttttttgc 13380 tgtgtaccgg cttgtcttgg tcctttgtcg atggcaacga cgacagctcg acatcccaat 13440
acatatataa tttgacgata tgcgagctga atgggaccga atggttgtcc ggtcattttg 13500
attgggcagt cgaaaccttt gtgctttacc cagttgccac tcatatcatt tcactgggtt 13560
ttctcacaac aagccatttc cttgatgcgc tcggtctcgg cgctgtgtcc gccacaggat 13620
tcattggcga gcggtatgta cttagcagca tgtacggcgt ttgcgccttc gcggcgttcg 13680
tatgttttgt catccgtgct gctaaaaatt gcatggcttg ccgctatgcc cgcacccggt 13740
ttaccaactt catcgtggac gaccggggaa gaatccatcg atggaagtct tcaatagtgg 13800
tggagaaatt gggcaaagct gaagtcggtg gtgaccttgt caacattaag catgttgtcc 13860
tcgaaggggt taaagctcaa cctttgacga ggacttcggc tgagcaatgg gaagcctaga 13920
cgacttttgc aacgatccca ccgccgcaca aaaactcgtg ctggccttta gcatcacata 13980
tacacccata atgatatacg cccttaaggt gtcacgcggc cgactcctgg ggctgttgca 14040
catcttgata tttctgaatt gttcctttac ttttgggtac atgacatatg tgcattttca 14100
atccaccaac cgtgtcgcat tcactctggg ggctgtagtc gcccttttgt ggggtgttta 14160
cagcctcaca gagtcatgga agttcatcac ttccagatgc agattgtgtt gcctaggccg 14220
gcgatacatt ctggcccctg cccatcacgt agaaagtgct gcaggcctcc attcaatccc 14280
agcgtctggt aaccgagcat acgctgtgag aaagcccgga ctaacatcag tgaacggcac 14340
tctagtacct gggcttcgga gcctcgtgct gggcggcaaa cgagctgtta aacgaggagt 14400
ggttaacctc gtcaagtatg gccggtaaga accagagcca gaagaaaaga agaaatgcag 14460
ctccgatggg gaaaggccag ccagtcaatc aactgtgcca gttgctgggt acaatgataa 14520
agtcccagcg ccagcaatct aggggaggac aggccaaaaa gaagaagcct gagaagccac 14580
attttcccct agctgctgaa gatgacattc ggcaccatct cacccaggcc gaacgttccc 14640
tctgcttgca atcgatccag acggctttca atcaaggcgc aggaactgcg tcgctttcat 14700
ccagcgggaa ggtcagtttc caggttgagt tcatgctgcc ggttgctcat acagtgcgcc 14760
tgattcgcgt gacttctaca tccgccagtc agggtgcaaa ttaatttgac agtcaggtga 14820
atggccgcga ttgacgtgtg gcctctaagt cacctattca attagggcga tcacatgggg 14880
gtcaaactta attaggcagg aaccatgtga ccgaaattaa aaaaaaaaaa aaaaaaaaaa 14940
aaaaa 14945

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: SEQ ID NO:39 with substitution N->Q at
position 9

<400> SEQUENCE: 50

Ser Ser His Leu Gln Leu Ile Tyr Gln Leu Thr Ile Cys Glu Leu Asn
1 5 10 15

Gly

<210> SEQ ID NO 51
<211> LENGTH: 11
<212> TYPE: PRT
<213> ORGANISM: Porcine reproductive and respiratory syndrome virus

<400> SEQUENCE: 51

Ser Ser His Leu Gln Leu Ile Tyr Asn Leu Thr
1 5 10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SEQ ID NO:51 with substitution N->Q at position 9

<400> SEQUENCE: 52

Ser Ser His Leu Gln Leu Ile Tyr Gln Leu Thr
1 5 10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SEQ ID NO:51 with Gly-Gly linker

<400> SEQUENCE: 53

Gly Ser Ser His Leu Gln Leu Ile Tyr Asn Leu Thr Gly
1 5 10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SEQ ID NO:52 with Gly-Gly linker

<400> SEQUENCE: 54

Gly Ser Ser His Leu Gln Leu Ile Tyr Gln Leu Thr Gly
1 5 10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: SEQ ID NO:53 with N-terminal P

<400> SEQUENCE: 55

Pro Gly Ser Ser His Leu Gln Leu Ile Tyr Asn Leu Thr Gly
1 5 10

<210> SEQ ID NO 56
<211> LENGTH: 14984

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SEQ ID NO:49 with insert coding for SEQ ID
      NO:53

<400> SEQUENCE: 56

atgatgtgta gggtattccc cctacataca cgacactctt agtgtttgtg taccttggag     60

gcgtgggtac agccctgccc caccctttgg tccctgttct agcccgacag gtacccttct    120

ctctcggggc gagcgcgccg cctgctgctc ccttgcggcg ggaaggacct cccgagtatt    180

tccggagagc acctgcttta cgggatctcc gccctttaac catgtctggg atgttctccc    240

ggtgcatgtg caccccggct gcccgggtat tttggaacgc cggccaagtc tattgcacac    300

ggtgtctcag tgcacggtct cttctctctc cagaacttca ggacacggac ctcggtgcag    360

ttggcttgtt tcacaagcct aaagacaagc tccattggaa agttcccatt ggtatccccc    420

aggtggaatg ttctccatct gggtgttgct ggctgtcaac cattttttcct ttagcgcgca    480

tgacctccgg caatcacaac ttccttcaac gactcgtgaa ggttgctgat gtattgtacc    540

gtgacggttg cttaacccct agacacctcc gtgaactcca agtttacgag cgtggttgca    600

attggtatcc gattacgggg cctgtgcctg ggatggctgt gtacgcgaac tccatgcacg    660

tgtccgacca accgttccct ggtgccactc atgtgttaac aaattcccct ttgcctcaac    720

gggcttgtcg gcagccgttc tgtccgttcg aagaggccca ttctagcata tacaggtggg    780

aaaaatttgt aatttttatg gattcctcct ccgacggtcg atctcgcatg atgtggactc    840

cggaatccga tgactccacg gctttggaag ttctgccgcc cgagctagaa caccaggtca    900

aggtccttgt tcggagcttt cccgcccatc accttgtcga ccttgccgat tgggagctca    960

ctgagtcccc tgataacggt tttccttca gcacgtcaca tccttgcggc taccttgttc   1020

gggacccggc tgtatccgaa ggcaagtgtt ggctttcctg ctttttgagc cagtcagccg   1080

aagtgctcag tcgcgaggcg catctggcta ccgcctatgg ttaccaaacc aagtggggtg   1140

tgcctggcaa gtacatccag cgcagacttc aagttcacgg tctccgtgct gtggtcgacc   1200

ctgatggtcc cattcacgtt gaagcattgt cttgccccca gtcttggatc aggcacttga   1260

ccctgaatga tgatgtcacc ccgggattcg ttcgcctaat gtctcttcgc attgtgccga   1320

acacagagcc taccacacac cggatctttc gttttggagt gcacaagtgg tatggtgccg   1380

ccggcaaacg ggcccgtggc aagcgtgccg ccaaaagtga gaaagactcg gcttccaccc   1440

tcaaggttgc ccgaccgact tccaccagtg gaatcgtcac ctactcccca cctgcggacg   1500

ggtcttgtgg ttggcatgcc cttgccgcca tactgaaccg gatgattaat aatgacttca   1560

cgtcccctct gcctcggtac aacaggccgg aggacgattg ggcttctgat ggtgaccttg   1620

ctcaggccat tcaatgtttg caactacctg ccgccatagc tcggaaccgc gcctgcccta   1680

acgccaaata cctcataaaa ctcaacggag ttcattggga ggtagaggtg aggcctggaa   1740

tggctcctcg ctccctctct cgtgagtgcg ttgttggcgt ctgctctgaa ggctgtgtcg   1800

cgtcgcctta cccggaggac gggttgccta aacgtgcact tgaggccctg gcgtctgctt   1860

atagactgcc ttcagactgt gtttgtgatg gtattattga cttccttgcc aatccacctc   1920

cccaggagtt ctggactctt gacaaaatgt tgacttcccc gtcaccggag cagtccggct   1980

tctctagtct gtataaattg ttgttagaga tcttgccgca gaaatgcgga tccacagaag   2040
```

-continued

```
gggaattcat ctatactgtt gagaggatgt tgaaggattg tccgagctcc aaacaggcca   2100
tggccctcct tgcaaaaatt aaggtcccat cctcaaaggc cccatccgtg actctgaacg   2160
agtgcttccc cacggatgtt ccagtcaact ctgagttaat atcttgggaa gagcccaaag   2220
accctggcgc tgctgttgtc ctatgtccat cggatgcaaa agaatctaag gaaacagccc   2280
ctgaagaagc tcaagcgaga aaccgtaagg tccttcaccc tgtggtcctt accgaggaac   2340
ttagcgagca acaggtgcag gtggttgagg gtgatcagga tatgccactg gatttgactt   2400
ggccaacctt aaccgctacg gcgacccctg ttagagggcc ggtaccggac aatttgagct   2460
ctggcattgg tgcccagccc gctaccgttc aagaactcat tctggcgagg cctgcacccc   2520
gtcttgttga gcgctgtggc acggagtcga acggcagcag ttcatttctg gatttgcctg   2580
acgtgcagac ctcggaccag cctttagacc tgtccctggc cgcgtggcct gtaagggcta   2640
ccgcgtctga ccccggttgg atccacggta ggcgtgagcc tgtctttgtg aagcctcgag   2700
gtgtttctc tgatggcgag tcggcccttc agttcggaga gctttccgaa gccagttctg   2760
tcgtcgatga ccggacaaaa gaagctccgg tggttgacgc cccccatcgat ttgacaactt   2820
cgaacgagac gctctctggg tctgacccct ttgaattcgc caaattcagg cgcccgcgtt   2880
tctccgcgca agctttaatc gaccgaggtg gtccgcttgc cgatgttcat gcaaagataa   2940
agagtcgggt atatgaacaa tgccttcaag cttgtgaacc tggtagtcgt gcgaccccag   3000
ccaccaagaa gtggctcgac aaaatgtggg acagggtgga catgaaaact tggcgctgca   3060
cctcgcagtt ccaagctggt cacattcttg agtccctcaa attcctccct gacatgattc   3120
aagacacacc gcctcctgtt cccaggaaga accgagctgg tgacagtgcc ggcctgaagc   3180
aactggtggc gcagtgggat aggaaatcga gtgtgacacc ccccacaaaa ccggttggac   3240
cggtgcttga ccaggccgtc cctctgccta tggacatcca gcaaggagat gccatctccg   3300
ctgacaagcc accccattcg caaaaccctt ctagtcaagt agatgtgggt ggaggttgga   3360
aaagttttat gctctccggc acccgtttcg cggggtccgt tagtcagcgc cttacgacat   3420
gggtttttga ggttctctcc catctcccag cttttatgct cacacttttc tcgccacggg   3480
gctctatggc tccaggtgat tggctgtttg caggtgctgt tctacttgct ctcctgctct   3540
gccgttctta cccaatactc ggatgccttc ccttattggg tgtcttttct ggttctgtgc   3600
ggtgtgttcg tttgggtgtt tttggttctt ggatggcttt tgctgtattt ttattctcga   3660
ctccacccga cccagtcggt tcttcttgtg accacgattc gccggagtgt catgctgagc   3720
ttttggctct tgagcagcgc caactttggg aacctgtgcg cagccttgtg gtcgggccat   3780
cgggcctctt atgcgtcatt cttggcaagt tactcggtgg gtcacgttgt ctctggtttg   3840
ttctcctacg tatatgcatg ctcgcagatt tggcaatttc tcttatttat gtggtgtccc   3900
aagggcgttg tcacaagtgt tggggaaagt gtataaggac ggctcctgca gaagtggccc   3960
ttaatgtgtt tcctttttcg cgcgccaccc gctcatctct tgtgtccttg tgtgatcggt   4020
tccaagcgcc aaaaggagtt gaccccgtgc acttggcgac aggctggcgc gggtgctggt   4080
gtggtgagag ccctattcat caatcacacc aaaaaccgat agcttatgcc aacttggatg   4140
aaaagaagat atccgcccag acggtgattg ctgtcccgta tgatcctagt caggccatta   4200
aatgcctgaa agttttgcag gcaggagggg ctattgtgga ccagcctacg cccgaggtcg   4260
tccgtgtgtc tgagattccc ttctcggccc catttttttcc gaaggtccca gtcaacccag   4320
actgcagggt tgtggtagat tcggacactt ttgtggctgc ggtccgctgc ggttattcga   4380
cagcacaact ggtccttggt cggggcaact ttgccaagct aaatcagacc cccctcagga   4440
```

-continued

```
actctgtccc caccaaaaca actggtgggg cctcatacac ccttgccgtg gcccaggtat   4500
ctgtgtggac tcttgttcat ttcatcctcg gcctttggtt aacgtcacct caagtgtgtg   4560
gtcgagggac ctctgacccg tggtgttcga accctttttc gtatcctact tatggccccg   4620
gagttgtgtg ttcctctcga ctctgcgtgt ctgccgacgg agttaccctg ccattgttct   4680
cagccgttgc ccatctttcc ggtagagagg tggggatttt tattttggtg cttgcctcct   4740
tgggcgcttt agcccaccgc ttggctctta aggcagacat gtcaatggtc tttttggcgt   4800
tttgtgctta cgcctggccc atgagctcct ggttaatttg cttctttcct atgctcttga   4860
ggtgggtaac ccttcatcct ctcactatgc tttgggtgca ctcatttttg gtgttttgcc   4920
taccagctgc cggcgttctc tcgctgggaa taaccggtct tctttgggca gttggccgtt   4980
tcacccaggt tgccggaatt atcacacctt atgacatcca ccagtatacc tccggaccac   5040
gtggtgcagc tgctgtagca acggctccag aaggtactta catggcggcc gttcggagag   5100
ccgctttgac tggacggact ttgatcttca caccatctgc agtcggatcc cttcttgaag   5160
gtgctttcag aactcaaaag ccctgcctta acaccgtgaa tgtcgtaggc tcttcccttg   5220
gttctggagg agttttcacc attgatggca gaagagtcat cgtcactgcc acccatgtgt   5280
tgaatggtaa cacagccagg gtcactggtg attcctacaa ccgcatgcac acgttcaata   5340
ctaatggtga ttatgcctgg tcccatgctg atgactggca aggcgttgcc cctatggtta   5400
agatcgctaa ggggtatcgc ggtcgtgcct actggcaaac gtcaaccgga gtcgaacctg   5460
gcatcatggg ggaaggattc gccttctgtt tcactaactg tggcgactca gggtcacctg   5520
tcatttcaga agctggtgac cttattggag tccataccgg ttcaaacaaa ctcggttctg   5580
gtcttgtgac aacccctgaa ggggagacct gctccatcaa ggaaactagg ctctctgacc   5640
tttctagaca ttttgcaggt ccaagcgtcc ctcttgggga cattaagttg agcccagcca   5700
tcatccctga tgtgacaact attccgagtg acttggcatc gctccttgct tctgtccccg   5760
tgatggaagg tggcctctca actgtccagc ttttgtgcgt ctttttcctt ctctggcgca   5820
tgatgggcca tgcctggaca cccattgttg ccgtaggctt ctttttgctg aatgaaattc   5880
tcccagcagt cttggtccga gctgtgttct cttttgcact ctttgtactt gcatgggcca   5940
ccccctggtc ggcacaagtg ttgatgatta gactcctcac ggcggctctc aaccgcaaca   6000
ggttgtccct ggcgttctac gcattcggag gtgtcgttgg cctggccaca gaaatcggga   6060
cttttgctgg tggatggcct gaactgtccc aagccctctc gacatactgc ttcctgccca   6120
ggttccttgc tgtgactagt tatgtcccca ccatcatcat cggtgggctc catgccctcg   6180
gcgtaatttt gtggttattc aaataccgat gcctccacaa catgctggtt ggtgatggga   6240
gtttctcaag cgctttcttc ctacggtatt ttgctgaggg taatcttagg aaaggcgtgt   6300
cgcagtcctg tggcatgaat aacgaatccc tgacagctgc tttggcttgc aagttgtcgc   6360
aagctgacct tgatttttg tccagtttaa cgaacttcaa gtgctttgtg tccgcttcaa   6420
acatgaaaaa tgcagctggc caatacatcg aggcggcgta tgctagagct ctgcgtcagg   6480
agctggcctc cttggttcag gttgacaaga tgaaaggagt attggccaag ctcgaggctt   6540
tcgctgagac ggccactccg tcacttgaca caggggacgt gattgttctg cttgggcaac   6600
acccccatgg atccatcctc gacattaatg tggggggtga aaggaaaact gtgtctgtgc   6660
aagaaacacg atgcctgggt ggttccaaat tcagtgtctg cactgtcgtg tccaacacgc   6720
ccgtggatac cttgaccggt atcccacttc agacgccaac cccacttttt gaaaatggcc   6780
```

-continued cgcgccatcg cagcgaggac gacgacctca aagttgagag aatgaaaaaa cactgtgtat 6840
ccctcggctt ccacaaaatc aatggtaaag tttactgcaa aatttgggac aagtctaacg 6900
gcgacacctt ttacacggat gattcccgat acactcaaga ccatgctttt caggacaggt 6960
caaccgacta tagagacagg gattatgaag gtgtacagac cgcccccaa cagggattcg 7020
atccaaagtc cgaagcccct gttggcactg ttgtaatcgg tggcattacg tataacaggc 7080
atctggtcaa aggtaaggag gtcctagttc ccaaacctga caactgcctt gaagctgcca 7140
gactgtccct tgagcaagct cttgctggga tgggccaaac ttgtgacctt acagctaccg 7200
aagtggagaa actaaagcgc atcattagtc aactccaagg tctgaccact gaacaggctt 7260
taaactgcta gccgccagcg gcttgacccg ctgtggccgc ggcggcctag ttgtaactga 7320
aacggcggta aaaatcgtaa aataccacag cagaactttc accttaggct ctttagacct 7380
aaaagtcacc tccgaggtgg aggtgaagaa atcaactgag caggggcacg ctgtcgtggc 7440
gaacttatgt tccggtgtcg tcttgatgag gcctcaccca ccgtcccttg ttgacgttct 7500
cctcaaaccc ggacttgaca caacacccgg cattcaacca gggcatgggg ccgggaatat 7560
gggcgtgaac ggttctattt gggattttga aactgcaccc acaaaggtag aactagagtt 7620
gtccaagcaa ataatccaag catgtgaagt caggcgcggg gacgccccta acctccaact 7680
cccctacaag ctttatcctg tcagggggga ccccgagcgg cgtaaaggtc gccttgtcaa 7740
cactaggttt ggagatttac cttacaaaac tccccaagac accaagtccg caattcatgc 7800
ggcttgttgc ctgcatccca atggggtcct cgtgtctgat ggcaaatcca cgctgggtac 7860
cactcttcaa catggtttcg agctttatgt ccccactgta ccttatagtg tcatggaata 7920
ccttgattca cgccctgaca ccccttttat gtgtactaaa catggcactt ccaaggctgc 7980
tgcagaggac ctccaaaaat atgacctatc cactcaaggg tttgtcttgc ctggggtcct 8040
acgcctagtg cgcaggttca tctttagcca tgttggtaag gcgccaccac tgttccttcc 8100
atcaacctac cctgccaaga actccatggc aggggtcaat ggccagaggt tcccaacaaa 8160
ggatgtccag agcatacctg aaattgatga aatgtgcgcc cgtgccgtca aggaaaattg 8220
gcagactgtg acaccttgca ccctcaaaaa acagtactgt tccaaaccta aaactagaac 8280
catcctaggt accaacaact tcatagcctt ggctcacagg tcagcactca gtggtgtcac 8340
ccaggcgttc atgaagaagg cctggaagtc cccaattgcc ttggggaaaa acaagtttaa 8400
ggaattgcat tgcactgtcg ccggcagatg ccttgaggct gacctggctt cctgcgatcg 8460
cagcaccccc gccattgtga ggtggtttgt tgccaacctc ctgtatgaac ttgcaggatg 8520
tgaagagtac ttgcctagct acgtgctcaa ctgttgccat gaccttgtgg caacgcagga 8580
tggcgctttc acaaaacgcg gtggcctgtc gtccggggac cccgtcacca gtgtgtccaa 8640
caccgtctac tcactgataa tttacgccca gcacatggtg ctttcggcct tgaagatggg 8700
tcatgaaatt ggtctcaagt tccttgagga acagctcaaa tttgaggacc ttcttgaaat 8760
ccagcccatg ttagtgtatt ctgatgacct cgtcttgtat gcggaaagac ccactttttcc 8820
caactaccat tggtgggtcg agcatcttga cctgatgttg ggctttaaaa cggacccaaa 8880
gaaaactgtc ataactgata aacccagttt tctcggctgc agaattgaag caggacggca 8940
gttagtcccc aatcgcgacc gtattctggc tgctcttgca tatcatatga aggcgcagaa 9000
cgcctcagag tattatgcgt ccgctgccgc aattctgatg gattcgtgtg cttgcattga 9060
ccatgacccc gagtggtatg aggatcttat ctgcggcatc gcccggtgtg ctcgccagga 9120
cggttaccgt tttccaggcc cggcattttt catgtccatg tgggagaagc tgaaaagtca 9180

-continued

```
taatgaaggg aagaaatgcc gtcactgcgg catctgcgac gccaaagccg actatgcgtc   9240
cgcctgtgga cttgatttgt gtttgttcca ttcacacttt catcaacact gcccagtcac   9300
tctgagctgt ggccaccatg ccggttcaaa ggaatgttcg cagtgtcagt cacctgtcgg   9360
ggctggcaaa tccccccttg acgctgtgct gaaacaaatc ccgtacaaac ctcctcgtac   9420
cattatcatg aaggtggaca acaaaacaac gacccttgac ccgggaagat atcagtcccg   9480
tcgaggtctt gttgcagtca aaagaggtat tgcaggtaat gaggttgatc tttctgatgg   9540
agactaccaa gtggtgcctc ttttgccgac ttgcaaagac ataaacatgg tgaaggtggc   9600
ttgcaacgta ctactcagca agtttatagt agggccgcca ggttccggaa aaaccacctg   9660
gctactgaac caagtccagg acgatgatgt catttacaca cctactcatc agacaatgtt   9720
tgacatagtc agtgctctta aagtttgcag gtattccatc ccaggagcct caggactccc   9780
ttttccacca cctgccaggt ccgggccgtg ggttaggctc atcgccagcg gacatgtccc   9840
tggccgagtg tcatatctcg atgaggcagg atattgcaat catctagaca ttctaaggct   9900
gctttccaaa acaccccttg tgtgtttggg tgaccttcag caacttcacc cggtcggctt   9960
tgattcctat tgttatgtgt tcgatcagat gcctcagaag cagctgacca ccatttatag  10020
atttggccct aacatctgtg cagccatcca gccttgttac agggagaaac ttgaatccaa  10080
ggccaggaac accagagtgg ttttcaccac ccggcctgtg gcctttggtc aggtcctgac  10140
accgtaccac aaagatcgta ccggctctgc aataactata gattcatccc agggggcgac  10200
cttcgacatt gtgacattgc atctaccatc gccaaagtcc ctaaacaaat cccgagcact  10260
tgtagccatc actcgggcaa gacatgggtt gttcatttat gaccctcatg accaactcca  10320
ggagtttttc aacttaaccc ccgagcgcac tgattgtaac cttgcgttca gccgtgggga  10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta gaagggagct gcatgccact accacaagta gcacataacc tggggtttta  10560
cttttccccg gacagcccag cttttgcacc cctgccaaaa gagctggcgc cacattggcc  10620
agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg gggcgagcc  10800
tcaggccctg ccagaaacac tcgtttcaac aggacgtata gccacagatt gtcgggaata  10860
tctcgacgcg gctgaggaag aggcagcgag agaacttccc cacgcattta ttggcgatgt  10920
caaaggcact acgatcgggg ggtgtcacca cattacatcg aaatacctac ctaggtccct  10980
gcctaaagac tctgttgctg tggttggggt gagttcgccc ggtagggctg ctaaagccgt  11040
gtgcactctc accgatgtgt acctccccga actccgacca tatttgcaac cggagacggc  11100
atcaaaatgc tggaaactta aactggattt cagggatgtt cgactgatgg tctggaaagg  11160
cgccacagcc tatttccagt tggaagggct gacatggtca gcgctgcccg attatgctag  11220
gttcattcag ctacccaagg atgccgttgt gtacatcgat ccgtgtatag ggccggcaac  11280
agccaatcgc aaggttgtgc gaaccacaga ctggcgggcc gacctggcag tgacaccgta  11340
tgattacggt gctcaggtca ttttgacaac agcctggttc gaggaccttg ggccgcagtg  11400
gaagattttg ggggttgcagc ctttcagacg aacatttggc tttgagaaca ctgaagattg  11460
ggcaattctc gcacgccgta tgaatgacgg caaagattac actgactata attggcattg  11520
```

-continued

```
tgtacgagaa cgcccacacg caatttacgg gcgcgcccgt gaccatacgt atcattttgc  11580
ccttggcact gaactgcaag tagagctggg cagaccccgg ctgcctcctg agcaagtgcc  11640
gtgaacgcgg agtgatgcaa tgggtttact gtggagtaaa atcagtcagt tgttcgtgga  11700
tgccttcact gagttccttg ttagtgtggt tgacattgtc atctttctcg ccatattgtt  11760
tgggttcact gttgcaggct ggttattggt cttccttctc agagtggttt gctccgcgtt  11820
tctccgttcg cgctctgcca ttcactcttc cgaactatcg aaggtcctat gagggcttgc  11880
tacccaactg cagaccggat gtcccacaat tcgcagttaa gcacccgttg ggtatacttt  11940
ggcatatgcg agtctcccac ctaattgacg aaatggtctc tcgccgcatt taccggacca  12000
tggaacattc gggtcaagcg gcctggaagc aggttgttag tgaagccact ctcacaaaac  12060
tgtcaaggct tgacgtagtc actcatttcc aacacctggc cgcagtggag gctgattctt  12120
gccgcttcct tagctcacga ctcgcgatgc tgaaaaacct tgccgttggc aatgtgagcc  12180
tggagtacaa cactactttg gaccgcgttg agctcatctt tcccacacca ggtacgaggc  12240
ccaagttgac cgattttagg caatggctta tcagcgtgca cgcttccatc ttctcctctg  12300
tggcttcgtc tgttaccttg ttcacagtgc tttggcttcg aattccagct ctacgctatg  12360
tttttggttt ccattggccc acggcaacac atcattcgaa ctaactatca attacactat  12420
atgtaagcca tgccctacca gtcaagctgc ccaacaaaga ctcgagcctg gccgtaacgt  12480
gtggtgcaaa atagggcacg acaggtgtga ggaacgtgac catgatgagt tgtcaatgtc  12540
cattccgtcc gggtacgaca acctcaaact tgagggttat tatgcttggc tggctttttt  12600
gtccttttcc tacgcggccc aattccatcc ggagctgttc ggaataggaa acgtgtcgcg  12660
cgtctttgtg gataagcgac accagttcat ttgcgccgag catgatggac aaaattcaac  12720
catatctgcc agacacaaca tctccgcgtc gtatgcggtg tattaccatc atcaaataga  12780
cgggggcaat tggtttcatt tggaatggct gcgaccattc ttttcctcct ggctggtgct  12840
caacatctca tggtttctga ggcgttcgcc tgcaagccct gcttctcgac gcatctatca  12900
gatattaaga ccaacacgac cgcggctgcc ggtttcatgg tccttcagaa catcaattgt  12960
ttccaatctc acggtagctc ccatttacag ttgatttata acttaacggg ctcatcccaa  13020
tgtcgtgaag ccgtcggcat tccccagtac atcacgataa cggctaatgt gaccgatgaa  13080
tcgtatttgt acaacgcgga cttgctgatg ctttccgcgt gccttttcta cgcctcggaa  13140
atgagcgaga aaggcttcaa agtcatcttt gggaatattt ctggcgttgt ttccgcttgt  13200
gttaatttca cagattatgt ggcccatgtg acccaacaca ctcagcagca ccatttggta  13260
attgatcaca ttcggttact acacttcttg acaccgtcta cgatgaggtg ggctacaacc  13320
attgcttgtt tgcttgccat tcttttggcg gtatgaaatg ttcttgcaag ttggggcatt  13380
tcttgactcc tcactcttgc ttctggtggc ttttttttgct gtgtaccggc ttgtcttggt  13440
cctttgtcga tggcaacgac gacagctcga catcccaata catatataat ttgacgatat  13500
gcgagctgaa tgggaccgaa tggttgtccg gtcattttga ttgggcagtc gaaacctttg  13560
tgctttaccc agttgccact catatcattt cactgggttt tctcacaaca agccatttcc  13620
ttgatgcgct cggtctcggc gctgtgtccg ccacaggatt cattggcgag cggtatgtac  13680
ttagcagcat gtacggcgtt tgcgccttcg cggcgttcgt atgttttgtc atccgtgctg  13740
ctaaaaattg catggcttgc cgctatgccc gcacccggtt taccaacttc atcgtggacg  13800
accggggaag aatccatcga tggaagtctt caatagtggt ggagaaattg ggcaaagctg  13860
aagtcggtgg tgaccttgtc aacattaagc atgttgtcct cgaaggggtt aaagctcaac  13920
```

ctttgacgag gacttcggct gagcaatggg aagcctagac gacttttgca acgatcccac 13980
cgccgcacaa aaactcgtgc tggcctttag catcacatat acacccataa tgatatacgc 14040
ccttaaggtg tcacgcggcc gactcctggg gctgttgcac atcttgatat ttctgaattg 14100
ttcctttact tttgggtaca tgacatatgt gcattttcaa tccaccaacc gtgtcgcatt 14160
cactctgggg gctgtagtcg cccttttgtg gggtgtttac agcctcacag agtcatggaa 14220
gttcatcact tccagatgca gattgtgttg cctaggccgg cgatacattc tggcccctgc 14280
ccatcacgta gaaagtgctg caggcctcca ttcaatccca gcgtctggta accgagcata 14340
cgctgtgaga aagcccggac taacatcagt gaacggcact ctagtacctg ggcttcggag 14400
cctcgtgctg ggcggcaaac gagctgttaa acgaggagtg gttaacctcg tcaagtatgg 14460
ccggtaagaa ccagagccag aagaaaagaa gaaatgcagc tccgatgggg aaaggccagc 14520
cagtcaatca actgtgccag ttgctgggta caatgataaa gtcccagcgc cagcaatcta 14580
ggggaggaca ggccaaaaag aagaagcctg agaagccaca ttttccccta gctgctgaag 14640
atgacattcg gcaccatctc acccaggccg aacgttccct ctgcttgcaa tcgatccaga 14700
cggctttcaa tcaaggcgca ggaactgcgt cgctttcatc cagcgggaag gtcagtttcc 14760
aggttgagtt catgctgccg gttgctcata cagtgcgcct gattcgcgtg acttctacat 14820
ccgccagtca gggtgcaaat taatttgaca gtcaggtgaa tggccgcgat tgacgtgtgg 14880
cctctaagtc acctattcaa ttagggcgat cacatggggg tcaaacttaa ttaggcagga 14940
accatgtgac cgaaattaaa aaaaaaaaaa aaaaaaaaaa aaaa 14984

<210> SEQ ID NO 57
<211> LENGTH: 14984
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SEQ ID NO:49 with insert coding for SEQ ID NO:54

<400> SEQUENCE: 57
atgatgtgta gggtattccc cctacataca cgacactctt agtgtttgtg taccttggag 60
gcgtgggtac agccctgccc cacccctttgg tccctgttct agcccgacag gtacccttct 120
ctctcggggc gagcgcgccg cctgctgctc ccttgcggcg ggaaggacct cccgagtatt 180
tccggagagc acctgcttta cgggatctcc gccctttaac catgtctggg atgttctccc 240
ggtgcatgtg caccccggct gcccgggtat tttggaacgc cggccaagtc tattgcacac 300
ggtgtctcag tgcacggtct cttctctctc cagaacttca ggacacggac ctcggtgcag 360
ttggcttgtt tcacaagcct aaagacaagc tccattggaa agttcccatt ggtatccccc 420
aggtggaatg ttctccatct gggtgttgct ggctgtcaac cattttttcct ttagcgcgca 480 tgacctccgg caatcacaac ttccttcaac gactcgtgaa ggttgctgat gtattgtacc 540
gtgacggttg cttaacccct agacacctcc gtgaactcca agtttacgag cgtggttgca 600
attggtatcc gattacgggg cctgtgcctg ggatggctgt gtacgcgaac tccatgcacg 660
tgtccgacca accgttccct ggtgccactc atgtgttaac aaattcccct ttgcctcaac 720
gggcttgtcg gcagccgttc tgtccgttcg aagaggccca ttctagcata tacaggtggg 780
aaaaatttgt aatttttatg gattcctcct ccgacggtcg atctcgcatg atgtggactc 840

-continued

```
cggaatccga tgactccacg gctttggaag ttctgccgcc cgagctagaa caccaggtca    900
aggtccttgt tcggagcttt cccgcccatc accttgtcga ccttgccgat tgggagctca    960
ctgagtcccc tgataacggt ttttccttca gcacgtcaca tccttgcggc taccttgttc   1020
gggacccggc tgtatccgaa ggcaagtgtt ggctttcctg ctttttgagc cagtcagccg   1080
aagtgctcag tcgcgaggcg catctggcta ccgcctatgg ttaccaaacc aagtggggtg   1140
tgcctggcaa gtacatccag cgcagacttc aagttcacgg tctccgtgct gtggtcgacc   1200
ctgatggtcc cattcacgtt gaagcattgt cttgcccca gtcttggatc aggcacttga   1260
ccctgaatga tgatgtcacc ccgggattcg ttcgcctaat gtctcttcgc attgtgccga   1320
acacagagcc taccacacac cggatctttc gttttggagt gcacaagtgg tatggtgccg   1380
ccggcaaacg ggcccgtggc aagcgtgccg ccaaaagtga gaaagactcg gcttccaccc   1440
tcaaggttgc ccgaccgact tccaccagtg gaatcgtcac ctactcccca cctgcggacg   1500
ggtcttgtgg ttggcatgcc cttgccgcca tactgaaccg gatgattaat aatgacttca   1560
cgtcccctct gcctcggtac aacaggccgg aggacgattg ggcttctgat ggtgaccttg   1620
ctcaggccat tcaatgtttg caactacctg ccgccatagc tcggaaccgc gcctgcccta   1680
acgccaaata cctcataaaa ctcaacggag ttcattggga ggtagaggtg aggcctggaa   1740
tggctcctcg ctccctctct cgtgagtgcg ttgttggcgt ctgctctgaa ggctgtgtcg   1800
cgtcgcctta cccggaggac gggttgccta aacgtgcact tgaggccctg gcgtctgctt   1860
atagactgcc ttcagactgt gtttgtgatg gtattattga cttccttgcc aatccacctc   1920
cccaggagtt ctggactctt gacaaaatgt tgacttcccc gtcaccggag cagtccggct   1980
tctctagtct gtataaattg ttgttagaga tcttgccgca gaaatgcgga tccacagaag   2040
gggaattcat ctatactgtt gagaggatgt tgaaggattg tccgagctcc aaacaggcca   2100
tggccctcct tgcaaaaatt aaggtcccat cctcaaaggc cccatccgtg actctgaacg   2160
agtgcttccc cacggatgtt ccagtcaact ctgagttaat atcttgggaa gagcccaaag   2220
accctggcgc tgctgttgtc ctatgtccat cggatgcaaa agaatctaag gaaacagccc   2280
ctgaagaagc tcaagcgaga aaccgtaagg tccttcaccc tgtggtcctt accgaggaac   2340
ttagcgagca acaggtgcag gtggttgagg gtgatcagga tatgccactg gatttgactt   2400
ggccaacctt aaccgctacg gcgacccctg ttagagggcc ggtaccggac aatttgagct   2460
ctggcattgg tgcccagccc gctaccgttc aagaactcat tctggcgagg cctgcacccc   2520
gtcttgttga gcgctgtggc acggagtcga acggcagcag ttcatttctg gatttgcctg   2580
acgtgcagac ctcggaccag cctttagacc tgtccctggc cgcgtggcct gtaagggcta   2640
ccgcgtctga ccccggttgg atccacggta ggcgtgagcc tgtctttgtg aagcctcgag   2700
gtgttttctc tgatggcgag tcggcccttc agttcggaga gctttccgaa gccagttctg   2760
tcgtcgatga ccggacaaaa gaagctccgg tggttgacgc cccccatcgat ttgacaactt   2820
cgaacgagac gctctctggg tctgacccct ttgaattcgc caaattcagg cgcccgcgtt   2880
tctccgcgca agctttaatc gaccgaggtg gtccgcttgc cgatgttcat gcaaagataa   2940
agagtcgggt atatgaacaa tgccttcaag cttgtgaacc tggtagtcgt gcgaccccag   3000
ccaccaagaa gtggctcgac aaaatgtggg acagggtgga catgaaaact tggcgctgca   3060
cctcgcagtt ccaagctggt cacattcttg agtccctcaa attcctccct gacatgattc   3120
aagacacacc gcctcctgtt cccaggaaga accgagctgg tgacagtgcc ggcctgaagc   3180
aactggtggc gcagtgggat aggaaatcga gtgtgacacc ccccacaaaa ccggttggac   3240
```

cggtgcttga ccaggccgtc cctctgccta tggacatcca gcaaggagat gccatctccg 3300
ctgacaagcc accccattcg caaaaccctt ctagtcaagt agatgtgggt ggaggttgga 3360
aaagttttat gctctccggc acccgtttcg cggggtccgt tagtcagcgc cttacgacat 3420
gggtttttga ggttctctcc catctcccag cttttatgct cacacttttc tcgccacggg 3480
gctctatggc tccaggtgat tggctgtttg caggtgctgt tctacttgct ctcctgctct 3540
gccgttctta cccaatactc ggatgccttc ccttattggg tgtcttttct ggttctgtgc 3600
ggtgtgttcg tttgggtgtt tttggttctt ggatggcttt tgctgtattt ttattctcga 3660
ctccacccga cccagtcggt tcttcttgtg accacgattc gccggagtgt catgctgagc 3720
ttttggctct tgagcagcgc caactttggg aacctgtgcg cagccttgtg gtcgggccat 3780
cgggcctctt atgcgtcatt cttggcaagt tactcggtgg gtcacgttgt ctctggtttg 3840
ttctcctacg tatatgcatg ctcgcagatt tggcaatttc tcttatttat gtggtgtccc 3900
aagggcgttg tcacaagtgt tggggaaagt gtataaggac ggctcctgca gaagtggccc 3960
ttaatgtgtt tcctttttcg cgcgccaccc gctcatctct tgtgtccttg tgtgatcggt 4020
tccaagcgcc aaaaggagtt gaccccgtgc acttggcgac aggctggcgc gggtgctggt 4080
gtggtgagag ccctattcat caatcacacc aaaaaccgat agcttatgcc aacttggatg 4140
aaaagaagat atccgcccag acggtgattg ctgtcccgta tgatcctagt caggccatta 4200
aatgcctgaa agttttgcag gcaggagggg ctattgtgga ccagcctacg cccgaggtcg 4260
tccgtgtgtc tgagattccc ttctcggccc catttttcc gaaggtccca gtcaacccag 4320
actgcagggt tgtggtagat tcggacactt ttgtggctgc ggtccgctgc ggttattcga 4380
cagcacaact ggtccttggt cggggcaact ttgccaagct aaatcagacc cccctcagga 4440
actctgtccc caccaaaaca actggtgggg cctcatacac ccttgccgtg gcccaggtat 4500
ctgtgtggac tcttgttcat ttcatcctcg gcctttggtt aacgtcacct caagtgtgtg 4560
gtcgagggac ctctgacccg tggtgttcga acccttttc gtatcctact tatggccccg 4620
gagttgtgtg ttcctctcga ctctgcgtgt ctgccgacgg agttaccctg ccattgttct 4680
cagccgttgc ccatctttcc ggtagagagg tggggatttt tattttggtg cttgcctcct 4740
tgggcgcttt agcccaccgc ttggctctta aggcagacat gtcaatggtc tttttggcgt 4800
tttgtgctta cgcctggccc atgagctcct ggttaatttg cttctttcct atgctcttga 4860
ggtgggtaac ccttcatcct ctcactatgc tttgggtgca ctcatttttg gtgttttgcc 4920
taccagctgc cggcgttctc tcgctgggaa taaccggtct tctttgggca gttggccgtt 4980
tcacccaggt tgccggaatt atcacacctt atgacatcca ccagtatacc tccggaccac 5040
gtggtgcagc tgctgtagca acggctccag aaggtactta catggcggcc gttcggagag 5100
ccgctttgac tggacggact ttgatcttca caccatctgc agtcggatcc cttcttgaag 5160
gtgctttcag aactcaaaag ccctgcctta acaccgtgaa tgtcgtaggc tcttcccttg 5220
gttctggagg agttttcacc attgatggca gaagagtcat cgtcactgcc acccatgtgt 5280
tgaatggtaa cacagccagg gtcactggtg attcctacaa ccgcatgcac acgttcaata 5340
ctaatggtga ttatgcctgg tcccatgctg atgactggca aggcgttgcc cctatggtta 5400
agatcgctaa ggggtatcgc ggtcgtgcct actggcaaac gtcaaccgga gtcgaacctg 5460
gcatcatggg ggaaggattc gccttctgtt tcactaactg tggcgactca gggtcacctg 5520
tcatttcaga agctggtgac cttattggag tccataccgg ttcaaacaaa ctcggttctg 5580

-continued gtcttgtgac aacccctgaa ggggagacct gctccatcaa ggaaactagg ctctctgacc 5640
tttctagaca ttttgcaggt ccaagcgtcc ctcttgggga cattaagttg agcccagcca 5700
tcatccctga tgtgacaact attccgagtg acttggcatc gctccttgct tctgtccccg 5760
tgatggaagg tggcctctca actgtccagc ttttgtgcgt ctttttcctt ctctggcgca 5820
tgatgggcca tgcctggaca cccattgttg ccgtaggctt ctttttgctg aatgaaattc 5880
tcccagcagt cttggtccga gctgtgttct cttttgcact ctttgtactt gcatgggcca 5940
ccccctggtc ggcacaagtg ttgatgatta gactcctcac ggcggctctc aaccgcaaca 6000
ggttgtccct ggcgttctac gcattcggag gtgtcgttgg cctggccaca gaaatcggga 6060
cttttgctgg tggatggcct gaactgtccc aagccctctc gacatactgc ttcctgccca 6120
ggttccttgc tgtgactagt tatgtcccca ccatcatcat cggtgggctc catgccctcg 6180
gcgtaatttt gtggttattc aaataccgat gcctccacaa catgctggtt ggtgatggga 6240
gtttctcaag cgctttcttc ctacggtatt ttgctgaggg taatcttagg aaaggcgtgt 6300
cgcagtcctg tggcatgaat aacgaatccc tgacagctgc tttggcttgc aagttgtcgc 6360
aagctgacct tgatttttg tccagtttaa cgaacttcaa gtgctttgtg tccgcttcaa 6420
acatgaaaaa tgcagctggc caatacatcg aggcggcgta tgctagagct ctgcgtcagg 6480
agctggcctc cttggttcag gttgacaaga tgaaaggagt attggccaag ctcgaggctt 6540
tcgctgagac ggccactccg tcacttgaca caggggacgt gattgttctg cttgggcaac 6600
acccccatgg atccatcctc gacattaatg tggggggtga aaggaaaact gtgtctgtgc 6660
aagaaacacg atgcctgggt ggttccaaat tcagtgtctg cactgtcgtg tccaacacgc 6720
ccgtggatac cttgaccggt atcccacttc agacgccaac cccacttttt gaaaatggcc 6780
cgcgccatcg cagcgaggac gacgacctca aagttgagag aatgaaaaaa cactgtgtat 6840
ccctcggctt ccacaaaatc aatggtaaag tttactgcaa aatttgggac aagtctaacg 6900
gcgacacctt ttacacggat gattcccgat acactcaaga ccatgctttt caggacaggt 6960
caaccgacta tagagacagg gattatgaag gtgtacagac cgcccccaa cagggattcg 7020 atccaaagtc cgaagcccct gttggcactg ttgtaatcgg tggcattacg tataacaggc 7080
atctggtcaa aggtaaggag gtcctagttc ccaaacctga caactgcctt gaagctgcca 7140
gactgtccct tgagcaagct cttgctggga tgggccaaac ttgtgacctt acagctaccg 7200
aagtggagaa actaaagcgc atcattagtc aactccaagg tctgaccact gaacaggctt 7260
taaactgcta gccgccagcg gcttgacccg ctgtggccgc ggcggcctag ttgtaactga 7320
aacggcggta aaaatcgtaa aataccacag cagaactttc accttaggct ctttagacct 7380
aaaagtcacc tccgaggtgg aggtgaagaa atcaactgag caggggcacg ctgtcgtggc 7440
gaacttatgt tccggtgtcg tcttgatgag gcctcaccca ccgtcccttg ttgacgttct 7500
cctcaaaccc ggacttgaca caacacccgg cattcaacca gggcatgggg ccgggaatat 7560
gggcgtgaac ggttctattt gggattttga aactgcaccc acaaaggtag aactagagtt 7620
gtccaagcaa ataatccaag catgtgaagt caggcgcggg gacgccccta acctccaact 7680
cccctacaag ctttatcctg tcagggggga ccccgagcgg cgtaaaggtc gccttgtcaa 7740
cactaggttt ggagatttac cttacaaaac tccccaagac accaagtccg caattcatgc 7800
ggcttgttgc ctgcatccca atggggtcct cgtgtctgat ggcaaatcca cgctgggtac 7860
cactcttcaa catggtttcg agctttatgt ccccactgta ccttatagtg tcatggaata 7920
ccttgattca cgccctgaca cccctttat gtgtactaaa catggcactt ccaaggctgc 7980

-continued tgcagaggac ctccaaaaat atgacctatc cactcaaggg tttgtcttgc ctggggtcct 8040
acgcctagtg cgcaggttca tctttagcca tgttggtaag gcgccaccac tgttccttcc 8100
atcaacctac cctgccaaga actccatggc aggggtcaat ggccagaggt tcccaacaaa 8160
ggatgtccag agcatacctg aaattgatga aatgtgcgcc cgtgccgtca aggaaaattg 8220
gcagactgtg acaccttgca ccctcaaaaa acagtactgt tccaaaccta aaactagaac 8280
catcctaggt accaacaact tcatagcctt ggctcacagg tcagcactca gtggtgtcac 8340
ccaggcgttc atgaagaagg cctggaagtc cccaattgcc ttggggaaaa acaagtttaa 8400
ggaattgcat tgcactgtcg ccggcagatg ccttgaggct gacctggctt cctgcgatcg 8460
cagcaccccc gccattgtga ggtggtttgt tgccaacctc ctgtatgaac ttgcaggatg 8520
tgaagagtac ttgcctagct acgtgctcaa ctgttgccat gaccttgtgg caacgcagga 8580
tggcgctttc acaaaacgcg gtggcctgtc gtccggggac cccgtcacca gtgtgtccaa 8640
caccgtctac tcactgataa tttacgccca gcacatggtg ctttcggcct tgaagatggg 8700
tcatgaaatt ggtctcaagt tccttgagga acagctcaaa tttgaggacc ttcttgaaat 8760
ccagcccatg ttagtgtatt ctgatgacct cgtcttgtat gcggaaagac ccacttttcc 8820
caactaccat tggtgggtcg agcatcttga cctgatgttg ggctttaaaa cggacccaaa 8880
gaaaactgtc ataactgata aacccagttt tctcggctgc agaattgaag caggacggca 8940
gttagtcccc aatcgcgacc gtattctggc tgctcttgca tatcatatga aggcgcagaa 9000
cgcctcagag tattatgcgt ccgctgccgc aattctgatg gattcgtgtg cttgcattga 9060
ccatgacccc gagtggtatg aggatcttat ctgcggcatc gcccggtgtg ctcgccagga 9120
cggttaccgt tttccaggcc cggcattttt catgtccatg tgggagaagc tgaaaagtca 9180
taatgaaggg aagaaatgcc gtcactgcgg catctgcgac gccaaagccg actatgcgtc 9240
cgcctgtgga cttgatttgt gtttgttcca ttcacacttt catcaacact gcccagtcac 9300
tctgagctgt ggccaccatg ccggttcaaa ggaatgttcg cagtgtcagt cacctgtcgg 9360
ggctggcaaa tccccccttg acgctgtgct gaaacaaatc ccgtacaaac ctcctcgtac 9420
cattatcatg aaggtggaca acaaaacaac gacccttgac ccgggaagat atcagtcccg 9480
tcgaggtctt gttgcagtca aaagaggtat tgcaggtaat gaggttgatc tttctgatgg 9540
agactaccaa gtggtgcctc ttttgccgac ttgcaaagac ataaacatgg tgaaggtggc 9600
ttgcaacgta ctactcagca agtttatagt agggccgcca ggttccggaa aaaccacctg 9660
gctactgaac caagtccagg acgatgatgt catttacaca cctactcatc agacaatgtt 9720
tgacatagtc agtgctctta aagtttgcag gtattccatc ccaggagcct caggactccc 9780
ttttccacca cctgccaggt ccgggccgtg ggttaggctc atcgccagcg gacatgtccc 9840
tggccgagtg tcatatctcg atgaggcagg atattgcaat catctagaca ttctaaggct 9900
gctttccaaa acaccccttg tgtgtttggg tgaccttcag caacttcacc cggtcggctt 9960
tgattcctat tgttatgtgt tcgatcagat gcctcagaag cagctgacca ccatttatag 10020
atttggccct aacatctgtg cagccatcca gccttgttac agggagaaac ttgaatccaa 10080
ggccaggaac accagagtgg ttttcaccac ccggcctgtg gcctttggtc aggtcctgac 10140
accgtaccac aaagatcgta ccggctctgc aataactata gattcatccc agggggcgac 10200
cttcgacatt gtgacattgc atctaccatc gccaaagtcc ctaaacaaat cccgagcact 10260
tgtagccatc actcgggcaa gacatgggtt gttcatttat gaccctcatg accaactcca 10320

```
ggagtttttc aacttaaccc ccgagcgcac tgattgtaac cttgcgttca gccgtgggga  10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta gaagggagct gcatgccact accacaagta gcacataacc tggggtttta  10560
cttttccccg gacagcccag cttttgcacc cctgccaaaa gagctggcgc cacattggcc  10620
agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg gggcgagcc   10800
tcaggccctg ccagaaacac tcgtttcaac aggacgtata gccacagatt gtcgggaata  10860
tctcgacgcg gctgaggaag aggcagcgag agaacttccc cacgcattta ttggcgatgt  10920
caaaggcact acgatcgggg ggtgtcacca cattacatcg aaatacctac ctaggtccct  10980
gcctaaagac tctgttgctg tggttggggt gagttcgccc ggtagggctg ctaaagccgt  11040
gtgcactctc accgatgtgt acctccccga actccgacca tatttgcaac cggagacggc  11100
atcaaaatgc tggaaactta aactggattt cagggatgtt cgactgatgg tctggaaagg  11160
cgccacagcc tatttccagt tggaagggct gacatggtca gcgctgcccg attatgctag  11220
gttcattcag ctacccaagg atgccgttgt gtacatcgat ccgtgtatag ggccggcaac  11280
agccaatcgc aaggttgtgc gaaccacaga ctggcgggcc gacctggcag tgacaccgta  11340
tgattacggt gctcaggtca ttttgacaac agcctggttc gaggaccttg ggccgcagtg  11400
gaagattttg ggggttgcagc ctttcagacg aacatttggc tttgagaaca ctgaagattg  11460
ggcaattctc gcacgccgta tgaatgacgg caaagattac actgactata attggcattg  11520
tgtacgagaa cgcccacacg caatttacgg gcgcgcccgt gaccatacgt atcattttgc  11580
ccttggcact gaactgcaag tagagctggg cagaccccgg ctgcctcctg agcaagtgcc  11640
gtgaacgcgg agtgatgcaa tgggtttact gtggagtaaa atcagtcagt tgttcgtgga  11700
tgccttcact gagttccttg ttagtgtggt tgacattgtc atctttctcg ccatattgtt  11760
tgggttcact gttgcaggct ggttattggt cttccttctc agagtggttt gctccgcgtt  11820
tctccgttcg cgctctgcca ttcactcttc cgaactatcg aaggtcctat gagggcttgc  11880
tacccaactg cagaccggat gtcccacaat tcgcagttaa gcacccgttg ggtatacttt  11940
ggcatatgcg agtctcccac ctaattgacg aaatggtctc tcgccgcatt taccggacca  12000
tggaacattc gggtcaagcg gcctggaagc aggttgttag tgaagccact ctcacaaaac  12060
tgtcaaggct tgacgtagtc actcatttcc aacacctggc cgcagtggag gctgattctt  12120
gccgcttcct tagctcacga ctcgcgatgc tgaaaaacct tgccgttggc aatgtgagcc  12180
tggagtacaa cactactttg gaccgcgttg agctcatctt tcccacacca ggtacgaggc  12240
ccaagttgac cgattttagg caatggctta tcagcgtgca cgcttccatc ttctcctctg  12300
tggcttcgtc tgttaccttg ttcacagtgc tttggcttcg aattccagct ctacgctatg  12360
tttttggttt ccattggccc acggcaacac atcattcgaa ctaactatca attacactat  12420
atgtaagcca tgccctacca gtcaagctgc ccaacaaaga ctcgagcctg gccgtaacgt  12480
gtggtgcaaa atagggcacg acaggtgtga ggaacgtgac catgatgagt tgtcaatgtc  12540
cattccgtcc gggtacgaca acctcaaact tgagggttat tatgcttggc tggctttttt  12600
gtccttttcc tacgcggccc aattccatcc ggagctgttc ggaataggaa acgtgtcgcg  12660
cgtctttgtg gataagcgac accagttcat ttgcgccgag catgatggac aaaattcaac  12720
```

```
catatctgcc agacacaaca tctccgcgtc gtatgcggtg tattaccatc atcaaataga  12780
cgggggcaat tggtttcatt tggaatggct gcgaccattc ttttcctcct ggctggtgct  12840
caacatctca tggtttctga ggcgttcgcc tgcaagccct gcttctcgac gcatctatca  12900
gatattaaga ccaacacgac cgcggctgcc ggtttcatgg tccttcagaa catcaattgt  12960
ttccaatctc acggtagctc ccatttacag ttgatttatc agttaacggg ctcatcccaa  13020
tgtcgtgaag ccgtcggcat tccccagtac atcacgataa cggctaatgt gaccgatgaa  13080
tcgtatttgt acaacgcgga cttgctgatg ctttccgcgt gccttttcta cgcctcggaa  13140
atgagcgaga aaggcttcaa agtcatcttt gggaatattt ctggcgttgt ttccgcttgt  13200
gttaatttca cagattatgt ggcccatgtg acccaacaca ctcagcagca ccatttggta  13260
attgatcaca ttcggttact acacttcttg acaccgtcta cgatgaggtg ggctacaacc  13320
attgcttgtt tgcttgccat tcttttggcg gtatgaaatg ttcttgcaag ttggggcatt  13380
tcttgactcc tcactcttgc ttctggtggc ttttttgct gtgtaccggc ttgtcttggt  13440
cctttgtcga tggcaacgac gacagctcga catcccaata catatataat ttgacgatat  13500
gcgagctgaa tgggaccgaa tggttgtccg gtcattttga ttgggcagtc gaaacctttg  13560
tgctttaccc agttgccact catatcattt cactgggttt tctcacaaca agccatttcc  13620
ttgatgcgct cggtctcggc gctgtgtccg ccacaggatt cattggcgag cggtatgtac  13680
ttagcagcat gtacggcgtt tgcgccttcg cggcgttcgt atgttttgtc atccgtgctg  13740
ctaaaaattg catggcttgc cgctatgccc gcacccggtt taccaacttc atcgtggacg  13800
accggggaag aatccatcga tggaagtctt caatagtggt ggagaaattg ggcaaagctg  13860
aagtcggtgg tgaccttgtc aacattaagc atgttgtcct cgaaggggtt aaagctcaac  13920
ctttgacgag gacttcggct gagcaatggg aagcctagac gacttttgca acgatcccac  13980
cgccgcacaa aaactcgtgc tggcctttag catcacatat acacccataa tgatatacgc  14040
ccttaaggtg tcacgcggcc gactcctggg gctgttgcac atcttgatat ttctgaattg  14100
ttcctttact tttgggtaca tgacatatgt gcattttcaa tccaccaacc gtgtcgcatt  14160
cactctgggg gctgtagtcg cccttttgtg gggtgtttac agcctcacag agtcatggaa  14220
gttcatcact tccagatgca gattgtgttg cctaggccgg cgatacattc tggcccctgc  14280
ccatcacgta gaaagtgctg caggcctcca ttcaatccca gcgtctggta accgagcata  14340
cgctgtgaga aagcccggac taacatcagt gaacggcact ctagtacctg ggcttcggag  14400
cctcgtgctg ggcggcaaac gagctgttaa acgaggagtg gttaacctcg tcaagtatgg  14460
ccggtaagaa ccagagccag aagaaaagaa gaaatgcagc tccgatgggg aaaggccagc  14520
cagtcaatca actgtgccag ttgctgggta caatgataaa gtcccagcgc cagcaatcta  14580
ggggaggaca ggccaaaaag aagaagcctg agaagccaca ttttccccta gctgctgaag  14640
atgacattcg gcaccatctc acccaggccg aacgttccct ctgcttgcaa tcgatccaga  14700
cggctttcaa tcaaggcgca ggaactgcgt cgctttcatc cagcgggaag gtcagtttcc  14760
aggttgagtt catgctgccg gttgctcata cagtgcgcct gattcgcgtg acttctacat  14820
ccgccagtca gggtgcaaat taatttgaca gtcaggtgaa tggccgcgat tgacgtgtgg  14880
cctctaagtc acctattcaa ttagggcgat cacatggggg tcaaacttaa ttaggcagga  14940
accatgtgac cgaaattaaa aaaaaaaaaa aaaaaaaaaa aaaa                  14984
```

<210> SEQ ID NO 58

<211> LENGTH: 14984
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SEQ ID NO:48 with deletion encoding ORF4 protein with deletion of 14 aa (aa 56-69), wherein insert coding for SEQ ID NO:55 is included

<400> SEQUENCE: 58

```
atgatgtgta gggtattccc cctacataca cgacactctt agtgtttgtg taccttggag     60

gcgtgggtac agccctgccc cacccttttgg tccctgttct agcccgacag gtacccttct    120

ctctcggggc gagcgcgccg cctgctgctc ccttgcggcg ggaaggacct cccgagtatt    180

tccggagagc acctgcttta cgggatctcc gccctttaac catgtctggg atgttctccc    240

ggtgcatgtg caccccggct gcccgggtat tttggaacgc cggccaagtc tattgcacac    300

ggtgtctcag tgcacggtct cttctctctc cagaacttca ggacacggac ctcggtgcag    360

ttggcttgtt tcacaagcct aaagacaagc tccattggaa agttcccatt ggtatccccc    420

aggtggaatg ttctccatct gggtgttgct ggctgtcaac catttttcct ttagcgcgca    480

tgacctccgg caatcacaac ttccttcaac gactcgtgaa ggttgctgat gtattgtacc    540

gtgacggttg cttaacccct agacacctcc gtgaactcca agtttacgag cgtggttgca    600

attggtatcc gattacgggg cctgtgcctg ggatggctgt gtacgcgaac tccatgcacg    660

tgtccgacca accgttccct ggtgccactc atgtgttaac aaattcccct ttgcctcaac    720

gggcttgtcg gcagccgttc tgtccgttcg aagaggccca ttctagcata tacaggtggg    780

aaaaatttgt aatttttatg gattcctcct ccgacggtcg atctcgcatg atgtggactc    840

cggaatccga tgactccacg gctttggaag ttctgccgcc cgagctagaa caccaggtca    900

aggtccttgt tcggagcttt cccgcccatc accttgtcga ccttgccgat tgggagctca    960

ctgagtcccc tgataacggt tttccttca gcacgtcaca tccttgcggc taccttgttc   1020

gggacccggc tgtatccgaa ggcaagtgtt ggctttcctg ctttttgagc cagtcagccg   1080

aagtgctcag tcgcgaggcg catctggcta ccgcctatgg ttaccaaacc aagtggggtg   1140

tgcctggcaa gtacatccag cgcagacttc aagttcacgg tctccgtgct gtggtcgacc   1200

ctgatggtcc cattcacgtt gaagcattgt cttgccccca gtcttggatc aggcacttga   1260

ccctgaatga tgatgtcacc ccgggattcg ttcgcctaat gtctcttcgc attgtgccga   1320

acacagagcc taccacacac cggatctttc gttttggagt gcacaagtgg tatggtgccg   1380

ccggcaaacg ggcccgtggc aagcgtgccg ccaaaagtga gaaagactcg gcttccaccc   1440

tcaaggttgc ccgaccgact tccaccagtg gaatcgtcac ctactcccca cctgcggacg   1500

ggtcttgtgg ttggcatgcc cttgccgcca tactgaaccg gatgattaat aatgacttca   1560

cgtcccctct gcctcggtac aacaggccgg aggacgattg ggcttctgat ggtgaccttg   1620

ctcaggccat tcaatgtttg caactacctg ccgccatagc tcggaaccgc gcctgcccta   1680

acgccaaata cctcataaaa ctcaacggag ttcattggga ggtagaggtg aggcctggaa   1740

tggctcctcg ctccctctct cgtgagtgcg ttgttggcgt ctgctctgaa ggctgtgtcg   1800

cgtcgcctta cccggaggac gggttgccta aacgtgcact tgaggccctg gcgtctgctt   1860

atagactgcc ttcagactgt gtttgtgatg gtattattga cttccttgcc aatccacctc   1920

cccaggagtt ctggactctt gacaaaatgt tgacttcccc gtcaccggag cagtccggct   1980
```

-continued

```
tctctagtct gtataaattg ttgttagaga tcttgccgca gaaatgcgga tccacagaag   2040
gggaattcat ctatactgtt gagaggatgt tgaaggattg tccgagctcc aaacaggcca   2100
tggccctcct tgcaaaaatt aaggtcccat cctcaaaggc cccatccgtg actctgaacg   2160
agtgcttccc cacggatgtt ccagtcaact ctgagttaat atcttgggaa gagcccaaag   2220
accctggcgc tgctgttgtc ctatgtccat cggatgcaaa agaatctaag gaaacagccc   2280
ctgaagaagc tcaagcgaga aaccgtaagg tccttcaccc tgtggtcctt accgaggaac   2340
ttagcgagca acaggtgcag gtggttgagg gtgatcagga tatgccactg gatttgactt   2400
ggccaacctt aaccgctacg gcgacccctg ttagagggcc ggtaccggac aatttgagct   2460
ctggcattgg tgcccagccc gctaccgttc aagaactcat tctggcgagg cctgcacccc   2520
gtcttgttga gcgctgtggc acggagtcga acggcagcag ttcatttctg gatttgcctg   2580
acgtgcagac ctcggaccag cctttagacc tgtccctggc cgcgtggcct gtaagggcta   2640
ccgcgtctga ccccggttgg atccacggta ggcgtgagcc tgtctttgtg aagcctcgag   2700
gtgttttctc tgatggcgag tcggcccttc agttcggaga gctttccgaa gccagttctg   2760
tcgtcgatga ccggacaaaa gaagctccgg tggttgacgc ccccatcgat ttgacaactt   2820
cgaacgagac gctctctggg tctgacccct ttgaattcgc caaattcagg cgcccgcgtt   2880
tctccgcgca agctttaatc gaccgaggtg gtccgcttgc cgatgttcat gcaaagataa   2940
agagtcgggt atatgaacaa tgccttcaag cttgtgaacc tggtagtcgt gcgaccccag   3000
ccaccaagaa gtggctcgac aaaatgtggg acagggtgga catgaaaact tggcgctgca   3060
cctcgcagtt ccaagctggt cacattcttg agtccctcaa attcctccct gacatgattc   3120
aagacacacc gcctcctgtt cccaggaaga accgagctgg tgacagtgcc ggcctgaagc   3180
aactggtggc gcagtgggat aggaaatcga gtgtgacacc ccccacaaaa ccggttggac   3240
cggtgcttga ccaggccgtc cctctgccta tggacatcca gcaaggagat gccatctccg   3300
ctgacaagcc accccattcg caaaaccctt ctagtcaagt agatgtgggt ggaggttgga   3360
aaagttttat gctctccggc acccgtttcg cggggtccgt tagtcagcgc cttacgacat   3420
gggtttttga ggttctctcc catctcccag cttttatgct cacacttttc tcgccacggg   3480
gctctatggc tccaggtgat tggctgtttg caggtgctgt tctacttgct ctcctgctct   3540
gccgttctta cccaatactc ggatgccttc ccttattggg tgtcttttct ggttctgtgc   3600
ggtgtgttcg tttgggtgtt tttggttctt ggatggcttt tgctgtattt ttattctcga   3660
ctccacccga cccagtcggt tcttcttgtg accacgattc gccggagtgt catgctgagc   3720
ttttggctct tgagcagcgc caactttggg aacctgtgcg cagccttgtg gtcgggccat   3780
cgggcctctt atgcgtcatt cttggcaagt tactcggtgg gtcacgttgt ctctggtttg   3840
ttctcctacg tatatgcatg ctcgcagatt tggcaatttc tcttatttat gtggtgtccc   3900
aagggcgttg tcacaagtgt tggggaaagt gtataaggac ggctcctgca gaagtggccc   3960
ttaatgtgtt tcctttttcg cgcgccaccc gctcatctct tgtgtccttg tgtgatcggt   4020
tccaagcgcc aaaaggagtt gaccccgtgc acttggcgac aggctggcgc gggtgctggt   4080
gtggtgagag ccctattcat caatcacacc aaaaaccgat agcttatgcc aacttggatg   4140
aaaagaagat atccgcccag acggtgattg ctgtcccgta tgatcctagt caggccatta   4200
aatgcctgaa agttttgcag gcaggagggg ctattgtgga ccagcctacg cccgaggtcg   4260
tccgtgtgtc tgagattccc ttctcggccc catttttttcc gaaggtccca gtcaacccag   4320
actgcagggt tgtggtagat tcggacactt ttgtggctgc ggtccgctgc ggttattcga   4380
```

-continued

```
cagcacaact ggtccttggt cggggcaact ttgccaagct aaatcagacc cccctcagga   4440
actctgtccc caccaaaaca actggtgggg cctcatacac ccttgccgtg gcccaggtat   4500
ctgtgtggac tcttgttcat ttcatcctcg gcctttggtt aacgtcacct caagtgtgtg   4560
gtcgagggac ctctgacccg tggtgttcga accctttttc gtatcctact tatggccccg   4620
gagttgtgtg ttcctctcga ctctgcgtgt ctgccgacgg agttaccctg ccattgttct   4680
cagccgttgc ccatctttcc ggtagagagg tggggatttt tattttggtg cttgcctcct   4740
tgggcgcttt agcccaccgc ttggctctta aggcagacat gtcaatggtc tttttggcgt   4800
tttgtgctta cgcctggccc atgagctcct ggttaatttg cttctttcct atgctcttga   4860
ggtgggtaac ccttcatcct ctcactatgc tttgggtgca ctcatttttg gtgttttgcc   4920
taccagctgc cggcgttctc tcgctgggaa taaccggtct tctttgggca gttggccgtt   4980
tcacccaggt tgccggaatt atcacacctt atgacatcca ccagtatacc tccggaccac   5040
gtggtgcagc tgctgtagca acggctccag aaggtactta catggcggcc gttcggagag   5100
ccgctttgac tggacggact ttgatcttca caccatctgc agtcggatcc cttcttgaag   5160
gtgctttcag aactcaaaag ccctgcctta acaccgtgaa tgtcgtaggc tcttcccttg   5220
gttctggagg agttttcacc attgatggca gaagagtcat cgtcactgcc acccatgtgt   5280
tgaatggtaa cacagccagg gtcactggtg attcctacaa ccgcatgcac acgttcaata   5340
ctaatggtga ttatgcctgg tcccatgctg atgactggca aggcgttgcc cctatggtta   5400
agatcgctaa ggggtatcgc ggtcgtgcct actggcaaac gtcaaccgga gtcgaacctg   5460
gcatcatggg ggaaggattc gccttctgtt tcactaactg tggcgactca gggtcacctg   5520
tcatttcaga agctggtgac cttattggag tccataccgg ttcaaacaaa ctcggttctg   5580
gtcttgtgac aacccctgaa ggggagacct gctccatcaa ggaaactagg ctctctgacc   5640
tttctagaca ttttgcaggt ccaagcgtcc ctcttgggga cattaagttg agcccagcca   5700
tcatccctga tgtgacaact attccgagtg acttggcatc gctccttgct tctgtccccg   5760
tgatggaagg tggcctctca actgtccagc ttttgtgcgt ctttttcctt ctctggcgca   5820
tgatgggcca tgcctggaca cccattgttg ccgtaggctt ctttttgctg aatgaaattc   5880
tcccagcagt cttggtccga gctgtgttct cttttgcact ctttgtactt gcatgggcca   5940
ccccctggtc ggcacaagtg ttgatgatta gactcctcac ggcggctctc aaccgcaaca   6000
ggttgtccct ggcgttctac gcattcggag gtgtcgttgg cctggccaca gaaatcggga   6060
cttttgctgg tggatggcct gaactgtccc aagccctctc gacatactgc ttcctgccca   6120
ggttccttgc tgtgactagt tatgtcccca ccatcatcat cggtgggctc catgccctcg   6180
gcgtaatttt gtggttattc aaataccgat gcctccacaa catgctggtt ggtgatggga   6240
gtttctcaag cgctttcttc ctacggtatt ttgctgaggg taatcttagg aaaggcgtgt   6300
cgcagtcctg tggcatgaat aacgaatccc tgacagctgc tttggcttgc aagttgtcgc   6360
aagctgacct tgattttttg tccagtttaa cgaacttcaa gtgctttgtg tccgcttcaa   6420
acatgaaaaa tgcagctggc caatacatcg aggcggcgta tgctagagct ctgcgtcagg   6480
agctggcctc cttggttcag gttgacaaga tgaaaggagt attggccaag ctcgaggctt   6540
tcgctgagac ggccactccg tcacttgaca caggggacgt gattgttctg cttgggcaac   6600
acccccatgg atccatcctc gacattaatg tggggggtga aaggaaaact gtgtctgtgc   6660
aagaaacacg atgcctgggt ggttccaaat tcagtgtctg cactgtcgtg tccaacacgc   6720
```

-continued

```
ccgtggatac cttgaccggt atcccacttc agacgccaac cccacttttt gaaaatggcc   6780
cgcgccatcg cagcgaggac gacgacctca aagttgagag aatgaaaaaa cactgtgtat   6840
ccctcggctt ccacaaaatc aatggtaaag tttactgcaa aatttgggac aagtctaacg   6900
gcgacacctt ttacacggat gattcccgat acactcaaga ccatgctttt caggacaggt   6960
caaccgacta tagagacagg gattatgaag gtgtacagac cgccccccaa cagggattcg   7020
atccaaagtc cgaagcccct gttggcactg ttgtaatcgg tggcattacg tataacaggc   7080
atctggtcaa aggtaaggag gtcctagttc ccaaacctga caactgcctt gaagctgcca   7140
gactgtccct tgagcaagct cttgctggga tgggccaaac ttgtgacctt acagctaccg   7200
aagtggagaa actaaagcgc atcattagtc aactccaagg tctgaccact gaacaggctt   7260
taaactgcta gccgccagcg gcttgacccg ctgtggccgc ggcggcctag ttgtaactga   7320
aacggcggta aaaatcgtaa aataccacag cagaactttc accttaggct ctttagacct   7380
aaaagtcacc tccgaggtgg aggtgaagaa atcaactgag caggggcacg ctgtcgtggc   7440
gaacttatgt tccggtgtcg tcttgatgag gcctcaccca ccgtcccttg ttgacgttct   7500
cctcaaaccc ggacttgaca caacacccgg cattcaacca gggcatgggg ccgggaatat   7560
gggcgtgaac ggttctattt gggattttga aactgcaccc acaaaggtag aactagagtt   7620
gtccaagcaa ataatccaag catgtgaagt caggcgcggg gacgccccta acctccaact   7680
cccctacaag ctttatcctg tcagggggga ccccgagcgg cgtaaaggtc gccttgtcaa   7740
cactaggttt ggagatttac cttacaaaac tccccaagac accaagtccg caattcatgc   7800
ggcttgttgc ctgcatccca atggggtcct cgtgtctgat ggcaaatcca cgctgggtac   7860
cactcttcaa catggtttcg agctttatgt ccccactgta ccttatagtg tcatggaata   7920
ccttgattca cgccctgaca cccctttat gtgtactaaa catggcactt ccaaggctgc   7980
tgcagaggac ctccaaaaat atgacctatc cactcaaggg tttgtcttgc ctggggtcct   8040
acgcctagtg cgcaggttca tctttagcca tgttggtaag gcgccaccac tgttccttcc   8100
atcaacctac cctgccaaga actccatggc aggggtcaat ggccagaggt tcccaacaaa   8160
ggatgtccag agcatacctg aaattgatga aatgtgcgcc cgtgccgtca aggaaaattg   8220
gcagactgtg acaccttgca ccctcaaaaa acagtactgt tccaaaccta aaactagaac   8280
catcctaggt accaacaact tcatagcctt ggctcacagg tcagcactca gtggtgtcac   8340
ccaggcgttc atgaagaagg cctggaagtc cccaattgcc ttggggaaaa acaagtttaa   8400
ggaattgcat tgcactgtcg ccggcagatg ccttgaggct gacctggctt cctgcgatcg   8460
cagcaccccc gccattgtga ggtggtttgt tgccaacctc ctgtatgaac ttgcaggatg   8520
tgaagagtac ttgcctagct acgtgctcaa ctgttgccat gaccttgtgg caacgcagga   8580
tggcgctttc acaaaacgcg gtggcctgtc gtccggggac cccgtcacca gtgtgtccaa   8640
caccgtctac tcactgataa tttacgccca gcacatggtg ctttcggcct tgaagatggg   8700
tcatgaaatt ggtctcaagt tccttgagga acagctcaaa tttgaggacc ttcttgaaat   8760
ccagcccatg ttagtgtatt ctgatgacct cgtcttgtat gcggaaagac ccacttttcc   8820
caactaccat tggtgggtcg agcatcttga cctgatgttg ggctttaaaa cggacccaaa   8880
gaaaactgtc ataactgata aacccagttt tctcggctgc agaattgaag caggacggca   8940
gttagtcccc aatcgcgacc gtattctggc tgctcttgca tatcatatga aggcgcagaa   9000
cgcctcagag tattatgcgt ccgctgccgc aattctgatg gattcgtgtg cttgcattga   9060
ccatgacccc gagtggtatg aggatcttat ctgcggcatc gcccggtgtg ctcgccagga   9120
```

-continued

```
cggttaccgt tttccaggcc cggcattttt catgtccatg tgggagaagc tgaaaagtca   9180
taatgaaggg aagaaatgcc gtcactgcgg catctgcgac gccaaagccg actatgcgtc   9240
cgcctgtgga cttgatttgt gtttgttcca ttcacacttt catcaacact gcccagtcac   9300
tctgagctgt ggccaccatg ccggttcaaa ggaatgttcg cagtgtcagt cacctgtcgg   9360
ggctggcaaa tcccccttg acgctgtgct gaaacaaatc ccgtacaaac ctcctcgtac   9420
cattatcatg aaggtggaca acaaaacaac gacccttgac ccgggaagat atcagtcccg   9480
tcgaggtctt gttgcagtca aaagaggtat tgcaggtaat gaggttgatc tttctgatgg   9540
agactaccaa gtggtgcctc ttttgccgac ttgcaaagac ataaacatgg tgaaggtggc   9600
ttgcaacgta ctactcagca agtttatagt agggccgcca ggttccggaa aaaccacctg   9660
gctactgaac caagtccagg acgatgatgt catttacaca cctactcatc agacaatgtt   9720
tgacatagtc agtgctctta aagtttgcag gtattccatc ccaggagcct caggactccc   9780
ttttccacca cctgccaggt ccgggccgtg ggttaggctc atcgccagcg gacatgtccc   9840
tggccgagtg tcatatctcg atgaggcagg atattgcaat catctagaca ttctaaggct   9900
gctttccaaa acacccttg tgtgtttggg tgaccttcag caacttcacc cggtcggctt   9960
tgattcctat tgttatgtgt tcgatcagat gcctcagaag cagctgacca ccatttatag  10020
atttggccct aacatctgtg cagccatcca gccttgttac agggagaaac ttgaatccaa  10080
ggccaggaac accagagtgg ttttcaccac ccggcctgtg gcctttggtc aggtcctgac  10140
accgtaccac aaagatcgta ccggctctgc aataactata gattcatccc aggggcgac  10200
cttcgacatt gtgacattgc atctaccatc gccaaagtcc ctaaacaaat cccgagcact  10260
tgtagccatc actcgggcaa gacatgggtt gttcatttat gaccctcatg accaactcca  10320
ggagtttttc aacttaaccc ccgagcgcac tgattgtaac cttgcgttca gccgtgggga  10380
tgagctggtt gttttgaatg tggataatgc ggtcacaact gtagcgaagg ccctagagac  10440
aggttcaccc cgatttcgag tatcggaccc gaggtgcaag tctctcttag ccgcttgttc  10500
ggccagtcta gaagggagct gcatgccact accacaagta gcacataacc tggggtttta  10560
cttttccccg gacagcccag cttttgcacc cctgccaaaa gagctggcgc cacattggcc  10620
agtggtcacc caccagaata atcgagcgtg gcctgatcga cttgtcgcta gtatgcgccc  10680
aattgatgcc cgctacagca agccaatggt cggtgcaggg tatgtggtcg ggccatccat  10740
ttttcttggc actcctggtg tggtgtcata ctatctcaca ttatacatcg ggggcgagcc  10800
tcaggccctg ccagaaacac tcgtttcaac aggacgtata gccacagatt gtcgggaata  10860
tctcgacgcg gctgaggaag aggcagcgag agaacttccc cacgcattta ttggcgatgt  10920
caaaggcact acgatcgggg ggtgtcacca cattacatcg aaatacctac ctaggtccct  10980
gcctaaagac tctgttgctg tggttggggt gagttcgccc ggtagggctg ctaaagccgt  11040
gtgcactctc accgatgtgt acctccccga actccgacca tatttgcaac cggagacggc  11100
atcaaaatgc tggaaactta aactggattt cagggatgtt cgactgatgg tctggaaagg  11160
cgccacagcc tatttccagt tggaagggct gacatggtca gcgctgcccg attatgctag  11220
gttcattcag ctacccaagg atgccgttgt gtacatcgat ccgtgtatag ggccggcaac  11280
agccaatcgc aaggttgtgc gaaccacaga ctggcgggcc gacctggcag tgacaccgta  11340
tgattacggt gctcaggtca ttttgacaac agcctggttc gaggaccttg ggccgcagtg  11400
gaagattttg ggttgcagc ctttcagacg aacatttggc tttgagaaca ctgaagattg  11460
```

-continued

```
ggcaattctc gcacgccgta tgaatgacgg caaagattac actgactata attggcattg  11520
tgtacgagaa cgcccacacg caatttacgg gcgcgcccgt gaccatacgt atcattttgc  11580
ccttggcact gaactgcaag tagagctggg cagaccccgg ctgcctcctg agcaagtgcc  11640
gtgaacgcgg agtgatgcaa tgggtttact gtggagtaaa atcagtcagt tgttcgtgga  11700
tgccttcact gagttccttg ttagtgtggt tgacattgtc atctttctcg ccatattgtt  11760
tgggttcact gttgcaggct ggttattggt cttccttctc agagtggttt gctccgcgtt  11820
tctccgttcg cgctctgcca ttcactcttc cgaactatcg aaggtcctat gagggcttgc  11880
tacccaactg cagaccggat gtcccacaat tcgcagttaa gcacccgttg ggtatacttt  11940
ggcatatgcg agtctcccac ctaattgacg aaatggtctc tcgccgcatt taccggacca  12000
tggaacattc gggtcaagcg gcctggaagc aggttgttag tgaagccact ctcacaaaac  12060
tgtcaaggct tgacgtagtc actcatttcc aacacctggc cgcagtggag gctgattctt  12120
gccgcttcct tagctcacga ctcgcgatgc tgaaaaacct tgccgttggc aatgtgagcc  12180
tggagtacaa cactactttg gaccgcgttg agctcatctt tcccacacca ggtacgaggc  12240
ccaagttgac cgattttagg caatggctta tcagcgtgca cgcttccatc ttctcctctg  12300
tggcttcgtc tgttaccttg ttcacagtgc tttggcttcg aattccagct ctacgctatg  12360
tttttggttt ccattggccc acggcaacac atcattcgaa ctaactatca attacactat  12420
atgtaagcca tgccctacca gtcaagctgc ccaacaaaga ctcgagcctg gccgtaacgt  12480
gtggtgcaaa atagggcacg acaggtgtga ggaacgtgac catgatgagt tgtcaatgtc  12540
cattccgtcc gggtacgaca acctcaaact tgagggttat tatgcttggc tggctttttt  12600
gtccttttcc tacgcggccc aattccatcc ggagctgttc ggaataggaa acgtgtcgcg  12660
cgtctttgtg gataagcgac accagttcat ttgcgccgag catgatggac aaaattcaac  12720
catatctgcc agacacaaca tctccgcgtc gtatgcggtg tattaccatc atcaaataga  12780
cgggggcaat tggtttcatt tggaatggct gcgaccattc ttttcctcct ggctggtgct  12840
caacatctca tggtttctga ggcgttcgcc tgcaagccct gcttctcgac gcatctatca  12900
gatattaaga ccaacacgac cgcggctgcc ggtttcatgg tccttcagaa catcaattgt  12960
ttccaatctc ccggtagctc ccatttacag ttgatttata acttaacggg ctcatcccaa  13020
tgtcgtgaag ccgtcggcat tccccagtac atcacgataa cggctaatgt gaccgatgaa  13080
tcgtatttgt acaacgcgga cttgctgatg ctttccgcgt gccttttcta cgcctcggaa  13140
atgagcgaga aaggcttcaa agtcatcttt gggaatattt ctggcgttgt ttccgcttgt  13200
gttaatttca cagattatgt ggcccatgtg acccaacaca ctcagcagca ccatttggta  13260
attgatcaca ttcggttact acacttcttg acaccgtcta cgatgaggtg ggctacaacc  13320
attgcttgtt tgcttgccat tcttttggcg gtatgaaatg ttcttgcaag ttggggcatt  13380
tcttgactcc tcactcttgc ttctggtggc tttttttgct gtgtaccggc ttgtcttggt  13440
cctttgtcga tggcaacgac gacagctcga catcccaata catatataat ttgacgatat  13500
gcgagctgaa tgggaccgaa tggttgtccg gtcattttga ttgggcagtc gaaacctttg  13560
tgctttaccc agttgccact catatcattt cactgggttt tctcacaaca agccatttcc  13620
ttgatgcgct cggtctcggc gctgtgtccg ccacaggatt cattggcgag cggtatgtac  13680
ttagcagcat gtacggcgtt tgcgccttcg cggcgttcgt atgttttgtc atccgtgctg  13740
ctaaaaattg catggcttgc cgctatgccc gcacccggtt taccaacttc atcgtggacg  13800
accggggaag aatccatcga tggaagtctt caatagtggt ggagaaattg ggcaaagctg  13860
```

aagtcggtgg tgaccttgtc aacattaagc atgttgtcct cgaaggggtt aaagctcaac 13920
ctttgacgag gacttcggct gagcaatggg aagcctagac gacttttgca acgatcccac 13980
cgccgcacaa aaactcgtgc tggcctttag catcacatat acacccataa tgatatacgc 14040
ccttaaggtg tcacgcggcc gactcctggg gctgttgcac atcttgatat ttctgaattg 14100
ttcctttact tttgggtaca tgacatatgt gcattttcaa tccaccaacc gtgtcgcatt 14160
cactctgggg gctgtagtcg cccttttgtg gggtgtttac agcctcacag agtcatggaa 14220
gttcatcact tccagatgca gattgtgttg cctaggccgg cgatacattc tggcccctgc 14280
ccatcacgta gaaagtgctg caggcctcca ttcaatccca gcgtctggta accgagcata 14340
cgctgtgaga aagcccggac taacatcagt gaacggcact ctagtacctg ggcttcggag 14400
cctcgtgctg ggcggcaaac gagctgttaa acgaggagtg gttaacctcg tcaagtatgg 14460
ccggtaagaa ccagagccag aagaaaagaa gaaatgcagc tccgatgggg aaaggccagc 14520
cagtcaatca actgtgccag ttgctgggta caatgataaa gtcccagcgc cagcaatcta 14580
ggggaggaca ggccaaaaag aagaagcctg agaagccaca ttttcccta gctgctgaag 14640 atgacattcg gcaccatctc acccaggccg aacgttccct ctgcttgcaa tcgatccaga 14700
cggctttcaa tcaaggcgca ggaactgcgt cgctttcatc cagcgggaag gtcagtttcc 14760
aggttgagtt catgctgccg gttgctcata cagtgcgcct gattcgcgtg acttctacat 14820
ccgccagtca gggtgcaaat taatttgaca gtcaggtgaa tggccgcgat tgacgtgtgg 14880
cctctaagtc acctattcaa ttagggcgat cacatggggg tcaaacttaa ttaggcagga 14940
accatgtgac cgaaattaaa aaaaaaaaaa aaaaaaaaaa aaaa 14984

<210> SEQ ID NO 59
<211> LENGTH: 6
<212> TYPE: PRT
<213> ORGANISM: Porcine reproductive and respiratory syndrome virus

<400> SEQUENCE: 59

Trp Tyr Gly Ala Gly Arg
1 5

<210> SEQ ID NO 60
<211> LENGTH: 6
<212> TYPE: PRT
<213> ORGANISM: Porcine reproductive and respiratory syndrome virus

<400> SEQUENCE: 60

Trp Tyr Gly Ala Ala Gly
1 5

<210> SEQ ID NO 61
<211> LENGTH: 9
<212> TYPE: PRT
<213> ORGANISM: Porcine reproductive and respiratory syndrome virus
<220> FEATURE:
<221> NAME/KEY: MOD_RES
<222> LOCATION: (6)..(6)
<223> OTHER INFORMATION: Any naturally occurring amino acid

<400> SEQUENCE: 61

Glu Cys Ala Met Ala Xaa Val Tyr Asp
1 5

<210> SEQ ID NO 62
<211> LENGTH: 9

```
<212> TYPE: PRT
<213> ORGANISM: Porcine reproductive and respiratory syndrome virus
<220> FEATURE:
<221> NAME/KEY: MOD_RES
<222> LOCATION: (6)..(6)
<223> OTHER INFORMATION: Any naturally occurring amino acid

<400> SEQUENCE: 62

Glu Glu Ala His Ser Xaa Val Tyr Arg
1               5


<210> SEQ ID NO 63
<211> LENGTH: 4
<212> TYPE: PRT
<213> ORGANISM: Porcine reproductive and respiratory syndrome virus

<400> SEQUENCE: 63

Ala Leu Glu Val
1


<210> SEQ ID NO 64
<211> LENGTH: 6
<212> TYPE: PRT
<213> ORGANISM: Porcine reproductive and respiratory syndrome virus

<400> SEQUENCE: 64

Ser Asp Gly Arg Ser Arg
1               5


<210> SEQ ID NO 65
<211> LENGTH: 64
<212> TYPE: PRT
<213> ORGANISM: Porcine reproductive and respiratory syndrome virus

<400> SEQUENCE: 65

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60


<210> SEQ ID NO 66
<211> LENGTH: 64
<212> TYPE: PRT
<213> ORGANISM: Porcine reproductive and respiratory syndrome virus

<400> SEQUENCE: 66

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60


<210> SEQ ID NO 67
<211> LENGTH: 64
<212> TYPE: PRT
<213> ORGANISM: Porcine reproductive and respiratory syndrome virus
```

<400> SEQUENCE: 67

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60
```

<210> SEQ ID NO 68
<211> LENGTH: 64
<212> TYPE: PRT
<213> ORGANISM: Porcine reproductive and respiratory syndrome virus

<400> SEQUENCE: 68

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60
```

<210> SEQ ID NO 69
<211> LENGTH: 64
<212> TYPE: PRT
<213> ORGANISM: Porcine reproductive and respiratory syndrome virus

<400> SEQUENCE: 69

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60
```

<210> SEQ ID NO 70
<211> LENGTH: 64
<212> TYPE: PRT
<213> ORGANISM: Porcine reproductive and respiratory syndrome virus

<400> SEQUENCE: 70

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60
```

<210> SEQ ID NO 71
<211> LENGTH: 64
<212> TYPE: PRT

<213> ORGANISM: Porcine reproductive and respiratory syndrome virus

<400> SEQUENCE: 71

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Arg Phe Thr Phe Met Thr
    50                  55                  60
```

<210> SEQ ID NO 72
<211> LENGTH: 64
<212> TYPE: PRT
<213> ORGANISM: Porcine reproductive and respiratory syndrome virus

<400> SEQUENCE: 72

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Glu Phe Thr Phe Met Thr
    50                  55                  60
```

<210> SEQ ID NO 73
<211> LENGTH: 64
<212> TYPE: PRT
<213> ORGANISM: Porcine reproductive and respiratory syndrome virus

<400> SEQUENCE: 73

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Glu Phe Thr Phe Met Thr
    50                  55                  60
```

<210> SEQ ID NO 74
<211> LENGTH: 64
<212> TYPE: PRT
<213> ORGANISM: Porcine reproductive and respiratory syndrome virus

<400> SEQUENCE: 74

```
Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Lys Phe Thr Phe Met Thr
    50                  55                  60
```

<210> SEQ ID NO 75
<211> LENGTH: 64

```
<212> TYPE: PRT
<213> ORGANISM: Porcine reproductive and respiratory syndrome virus

<400> SEQUENCE: 75

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Lys Phe Thr Phe Met Thr
    50                  55                  60


<210> SEQ ID NO 76
<211> LENGTH: 64
<212> TYPE: PRT
<213> ORGANISM: Porcine reproductive and respiratory syndrome virus

<400> SEQUENCE: 76

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Lys Phe Thr Phe Ile Thr
    50                  55                  60


<210> SEQ ID NO 77
<211> LENGTH: 68
<212> TYPE: PRT
<213> ORGANISM: Porcine reproductive and respiratory syndrome virus

<400> SEQUENCE: 77

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65


<210> SEQ ID NO 78
<211> LENGTH: 68
<212> TYPE: PRT
<213> ORGANISM: Porcine reproductive and respiratory syndrome virus

<400> SEQUENCE: 78

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60
```

```
Glu Leu Thr Glu
65


<210> SEQ ID NO 79
<211> LENGTH: 68
<212> TYPE: PRT
<213> ORGANISM: Porcine reproductive and respiratory syndrome virus

<400> SEQUENCE: 79

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65


<210> SEQ ID NO 80
<211> LENGTH: 68
<212> TYPE: PRT
<213> ORGANISM: Porcine reproductive and respiratory syndrome virus

<400> SEQUENCE: 80

Ser Ser Val Tyr Arg Trp Lys Lys Phe Val Val Phe Thr Asp Ser Ser
1               5                   10                  15

Pro Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65


<210> SEQ ID NO 81
<211> LENGTH: 68
<212> TYPE: PRT
<213> ORGANISM: Porcine reproductive and respiratory syndrome virus

<400> SEQUENCE: 81

Ser Ser Val Tyr Arg Trp Lys Lys Phe Val Val Phe Thr Asp Ser Ser
1               5                   10                  15

Pro Asn Gly Arg Ser Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Ile Arg Ser Phe Pro Ala His His Pro Val Asp Leu Ala Asp Trp
    50                  55                  60

Glu Leu Thr Glu
65


<210> SEQ ID NO 82
<211> LENGTH: 68
<212> TYPE: PRT
<213> ORGANISM: Porcine reproductive and respiratory syndrome virus
```

<400> SEQUENCE: 82

Ser Ser Val Tyr Arg Trp Lys Arg Phe Val Val Phe Thr Asp Ser Ser
1 5 10 15

Pro Asn Gly Arg Ser Arg Met Met Trp Thr Pro Glu Ser Asp Asp Ser
20 25 30

Ala Ala Leu Glu Val Leu Pro Pro Glu Leu Glu Arg Gln Val Glu Ile
35 40 45

Leu Ile Arg Ser Phe Pro Ala His His Pro Val Asn Leu Ala Asp Trp
50 55 60

Glu Leu Thr Glu
65

<210> SEQ ID NO 83
<211> LENGTH: 68
<212> TYPE: PRT
<213> ORGANISM: Porcine reproductive and respiratory syndrome virus

<400> SEQUENCE: 83

Ser Ser Val Tyr Arg Trp Lys Arg Phe Val Val Phe Thr Asp Ser Ser
1 5 10 15

Pro Asn Gly Arg Ser Arg Met Met Trp Thr Pro Glu Ser Asp Asp Ser
20 25 30

Ala Ala Leu Glu Val Leu Pro Pro Glu Leu Glu Arg Gln Val Glu Ile
35 40 45

Leu Ile Arg Ser Phe Pro Ala His His Pro Val Asn Leu Ala Asp Trp
50 55 60

Glu Leu Thr Glu
65

<210> SEQ ID NO 84
<211> LENGTH: 68
<212> TYPE: PRT
<213> ORGANISM: Porcine reproductive and respiratory syndrome virus

<400> SEQUENCE: 84

Ser Ser Val Tyr Arg Trp Lys Arg Phe Val Val Phe Thr Asp Ser Ser
1 5 10 15

Pro Asn Gly Arg Ser Arg Met Met Trp Thr Pro Glu Ser Asp Asp Ser
20 25 30

Ala Ala Leu Glu Val Leu Pro Pro Glu Leu Glu Arg Gln Val Glu Ile
35 40 45

Leu Ile Arg Ser Phe Pro Ala His His Pro Val Asn Leu Ala Asp Trp
50 55 60

Glu Leu Thr Glu
65

<210> SEQ ID NO 85
<211> LENGTH: 68
<212> TYPE: PRT
<213> ORGANISM: Porcine reproductive and respiratory syndrome virus

<400> SEQUENCE: 85

Ser Asp Val Tyr Arg Trp Lys Lys Phe Val Ile Phe Thr Asp Ser Ser
1 5 10 15

Pro Asn Gly Arg Phe Arg Met Met Trp Thr Pro Glu Ser Asp Asp Ser
20 25 30

Ala Ala Leu Glu Val Leu Pro Pro Glu Leu Glu Arg Gln Val Glu Ile
35 40 45

Leu Thr Arg Ser Phe Pro Ala His His Pro Ile Asn Leu Ala Asp Trp
    50                  55                  60

Glu Leu Thr Glu
65

<210> SEQ ID NO 86
<211> LENGTH: 68
<212> TYPE: PRT
<213> ORGANISM: Porcine reproductive and respiratory syndrome virus

<400> SEQUENCE: 86

Ser Asp Val Tyr Arg Trp Lys Lys Phe Val Ile Phe Thr Asp Ser Ser
1               5                   10                  15

Pro Asn Gly Arg Phe Arg Met Met Trp Thr Pro Glu Ser Asp Asp Ser
            20                  25                  30

Ala Ala Leu Glu Val Leu Pro Pro Glu Leu Glu Arg Gln Val Glu Ile
        35                  40                  45

Leu Thr Arg Ser Phe Pro Ala His His Pro Ile Asn Leu Ala Asp Trp
    50                  55                  60

Glu Leu Thr Glu
65

<210> SEQ ID NO 87
<211> LENGTH: 68
<212> TYPE: PRT
<213> ORGANISM: Porcine reproductive and respiratory syndrome virus

<400> SEQUENCE: 87

Ser Ser Val Tyr Arg Trp Lys Lys Phe Val Val Phe Thr Asp Ser Ser
1               5                   10                  15

Pro Asn Gly Arg Pro Arg Met Met Trp Thr Pro Glu Ser Asp Asp Ser
            20                  25                  30

Ala Asp Leu Glu Ala Leu Pro Pro Glu Leu Glu Arg Gln Val Glu Ile
        35                  40                  45

Leu Ile Arg Ser Phe Pro Ala His His Pro Val Ser Leu Ala Asp Trp
    50                  55                  60

Glu Leu Ala Glu
65

<210> SEQ ID NO 88
<211> LENGTH: 68
<212> TYPE: PRT
<213> ORGANISM: Porcine reproductive and respiratory syndrome virus

<400> SEQUENCE: 88

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Leu Glu Val Leu Pro Pro Glu Leu Glu His Gln Val Lys Val
        35                  40                  45

Leu Val Arg Ser Phe Pro Ala His His Leu Val Asp Leu Ala Asp Trp
    50                  55                  60

Glu Leu Thr Glu
65

<210> SEQ ID NO 89
<211> LENGTH: 65

```
<212> TYPE: PRT
<213> ORGANISM: Porcine reproductive and respiratory syndrome virus

<400> SEQUENCE: 89

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Leu Pro Pro Glu Leu Glu His Gln Val Lys Val Leu Val Arg Ser
        35                  40                  45

Phe Pro Ala His His Leu Val Asp Leu Ala Asp Trp Glu Leu Thr Glu
    50                  55                  60

Ser
65


<210> SEQ ID NO 90
<211> LENGTH: 67
<212> TYPE: PRT
<213> ORGANISM: Porcine reproductive and respiratory syndrome virus

<400> SEQUENCE: 90

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Leu Leu Pro Pro Glu Leu Glu His Gln Val Lys Val Leu Val
        35                  40                  45

Arg Ser Phe Pro Ala His His Leu Val Asp Leu Ala Asp Trp Glu Leu
    50                  55                  60

Thr Glu Ser
65


<210> SEQ ID NO 91
<211> LENGTH: 65
<212> TYPE: PRT
<213> ORGANISM: Porcine reproductive and respiratory syndrome virus

<400> SEQUENCE: 91

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Pro Pro Glu Leu Glu His Gln Val Lys Val Leu Val Arg Ser
        35                  40                  45

Phe Pro Ala His His Leu Val Asp Leu Ala Asp Trp Glu Leu Thr Glu
    50                  55                  60

Ser
65


<210> SEQ ID NO 92
<211> LENGTH: 67
<212> TYPE: PRT
<213> ORGANISM: Porcine reproductive and respiratory syndrome virus

<400> SEQUENCE: 92

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30
```

```
Thr Ala Val Leu Pro Pro Glu Leu Glu His Gln Val Lys Val Leu Val
        35                  40                  45

Arg Ser Phe Pro Ala His His Leu Val Asp Leu Ala Asp Trp Glu Leu
    50                  55                  60

Thr Glu Ser
65


<210> SEQ ID NO 93
<211> LENGTH: 67
<212> TYPE: PRT
<213> ORGANISM: Porcine reproductive and respiratory syndrome virus

<400> SEQUENCE: 93

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Ser Thr Ala
            20                  25                  30

Leu Glu Val Leu Pro Pro Glu Leu Glu His Gln Val Lys Val Leu Val
        35                  40                  45

Arg Ser Phe Pro Ala His His Leu Val Asp Leu Ala Asp Trp Glu Leu
    50                  55                  60

Thr Glu Ser
65


<210> SEQ ID NO 94
<211> LENGTH: 65
<212> TYPE: PRT
<213> ORGANISM: Porcine reproductive and respiratory syndrome virus

<400> SEQUENCE: 94

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Thr Ala Leu Glu
            20                  25                  30

Val Leu Pro Pro Glu Leu Glu His Gln Val Lys Val Leu Val Arg Ser
        35                  40                  45

Phe Pro Ala His His Leu Val Asp Leu Ala Asp Trp Glu Leu Thr Glu
    50                  55                  60

Ser
65


<210> SEQ ID NO 95
<211> LENGTH: 67
<212> TYPE: PRT
<213> ORGANISM: Porcine reproductive and respiratory syndrome virus

<400> SEQUENCE: 95

Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30

Thr Ala Leu Glu Val Leu Pro Pro Glu Leu Glu His Gln Val Lys Val
        35                  40                  45

Leu Val Arg Ser Phe Pro Ala Leu Val Asp Leu Ala Asp Trp Glu Leu
    50                  55                  60

Thr Glu Ser
65
```

<210> SEQ ID NO 96
<211> LENGTH: 65
<212> TYPE: PRT
<213> ORGANISM: Porcine reproductive and respiratory syndrome virus

<400> SEQUENCE: 96

```
Ser Ser Ile Tyr Arg Trp Glu Lys Phe Val Ile Phe Met Asp Ser Ser
1               5                   10                  15

Ser Asp Met Met Trp Thr Pro Glu Ser Asp Asp Ser Thr Ala Leu Glu
            20                  25                  30

Val Leu Pro Pro Glu Leu Glu His Gln Val Lys Val Leu Val Arg Ser
        35                  40                  45

Phe Pro Ala His His Leu Val Asp Leu Ala Asp Trp Glu Leu Thr Glu
    50                  55                  60

Ser
65
```

<210> SEQ ID NO 97
<211> LENGTH: 66
<212> TYPE: PRT
<213> ORGANISM: Porcine reproductive and respiratory syndrome virus

<400> SEQUENCE: 97

```
Ser Ser Ile Tyr Arg Trp Glu Lys Phe Val Ile Phe Met Asp Ser Ser
1               5                   10                  15

Ser Asp Gly Met Met Trp Thr Pro Glu Ser Asp Asp Ser Thr Ala Leu
            20                  25                  30

Glu Val Leu Pro Pro Glu Leu Glu His Gln Val Lys Val Leu Val Arg
        35                  40                  45

Ser Phe Pro Ala His His Leu Val Asp Leu Ala Asp Trp Glu Leu Thr
    50                  55                  60

Glu Ser
65
```

<210> SEQ ID NO 98
<211> LENGTH: 63
<212> TYPE: PRT
<213> ORGANISM: Porcine reproductive and respiratory syndrome virus

<400> SEQUENCE: 98

```
Ser Ser Ile Tyr Arg Trp Glu Lys Phe Val Ile Phe Met Asp Ser Ser
1               5                   10                  15

Met Met Trp Thr Pro Glu Ser Asp Asp Ser Thr Ala Leu Glu Val Leu
            20                  25                  30

Pro Pro Glu Leu Glu His Gln Val Lys Val Leu Val Arg Ser Phe Pro
        35                  40                  45

Ala His His Leu Val Asp Leu Ala Asp Trp Glu Leu Thr Glu Ser
    50                  55                  60
```

<210> SEQ ID NO 99
<211> LENGTH: 69
<212> TYPE: PRT
<213> ORGANISM: Porcine reproductive and respiratory syndrome virus

<400> SEQUENCE: 99

```
Ser Ser Ile Tyr Arg Trp Glu Lys Phe Val Ile Phe Met Asp Ser Ser
1               5                   10                  15

Ser Asp Gly Arg Ser Arg Met Met Trp Thr Pro Glu Ser Asp Asp Ser
            20                  25                  30
```

-continued

```
Thr Ala Leu Glu Val Leu Pro Pro Glu Leu Glu His Gln Val Lys Val
        35                  40                  45

Leu Val Arg Ser Phe Pro Ala His His Leu Val Asp Leu Ala Asp Trp
    50                  55                  60

Glu Leu Thr Glu Ser
65
```

PRRS VIRUS VARIANT, EUROPEAN PRRS VIRUS CDNA CLONE, AND USES THEREOF

CROSS-REFERENCE TO RELATED APPLICATIONS

This application is a divisional of U.S. patent application Ser. No. 15/105,760, filed Jun. 17, 2016, which claims the benefit of PCT Application No. PCT/EP2014/078929, filed Dec. 19, 2014, the entire contents of which are hereby incorporated by reference herein.

SEQUENCE LISTING

This application contains a sequence listing in accordance with 37 C.F.R. 1.821-1.825. The Sequence Listing which has been submitted electronically in ASCII format was created on Jan. 31, 2018, is named 01-2959-US-1-AMND-SEQ.txt, and is 225,201 bytes in size. The sequence listing accompanying this application is hereby incorporated by reference in its entirety.

TECHNICAL FIELD

The present invention belongs to the field of animal health.

In a first consideration, the invention relates to a new PRRS virus variant. The invention also relates to the use of such PRRS virus to study Porcine Reproductive and Respiratory Syndrome (PRRS), a viral disease affecting swine, and in the development of vaccines, therapeutics and diagnostics for the prophylaxis, treatment and diagnosis of PRRS.

In a second consideration, the invention relates to a nucleic acid sequence which comprises the genome of an infectious genotype I (EU) PRRS virus clone. The invention also relates to the use of the nucleic acid sequence of the infectious genotype I PRRS virus clone to produce attenuated live viruses useful for preventing or treating Porcine Reproductive and Respiratory Syndrome (PRRS) in swine and in the development of vaccines, therapeutics and diagnostics for the prophylaxis, treatment and diagnosis of PRRS.

Combining said both considerations, furthermore novel PRRS viruses with improved properties are provided under a third consideration of the invention.

BACKGROUND INFORMATION

Porcine reproductive and respiratory syndrome virus (PRRSV) is a member of the virus family Arteriviridae and belongs, together with the Coronaviridae, to the virus order Nidovirales. PRRSV is an enveloped virus with a single-stranded, positive-sense RNA genome of about 15 kilobases comprising nine open reading frames (ORFs), namely ORF1a, ORF1ab, ORF2a, ORF2ab, and ORFs 3 through ORF7. ORFs 1a and 1ab encode large polyproteins that are processed into the viral nonstructural proteins (nsp) by auto- and transcleavages of viral proteases nsp1, nsp2, and nsp4 (Snijder and Meulenberg, 1998). ORF4 encodes a minor glycoprotein (GP4) which is, next to a major glycoprotein (GP5) and two other minor glycoproteins (GP2a and GP3), found in the viral envelope, wherein all of said glycoproteins are important for infectious virus production.

PRRSV is considered one of the economically most important infectious agents in pigs causing late-term reproductive failure in sows and respiratory disease in growing pigs. Often, PRRSV infection is complicated by secondary bacterial infections being attributed to the immunosuppressive nature of the virus. Also, PRRSV viremia lasts for weeks, and virus then still can be detected in lymphoid organs for several months, demonstrating difficulties or failure of the host's immune response to clear the virus (Allende et al., 2000).

There are two distinct viral PRRSV genotypes causing similar clinical symptoms that diverge by about 40% on nucleotide sequence level, genotype I (EU) and genotype II (US). The North American (US) prototype strain is VR-2332, while the European (EU) prototype strain is Lelystad virus.

However, in a first consideration, as PRRS virus strains have a high biological diversity and evolve rapidly on individual farms (Badaoui et al. *BMC Veterinary Research* 2013, 9:58), new PRRSV isolates are needed for a better understanding of PRRS, for reproducing said disease in its different forms, for comparative tests, and as platform for the development of new vaccines, medications and diagnostics for the prophylaxis, treatment and diagnosis of PRRS.

In a second consideration, a growing number of infectious cDNA clones of the PRRS virus are becoming available to the scientific community, most of which are based on the US type of the virus. For the EU type, however, only few clones are available. Thus, there is a strong need for new infectious cDNA clones of European (genotype I) PRRS virus, for a better understanding of PRRS, for comparative tests, as platform for the development of new vaccines, medications and diagnostics for the prophylaxis, treatment and diagnosis of PRRS, wherein the use of the cDNA clone results in a high yield of virus production. Thus, for experimental convenience in the PRRS vaccine research an infectious cDNA clone would be needed enabling the production of genotype I PRRS virus in high amounts

DESCRIPTION OF THE INVENTION

The solution to the above technical problems is achieved by the description and the embodiments characterized in the claims.

Thus, the invention in its different aspects and embodiments is implemented according to the claims.

1. First Consideration of the Present Invention

According to a first consideration, which is detailed in this section, the invention is based on the isolation of a new PRRS virus which is surprisingly capable to induce severe clinical signs in boars. Closer analyses of this PRRS virus variant revealed a significant deletion within the ORF4 gene of said virus.

In one aspect, the invention thus relates to a Porcine Reproductive and Respiratory Syndrome (PRRS) virus, wherein said virus is selected from the group consisting of the following (a), (b), (c), (d), (e), and (f):

(a) a PRRS virus comprising an ORF4 protein which comprises an amino acid sequence selected from the group consisting of SEQ ID NOs: 1-12;

(b) a PRRS virus, preferably a genotype I PRRS virus, comprising an ORF4 protein having a deletion of 9, 10, 11 or more amino acid residues in the region located between the first two predicted N-terminal ß-sheets, as compared to the ORF4 protein of a wild type genotype I PRRS virus;

(c) a genotype II PRRS virus, comprising an ORF4 protein having a deletion of 5, 6, 7 or more amino acid residues in the region between the first two predicted N-terminal ß-sheets, as compared to a wild type genotype II PRRS virus;

(d) a PRRS virus, preferably a genotype I PRRS virus, comprising an ORF4 protein having a deletion of 9, 10, 11 or more amino acid residues between amino acid positions 50 to 71, wherein the numbering of the amino acid positions refers to the amino acid sequence of ORF4 protein of the Lelystad virus;

(e) a genotype II PRRS virus, comprising an ORF4 protein having a deletion of 5, 6, 7 or more amino acid residues between amino acid positions 50 to 67, wherein the numbering of the amino acid positions refers to the amino acid sequence of ORF4 protein of the PRRS virus VR2332;

(f) a combination of any of (a), (b), (c), (d), and (e);

and, in a further aspect, the invention relates, respectively, to a Porcine Reproductive and Respiratory Syndrome (PRRS) virus selected from the group consisting of the following A), B), C), D), E), and F):

A) a PRRS virus whose genome comprises a nucleic acid molecule which encodes an ORF4 protein comprising an amino acid sequence selected from the group consisting of SEQ ID NO: 1-12;

B) a PRRS virus, preferably a genotype I PRRS virus, whose genome comprises a nucleic acid molecule which encodes an ORF4 protein having a deletion of 9, 10, 11 or more amino acid residues in the region located between the first two predicted N-terminal ß-sheets, as compared to the ORF4 protein of a wild type genotype I PRRS virus;

C) a genotype II PRRS virus whose genome comprises a nucleic acid molecule which encodes an ORF4 protein having a deletion of 5, 6, 7 or more amino acid residues in the region between the first two predicted N-terminal ß-sheets, as compared to a wild type genotype II PRRS virus;

D) a PRRS virus, preferably a genotype I PRRS virus, whose genome comprises a nucleic acid molecule which encodes an ORF4 protein having a deletion of 9, 10, 11 or more amino acid residues between amino acid positions 50 to 71, wherein the numbering of the amino acid positions refers to the amino acid sequence of ORF4 protein of the Lelystad virus;

E) a genotype II PRRS virus whose genome comprises a nucleic acid molecule which encodes an ORF4 protein having a deletion of 5, 6, 7 or more amino acid residues between amino acid positions 50 to 67, wherein the numbering of the amino acid positions refers to the amino acid sequence of ORF4 protein of the PRRS virus VR2332;

F) a combination of any of A), B), C), D), and E).

Preferably, said PRRS virus, which is also termed “PRRS virus of the present invention” hereinafter, is an isolated PRRS virus.

Within the context of the invention, it is in particular understood that the phrase “amino acid residues in the region” is equivalent to the phrase “amino acid residues located in the region” and, respectively, it is particularly understood that the term “amino acid residues between amino acid positions” is interchangeable with the term “amino acid residues located in the region between amino acid positions”.

It is further understood that the terms “genotype I” and “genotype II” are equivalent to the terms “genotype 1” and “genotype 2” or to the terms “type 1” and “type 2”, as frequently used in the literature in the context of PRRSV.

According to the first aspect ((a)), the PRRS virus of the present invention is thus a PRRS virus comprising an ORF4 protein which comprises an amino acid sequence selected from the group consisting of SEQ ID NOs: 1-12, wherein said ORF4 protein preferably comprises an amino acid sequence selected from the group consisting of SEQ ID NO: 13-24, and wherein said ORF4 protein in an exemplary non-limiting embodiment comprises the amino acid sequence of SEQ ID NO: 31.

Respectively, according to the first aspect ((A)), the PRRS virus of the present invention is a PRRS virus whose genome comprises a nucleic acid molecule which encodes an ORF4 protein comprising an amino acid sequence selected from the group consisting of SEQ ID NOs: 1-12, wherein said ORF4 protein preferably comprises an amino acid sequence selected from the group consisting of SEQ ID NO: 13-24, and wherein said ORF4 protein in an exemplary non-limiting embodiment comprises the amino acid sequence of SEQ ID NO: 31.

According to the second aspect ((b)), the PRRS virus of the present invention is a PRRS virus, in particular a genotype I PRRS virus, comprising an ORF4 protein having a deletion of 9, 10, 11 or more amino acid residues in the region between the first two predicted N-terminal ß-sheets, as compared to the ORF4 protein of a wild type genotype I PRRS virus, wherein said first two predicted N-terminal ß-sheets are preferably the two amino acid sequences set forth in SEQ ID NO:25 and SEQ ID NO:26, or are preferably the two amino acid sequences set forth in SEQ ID NO:29 and SEQ ID NO:30, and wherein in an exemplary non-limiting embodiment said ORF4 protein comprises the amino acid sequence of SEQ ID NO:32.

Respectively, according to the second aspect ((B)), the PRRS virus of the present invention is a PRRS virus, in particular a genotype I PRRS virus, whose genome comprises a nucleic acid molecule which encodes an ORF4 protein having a deletion of 9, 10, 11 or more amino acid residues in the region between the first two predicted N-terminal ß-sheets, as compared to the ORF4 protein of a wild type genotype I PRRS virus, wherein said first two predicted N-terminal ß-sheets are preferably the two amino acid sequences set forth in SEQ ID NO:25 and SEQ ID NO:26, or are preferably the two amino acid sequences set forth in SEQ ID NO:29 and SEQ ID NO:30, and wherein in an exemplary non-limiting embodiment said ORF4 protein comprises the amino acid sequence of SEQ ID NO:32.

As described herein, for purposes of comparison, the wild type genotype I PRRS virus is preferably the prototype genotype I Lelystad virus. The genome of the Lelystad virus is encoded by the nucleic acid sequence of SEQ ID NO:41.

According to the third aspect ((c)), the PRRS virus of the present invention is a genotype II PRRS virus, comprising an ORF4 protein having a deletion of 5, 6, 7 or more amino acid residues in the region between the first two predicted N-terminal ß-sheets, as compared to a wild type genotype II PRRS virus, wherein the first two predicted N-terminal ß-sheets are preferably the two amino acid sequences set forth in SEQ ID NO: 27 and SEQ ID NO: 28, and wherein said ORF4 protein in an exemplary non-limiting example comprises the amino acid sequence of SEQ ID NO:33.

Respectively, according to the third aspect ((C)), the PRRS virus of the present invention is a genotype II PRRS virus whose genome comprises a nucleic acid molecule which encodes an ORF4 protein having a deletion of 5, 6, 7 or more amino acid residues in the region between the first two predicted N-terminal ß-sheets, as compared to a wild type genotype II PRRS virus, wherein the first two predicted N-terminal ß-sheets are preferably the two amino acid sequences set forth in SEQ ID NO: 27 and SEQ ID NO: 28, and wherein said ORF4 protein in an exemplary non-limiting example comprises the amino acid sequence of SEQ ID NO:33.

As mentioned herein, for purposes of comparison, the wild type genotype II PRRS virus is preferably the prototype genotype II virus VR2332. The genome of the virus VR2332 is encoded by the nucleic acid sequence of SEQ ID NO:42.

In the context of the invention, a deletion of amino acid residues is preferably a deletion of consecutive amino acid residues. Thus, for example, a deletion of 9, 10, 11 or more amino acid residues, as described herein, is preferably a deletion of 9, 10, 11 or more consecutive amino acid residues and, respectively, a deletion of 5, 6, 7 or more amino acid residues, as described herein, is preferably a deletion of 5, 6, 7 or more consecutive amino acid residues.

According to the fourth aspect ((d)), the PRRS virus of the present invention is a PRRS virus, preferably a genotype I PRRS virus, comprising an ORF4 protein having a deletion of 9, 10, 11 or more amino acid residues, or preferably a deletion of 11, 12, 13, 14, 15, 16, or 17 amino acid residues, between amino acid positions 50 to 71, wherein the numbering of the amino acid positions refers to the amino acid sequence of ORF4 protein of the Lelystad virus, and wherein in a non-limiting exemplary embodiment an ORF4 protein having a deletion of 11 amino acid residues between amino acid positions 50 to 71 is an ORF4 protein which comprises the amino acid sequence of SEQ ID NO:34.

Respectively, according to the fourth aspect ((D)), the PRRS virus of the present invention is a PRRS virus, preferably a genotype I PRRS virus, whose genome comprises a nucleic acid molecule which encodes an ORF4 protein having a deletion of 9, 10, 11 or more amino acid residues, or preferably a deletion of 11, 12, 13, 14, 15, 16, or 17 amino acid residues, between amino acid positions 50 to 71, wherein the numbering of the amino acid positions refers to the amino acid sequence of ORF4 protein of the Lelystad virus, and wherein in a non-limiting exemplary embodiment an ORF4 protein having a deletion of 11 amino acid residues between amino acid positions 50 to 71 is an ORF4 protein which comprises the amino acid sequence of SEQ ID NO:34.

As described herein, the numbering of amino acid positions relating to the Lelystad virus refers to the amino acid sequence of full length ORF4 protein of the Lelystad virus. Hence, the numbering of the amino positions as mentioned in this context is with reference to the ORF4 protein of the Lelystad protein having 183 amino acid residues, including a methionine residue at the (N-terminal) amino acid position 1.

Thus, the phrase “wherein the numbering of the amino acid positions refers to the amino acid sequence of ORF4 protein of the Lelystad virus”, as used in the context of the present invention, relates to the sequence of ORF4 protein as set forth in SEQ ID NO:43.

According to the fifth aspect ((e)), the PRRS virus of the present invention is a genotype II PRRS virus, comprising an ORF4 protein having a deletion of 5, 6, 7 or more amino acid residues, or preferably a deletion of 8, 9, 10, 11 or more amino acid residues, between amino acid positions 50 to 67, wherein the numbering of the amino acid positions refers to the amino acid sequence of ORF4 protein of the PRRS virus VR2332, and wherein in a non-limiting exemplary embodiment an ORF4 protein having a deletion of 7 amino acid residues between amino acid positions 50 to 67 is an ORF4 protein which comprises the amino acid sequence of SEQ ID NO:35.

Respectively, according to the fifth aspect ((E)), the PRRS virus of the present invention is a genotype II PRRS virus whose genome comprises a nucleic acid molecule which encodes an ORF4 protein having a deletion of 5, 6, 7 or more amino acid residues, or preferably a deletion of 8, 9, 10, 11 or more amino acid residues, between amino acid positions 50 to 67, wherein the numbering of the amino acid positions refers to the amino acid sequence of ORF4 protein of the PRRS virus VR2332, and wherein in a non-limiting exemplary embodiment an ORF4 protein having a deletion of 7 amino acid residues between amino acid positions 50 to 67 is an ORF4 protein which comprises the amino acid sequence of SEQ ID NO:35.

As described herein, the numbering of amino acid positions relating to the PRRS virus VR2332 refers to the amino acid sequence of full length ORF4 protein of the PRRS virus VR2332. Hence, the numbering of the amino positions as mentioned in this context is with reference to the ORF4 protein of the VR2332 virus having 178 amino acid residues, including a methionine residue at the (N-terminal) amino acid position 1.

Thus, the phrase “wherein the numbering of the amino acid positions refers to the amino acid sequence of ORF4 protein of the PRRS virus VR2332 having 178 amino acid residues, as used in the context of the present invention, relates to the sequence of ORF4 protein as set forth in SEQ ID NO:44.

According to the sixth aspect ((f)), the PRRS virus of the present invention is a combination of any of the aspects (a), (b), (c), (d), and (e), as described herein, preferably a combination of any of the aspects (a), (b), and (d) or a combination of any of the aspects (a), (c), and (e). Within this context it is in particular understood that the phrase “combination of any of (a), (b), (c), (d), and (e)” and “combination of any of the aspects (a), (b), (c), (d), and (e)”, respectively, means a PRRS virus having a combination of the features of any PRRS viruses of (a), (b), (c), (d), and (e), as described herein, wherein a combination of the features of any of the PRRS viruses of the aspects (a), (b) and/or (c) or a combination of the features of any of the PRRS viruses of the aspects (a), (c), and (e) is in particular preferred.

Respectively, according to the sixth aspect ((F)), the PRRS virus of the present invention is a combination of any of the aspects (A), (B), (C), (D), and (E), as described herein, preferably a combination of any of the aspects (A), (B), and (D) or a combination of any of the aspects (A), (C), and (E). Within this context it is in particular understood that the phrase “combination of any of (A), (B), (C), (D), and (E)” and “combination of any of the aspects (A), (B), (C), (D), and (E)”, respectively, means a PRRS virus having a combination of the features of any PRRS viruses of (A), (B), (C), (D), and (E), as described herein, wherein a combination of the features of any of the PRRS viruses of the aspects (A), (B) and/or (D) or a combination of the features of any of the PRRS viruses of the aspects (A), (C), and (E) is in particular preferred.

The PRRS virus of the present invention preferably comprises

- an ORF4 protein which comprises or consists of an amino acid sequence having a least 84.5% preferably at least 90%, more preferably at least 95%, still more preferably at least 97%, and in particular preferably at least 99% sequence identity with the amino acid sequence of SEQ ID NO:36, or an ORF4 protein which comprises or consists of an amino acid sequence encoded by a nucleic acid sequence having a least 83.5% preferably at least 90%, more preferably at least 95%, still more preferably at least 97%, and in particular preferably at least 99% sequence identity with the nucleic acid sequence of SEQ ID NO:37, wherein said PRRS virus is preferably a genotype I PRRS virus, and wherein said PRRS virus is in particular a genotype I PRRS virus.

As used herein, it is in particular understood that the term "sequence identity with the amino acid sequence of SEQ ID NO: 36" is equivalent to the term "sequence identity with the amino acid sequence of SEQ ID NO: 36 over the length of SEQ ID NO: 36" or to the term "sequence identity with the amino acid sequence of SEQ ID NO: 36 over the whole length of SEQ ID NO: 36", respectively.

Further, as used herein, it is particularly understood that the term "sequence identity with the nucleic acid sequence of SEQ ID NO: 37" is equivalent to the term "sequence identity with the nucleic acid sequence of SEQ ID NO: 37 over the length of SEQ ID NO: 37" or to the term "sequence identity with the nucleic acid sequence of SEQ ID NO: 37 over the whole length of SEQ ID NO: 37", respectively.

Sequence identity in the context of the first consideration of the invention is understood as being based on progressive alignment (Feng, D. F. and Doolittle, R. F. (1987). Progressive sequence alignment as a prerequisite to correct phylogenetic trees. J. Mol. Evol., 25(4):351-360, herein incorporated by reference). This method is based on combining sequences into alignments, which can in turn be combined with other sequences or alignments to form larger alignments. The procedure is repeated until all the input sequences have been joined in a single multiple alignment. For purposes of the present invention, percent sequence identity is determined with the software CLC MAIN WORKBENCH 4.1.1 (CLC BIO).

In one exemplary and non-limiting embodiment the PRRS virus of the present invention is a genotype I PRRS whose genome comprises an RNA molecule encoded by a nucleic acid molecule having at least 84.5%, preferably at least 90%, more preferably at least 95%, still more preferably at least 97%, and in particular preferably at least 99% sequence identity with the nucleic acid sequence of SEQ ID NO: 38.

As used herein, it is in particular understood that the term "sequence identity with the nucleic acid sequence of SEQ ID NO: 38" is equivalent to the term "sequence identity with the nucleic acid sequence of SEQ ID NO: 38 over the length of SEQ ID NO: 38" or to the term "sequence identity with the nucleic acid sequence of SEQ ID NO: 38 over the whole length of SEQ ID NO: 38", respectively.

According to another preferred aspect, the PRRS virus of the present invention is able to induce reproductive symptoms in pregnant sows and/or respiratory symptoms in piglets.

According to further preferred aspect, the PRRS virus of the present invention is able to induce respiratory symptoms in boars.

Thus, the PRRS virus of the present invention is preferably an infectious PRRS virus.

The term "infectious PRRS virus" according to the invention is particularly understood as a PRRS virus which infects swine, causing the associated disease, Porcine reproductive and respiratory syndrome (PRRS).

Said infection of swine by the PRRS virus of the present invention in particular includes attachment of the virus to a host cell, entry of the virus into the cell, disassembly of the virion, replication and transcription of the viral genome, expression of viral proteins and assembly and release of new infectious viral particles.

In another aspect, the invention further relates to a PRRS virus, preferably the PRRS virus of the present invention, genetically modified to contain therein exogenous RNA, wherein the exogenous RNA is inserted into the ORF4 gene of said virus, and wherein the exogenous RNA is preferably inserted a) into the region of the ORF4 gene of said virus encoding the amino acid sequence selected from the group consisting of SEQ ID NOs: 1-12 or 13-24;
b) into the region of the ORF4 gene of said virus encoding the region located between the first two predicted N-terminal ß-sheets, as compared to the ORF4 protein of a wild type genotype I PRRS virus;
c) into the region of the ORF4 gene of said virus encoding the region located between the first two predicted N-terminal ß-sheets, as compared to the ORF4 protein of a wild type genotype II PRRS virus;
d) into the region of the ORF4 gene of said virus encoding the region located between amino acid positions 50 to 71, wherein the numbering of the amino acid positions refers to the amino acid sequence of ORF4 protein of the Lelystad virus; or
e) into the region of the ORF4 gene of said virus encoding the region located between amino acid positions 50 to 67, wherein the numbering of the amino acid positions refers to the amino acid sequence of ORF4 protein of the PRRS virus VR2332.

As used herein, the term "exogenous RNA" or "exogenous nucleic acid sequence" in particular refers to a nucleic acid sequence that was introduced into the genome of a PRRS virus from an external source, such as from a recombinant sequence. Examples of such external source comprise PRRSV derived sequences as well as non PRRSV derived sequences. More particular, the introduction of the exogenous nucleic acid sequence results in a genome or a gene, respectively, having a non-naturally occuring portion. As used herein, the term "exogenous RNA" thus in particular refers to a nucleotide sequence, which is not naturally found in the PRRS virus genome. Such non-naturally occuring portion or not naturally found sequence, respectively, can also be the result of the insertion of one naturally occuring nucleotide sequence into another naturally occuring nucleotide sequence.

The exogenous RNA, as described herein, in particular encodes an expression product selected from the group consisting of an epitope of interest, a biological response modulator, a growth factor, a recognition sequence, and a fusion protein, and wherein said epitope of interest is preferably an epitope of interest from an antigen or a veterinary pathogen or toxin.

In one preferred embodiment, said epitope of interest is a peptide encoded by the ORF5 gene of PRRS virus, wherein said peptide encoded by the ORF5 gene of PRRS virus in particular comprises or consists of at least 4 consecutive amino acid residues of the sequence set forth in SEQ ID NO: 39 or, more particular, said peptide encoded by the ORF5 gene of PRRS virus comprises or consists of the amino acid sequence of SEQ ID NO:39.

In another preferred embodiment, said epitope of interest is the ectodomain of the ORF4 protein (GP4) of a different PRRS virus strain, wherein said ectodomain of GP4 of a different PRRS virus strain in particular comprises or consists of at least 4 consecutive amino acid residues of the sequence set forth in SEQ ID NO:40 or, more particular, said ectodomain of GP4 of a different PRRS virus strain comprises or consists of the amino acid sequence of SEQ ID NO:40.

The invention further provides the PRRS virus genetically modified to contain therein exogenous RNA, as described herein, for use as a medicament.

The present invention also provides the PRRS virus described herein for use as a challenge virus, in particular if said PRRS virus inherently induces a vaccinating effect when administered to an animal.

The present invention additionally provides the use of the PRRS virus of the present invention as a challenge virus, in particular if said PRRS virus does not induce a vaccinating effect when administered to an animal.

The term "animal", as mentioned herein, is in particular directed to swine, more particular to a pig, preferably a domestic pig.

Preferably, the PRRS virus is to be administered, or is administered, respectively, via the intranasal, intramuscular, oral, or intrauterine route to an animal.

Also, the present invention provides the use of the PRRS virus described herein as a detection marker, preferably for the differentiation between infected and vaccinated animals (DIVA).

According to a further aspect, the invention also relates to a DNA molecule which encodes the PRRS virus described herein, wherein said DNA molecule is preferably an isolated DNA molecule and/or wherein said DNA molecule preferably comprises a nucleic acid molecule having at least 84.5%, preferably at least 90%, more preferably at least 95%, still more preferably at least 97%, and in particular preferably at least 99% sequence identity with the nucleic acid sequence of SEQ ID NO: 38.

The present invention further provides a DNA construct comprising the DNA molecule described herein, wherein said DNA construct is in particular a DNA vector such as a plasmid. DNA vectors or plasmids into which the DNA molecule of the present invention can be inserted will be recognized by those of ordinary skill in the art. The DNA construct, as described herein, is preferably an isolated DNA construct. As used herein, the term "comprising the DNA molecule" is in particular understood to be equivalent to the term "comprising the sequence of the DNA molecule".

Further, the present invention provides a RNA transcript of the DNA construct described herein, wherein said RNA transcript is preferably an isolated RNA transcript.

The present invention also provides a cell transfected with the DNA construct described herein, wherein said cell is preferably an isolated cell.

Further, the present invention provides a cell transfected with the RNA transcript mentioned herein, wherein said cell is preferably an isolated cell.

The term "cells" or "cell", as mentioned herein, is preferably directed to mammalian cells, in particular porcine or simian cells, such as MA-104 cells or MARC-145 cells or Vero cells, more preferably it is understood that the term "cells" or "cell" is directed to the host cells of PRRS virus, namely to porcine macrophages. Hence, a cell, as mentioned herein, is preferably selected from the group consisting of porcine cell, simian cell, MA-104 cell, MARC-145 cell, Vero cell and porcine macrophage.

In a further aspect, the invention provides a method for producing the PRRS virus described herein, wherein the method comprises the step of transfecting a cell with the DNA construct described herein and optionally harvesting the virus from the cell and/or the medium.

In another aspect, the invention provides a method for producing the PRRS virus described herein, wherein the method comprises the step of transfecting a host cell with the RNA transcript described herein and optionally harvesting the virus from the cell and/or the medium.

Production of the nucleic acid/DNA molecules described herein, is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, N.Y.; Ausubel, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

2. Second Consideration of the Present Invention

According to a second consideration, which is detailed in this section, the invention provides, in one aspect, a nucleic acid molecule which encodes a genotype I PRRS virus and which is capable of producing live virus when transfected into cells, wherein said molecule comprises

- a first nucleic acid sequence having at least 95% sequence identity with the nucleic acid sequence of SEQ ID NO:45,
- a second nucleic acid sequence flanking the 5' end of the first nucleic acid sequence and having at least 95% sequence identity with the nucleic acid sequence of SEQ ID NO:46,
- a third nucleic acid sequence flanking the 3' end of the first nucleic acid sequence and having at least 95% sequence identity with the nucleic acid sequence of SEQ ID NO:47, and
- a polyadenine nucleotide sequence flanking the 3' end of the third nucleic acid sequence.

Preferably,

- said first nucleic acid sequence has at least 96%, preferably at least 97%, more preferably at least 98%, still more preferably at least 99%, and in particular preferably 100% sequence identity with the nucleic acid sequence of SEQ ID NO:45; and/or
- said second nucleic acid sequence having at least 96%, preferably at least 97%, more preferably at least 98%, still more preferably at least 99%, and in particular preferably 100% sequence identity with the nucleic acid sequence of SEQ ID NO:46; and/or
- said third nucleic acid sequence having at least 96%, preferably at least 97%, more preferably at least 98%, still more preferably at least 99%, and in particular preferably 100% sequence identity with the nucleic acid sequence of SEQ ID NO:47; and/or
- said polyadenine nucleotide sequence is composed of n adenine nucleotides, wherein n is any integer between 1 and 51, and wherein n is preferably 12, 13 or 14.

The nucleic acid molecule of the present invention is preferably a DNA molecule. Preferably, said nucleic acid molecule is an isolated nucleic acid molecule.

Within the context of the present invention it is in particular understood that the term "polyadenine nucleotide sequence" is equivalent to the term "polyadenylic acid sequence" or "poly (A) tail", respectively. The term "adenine nucleotide(s)", as described herein, is in particular understood to be equivalent to the term "deoxyadenylate(s)".

The phrase "nucleotide sequence flanking the 5' end of" as described herein is in particular equivalent to the phrase "nucleotide sequence covalently linked with the 5' end of" or, respectively, with the phrase "nucleotide sequence, wherein the 3' terminal nucleotide thereof is covalently linked with the 5' terminal nucleotide of", and wherein it is particularly understood that said two terminal nucleotides are linked covalently between the phosphate group attached to the 5' carbon of the pentose and the 3' carbon atom of the adjacent pentose.

The phrase "nucleotide sequence flanking the 3' end of" as described herein is in particular equivalent to the phrase "nucleotide sequence covalently linked with the 3' end of" or, respectively, to the phrase "nucleotide sequence, wherein the 5' terminal nucleotide thereof is covalently linked with the 3' terminal nucleotide of", and wherein it is particularly understood that said two terminal nucleotides are linked covalently between the 3' carbon atom of the pentose and the phosphate group attached to the 5' carbon of the adjacent pentose.

It is further particularly understood that the phrase "having 100% sequence identity with the nucleic acid sequence of", as used herein, is equivalent to the phrase "being identical to the the nucleic acid sequence of" or "consisting of the nucleic acid sequence of", respectively.

In a particular preferred aspect, the nucleic acid molecule of the present invention comprises a nucleic acid sequence having at least 99% sequence identity with the nucleic acid sequence of SEQ ID NO:48, or wherein said nucleic acid molecule comprises or consists of a RNA copy of a nucleic acid sequence having at least 99% sequence identity with the nucleic acid sequence of SEQ ID NO:48.

The term "cells" or "cell", as mentioned herein, is preferably directed to mammalian cells, in particular porcine or simian cells, such as MA-104 cells or MARC-145 cells or Vero cells, more preferably it is understood that the term "cells" or "cell" is directed to the host cells of PRRS virus, namely to porcine macrophages. Hence, a cell, as mentioned herein, is preferably selected from the group consisting of porcine cell, simian cell, MA-104 cell, MARC-145 cell, Vero cell and porcine macrophage.

The term "live virus" according to the invention is particularly understood as a PRRS virus having the ability of infecting an appropriate subject (as opposed to an inactivated (killed) virus) and/or whose infectivity is similar or identical to a native virus. In particular, a live virus can infect its native host cells.

Said infection of host cells by the PRRS virus produced by the nucleic acid molecule of the present invention in particular includes attachment of the virus to a host cell, entry of the virus into the cell, disassembly of the virion, replication and transcription of the viral genome, expression of viral proteins and assembly and release of new infectious viral particles. Said infection of host cells by the PRRS virus produced by the nucleic acid molecule of the present invention further preferably includes the transcription of the cDNA sequence, in particular in BHK cells, to yield a functional RNA molecule, transfection of cultured cells, preferably porcine cell, simian cell, MA-104 cell, MARC-145 cell, Vero cell and porcine macrophage, with said RNA molecule, generation of live virions by viral replication in said cultured cells, isolation of such virions and infection of host cells.

In particular, the nucleic acid molecule of the present invention preferably encodes an attenuated genotype I PRRS virus or, respectively, the nucleic acid molecule of the present invention is capable of producing live attenuated virus when transfected into cells.

More particular the nucleic acid molecule of the present invention encodes a genotype I PRRS virus which is not able to induce a severe Porcine Reproductive and Respiratory Syndrome (PRRS) in swine or, respectively, the nucleic acid molecule of the present invention is capable of producing live virus when transfected into cells, wherein said live virus is not able to induce a severe, wild-type virus-like Porcine Reproductive and Respiratory Syndrome (PRRS) in swine as caused by virulent field PRRS viruses.

In one particular embodiment, the nucleic acid molecule of the present invention encodes a genotype I PRRS virus which is able to reach titers of at least $5\times10^5$ to $1\times10^6$ tissue culture infectious dose 50 ($TCID_{50}$) per milliliter (ml) within 24 hours post infection of MA104 cells, wherein said MA104 cells are preferably infected with said virus at an MOI (multiplicity of infection) of 0.001 to 0.1.

Particularly, the nucleic acid molecule of the present invention encodes a genotype I PRRS virus which is able to reach titers of $5\times10^6$ to $1\times10^7$ or more tissue culture infectious dose 50 ($TCID_{50}$) per milliliter (ml) within 48 hours post infection of MA104 cells, wherein said MA104 cells are preferably infected with said virus at an MOI (multiplicity of infection) of 0.001 to 0.1.

Thus, the nucleic acid molecule of the present invention preferably encodes a genotype I PRRS virus which is able to
- reach titers of at least $5\times10^5$ to $1\times10^6$ tissue culture infectious dose 50 ($TCID_{50}$) per milliliter (ml) within 24 hours and/or
- reach titers of at least $5\times10^6$ to $1\times10^7$ tissue culture infectious dose 50 ($TCID_{50}$) per milliliter (ml) within 48 hours post infection of MA104 cells at an MOI (multiplicity of infection) of 0.001 to 0.1, in particular at an MOI of 0.001 or 0.01 or 0.1.

In the context of the PRRS virus as described herein, it is understood that the term "genotype I" is equivalent to the terms "genotype 1" or "type 1" or "European (EU)" as frequently used in the literature in the context of PRRSV.

In another preferred embodiment, the nucleic acid molecule of the present invention comprises a nucleic acid sequence having at least 99.1% or 99.2%, preferably at least 99.3% or 99.4%, more preferably at least 99.5% or 99.6%, still more preferably at least 99.8% or 99.9%, and in particular preferably at least 99.95% sequence identity with the nucleic acid sequence set forth in SEQ ID NO:48.

Sequence identity in the context of the second consideration of the invention is understood as being based on pairwise determined similarity between nucleotide sequences. The determination of percent identity between two sequences is preferably accomplished using a mathematical algorithm, in particular the well-known Smith-Waterman algorithm (Smith and Waterman, M. S. (1981) J Mol Biol, 147(1):195-197). For purposes of the present invention, percent sequence identity of a nucleotide sequence is determined using the Smith-Waterman homology search algorithm using a gap open penalty of 25 and a gap extension penalty of 5. The Smith-Waterman homology search algorithm is taught in Smith and Waterman (1981) Adv. Appl. Math 2:482-489, herein incorporated by reference. Such a determination of sequence identity can be performed using, for example, the DeCypher Hardware Accelerator from TimeLogic Version G, or the sequence identity is determined with the software CLC MAIN WORKBENCH 4.1.1 (CLC BIO).

As used herein, it is in particular understood that the term "having at least X % sequence identity with the nucleic acid sequence of SEQ ID NO:Y" (or, alternatively, the term "having at least X % sequence identity with the nucleic acid sequence set forth in SEQ ID NO:Y") is equivalent to the term "having at least X % sequence identity with the nucleic acid sequence of SEQ ID NO:Y over the length of SEQ ID NO:Y" or to the term "having at least X % sequence identity with the nucleic acid sequence of SEQ ID NO:Y over the whole length of SEQ ID NO:Y", respectively. In this context, "X" is any number from 95 to 100, in particular any integer selected from 95 to 99, such that "X % sequence identity" represents any of the percent sequence identities mentioned herein. Respectively, "Y" in this context is any integer selected from 1 to 6, such that "SEQ ID NO:Y" represents any of the SEQ ID NOs mentioned herein.

In a particular preferred embodiment, the nucleic acid molecule of the present invention comprises the nucleic acid sequence of SEQ ID NO:48.

In another preferred embodiment, the nucleic acid molecule of the present invention encodes a genotype I PRRS virus which is not able to induce Porcine Reproductive and Respiratory Syndrome (PRRS) in swine or, respectively, the nucleic acid molecule of the present invention is capable of producing live virus when transfected into cells, wherein said infectious virus is not able to induce Porcine Reproductive and Respiratory Syndrome (PRRS) in swine.

As used herein, the term "is not able to induce Porcine Reproductive and Respiratory Syndrome (PRRS)" in particular refers to a reduction of the clinical signs of PRRS or of signs associated with PRRSV infection, respectively, such as lung lesions in piglets, reproductive failure in pregnant sows, and/or prolonged PRRSV viremia, when compared to a wild-type PRRS virus. In one aspect, the genotype I PRRS virus which is not able to induce PRRS in swine is thus a virus showing one or more reduced clinical signs when administered to swine, in comparison with a wild type PRRS virus administered to swine. The term "wild type PRRS virus", as mentioned herein, in particular relates to a wild type genotype I PRRS virus.

The present invention further provides a DNA construct comprising the nucleic acid molecule according to the invention, wherein said DNA construct is in particular a DNA vector such as a plasmid. DNA vectors or plasmids into which the nucleotide molecule of the present invention can be inserted will be recognized by those of ordinary skill in the art. The DNA construct, as described herein, is preferably an isolated DNA construct. As used herein, the term "comprising the nucleic acid molecule" or "comprising a DNA molecule", respectively, is in particular understood to be equivalent to the term "comprising the sequence of the nucleic acid molecule" or "comprising the sequence of a DNA molecule", respectively.

Further, the present invention provides a RNA transcript of the DNA construct described herein, wherein said RNA transcript is preferably an isolated RNA transcript.

The present invention also provides a cell transfected with the DNA construct described herein, wherein said cell is preferably an isolated cell.

Thus, the present invention also provides genotype I PRRS virus produced by the aforementioned cell, wherein said genotype I PRRS virus is preferably an isolated genotype I PRRS virus.

Further, the present invention provides a cell transfected with the RNA transcript mentioned herein, wherein said cell is preferably an isolated cell.

Hence, the present invention also provides genotype I PRRS virus produced by the aforementioned cell, wherein said genotype I PRRS virus is preferably an isolated genotype I PRRS virus.

The present invention further provides a genotype I PRRS virus whose genome comprises the nucleic acid molecule of the present invention or whose genome comprises an RNA molecule encoded by a nucleic acid molecule of the present invention, wherein said genotype I PRRS virus is preferably an isolated genotype I PRRS virus.

In another aspect, the present invention provides a method for producing a genotype I PRRS virus, said method comprising transfecting a cell with the DNA construct described herein.

Moreover, the present invention provides a method for producing a genotype I PRRS virus, said method comprising transfecting a cell with the RNA transcript mentioned herein.

In yet another aspect, the present invention provides a composition, said composition comprising the nucleic acid molecule according to the invention suspended in a suitable amount of a pharmaceutically acceptable diluent or excipient.

Production of the nucleic acid molecules described herein is within the skill in the art and can be carried out according to recombinant techniques described, among other places, in Sambrook et al., 2001, Molecular Cloning, A Laboratory Manual, Cold Spring Harbor Laboratory Press, Cold Spring Harbor, NY; Ausubel, et al., 2003, Current Protocols In Molecular Biology, Greene Publishing Associates & Wiley Interscience, NY; Innis et al. (eds), 1995, PCR Strategies, Academic Press, Inc., San Diego; and Erlich (ed), 1994, PCR Technology, Oxford University Press, New York, all of which are incorporated herein by reference.

In still another aspect, the invention further relates to the use of the nucleic acid molecule according to the invention or of the DNA construct described herein for producing an attenuated genotype I PRRS virus, wherein one or more mutations are introduced into the nucleic acid molecule or into the DNA construct.

The invention also provides a method of producing an attenuated genotype I PRRS virus comprising the step of introducing one or more mutations into the nucleic acid molecule according to the invention or into the DNA construct described herein.

Preferably, the one or more mutations described herein are introduced into the first nucleic acid sequence having at least 95% sequence identity with the nucleic acid sequence of SEQ ID NO:45.

The term "attenuated PRRS virus", as described herein, is in particular directed to a PRRS virus which is attenuated in vitro and/or in vivo, more particular in susceptible cell lines and/or the host.

The term "host", as used herein, is in particular directed to animals infectable with PRRS virus, in particular swine, more particular pigs, such as domestic pigs.

As mentioned herein, "attenuated" particularly relates to a reduced virulence of a pathogen, in particular of a wild type PRRS virus, wherein "virulence" is understood to be the degree of pathogenicity, and wherein "pathogenicity" is directed to the ability of the pathogen to induce clinical signs in the host or the offspring of the host, such as reproductive failure.

The term "wild type PRRS virus" or "wild type PRRSV", respectively, as used herein, is in particular directed to an infectious pathogenic PRRS virus, which is particularly capable of causing PRRS in swine. In one particular preferred embodiment, the term "wild type PRRS virus" is directed to a PRRS virus whose genome comprises a RNA sequence or consists of a RNA polynucleotide, wherein said RNA sequence or RNA polynucleotide is a RNA copy of SEQ ID NO:41 (corresponding to Lelystad virus complete genome).

Preferably, the one or more mutations, as described herein, comprise or consist of one or more point mutations and/or one or more genomic deletions and/or one or more insertions.

Also, the invention provides an attenuated genotype I PRRS virus whose genome comprises an RNA molecule encoded by a nucleic acid molecule according to the invention but wherein said first nucleic acid sequence having at least 95% sequence identity with the nucleic acid sequence of SEQ ID NO:45 contains one or more mutations that attenuate the encoded PRRS virus and/or that disable the encoded PRRS virus to suppress the interferon type I production and secretion by a cell infected by said virus, and wherein said attenuated genotype I PRRS virus is preferably an isolated attenuated genotype I PRRS virus.

The invention further provides the use of the attenuated genotype I PRRS virus described herein for the preparation of a medicament, in particular of a vaccine or vaccine composition, for preventing an animal from clinical signs of a PRRSV infection, such as by reducing the clinical signs of a PRRSV infection, e.g. reducing the duration of PRRSV viremia.

The term "preventing" or "reducing", respectively, as used herein, means, but is not limited to, a process which includes the administration of a PRRSV antigen, namely of the attenuated genotype I PRRS virus described herein, to an animal, wherein said PRRSV antigen, when administered to said animal elicits or is able to elicit an immune response in said animal against PRRSV. Altogether, such treatment results in reduction of the clinical signs of PRRS or of signs associated with PRRSV infection, respectively. More specifically, the term "preventing, as used herein, means generally a process of prophylaxis in which an animal is exposed to the immunogenic composition of the present invention prior to the induction or onset of the disease process (PRRS).

Herein, "reducing the clinical signs of a PRRSV infection" means, but is not limited to, reducing the number of infected subjects in a group, reducing or eliminating the number of subjects exhibiting clinical signs of infection, or reducing the severity of any clinical signs that are present in the subjects, in comparison to wild type PRRS virus infection. For example, it should refer to any reduction of pathogen load, pathogen shedding, reduction in pathogen transmission, or reduction of any clinical sign typical of PRRSV infection, in particular of reproductive failure and/or induction of lung lesions. Preferably these clinical signs are reduced in subjects receiving the attenuated genotype I PRRS virus of the present invention by at least 10% in comparison to subjects not receiving the composition and may become infected. More preferably, clinical signs are reduced in subjects receiving the composition of the present invention by at least 20%, preferably by at least 30%, more preferably by at least 40%, even more preferably by at least 50%, even more preferably by at least 60%, even more preferably by at least 70%, even more preferably by at least 80%, even more preferably by at least 90%, and most preferably by 100%.

The term "subject", as mentioned herein, in particular relates to an animal.

The term "animal", as mentioned herein, is in particular directed to swine, more particular to a pig, preferably a domestic pig.

The term "reducing the duration of PRRSV viremia" means, but is not limited to, the reduction of the duration of PRRS virus entering the bloodstream of an animal by at least one day in comparison to subjects not receiving the composition and become infected by a wild type PRRSV.

The term "viremia" refers to the presence of PRRSV in the blood of infected animals as reflected by e.g. the detection of PRRSV RNA copies in blood serum.

Also, the invention relates to a vaccine composition comprising the attenuated genotype I PRRS virus described herein suspended in a suitable amount of a pharmaceutically acceptable diluent or excipient.

The one or more pharmaceutically acceptable carriers or excipients, as mentioned herein, are preferably selected from the group consisting of solvents, dispersion media, adjuvants, stabilizing agents, diluents, preservatives, antibacterial and antifungal agents, isotonic agents, and adsorption delaying agents.

In a preferred aspect, the immunogenic composition of the invention comprises an amount of $10^1$ to $10^7$ viral particles of the attenuated genotype I PRRS virus described herein per dose, preferably $10^3$ to $10^6$ particles per dose, more preferably $10^4$ to $10^6$ particles per dose.

In another preferred aspect, the immunogenic composition of the invention comprises an amount of the PRRS virus according to the invention which is equivalent to a virus titer of at least about $10^3$ $TCID_{50}$/mL per dose, preferably between $10^3$ to $10^5$ $TCID_{50}$/mL per dose As used herein, the term "vaccine composition" in particular refers to a composition that will elicit a protective immune response in an animal that has been exposed to the composition. An immune response may include induction of antibodies and/or induction of a T-cell response.

Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the clinical signs associated with the infection of the pathogen, in the delay of onset of viremia, in a reduced viral persistence, in a reduction of the overall viral load and/or in a reduction of viral excretion.

Thus, an "immune response" in particular means but is not limited to the development in a subset of a cellular and/or antibody-mediated immune response to the composition or vaccine of interest.

Further, the invention relates to the vaccine composition of the invention for use in a method for preventing an animal from clinical signs of a PRRSV infection, such as by reducing the clinical signs of a PRRSV infection, e.g. reducing the duration of PRRSV viremia.

Moreover, the invention provides a method for preventing an animal from clinical signs of a PRRSV infection, such as by reducing the clinical signs of a PRRSV infection, e.g. reducing the duration of PRRSV viremia, wherein said method comprises the step of administering the vaccine of the invention to an animal in need thereof.

EMBODIMENTS According to the Second Consideration of the Present Invention

The following clauses are also described herein:

1. A nucleic acid molecule which encodes a genotype I PRRS virus and which is capable of producing live virus when transfected into cells, wherein said molecule comprises a first nucleic acid sequence having at least 95% sequence identity with the nucleic acid sequence of SEQ ID NO:45, a second nucleic acid sequence flanking the 5' end of the first nucleic acid sequence and having at least 95% sequence identity with the nucleic acid sequence of SEQ ID NO:46, a third nucleic acid sequence flanking the 3' end of the first nucleic acid sequence and having at least 95% sequence identity with the nucleic acid sequence of SEQ ID NO:47, and a polyadenine nucleotide sequence flanking the 3' end of the third nucleic acid sequence.

2. The nucleic acid molecule of clause 1, wherein said first nucleic acid sequence having at least 96%, preferably at least 97%, more preferably at least 98%, still more preferably at least 99%, and in particular preferably 100% sequence identity with the nucleic acid sequence of SEQ ID NO:45; and/or said second nucleic acid sequence having at least 96%, preferably at least 97%, more preferably at least 98%, still more preferably at least 99%, and in particular preferably 100% sequence identity with the nucleic acid sequence of SEQ ID NO:46; and/or said third nucleic acid sequence having at least 96%, preferably at least 97%, more preferably at least 98%, still more preferably at least 99%, and in particular preferably 100% sequence identity with the nucleic acid sequence of SEQ ID NO:47; and/or said polyadenine nucleotide sequence is composed of n adenine nucleotides, wherein n is any integer between 1 and 51, and wherein n is preferably 12, 13 or 14.

3. The nucleic acid molecule of clause 1 or 2, wherein said virus is attenuated and/or wherein said virus is able to induce a protective immune response against respiratory and/or reproductive signs of disease after infection with Porcine Reproductive and Respiratory Syndrome (PRRS) virus in swine.
4. The nucleic acid molecule of any one of clauses 1 to 3, wherein said virus is able to reach titers of at least $5\times10^5$ to $1\times10^6$ tissue culture infectious dose 50 ($TCID_{50}$) per milliliter (ml) within 24 hours post infection of MA104 cells, preferably at an MOI (multiplicity of infection) of 0.001 to 0.1.
5. The nucleic acid molecule of any one of clauses 1 to 4, wherein said virus is able to reach titers of at least $5\times10^6$ to $1\times10^7$ tissue culture infectious dose 50 ($TCID_{50}$) per milliliter (ml) within 48 hours post infection of MA104 cells, preferably at an MOI (multiplicity of infection) of 0.001 to 0.1.
6. The nucleic acid molecule of any one of clauses 1 to 5, wherein said molecule comprises a nucleic acid sequence having at least 91% or 92%, preferably at least 93% or 94%, more preferably at least 95% or 96%, still more preferably at least 98% or 99%, and in particular preferably at least 99% sequence identity with the nucleic acid sequence of SEQ ID NO:48.
7. The nucleic acid molecule of any one of clauses 1 to 6, wherein said molecule comprises a nucleic acid sequence having at least 99.1% or 99.2%, preferably at least 99.3% or 99.4%, more preferably at least 99.5% or 99.6%, still more preferably at least 99.8% or 99.9%, and in particular preferably at least 99.95% sequence identity with the nucleic acid sequence of SEQ ID NO:48.
8. The nucleic acid molecule of any one of clauses 1 to 7, wherein said molecule comprises the nucleic acid sequence of SEQ ID NO:48.
9. The nucleic acid molecule of any one of clauses 1 to 8, wherein said virus is not able to induce a severe, Porcine Reproductive and Respiratory Syndrome (PRRS) in swine as caused by virulent field PRRS viruses.
10. The nucleic acid molecule of any one of clauses 1 to 9, wherein said molecule is a DNA molecule.
11. A DNA construct comprising a DNA molecule according to clause 10.
12. An RNA transcript of the DNA construct of clause 11.
13. A cell transfected with the DNA construct of clause 11.
14. A cell transfected with the RNA transcript of clause 12.
15. A genotype I PRRS virus produced by the cell of clause 13.
16. A genotype I PRRS virus produced by the cell of clause 14.
17. A genotype I PRRS virus whose genome comprises a nucleic acid molecule according to any one of clauses 1 to 9 or whose genome comprises an RNA molecule encoded by a nucleic acid molecule according to any one of clauses 1 to 10.
18. A method for producing a genotype I PRRS virus comprising transfecting a cell with the DNA construct of clause 11.
19. A method for producing a genotype I PRRS virus comprising transfecting a host cell with the RNA transcript of clause 12.
20. A composition comprising a nucleic acid molecule of any one of clauses 1 to 10 suspended in a suitable amount of a pharmaceutically acceptable diluent or excipient.
21. Use of the nucleic acid molecule of any one of clauses 1 to 10 or of the DNA construct of clause 11 for producing an attenuated genotype I PRRS virus, wherein one or more mutations are introduced into the nucleic acid molecule or into the DNA construct.
22. Method of producing an attenuated genotype I PRRS virus comprising the step of introducing one or more mutations into the nucleic acid molecule of any one of clauses 1 to 10 or into the DNA construct of clause 11.
23. An attenuated genotype I PRRS virus whose genome comprises an RNA molecule encoded by a nucleic acid molecule according to any one of clauses 1 to 10 but wherein said first nucleic acid sequence having at least 95% sequence identity with the nucleic acid sequence of SEQ ID NO:45 contains one or more mutations that disable the encoded PRRS virus to suppress the interferon type I production and secretion by a cell infected by said virus.
24. Use of the attenuated genotype I PRRS virus of any one of clauses 21 to 23 for the preparation of a medicament for preventing an animal from clinical signs of a PRRSV infection.
25. A vaccine composition comprising the attenuated genotype I PRRS virus of any one of clauses 21 to 23 suspended in a suitable amount of a pharmaceutically acceptable diluent or excipient.

26. The vaccine composition of clause 25 for use in a method for preventing an animal from clinical signs of a PRRSV infection.
27. Method for preventing an animal from clinical signs of a PRRSV infection comprising the step of administering the vaccine composition of clause 26 to an animal in need thereof.

3. Third Consideration of the Present Invention

According to a third consideration, which is detailed in this section, the invention is based on the finding that the first consideration of the present invention can be combined with the second consideration of the present invention. Thus, the third consideration of the present invention relates to a combination of (1) the aspects and embodiments of the first consideration of the present invention and (2) the aspects and embodiments of the second consideration of the present invention. Hence, it is understood that all possible features and definitions, in particular the features and definitions relating to a genotype I PRRS virus, of the first consideration of the present invention can be arbitrarily combined with all features and definitions of the second consideration of the present invention.

In one aspect, the nucleic acid molecule according to the second consideration of the present invention thus encodes the Porcine Reproductive and Respiratory Syndrome (PRRS) virus according to the first consideration of the present invention, as recited.

In another aspect, respectively, the Porcine Reproductive and Respiratory Syndrome (PRRS) virus according to the first consideration of the present invention is thus encoded by the nucleic acid molecule according to the second consideration of the present invention, as recited.

Hence, the combination of all possible aspects of the first consideration of the present invention with all possible aspects of the second consideration of the present invention is in particular also reflected by said claims and the claims depending thereon.

The invention is directed, furthermore, to a genotype I PRRS virus, in particular the aforementioned PRRS virus, whose genome is encoded by a nucleic acid molecule which encodes a genotype I PRRS virus and which is capable of producing live virus when transfected into cells, wherein said molecule comprises a nucleic acid sequence having at least 91% or 92%, preferably at least 93% or 94%, more preferably at least 95% or 96%, still more preferably at least 98% or 99%, and in particular preferably at least 99% or 100% sequence identity with the nucleic acid sequence of SEQ ID NO:48, but wherein said nucleic acid sequence contains a mutation resulting in the production of said virus comprising an ORF4 protein having a deletion of 9, 10, 11 or more amino acid residues between amino acid positions 50 to 71, wherein the numbering of the amino acid positions refers to the amino acid sequence of ORF4 protein of the Lelystad virus.

The invention also concerns a genotype I PRRS virus, whose genome is encoded by a nucleic acid molecule which encodes a genotype I PRRS virus and which is capable of producing live virus when transfected into cells, wherein said molecule comprises a nucleic acid sequence having at least 91% or 92%, preferably at least 93% or 94%, more preferably at least 95% or 96%, still more preferably at least 98% or 99%, and in particular preferably at least 99% or 100% sequence identity with the nucleic acid sequence of the nucleic acid sequence of SEQ ID NO:48, but wherein said nucleic acid sequence contains a mutation resulting in the production of said virus comprising an ORF4 protein having a deletion of 11, 12, 13, 14, 15, 16, or 17 amino acid residues between amino acid positions 50 to 71, wherein the numbering of the amino acid positions refers to the amino acid sequence of ORF4 protein of the Lelystad virus.

The invention moreover contemplates a genotype I PRRS virus, whose genome is encoded by a nucleic acid molecule which encodes a genotype I PRRS virus and which is capable of producing live virus when transfected into cells, wherein said molecule comprises a nucleic acid sequence having at least 91% or 92%, preferably at least 93% or 94%, more preferably at least 95% or 96%, still more preferably at least 98% or 99%, and in particular preferably at least 99% or 100% sequence identity with the nucleic acid sequence of the nucleic acid sequence of SEQ ID NO:48, but wherein said nucleic acid sequence contains a mutation resulting in the production of said virus comprising an ORF4 protein having a deletion of 13 amino acid residues between amino acid positions 56 to 70 or between amino acid positions 57 to 69, wherein the numbering of the amino acid positions refers to the amino acid sequence of ORF4 protein of the Lelystad virus.

The mutation, as referred to herein, is preferably a deletion.

Peferably, the PRRS virus of the invention is genetically modified to contain therein exogenous RNA, wherein the exogenous RNA is inserted into the orf4 gene of said virus, and wherein the exogenous RNA is in particular inserted into the region of the orf4 gene of said virus encoding the region located between amino acid positions 50 to 71, wherein the numbering of the amino acid positions refers to the amino acid sequence of ORF4 protein of the Lelystad virus.

In another preferred aspect, the exogenous RNA is inserted into the orf4 gene of the virus and replaces the nucleotide sequence encoding the amino acid residues deleted within the context of the invention.

According to a further preferred aspect, the exogenous RNA encodes an expression product selected from the group consisting of an epitope of interest, a biological response modulator, a growth factor, a recognition sequence, a fusion protein, wherein the epitope of interest is preferably an epitope of interest from an antigen or a veterinary pathogen or toxin.

In particular, the epitope of interest is a peptide encoded by the orf5 gene of PRRS virus or is an amino acid sequence encoded by the orf5 gene of PRRS virus, wherein said peptide or amino acid sequence encoded by the orf5 gene of PRRS virus preferably comprises or consists of the amino acid sequence of SEQ ID NO:39 or SEQ ID NO:50 or preferably comprises or consists of at least 4 consecutive amino acid residues of the sequence set forth in SEQ ID NO: 39 or SEQ ID NO:50, or preferably comprises or consists of the amino acid sequence of SEQ ID NO:51 or SEQ ID NO:52.

According to a another preferred aspect, the exogenous RNA encodes an amino acid sequence selected from the group consisting of SEQ ID NOs: 53-55.

In a particular preferred aspect, the invention provides, as a non limiting example, a genotype I PRRS virus, whose genome is encoded by a nucleic acid molecule comprising a nucleic acid sequence selected from the group consisting of any one of SEQ ID NOs:56-59.

The PRRS virus, as mentioned to herein, is preferably an isolated virus and/or a non-naturally occurring virus.

The invention is directed, furthermore, to a genotype I PRRS virus, wherein said virus comprises an ORF4 protein having a proline residue at amino acid position 56 and/or having a glutamine residue at amino acid position 66, wherein the numbering of the amino acid positions refers to the amino acid sequence of ORF4 protein of the Lelystad virus, and wherein the amino acid sequence of ORF4 protein of the Lelystad virus is the sequence set forth in SEQ ID NO:43.

The invention also concerns a genotype I PRRS virus, whose genome comprises a nucleic acid molecule which encodes an ORF4 protein having a proline residue at amino acid position 56 and/or having a glutamine residue at amino acid position 66, wherein the numbering of the amino acid positions refers to the amino acid sequence of ORF4 protein of the Lelystad virus, and wherein the genome of said virus is preferably is encoded by a nucleic acid molecule, wherein said molecule comprises a nucleic acid sequence having at least 91% or 92%, preferably at least 93% or 94%, more preferably at least 95% or 96%, still more preferably at least 98% or 99%, and in particular preferably at least 99% sequence identity with the nucleic acid sequence of the nucleic acid sequence of SEQ ID NO:45 or SEQ ID NO:48.

Such a genotype I PRRS virus, whose genome comprises a nucleic acid molecule which encodes an ORF4 protein having a proline residue at amino acid position 56, is in an exemplary non-limiting aspect a PRRS virus, whose genome is encoded by a nucleic acid molecule comprising the nucleic acid sequence SEQ ID NO:58.

In another exemplary non-limiting aspect, such a genotype I PRRS virus, whose genome comprises a nucleic acid molecule which encodes an ORF4 protein having a glutamine residue at amino acid position 66, is a PRRS virus, whose genome is encoded by a nucleic acid molecule comprising the nucleic acid sequence SEQ ID NO:57.

The PRRS virus of the invention is preferably for use as a medicament or for use in the prophylaxis or treatment of Porcine Reproductive and Respiratory Syndrome, in particular in swine, and wherein optionally said virus is to be administered, or is administered, respectively, via the intranasal, intramuscular, oral, or intrauterine route to an animal, in particular to a pig.

A medicament as referred to throughout this disclosure is preferably a vaccine.

According to another aspect, the PRRS virus of the invention is preferably used as a detection marker, preferably for the differentiation between infected and vaccinated animals (DIVA).

In still a further aspect, the invention relates to a DNA molecule which encodes the PRRS virus of the invention, and wherein said DNA molecule preferably comprises a nucleic acid molecule having a sequence selected from the group consisting of SEQ ID NOs:56-58.

In yet a further aspect, the invention relates to a preferably isolated DNA construct comprising said DNA molecule and to a preferably isolated RNA transcript thereof.

According to still another aspect the invention also relates to a preferably isolated cell transfected with said DNA construct or said RNA transcript.

The invention furthermore relates to a method for producing the PRRS virus of the invention, wherein said method comprises the step of transfecting a cell with said DNA construct or comprises the step of transfecting a host cell with said RNA transcript.

In conclusion, the knowledge of having the possibility to insert a deletion to the extent according to the present invention into the sequence coding for the ectodomain of GP4 of a PRRS virus, such as a genotype I PRRSV, now provides a number of beneficial uses:

The virus based on this knowledge can be used as a challenge isolate for parenteral, oral, intranasal, intrauterine infection and for infection by means of sperm in PRRSV positive and PRRSV naive and/or PRRSV sensitive species.

The invention provides deletion markers for serological differentiation or for sequence differentiation (DIVA concept), of each conceivable PRRSV strain, to PRRSV strains of the genotype II, regardless of whether deletions are already present at the respective site or not.

Further, deletion markers are provided for serological differentiation also in connection or in combination with other epitopes. For example, PRRS viruses without deletion could be distinguished serologically from PRRS viruses with a complete or partial deletion of these epitopes (e.g. Lelystad GP4 aa60-aa70: AAQEKISFGKS as included in SEQ ID NO:43) by using antibodies directed against this epitope. For instance, two PRRS viruses having a deletion in this region/domain could be differentiated from each other in conjunction with other epitopes.

The invention further provides an insertion region/domain for the introduction of foreign RNA instead of the viral RNA at the position, where the deletion according to the invention is located (ectodomain of GP4).

The insertion can be done for various purposes and for every conceivable PRRSV strain, also for PRRSV strains of the genotype II which already have a small deletion in this region.

The insertion of the foreign sequence can take place e.g. in the PRRSV genotype I strain BI EU described herein and replace the sequence coding for the ectodomain of GP4 of said strain with the amino acid (aa) sequence aa54-aa70 (QSHRASTAQGTTPLRRS (SEQ ID NO:40)) or with shortened or mutagenized derivatives thereof.

Moreover, for the improvement of the immune response it is also possible to insert one or more sequential T-oder B-cell epitopes a) from other gene/genomic regions of PRRSV, e.g. from (i) the region coding for the glycoprotein 5 (aa) of the PRRSV genotype I strain BI EU described herein, e.g. sequences coding for the amino acids (aa) aa36-aa52 (SSHLQLIYNLTICELNG (SEQ ID NO:39)) or for shortened or for mutagenized derivatives thereof, also with suitable linker(s), for instance with the aa motif GSS; accordingly also from other PRRSV isolates, e.g. from the PRRSV genotype I protype isolate Lelystad or, accordingly, from other genotypes of PRRSV, such as e.g. from the PRRSV genotype II prototype isolate VR2332;

b) from other pathogens, e.g. from another swine pathogen, for establishing an or enhancing the immune response against said pathogen(s);

c) from non-PRRSV-specific T-oder B-cell epitopes as a genetic or serological positive marker, also in combination with a);

d) from immuno-enhancers different from a), e.g. cytokines, as for instance interleukins, also in combination with b).

For the improvement of the immune response it is also possible to insert one or more sequential T-oder B-cell epitopes for the reduction of the pathogenicity of the virus.

EXAMPLES

Example 1 a) Isolation of PRRSV

PRRSV was isolated from blood samples (bS-720789) previously tested positive in a PRRSV EU-type detection PCR. Isolation of virus was performed on MA104 cells. After propagation of the isolated EU-type PRRSV on MA104 cells, a virus stock for full genome sequencing was prepared by ultracentrifugation on a sucrose cushion, followed by RNase and DNase treatment. Finally, viral RNA was extracted from the virus stock and submitted for full genome sequencing (Roche 454 platform). The genome sequence obtained (14 854 nucleotides) was compared to the EU-type reference genome sequence of strain Lelystad, revealing a deletion of 33 nucleotides in ORF4.

b) Infection

Infection of boars with the virus of a) produces severe clinical signs of PRRS.

Example 2 a) Generation and Characterization of a Novel EU Type PRRSV Infectious cDNA Clone This example describes the generation and characterization of a novel EU type PRRSV infectious cDNA clone which is designated "BI EU" in the following. BI EU is based on but not identical to an attenuated EU type PRRSV strain and is 89% identical on nucleotide level to the EU prototype strain Lelystad virus or 87% identical to the PRRSV cDNA insert of the EU type PRRSV infectious cDNA clone LoN94-13 (WO 2013017568 A1) respectively. The cDNA sequence of BI EU is provided in SEQ ID NO:48.

Live virus was recovered from cDNA clone BI EU after transfecting synthetic capped transcripts into BHK21 cells and subsequent transfer of cell culture supernatant from transfected cells onto PRRSV-susceptible MA104 cells. A strong cytopathic effect (CPE) was detectable within 3 to 4 days post transfer of cell culture supernatant from transfected BHK21 cells to MA104 cells (FIG. 1A). After staining the cells with the PRRSV capsid protein-specific monoclonal antibody SDOW17 (Rural Technologies), a strong signal was detectable in the CPE positive MA104 cells (FIG. 1 B) but not in cells which received supernatants of mock transfected BHK21 cells (not shown).

To test growth of the BI EU cDNA clone-derived virus, MA104 cells were infected with the recovered virus using a multiplicity of infection (MOI) of 0.001, 0.01 or 0.1, respectively.

Figure 2:
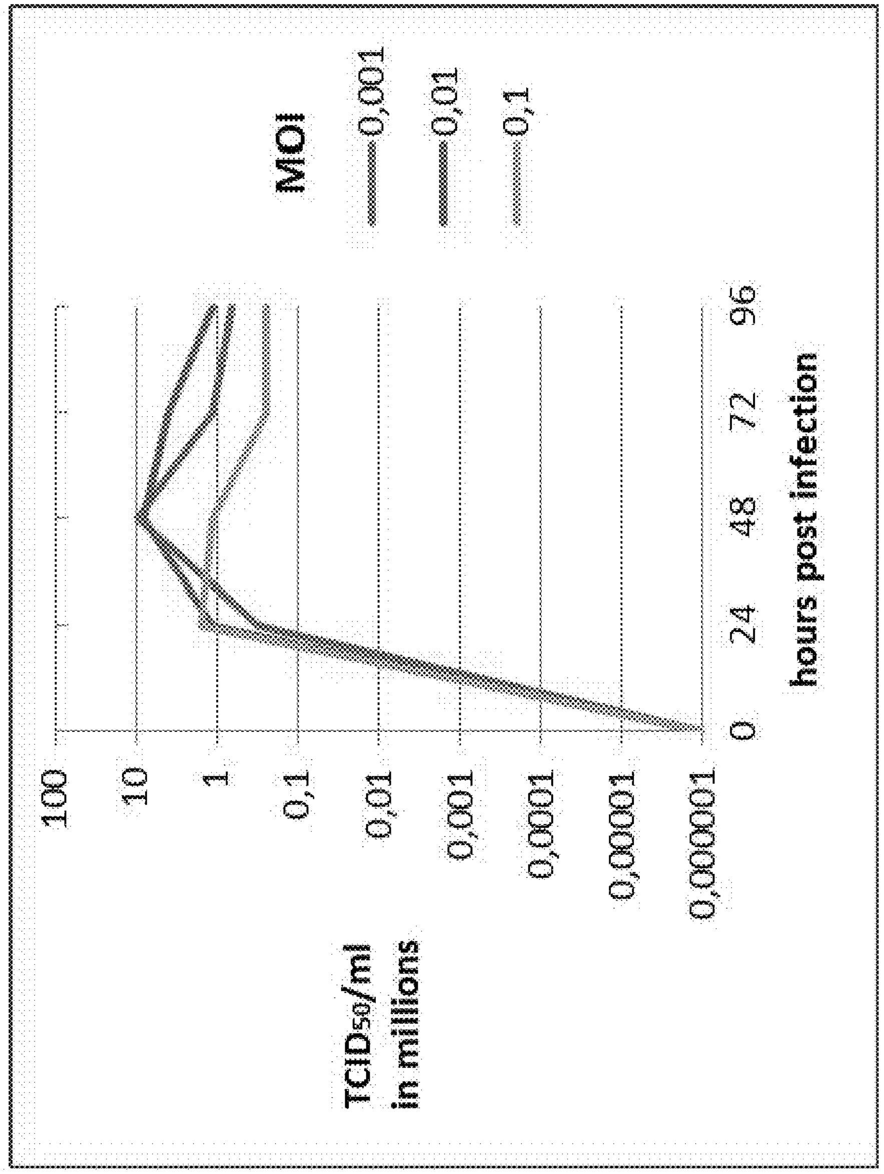

Supernatants of infected cells were collected at 0, 24, 48, 72 and 96 hours post infection and virus titers were determined by serial virus dilutions on 96-well plates containing MA104 cells. The resulting growth curve for virus recovered from BI EU is shown in FIG. 2.

Independent of the MOI used for infection of MA104 cells, the virus BI EU reached titers of $5\times10^5$ to $1\times10^6$ tissue culture infectious dose 50 ($TCID_{50}$) per milliliter (ml) within 24 hours post infection. Titers peaked around 48 hours post infection with $1\times10^6$ to $1\times10^7$ $TCID_{50}$/ml, demonstrating highly efficient replication of the BI EU virus on MA104 cells.

This finding allows to use BI EU as a platform for PRRSV vaccine research, e.g., as one of many applications, to investigate the PRRSV interplay with host immune responses to viral infection.

b) Use of the Novel EU Type PRRSV Infectious cDNA Clone in PRRS Vaccine Research The specific immune response to PRRSV infection is characterized by delayed induction of neutralizing antibodies (Lopez and Osorio, 2004) and short cell-mediated immune response (Xiao et al., 2004). It is commonly accepted that these effects can in part be attributed, along with presentation of decoy epitopes (Ostrowski et al., 2002; Ansari et al., 2006) and glycan shielding of viral envelope proteins (Ansari et al., 2006), to the viral inhibition of the host's innate immune system. It has been demonstrated that PRRSV infection does not or only weakly or delayedly induce production of type I interferon (IFN), (interferon-α and interferon-β; (Miller et al., 2004)) or type II IFN, (interferon-γ; (Meier et al., 2003)) in susceptible cell lines (swine pumonary alveolar macrophages, monkey kidney cells MARC-145) and/or pigs (Buddaert et al., 1998).

IFNs play an important role in establishing an effective adaptive immune response against viral infections, and many viruses therefore have developed strategies to counteract onset of the host's innate immune system (Haller and Weber, 2009). In the interest to identify the anticipated PRRSV IFN antagonist(s), extensive screening analyses based on cell lines stably expressing genes of interest or on cells transfected with protein-expressing plasmids have identified several PRRSV nonstructural proteins (nsps) including nsp1 (see below), nsp2 (Beura et al., 2010; Li et al., 2010), nsp4 (Beura et al., 2010), and nsp11 (Beura et al., 2010; Shi et al., 2011a) to be involved in blocking the induction of type I IFN.

nsp1 is located at the N-terminus of the PRRSV ORF1a-derived polyprotein 1a and is processed into two multifunctional subunits, nsp1α and nsp1β, each of which contains a papain-like cystein protease (PCP) domain essential for self-release from the viral polyprotein (den Boon et al., 1995; Chen et al., 2010). nsp1α contains an N-terminal zinc-finger domain and the PCPα protease domain, while nsp1β contains PCPβ. For both nsp1 subunits, nsp1α and nsp1β, the tree-dimensional crystal structure has been resolved (Sun et al., 2009; Xue et al., 2010). According to these analyses, nsp1β consists of an N-terminal domain (NTD), a linker domain (LKD), the PCP domain (PCP beta), and a C-terminal extension (CTE); (Xue et al., 2010). C-terminal, nsp1β-mediated cleavage of nsp1 from nsp2 occurs at site WYG/AGR (SEQ ID NO: 59) for PRRSV US strains (Kroese et al., 2008) or is predicted at site WYG/AAG (SEQ ID NO: 60) for PRRSV EU strains (Chen et al., 2010), while nsp1α/nsp1β cleavage occurs at site ECAM/AxVYD (SEQ ID NO: 61) for PRRSV US strains or is predicted at site EEAH/SxVYR (SEQ ID NO: 62) for PRRSV EU strains (Chen et al., 2010).

Several studies demonstrated to the mechanistic detail that PRRSV nsp1 and/or its autocleavage-derived subunits nsp1α and/or nsp1β inhibit type I IFN production by interfering with IFN transcription (Song et al., 2010; Kim et al., 2010; Chen et al., 2010; Beura et al., 2010). In addition, it has been demonstrated that nsp1β interferes with the cellular response to interferon (interferon signaling); (Chen et al., 2010). Moreover, it was demonstrated that PRRSV infection inhibits IFN-α and/or IFN-β production in PRRSV infected cells in vitro (Kim et al., 2010; Beura et al., 2010), the subcellular localization of nsp1 (subunits) was determined (Song et al., 2010; Chen et al., 2010), and mechanistic aspects of type I IFN inhibition that were obtained by others from single protein expression experiments were confirmed in cells infected with PRRSV (Shi et al., 2010). Finally, a nsp1 mutagenesis study based on nsp1 protein expression investigated effects on viral IFN inhibition (Shi et al., 2011b).

Previously viable PRRSV (EU) strains have been generated (as described in WO 2013017570 A1) that contained mutations (deletions) in the nsp1β gene that induced type I IFN (IFN-β) production in susceptible cells (MARC145) and that are sensitive to type I IFN (IFN-β).

Figure 3:
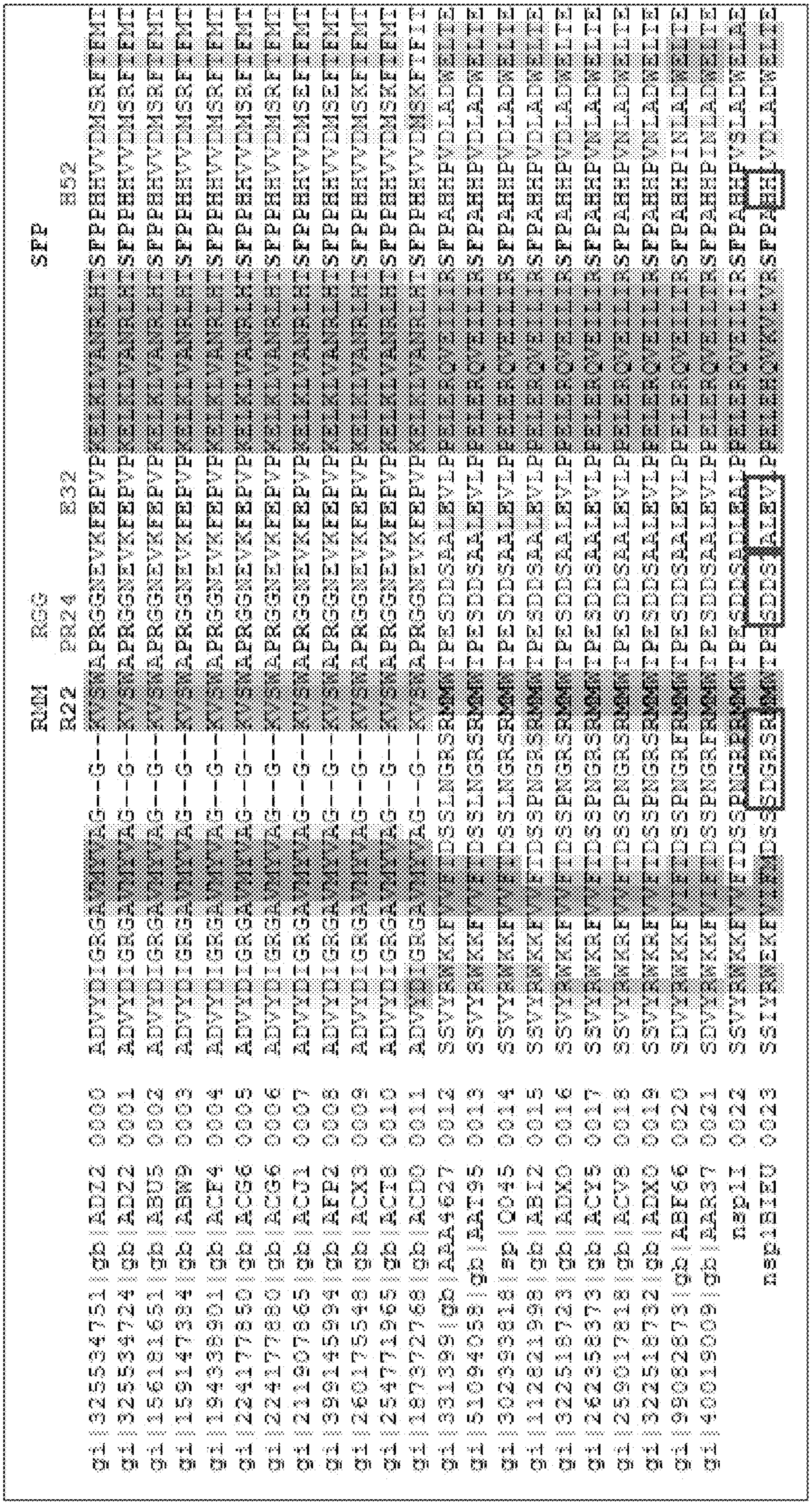

To test whether such and also different IFN inducing virus mutants could get generated based on the novel infectious clone BI EU, a set of viruses harboring deletions in the nsp1β gene was designed. More precisely, these deletions were located in the N-terminal domain (NTD) of nsp1β which has been shown to be required for homodimerization of the protein (Xue et al., 2010). FIG. 3 shows an nsp1β aminoacid sequence alignment of several US and EU type PRRSV strains. Indicated are aminoacids predicted to form strands (blue) or alpha helices (red) formation.

Ten nsp1β deletion mutants were generated on the basis of the infectious cDNA clone BI EU. Deletions included aminoacids that were predictedly not involved in beta strand or alpha helix formation and that were (partially) conserved within all EU type PRRSV strains analyzed in the alignment (framed in red in FIG. 3).

Figure 4:
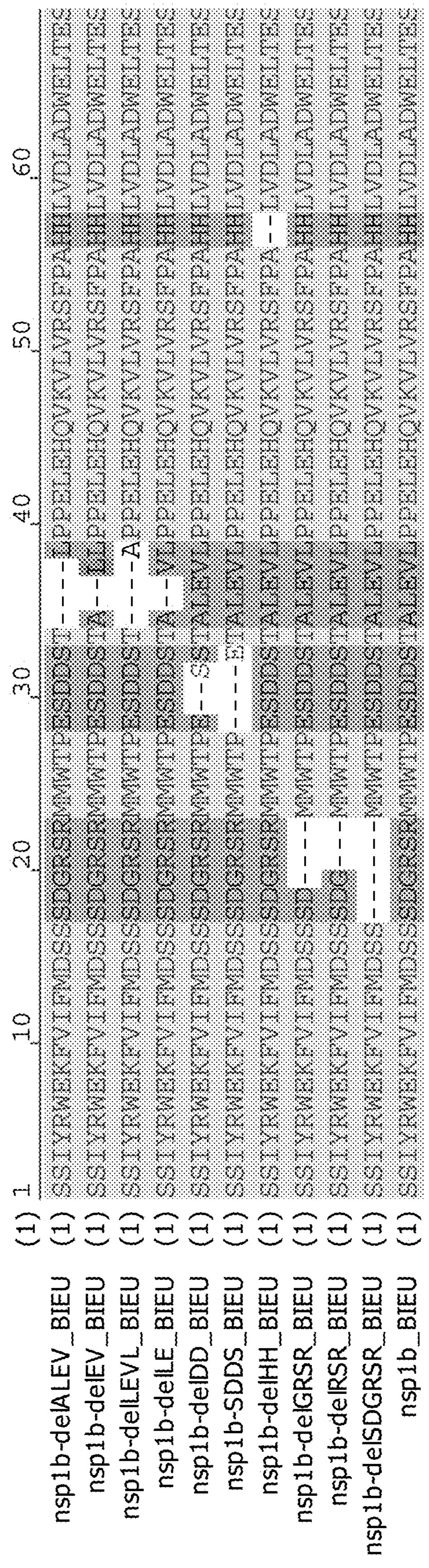

The deletions introduced in the nsp1β gene are visualized in the aminoacid sequence alignment shown in FIG. 4. The BI EU-nsp1β deletion mutants are designated BI EU-nsp1β-delALEV (SEQ ID NO: 89), BI EU-nsp1β-delEV (SEQ ID NO: 90), BI EU-nsp1β-delLEVL (SEQ ID NO: 91), BI EU-nsp1β-delLE (SEQ ID NO: 92), BI EU-nsp1β-delDD (SEQ ID NO: 93), BI EU-nsp1β-delSDDS (SEQ ID NO: 94), BI EU-nsp1β-delHH (SEQ ID NO: 95), BI EU-nsp1β-delGRSR (SEQ ID NO: 96), BI EU-nsp1β-delRSR (SEQ ID NO: 97), and BI EU-nsp1β-delSDGRSR (SEQ ID NO: 98), respectively.

Figure 5:
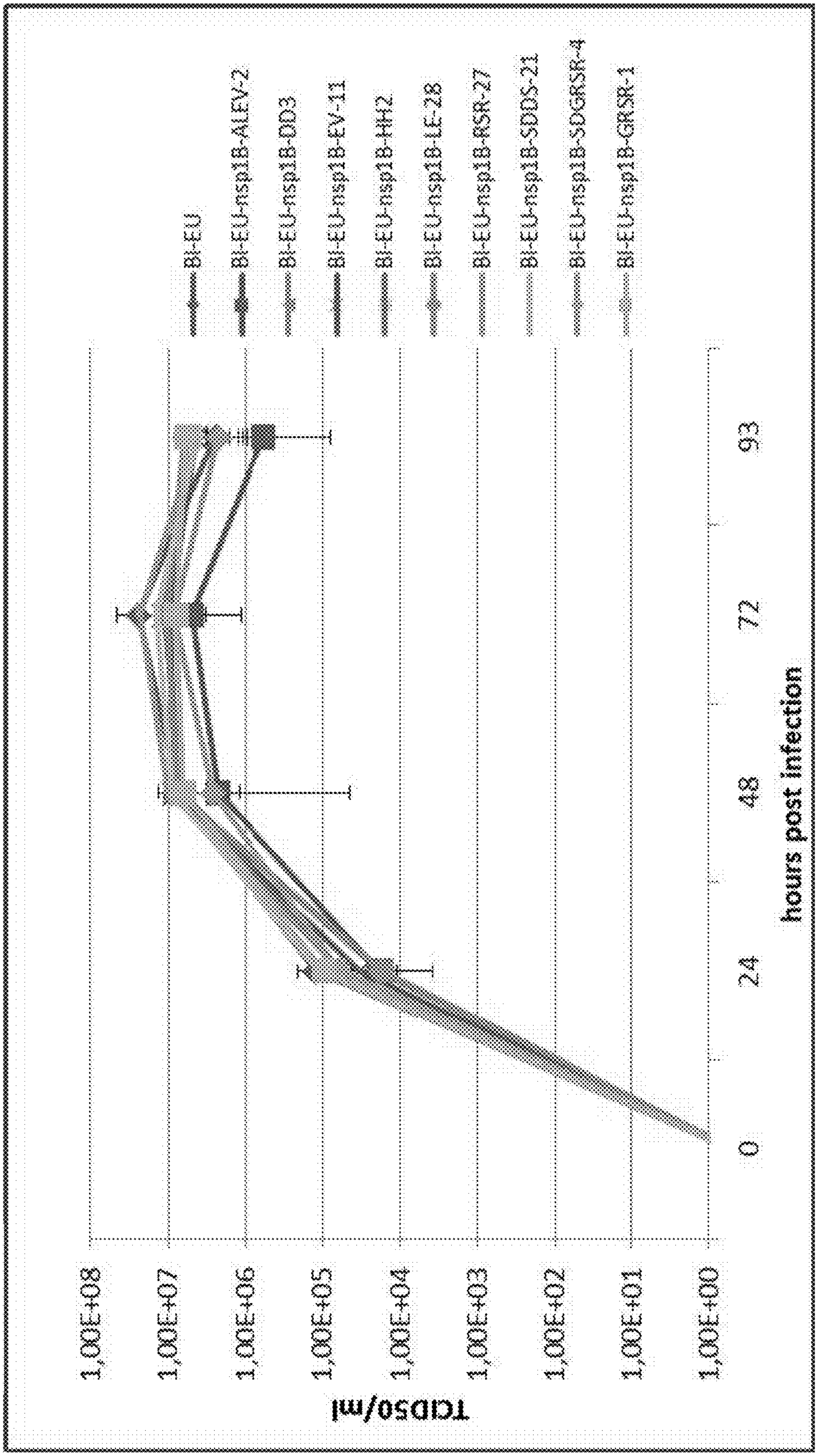

To test viability of the nsp1β deletion mutants, synthetic transcripts of BI EU cDNAs harbouring the respective deletion were transfected into BHK21 cells. After transfer of cell culture supernatant from transfected cells onto PRRSV-susceptible MA104 cells, cytopathic effects (CPE) and nucleocapsid-specific immunofluorescence staining indicating PRRSV mutant viability were detectable for nine of the ten nsp1β deletion mutants generated (not shown). These findings demonstrated that, with the exception of BI EU-nsp1β-delLEVL (SEQ ID NO: 91), all nsp1β deletion mutants were viable. To further analyze whether the nsp1β deletion mutants could be grown to high titers on IFN-competent MA104 cells, growth curves were performed essentially as described above for the BI EU virus. Briefly, MA104 cells were infected with one of the nine nsp1β deletion mutants or the virus BI EU as control. Cell culture supernatants were harvested at 0, 24, 48, 72 and 93 hours post infection and titrated on MA104 cells on 96-well plates. Viral titers were calculated based on CPE-positive wells. FIG. 5 shows the result of two independent experiments and demonstrates that BI EU-nsp1β deletion mutants can be grown on MA104 cells as efficiently as the parent BI EU virus. Peak titers of $5\times10^6$ to $1\times10^7$ $TCID_{50}$/ml were observed at 48 hours post infection.

It was next analyzed whether the deletions introduced into the nsp1β gene would indeed abolish the IFN antagonistic activity of the nsp1β protein. Therefore IFN-β levels in 100 μl samples collected at 0, 24, 48, 72 and 93 hours post infection throughout the growth curve experiment described above were measured using a commercial ELISA specific for human IFN-β (Invitrogen). According to the manufacturer, this ELISA can also be applied for the detection of non-human primate IFN-β and worked well for samples from MA104 cells which are epithelial Green Monkey kidney cells (see FIG. 6). For quantification of the obtained results, a calibration curve was included using a positive control of the ELISA manufacturer.

Figure 6:
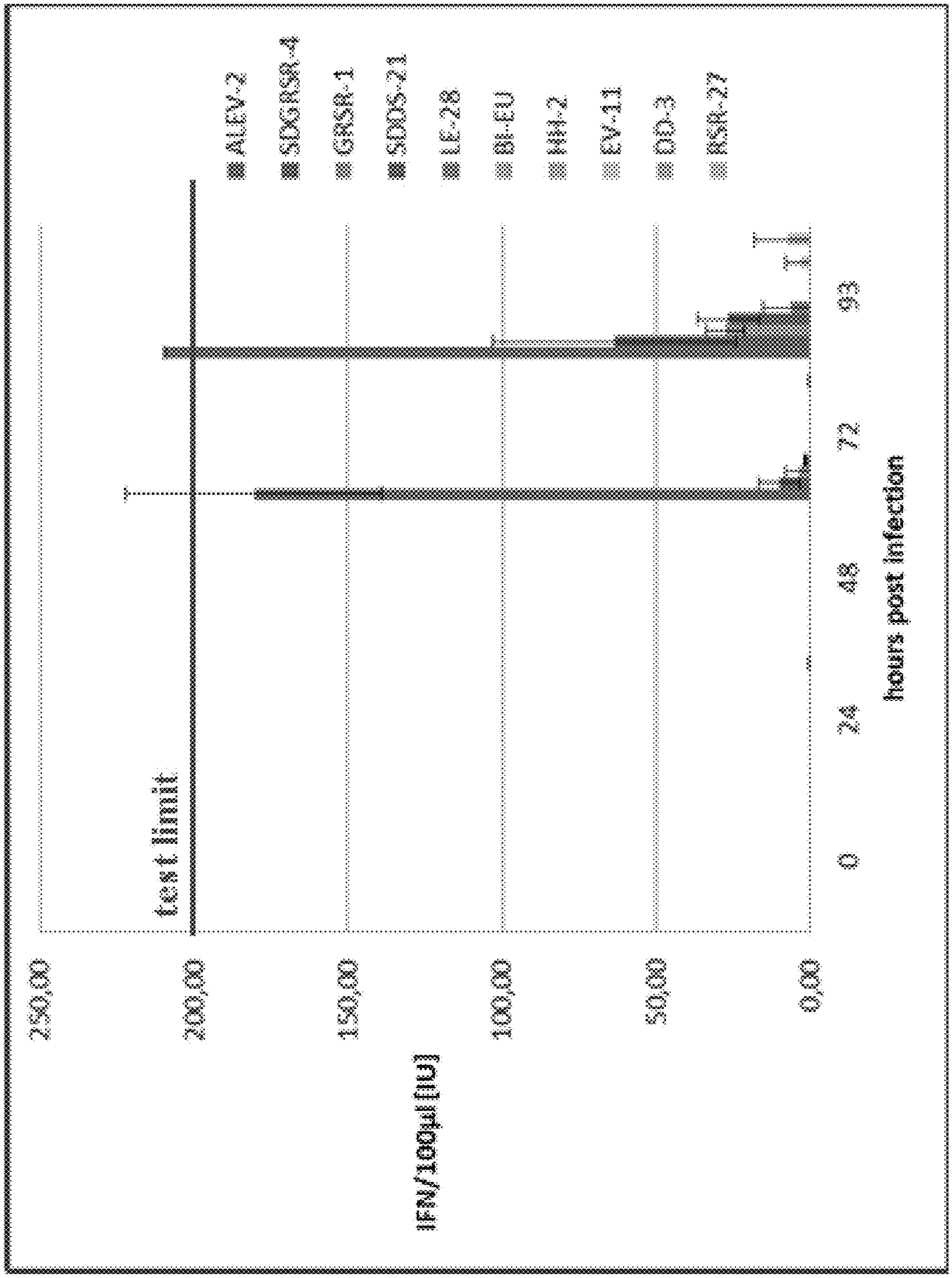

IFN-β levels measured in the supernatants of MA104 cells infected with one of the nine viable nsp1β deletion mutants or with the parent BI EU virus and obtained from two independent experiments are shown in FIG. 6.

As expected, parental BI EU efficiently blocked the secretion of IFN-β throughout the course of infection which is attributed to functional viral IFN antagonist(s). No or only little amounts of IFN-β were detectable in the cell culture supernatant at 0, 24 and 48 hours post infection with the various BI EU-nsp1β deletion mutants. At later timepoints however, some mutants were unable to inhibit the expression of IFN-β in infected MA104 cells, indicating a defect in the nsp1β IFN antagonistic activity. Interestingly, this defect varied significantly between the nine BI EU-nsp1β deletion mutants analyzed. While most of the mutants induced IFN-β levels below 50 international units (IU) per 100 μl cell culture supernatant, the mutant BI EU-nsp1β-delALEV (SEQ ID NO: 89) was completely unable to antagonize the expression of IFN-β in infected MA104 cells. The amounts of IFN-β measured at 72 and 93 hours post infection even exceeded the limit of the ELISA test which is set at ~200 IU per 100 μl. This result clearly demonstrated that the IFN antagonistic activity of the nsp1β protein can be abolished by deleting the aminoacids $A_{30}LEV_{33}$ (SEQ ID NO: 63) in the BI EU infectious cDNA clone.

Taken together, a novel EU type PRRSV infectious cDNA clone was generated that can be efficiently grown to titers of $1\times10^7$ $TCID_{50}$/ml in Green Monkey kidney MA104 cells. Based on this clone, nine viable BI EU-nsp1β mutants were generated which harboured deletions in the NTD of nsp1β which has been shown to be required for homodimerization of the protein (Xue et al., 2010). These mutants could all be grown to high titers on MA104 cells. Mutants BI EU-nsp1β-delALEV (SEQ ID NO: 89), BI EU-nsp1β-delEV (SEQ ID NO: 90), BI EU-nsp1β-delLE (SEQ ID NO: 92), BI EU-nsp1β-delSDDS (SEQ ID NO: 94), BI EU-nsp1β-delGRSR (SEQ ID NO: 96), BI EU-nsp1β-delRSR (SEQ ID NO: 97), and BI EU-nsp1β-delSDGRSR (SEQ ID NO: 98) all induced the secretion of IFN-β at late timepoints of infection which is in strict contrast to the parent BI EU virus. Out of these seven mutants, the four mutants BI EU-nsp1β-delALEV (SEQ ID NO: 89), BI EU-nsp1β-delEV (SEQ ID NO: 90), BI EU-nsp1β-delLE (SEQ ID NO: 92), and BI EU-nsp1β-delSDDS (SEQ ID NO: 94) represent a new class of mutants that has not previously been described in WO 2013017570 A1. In particular, infection with the mutant BI EU-nsp1β-delALEV (SEQ ID NO: 89) induced extremely high amounts of IFN-β in MA104 cells which leads to the conclusion that this virus is severely impaired in blocking the induction of IFN type I.

This finding has strong implications for PRRSV vaccine development since it can be assumed that the immune response of the natural host against PRRSV can be significantly enhanced by introducing deletions, e.g. by deleting aminoacids $A_{30}LEV_{33}$ (SEQ ID NO: 63) in the nsp1β protein of genotype I PRRSV strains.

The nsp1β deletion mutants described therein, either alone or in combination with other attenuating mutations, represent promising candidates for life attenuated PRRSV vaccines.

Example 3 a) Introducing a Deletion Within the ORF4 Protein of the EU Type PRRSV Infectious cDNA Clone BI EU It was tested whether a deletion, as described according to the first consideration of the present invention, could be introduced into the ORF4 gene of any PRRS virus strain without negatively affecting viral replication. Therefore, a deletion was introduced into the genomic region coding for the ectodomain of the ORF4 protein between amino acid positions 50 to 71 of the EU type PRRSV infectious cDNA clone BI EU (comprising the sequence of SEQ ID NO:48). The deletion within the ORF4 protein of BI EU included amino acids 57-69 (as encoded by SEQ ID NO:49).

To test viability of the ORF4 deletion mutant, a synthetic transcript of BI EU cDNA harboring the deletion was transfected into BHK21 cells. After transfer of cell culture supernatants from transfected cells onto PRRSV-susceptible MA104 cells, a cytopathic effect (CPE) was detectable within 3 to 4 days post transfer of cell culture supernatants from transfected BHK21 cells to MA104 cells. After staining the cells with the PRRSV capsid protein-specific monoclonal antibody SDOW17 (Rural Technologies), a strong signal was detectable in the CPE positive MA104 cells but not in cells which received supernatants of mock transfected BHK21 cells (not shown). These findings demonstrated that the BI EU-ORF4 deletion mutant was viable. The recovered mutant virus is designated as BI EU-GP5-36-46-ctr (compare example b) in the following.

Figure 7:
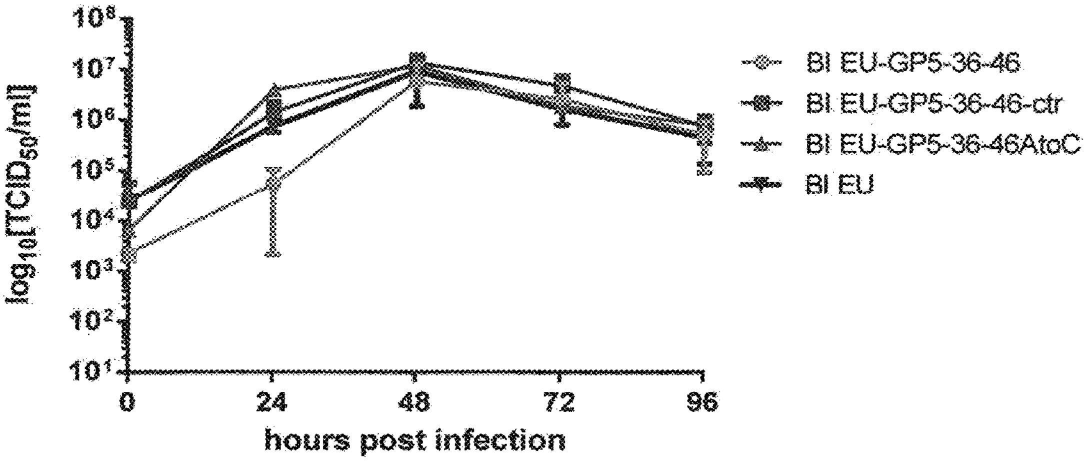

To further analyze whether BI EU-GP5-36-46-ctr could be grown to high titers on MA104 cells, growth kinetics were performed. Therefore, MA104 cells were infected with the recovered virus and with the parental BI EU virus as control using a multiplicity of infection (MOI) of 0.01. Supernatants of infected cells were collected at 0, 24, 48, 72 and 96 hours post infection and virus titers were determined by serial virus dilutions on 96-well plates containing MA104 cells. FIG. 7 shows the result of three independent experiments and demonstrates that BI EU-GP5-36-46-ctr can be grown on MA104 cells as efficiently as the parental BI EU virus. Peak titers of ~$1\times10^7$ $TCID_{50}$/ml were observed for both viruses at 48 hours post infection.

Taken together, deletion of amino acids 57-69 within the ORF4 protein does not negatively influence growth of BI EU, indicating that sequence variations within this region are well tolerated by PRRSV in vitro. Concluding from these results, the region located between amino acid positions 50 to 71 of the BI EU ORF4 protein might also be used as insertion site for exogenous sequences.

b) Use of the ORF4 Protein Deletion Site For Inserting Exogenous RNA: Insertion of the PRRSV ORF5 Protein Neutralizing Epitope Sequence Into the ORF4 Gene of the Infectious cDNA Clone BI EU This example describes the insertion of an exogenous RNA into the region located between amino acid positions 50 to 71 of the BI EU ORF4 protein. The exogenous RNA in this example codes for the neutralizing epitope located within the ORF5 protein of PRRS virus (Ostrowski, M. et al.) and consists of amino acids 1-11 of SEQ ID NO:39. This sequence (SEQ ID NO:51) was chosen to be inserted into the ectodomain of the ORF4 protein in order to increase accessibility of the ORF5 neutralizing epitope in a potential vaccine candidate allowing improved immune responses in vaccinated animals.

For generating the recombinant virus, the exogenous sequence was introduced into the ORF4 deletion site described in example a) and replaced amino acids 57-69 of the BI EU ORF4 protein by amino acids 1-11 of SEQ ID NO: 39 (representing amino acids 36-46 within the ORF5 protein of type 2 PRRSV strains) flanked by a G-G linker. The insertion resulted in a final sequence of $Gly_{57}$-Ser-Ser-His-Leu-Gln-Leu-Ile-Tyr-Asn-Leu-Thr-$Gly_{69}$ (SEQ ID NO:53) within the ORF4 protein of BI EU. The recombinant virus harboring the insertion is designated as BI EU-GP5-36-46 (comprising the sequence of SEQ ID NO:56) in the following.

In order to test whether BI EU-GP5-36-46 could be recovered, a synthetic transcript of BI EU cDNA harboring the mutation was transfected into BHK21 cells. The recombinant virus could be rescued by the same method as described above. A cytopathic effect (CPE) was observable within 3 to 4 days post transfer of cell culture supernatants from transfected BHK21 cells to PRRSV susceptible MA104 cells. Furthermore, PRRSV capsid protein-specific staining was detectable in CPE positive MA104 cells but not in cells which received supernatants of mock transfected BHK21 cells (not shown).

Growth kinetics were performed in order to test whether the recombinant virus could be grown to high titers. Therefore, MA104 cells were infected with BI EU-GP5-36-46 and with the parental BI EU virus as control using a MOI of 0.01. Supernatants of infected cells were collected at 0, 24, 48, 72 and 96 hours post infection and virus titers were determined by serial virus dilutions on 96-well plates containing MA104 cells. The result of three independent experiments is depicted in FIG. 7. At 48 hours post infection the virus mutant BI EU-GP5-36-46 reached the same peak titer of ~$1\times10^7$ $TCID_{50}$/ml as the parental BI EU virus showing that the inserted sequence within the ORF4 protein does not negatively influence high titer virus growth.

Further experiments on MA104 cells revealed that the exogenous RNA sequence was stably maintained over multiple passages. Sequence analyses demonstrated stability of the insert over all passages analyzed. Interestingly a single nucleotide mutation of adenine to thymine, resulting in an amino acid exchange of His to Pro at position 56, upstream of the insertion site was detectable after passage 1 in independent experiments. Therefore, this additional mutation was inserted into BI EU-GP5-36-46 by reverse genetics. For generating this recombinant virus, an exogenous sequence was introduced into the ORF4 deletion site described in example a) and replaced amino acids 56-69 of the BI EU ORF4 protein by amino acids 1-11 of SEQ ID NO: 39 (representing amino acids 36-46 within the ORF5 protein of type 2 PRRSV strains) N-terminally flanked by the amino acid sequence PG and C-terminally flanked by a G-linker. The insertion resulted in a final sequence of $Pro_{56}$-Gly-Ser-Ser-His-Leu-Gln-Leu-Ile-Tyr-Asn-Leu-Thr-$Gly_{69}$(SEQ ID NO:55) within the ORF4 protein of BI EU. The resulting recombinant virus is designated as BI EU-GP5-36-46-AtoC (comprising the sequence of SEQ ID NO:58) in the following. Growth kinetics depicted in FIG. 7 demonstrated that BI EU-GP5-36-46-AtoC could be grown to similar titers as BI EU-GP5-36-46 and BI EU wild type, respectively.

To test whether the ORF5-derived sequences in the ectodomain-encoding region of ORF4 in BI EU-GP5-36-46-AtoC would render the mutant virus more sensitive to serum neutralization, serum neutralization tests (SNTs) were performed. It was postulated that increased accessibility of the inserted ORF5-derived neutralizing epitope located in the ORF4 protein ectodomain would result in enhanced sensitivity of the recombinant virus to the action of neutralizing antibodies as compared to the parental virus BI EU.

For the SNTs sera taken from six sows at 48 days post vaccination with BI EU wild type virus were serially diluted and mixed either with BI EU-GP5-36-46-AtoC or with wild type BI EU.

Figure 8:
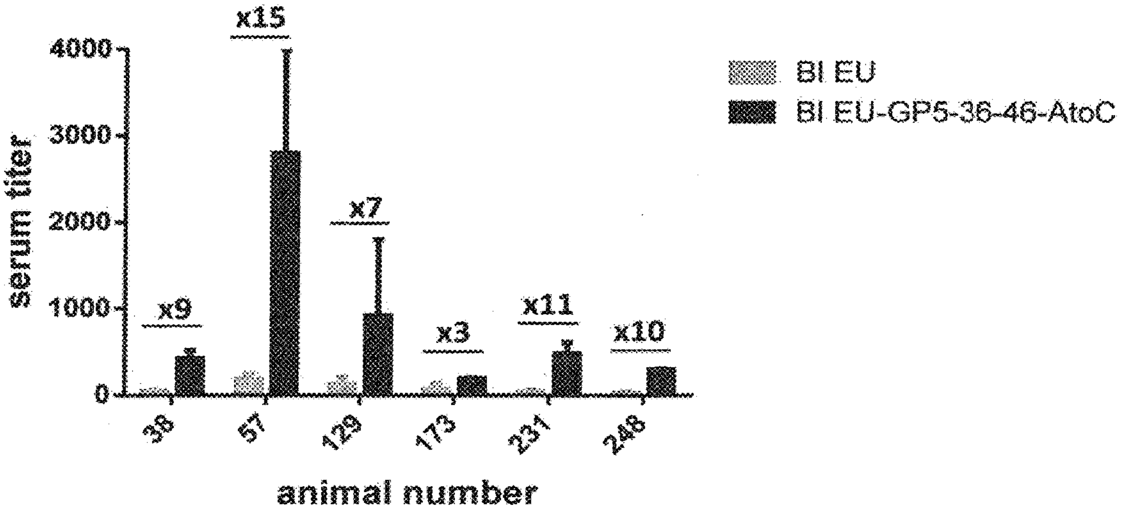

After incubation for one hour at 37° C. and 5% $CO_2$, MA104 cells were added to the samples. Serum titers were determined four days later based on CPE induced by non-neutralized virus. Sera taken from the same animals previous to vaccination served as negative controls (not shown). Mean values and standard deviations of two independent experiments are depicted in FIG. 8.

It could be demonstrated that BI EU-GP5-36-46-AtoC was consistently more sensitive to in vitro neutralization when compared to BI EU wild type virus despite variations that were observable between the six animals analyzed. Serum titers measured for BI EU-GP5-36-46-AtoC were 3 to 15 fold higher than the titers determined for the parental virus BI EU (FIG. 8). Data obtained from a different experiment further suggested that serum titers for BI EU-GP5-36-46-AtoC might be even more increasable by mutating the N-glycosylation site (amino acid $N_9$ of SEQ ID NO: 39) present in the ORF5-derived sequence from $Asn_9$ to $Gln_9$ (SEQ ID NO: 50 and 52) as N-glycosylation naturally shields the ORF5 neutralizing epitope ((Ansari et al., 2006) and data not shown). In summary, the findings depicted in FIG. 8 strongly indicated that the ORF5-derived neutralizing epitope inserted into the ORF4 protein ectodomain is highly accessible in the recombinant virus BI EU-GP5-36-46-AtoC making the latter a promising vaccine candidate. The demonstrated higher sensitivity to sera containing PRRSV-specific neutralizing antibodies should allow faster clearance and increased safety of the vaccine virus.

Also, it can be expected that PRRSV-specific neutralizing antibodies will be induced to higher levels and at earlier time points in piglets or sows that were vaccinated with BI EU-GP5-36-46-AtoC when compared to animals that were vaccinated with the parental virus BI EU. Early induction of neutralizing antibodies after vaccination should result in faster clearance and therefore less shedding of the vaccine virus (increased safety) and in a more efficient immune response after natural infection with PRRSV (increased efficacy).

The recombinant virus BI EU-GP5-36-46-AtoC therefore represents a promising candidate for a life attenuated PRRSV vaccine with improved safety and efficacy.

LIST OF FIGURES

FIG. 1: A. Infectious virus recovered from the BI EU cDNA clone induced a strong CPE on MA104 cells as shown by bright field microscopy. B. PRRSV capsid protein-specific immunofluorescence (IF) staining of BI EU-infected MA104 cells.

FIG. 2: Growth of virus recovered from the infectious cDNA clone BI EU on MA104 cells.

FIG. 3: nsp1β N-terminal domain (NTD) amino acid sequence alignment of several US (type II, top) and EU (type I, bottom) PRRSV strains. The NTD aminoacid sequence of BI EU is given at the very bottom. Amino acids R22, PR24, E32, SFP and H52 are indicated above the alignment and have been shown to be crucial for nsp1β homodimerization (Xue et al., 2010). Target regions for nsp1β mutagenesis are framed in red. The SDGRSR (SEQ ID NO: 64) motif corresponds to the region described in WO 2013017570 A1 using PRRSV EU cDNA clone LoN94-13. FIG. 3 discloses SEQ ID NOS: 65-88, respectively, in order of appearance.

FIG. 4: Amino acid sequence alignment of BI EU-nsp1β deletion mutants. FIG. 4 discloses SEQ ID NOS: 89-99, respectively, in order of appearance.

FIG. 5: Growth of BI EU-nsp1β deletion mutants on IFN-competent MA104 cells. FIG. 5 references SEQ ID NOS: 99, 89, 93, 90, 95, 92, 97, 94, 98, and 96, respectively, in order of appearance.

FIG. 6: IFN-β levels measured at different timepoints in the cell culture supernatant of MA104 cells infected with the BI EU-nsp1β deletion mutants or with parent BI EU virus. FIG. 6 references SEQ ID NOS: 89, 98, 96, 94, 92, 99, 95, 90, 93, and 97, respectively, in order of appearance.

FIG. 7: Growth kinetics of recombinant BI EU viruses harboring deletions or insertions within the ORF4 protein.

FIG. 8: Serum neutralization tests for the recombinant virus BI EU-GP5-36-46-AtoC and the parental virus BI EU.

In the sequence listing:

SEQ ID NOs:1-24 correspond to sequences of the ectodomain of PRRSV ORF4 protein with a deletion;

SEQ ID NO:25 and SEQ ID NO:26 correspond to sequences of the first two predicted N-terminal ß-sheets of PRRSV (genotype I) ORF4 protein;

SEQ ID NO:27 and SEQ ID NO:28 correspond to sequences of the first two predicted N-terminal ß-sheets of PRRSV (genotype II) ORF4 protein;

SEQ ID NO:29 and SEQ ID NO:30 correspond to sequences of the first two predicted N-terminal ß-sheets of PRRSV (genotype I) ORF4 protein;

SEQ ID NO:31 and SEQ ID NO:32 correspond to sequences of the first two predicted N-terminal ß-sheets of PRRSV (genotype II) ORF4 protein;

SEQ ID NO:32 corresponds to a (partial) sequence of a PRRSV (genotype I) ORF4 protein having a deletion of 11 amino acid residues in the region between the first two predicted N-terminal ß-sheets;

SEQ ID NO:33 corresponds to a (partial) sequence of a PRRSV (genotype II) ORF4 protein having a deletion of 7 amino acid residues in the region between the first two predicted N-terminal ß-sheets;

SEQ ID NO:34 corresponds to the sequence of the ectodomain of a PRRSV (genotype I) ORF4 protein having a deletion of 11 amino acid residues;

SEQ ID NO:35 corresponds to the sequence of the ectodomain of a PRRSV (genotype II) ORF4 protein having a deletion of 7 amino acid residues;

SEQ ID NO:36 corresponds to the sequence of a PRRSV (genotype I) ORF4 protein having a deletion of 11 amino acid residues (and including the sequence of SEQ ID NO:34, respectively);

SEQ ID NO:37 corresponds to a nucleotide sequence encoding the sequence of SEQ ID NO:36;

SEQ ID NO:38 corresponds to a nucleotide sequence encoding a genotype I PRRSV whose genome comprises a nucleic acid molecule which codes for the sequence of SEQ ID NO:36;

SEQ ID NO:39 corresponds to the sequence of a peptide encoded by the ORF5 gene of PRRS virus;

SEQ ID NO:40 corresponds to the sequence of a peptide encoded by the ORF5 gene of PRRS virus;

SEQ ID NO:41 corresponds to Lelystad virus complete genome;

SEQ ID NO:42 corresponds to VR2332 virus complete genome;

SEQ ID NO:43 corresponds to the sequence of ORF4 protein of the Lelystad virus;

SEQ ID NO:44 corresponds to the sequence of ORF4 protein of the VR2332 virus;

SEQ ID NO:45 corresponds to a first nucleic acid sequence as described herein;

SEQ ID NO:46 corresponds to a second nucleic acid sequence as described herein, which flanks the 5' end of the first nucleic acid sequence;

SEQ ID NO:47 corresponds to a third nucleic acid sequence as described herein, which flanks the 3' end of the first nucleic acid sequence;

SEQ ID NO:48 corresponds to BI EU complete viral cDNA insert;

SEQ ID NO:49 corresponds to the sequence of SEQ ID NO:48 with a deletion, thereby encoding an ORF4 protein having a deletion of 13aa (aa 57-69);

SEQ ID NO:50 corresponds to the sequence of SEQ ID NO:39 with the substitution N–>Q at position 9;

SEQ ID NO:51 corresponds to the sequence of aa 1-11 of SEQ ID NO:39;

SEQ ID NO:52 corresponds to the sequence of SEQ ID NO:51 with the substitution N–>Q at position 9;

SEQ ID NO:53 corresponds to the sequence of SEQ ID NO:51 with a Gly-Gly linker;

SEQ ID NO:54 corresponds to the sequence of SEQ ID NO:52 with a Gly-Gly linker;

SEQ ID NO:55 corresponds to the sequence of SEQ ID NO:53 with an N-terminal proline residue;

SEQ ID NO:56 corresponds to the sequence of SEQ ID NO:49 with an insert, thereby encoding the sequence of SEQ ID NO:53;

SEQ ID NO:57 corresponds to the sequence of SEQ ID NO:49 with an insert, thereby encoding the sequence of SEQ ID NO:54;

SEQ ID NO:58 corresponds to the sequence of SEQ ID NO:48 with a deletion, thereby encoding an ORF4 protein having a deletion of 14aa (aa 56-69), wherein an insert coding for the sequence of SEQ ID NO: 55 is included.

REFERENCE LIST

Allende, R., Laegreid, W. W., Kutish, G. F., Galeota, J. A., Wills, R. W., Osorio, F. A., 2000. Porcine reproductive and respiratory syndrome virus: description of persistence in individual pigs upon experimental infection. J. Virol. 74, 10834-10837.

Ansari, I. H., Kwon, B., Osorio, F. A., Pattnaik, A. K., 2006. Influence of N-linked glycosylation of porcine reproductive and respiratory syndrome virus GP5 on virus infectivity, antigenicity, and ability to induce neutralizing antibodies. J. Virol. 80, 3994-4004.

Beura, L. K., Sarkar, S. N., Kwon, B., Subramaniam, S., Jones, C., Pattnaik, A. K., Osorio, F. A., 2010. Porcine reproductive and respiratory syndrome virus nonstructural protein 1beta modulates host innate immune response by antagonizing IRF3 activation. J. Virol. 84, 1574-1584.

Buddaert, W., Van, R. K., Pensaert, M., 1998. In vivo and in vitro interferon (IFN) studies with the porcine reproductive and respiratory syndrome virus (PRRSV). Adv. Exp. Med. Biol. 440, 461-467.

Chen, Z., Lawson, S., Sun, Z., Zhou, X., Guan, X., Christopher-Hennings, J., Nelson, E. A., Fang, Y., 2010. Identification of two auto-cleavage products of nonstructural protein 1 (nsp1) in porcine reproductive and respiratory syndrome virus infected cells: nsp1 function as interferon antagonist. Virology 398, 87-97.

den Boon, J. A., Faaberg, K. S., Meulenberg, J. J., Wassenaar, A. L., Plagemann, P. G., Gorbalenya, A. E., Snijder, E. J., 1995. Processing and evolution of the N-terminal region of the arterivirus replicase ORF1a protein: identification of two papainlike cysteine proteases. J. Virol. 69, 4500-4505.

Haller, O., Weber, F., 2009. The interferon response circuit in antiviral host defense. Verh. K. Acad. Geneeskd. Belg. 71, 73-86.

Kim, O., Sun, Y., Lai, F. W., Song, C., Yoo, D., 2010. Modulation of type I interferon induction by porcine reproductive and respiratory syndrome virus and degradation of CREB-binding protein by non-structural protein 1 in MARC-145 and HeLa cells. Virology 402, 315-326.

Kroese, M. V., Zevenhoven-Dobbe, J. C., Bos-de Ruijter, J. N., Peeters, B. P., Meulenberg, J. J., Cornelissen, L. A., Snijder, E. J., 2008. The nsp1alpha and nsp1 papain-like autoproteinases are essential for porcine reproductive and respiratory syndrome virus RNA synthesis. J. Gen. Virol. 89, 494-499.

Li, H., Zheng, Z., Zhou, P., Zhang, B., Shi, Z., Hu, Q., Wang, H., 2010. The cysteine protease domain of porcine reproductive and respiratory syndrome virus non-structural protein 2 antagonizes interferon regulatory factor 3 activation. J. Gen. Virol. 91, 2947-2958.

Lopez, O. J., Osorio, F. A., 2004. Role of neutralizing antibodies in PRRSV protective immunity. Vet. Immunol. Immunopathol. 102, 155-163.

Meier, W. A., Galeota, J., Osorio, F. A., Husmann, R. J., Schnitzlein, W. M., Zuckermann, F. A., 2003. Gradual development of the interferon-gamma response of swine to porcine reproductive and respiratory syndrome virus infection or vaccination. Virology 309, 18-31.

Miller, L. C., Laegreid, W. W., Bono, J. L., Chitko-McKown, C. G., Fox, J. M., 2004. Interferon type I response in porcine reproductive and respiratory syndrome virus-infected MARC-145 cells. Arch. Virol. 149, 2453-2463.

Ostrowski, M., Galeota, J. A., Jar, A. M., Platt, K. B., Osorio, F. A., Lopez, O. J., 2002. Identification of neutralizing and nonneutralizing epitopes in the porcine reproductive and respiratory syndrome virus GP5 ectodomain. J. Virol. 76, 4241-4250.

Shi, X., Wang, L., Li, X., Zhang, G., Guo, J., Zhao, D., Chai, S., Deng, R., 2011a. Endoribonuclease activities of porcine reproductive and respiratory syndrome virus nsp11 was essential for nsp11 to inhibit IFN-beta induction. Mol. Immunol. 48, 1568-1572.

Shi, X., Wang, L., Zhi, Y., Xing, G., Zhao, D., Deng, R., Zhang, G., 2010. Porcine reproductive and respiratory syndrome virus (PRRSV) could be sensed by professional beta interferon-producing system and had mechanisms to inhibit this action in MARC-145 cells. Virus Res. 153, 151-156.

Shi, X., Zhang, G., Wang, L., Li, X., Zhi, Y., Wang, F., Fan, J., Deng, R., 2011b. The Nonstructural Protein 1 Papain-Like Cysteine Protease Was Necessary for Porcine Reproductive and Respiratory Syndrome Virus Nonstructural Protein 1 to Inhibit Interferon-beta Induction. DNA Cell Biol. 30, 355-362.

Snijder, E. J., Meulenberg, J. J., 1998. The molecular biology of arteriviruses. J. Gen. Virol. 79 (Pt 5), 961-979.

Song, C., Krell, P., Yoo, D., 2010. Nonstructural protein 1alpha subunit-based inhibition of NF-kappaB activation and suppression of interferon-beta production by porcine reproductive and respiratory syndrome virus. Virology 407, 268-280.

Sun, Y., Xue, F., Guo, Y., Ma, M., Hao, N., Zhang, X. C., Lou, Z., Li, X., Rao, Z., 2009. Crystal structure of porcine reproductive and respiratory syndrome virus leader protease Nsplalpha. J. Virol. 83, 10931-10940.

Xiao, Z., Batista, L., Dee, S., Halbur, P., Murtaugh, M. P., 2004. The level of virus-specific T-cell and macrophage recruitment in porcine reproductive and respiratory syndrome virus infection in pigs is independent of virus load. J. Virol. 78, 5923-5933.

Xue, F., Sun, Y., Yan, L., Zhao, C., Chen, J., Bartlam, M., Li, X., Lou, Z., Rao, Z., 2010. The crystal structure of porcine reproductive and respiratory syndrome virus nonstructural protein Nsp1beta reveals a novel metal-dependent nuclease. J. Virol. 84, 6461-6471.

The invention claimed is:

1. A genotype I Porcine Reproductive and Respiratory Syndrome (PRRS) virus whose genome is encoded by a nucleic acid molecule comprising a sequence selected from SEQ ID NOS: 49, 56, 57, and 58.

2. The virus of claim 1, wherein the nucleic acid comprises the sequence of SEQ ID NO: 49.

3. The virus of claim 1, wherein the nucleic acid comprises the sequence of SEQ ID NO: 56.

4. The virus of claim 1, wherein the nucleic acid comprises the sequence of SEQ ID NO: 57.

5. The virus of claim 1, wherein the nucleic acid comprises the sequence of SEQ ID NO: 58.

6. A vaccine comprising the virus according to claim 1.

7. The vaccine of claim 6, further comprising a pharmaceutically acceptable excipient.

8. The vaccine of claim 7, wherein the pharmaceutically acceptable excipient is selected from a solvent, a dispersion media, an adjuvant, a stabilizing agent, a diluent, a preservative, an antibacterial agent, an antifungal agent, and an isotonic agent.

9. The vaccine of claim 6, wherein the vaccine comprises $10^4$ to $10^6$ particles of the virus per dose.

10. The vaccine of claim 6, wherein the nucleic acid comprises the sequence of SEQ ID NO: 49.

11. The vaccine of claim 6, wherein the nucleic acid comprises the sequence of SEQ ID NO: 56.

12. The vaccine of claim 6, wherein the nucleic acid comprises the sequence of SEQ ID NO: 57.

13. The vaccine of claim 6, wherein the nucleic acid comprises the sequence of SEQ ID NO: 58.

14. A method for treating and/or prophylaxis of PRRS in swine, comprising administering to the swine the vaccine according to claim 6.

15. The method of claim 14, wherein the vaccine is administered by an intranasal, an intramuscular, an oral, or an intrauterine route.

16. The method of claim 14, wherein the administration induces a protective immune response against PRRS in the swine that reduces and/or prevents PRRS symptoms.

17. The method of claim 14, wherein the nucleic acid comprises the sequence of SEQ ID NO: 56.

18. The method of claim 14, wherein the nucleic acid comprises the sequence of SEQ ID NO: 58.

19. A method for differentiating between infection and vaccination of a swine, comprising detecting for a vaccine marker in the swine that differentiates between native infection with PRRS and the vaccine according to claim 1.

20. The method of claim 19, wherein the vaccine marker is a deletion or insertion marker that permits serological and/or sequence differentiation.

* * * * *